(12) United States Patent
He et al.

(10) Patent No.: US 10,597,391 B2
(45) Date of Patent: Mar. 24, 2020

(54) UREA-CONTAINING ISOXAZOLE DERIVATIVES AS FXR AGONISTS AND METHODS OF USE THEREOF

(71) Applicant: Enanta Pharmaceuticals, Inc., Watertown, MA (US)

(72) Inventors: Jing He, Somerville, MA (US); Guoqiang Wang, Belmont, MA (US); Ruichao Shen, West Roxbury, MA (US); Xuechao Xing, Wilmington, MA (US); Bin Wang, Brighton, MA (US); Jun Ma, Belmont, MA (US); Yat Sun Or, Watertown, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 15/793,554

(22) Filed: Oct. 25, 2017

(65) Prior Publication Data

US 2018/0141941 A1    May 24, 2018

Related U.S. Application Data

(60) Provisional application No. 62/413,372, filed on Oct. 26, 2016.

(51) Int. Cl.
| | | |
|---|---|---|
| *C07D 451/02* | (2006.01) | |
| *A61P 1/16* | (2006.01) | |
| *A61P 3/00* | (2006.01) | |
| *A61P 1/00* | (2006.01) | |
| *A61P 11/00* | (2006.01) | |
| *A61P 9/00* | (2006.01) | |
| *A61P 13/12* | (2006.01) | |

(52) U.S. Cl.
CPC .............. *C07D 451/02* (2013.01); *A61P 1/00* (2018.01); *A61P 1/16* (2018.01); *A61P 3/00* (2018.01); *A61P 9/00* (2018.01); *A61P 11/00* (2018.01); *A61P 13/12* (2018.01)

(58) Field of Classification Search
None
See application file for complete search history.

(56) References Cited

U.S. PATENT DOCUMENTS

| | | | |
|---|---|---|---|
| 5,571,809 A | 11/1996 | Hargrave et al. | |
| 6,974,830 B2 | 12/2005 | Bauer et al. | |
| 7,319,109 B2 | 1/2008 | Boggs et al. | |
| 7,846,960 B2 | 12/2010 | Bell et al. | |
| 7,863,302 B2 | 1/2011 | Bell et al. | |
| 7,897,773 B2 | 3/2011 | Aletru et al. | |
| 7,902,373 B2 | 3/2011 | Blake et al. | |
| 8,952,042 B2 | 2/2015 | Kremoser et al. | |
| 9,751,874 B2 | 9/2017 | Gege et al. | |
| 2004/0048316 A1 | 3/2004 | Haffner et al. | |
| 2007/0054902 A1 | 3/2007 | Fukui et al. | |
| 2008/0167356 A1 | 7/2008 | Caldwell et al. | |
| 2009/0163474 A1 | 6/2009 | Zhang et al. | |
| 2010/0015063 A1 | 1/2010 | Carter et al. | |
| 2010/0063697 A1 | 3/2010 | Lindgren et al. | |
| 2010/0099703 A1 | 4/2010 | Garcia-Lopez et al. | |
| 2010/0120775 A1 | 5/2010 | Bass, III et al. | |
| 2010/0152166 A1 | 6/2010 | Genin et al. | |
| 2010/0184809 A1 | 7/2010 | Kremoser et al. | |
| 2010/0210660 A1 | 8/2010 | Kremoser et al. | |
| 2010/0249179 A1 | 9/2010 | Deaton et al. | |
| 2010/0292212 A1 | 11/2010 | Ackermann et al. | |
| 2011/0034507 A1 | 2/2011 | Akwabi-Ameyaw et al. | |
| 2011/0275595 A1 | 11/2011 | Eckhardt et al. | |
| 2012/0004164 A1 | 1/2012 | Dales et al. | |
| 2013/0261108 A1 | 10/2013 | Bass, III et al. | |
| 2014/0038947 A1 | 2/2014 | Glick et al. | |
| 2014/0221659 A1 | 8/2014 | Kinzel et al. | |
| 2015/0299210 A1 | 10/2015 | Bailey et al. | |
| 2015/0366856 A1 | 12/2015 | Tully et al. | |
| 2016/0130297 A1 | 5/2016 | Or et al. | |

(Continued)

FOREIGN PATENT DOCUMENTS

| | | | |
|---|---|---|---|
| CN | 106588804 A | 4/2017 | |
| CN | 106632294 A | 5/2017 | |

(Continued)

OTHER PUBLICATIONS

Merck Manual, Diabetes Mellitus. (2017. Web: <http://www.merck.com/mmpe/print/sec12/ch158/ch158b.html>.*

(Continued)

*Primary Examiner* — Emily A Bernhardt
*Assistant Examiner* — Laura M Daniel
(74) *Attorney, Agent, or Firm* — Edgar W. Harlan; Carolyn S. Elmore; Elmore Patent Law Group, P.C.

(57) ABSTRACT

The present invention provides compounds of Formula I,

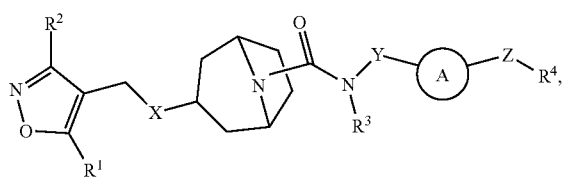

Pharmaceutically acceptable salts thereof, pharmaceutical compositions comprising these compounds and methods of using these compounds to prevent or treat FXR-mediated or TGR5-mediated diseases or conditions.

25 Claims, No Drawings

(56) References Cited

U.S. PATENT DOCUMENTS

| | | |
|---|---|---|
| 2017/0298068 A1 | 10/2017 | Gege et al. |
| 2017/0304270 A1 | 10/2017 | Or et al. |
| 2017/0304271 A1 | 10/2017 | Or et al. |
| 2017/0304272 A1 | 10/2017 | Or et al. |
| 2017/0355685 A1 | 12/2017 | Blomgren et al. |
| 2017/0355693 A1 | 12/2017 | Blomgren et al. |
| 2017/0355694 A1 | 12/2017 | Gege |
| 2017/0368038 A1 | 12/2017 | Badman et al. |
| 2018/0030003 A1 | 2/2018 | Wang et al. |
| 2018/0099957 A1 | 4/2018 | Ma et al. |
| 2018/0141941 A1 | 5/2018 | He et al. |

FOREIGN PATENT DOCUMENTS

| | | |
|---|---|---|
| CN | 106946867 A | 7/2017 |
| CN | 106995416 A | 8/2017 |
| CN | 107021957 A | 8/2017 |
| CN | 108017636 A | 5/2018 |
| CN | 108341822 A | 7/2018 |
| CN | 109053751 A | 12/2018 |
| WO | 2004046162 A2 | 6/2004 |
| WO | 2009149795 A2 | 12/2009 |
| WO | 2011020615 A1 | 2/2011 |
| WO | 2011021645 A1 | 2/2011 |
| WO | 2012087519 A1 | 6/2012 |
| WO | 2012087520 A1 | 6/2012 |
| WO | 2012087521 A1 | 6/2012 |
| WO | 2013007387 A1 | 1/2013 |
| WO | 2013037482 A1 | 3/2013 |
| WO | 2013166176 A1 | 11/2013 |
| WO | 2015036442 A1 | 3/2015 |
| WO | 2017118294 A1 | 7/2017 |
| WO | 2017128896 A1 | 8/2017 |
| WO | 2017133521 | 8/2017 |
| WO | 2017145041 | 8/2017 |
| WO | 2017201150 A1 | 11/2017 |
| WO | 2018024224 A1 | 2/2018 |
| WO | 2018039386 A1 | 3/2018 |
| WO | 2018067704 A1 | 4/2018 |
| WO | 2018075207 A1 | 4/2018 |
| WO | 2018085148 A1 | 5/2018 |
| WO | 2018133730 A1 | 7/2018 |
| WO | 2018170173 A1 | 9/2018 |
| WO | 2018190643 A1 | 10/2018 |
| WO | 2018214959 A1 | 11/2018 |
| WO | 2019007418 A1 | 1/2019 |

OTHER PUBLICATIONS

Medline Plus. Hardening of the Arteries. (2018). Web: <http://www.nlm.nih.gov/medlineplus/ency/article/000171.htm>.*

Ruano, J., L. G., et al., Synthesis of alkyl 4-(diethoxymethyl)-3-pyridin-3-ylisoxazole-5-carboxylates: useful scaffold for highly functionalised 3-(pyridin-3-yl)isoxazoles, Tetrahedron, 61: 4363-4371 (2005).

Ali, et al., "Recent advances in the development of farnesoid X receptor agonists," Ann Transl Med, 3(1):5, pp. 1-16, 2015.

Crawley, "Farnesoid X Receptor Modulators: a patent review," Expert Opinion on Therapeutic Patents, 20(8): 1047-1057, 2010.

U.S. Appl. No. 15/597,431, filed May 17, 2017.

U.S. Appl. No. 15/597,417, filed May 17, 2017.

U.S. Appl. No. 15/597,423, filed May 17, 2017.

Sepe, et al., "Farnesoid X receptor modulators (2011-2014): a patent review," Expert Opinion on Therapeutic Patents, 25:8, 885-896, 2015.

Buijsman, et al., "Non-Steroidal Steroid Receptor Modulators," Current Medicinal Chemistry, 12:1017-1075, 2005.

U.S. Appl. No. 15/497,359, filed Apr. 26, 2017.

U.S. Appl. No. 15/724,919, filed Oct. 4, 2017.

U.S. Appl. No. 15/497,307, filed Apr. 26, 2017.

U.S. Appl. No. 15/497,268, filed Apr. 26, 2017.

"Pubchem CID 123486225" Create Date: Jan. 25, 2017 (Jan. 25, 2017) Date Accessed: Apr. 1, 2019 (Apr. 1, 2019).

\* cited by examiner

UREA-CONTAINING ISOXAZOLE DERIVATIVES AS FXR AGONISTS AND METHODS OF USE THEREOF

RELATED APPLICATIONS

This application claims the benefit of U.S. Provisional Application No. 62/413,372, filed on Oct. 26, 2016. The entire teachings of the above application are incorporated herein by reference.

TECHNICAL FIELD

The present invention relates generally to compounds and pharmaceutical compositions useful as FXR agonists. Specifically, the present invention relates to isoxazole compounds containing a urea moiety and methods for their preparation and use.

BACKGROUND OF THE INVENTION

Farnesoid X Receptor (FXR, NR1H4) is a member of the nuclear receptor family of ligand-activated transcription factors that includes receptors for the steroid, retinoid, and thyroid hormones (D. J. Mangelsdorf, et al., *Cell,* 1995, 83(6), 841-850). FXR was originally identified from a rat liver cDNA library. Farnesol and derivatives, collectively termed farnesoids, activate the rat ortholog at high concentration, but they do not modulate the human or mouse receptors. FXR is primarily expressed in the liver, kidney, and intestine (W. Seol, et al., *Mol. Endocrinol.,* 1995, 9(1), 72-85; B. M. Forman, et al., *Cell,* 1995, 81(5), 687-693). The relevant physiological ligands of FXR include the primary bile acids cholic acid (CA) and chenodeoxycholic acid (CDCA) and the secondary bile acids deoxycholic acid (DCA) and lithocholic acid (LCA) (D. Parks, et al., *Science,* 1999, 284(5418), 1362-1365). The most potent physiological ligand for FXR is CDCA, which plays a key role in regulating the expression of several genes that participate in bile acid homeostasis. FXR functions as a heterodimer with the retinoid X receptor (RXR) and binds to response elements in the promoter region of target genes to regulate gene transcription. FXR seems to be also involved in paracrine and endocrine signaling by upregulating the expression of the cytokine Fibroblast Growth Factor (J. Holt, et al., *Genes Dev.,* 2003, 17(13), 1581-1591; T. Inagaki, et al., *Cell Metab.,* 2005, 2(4), 217-225).

Small molecule compounds which act as FXR modulators have been disclosed in the following publications: WO 2000/037077, WO 2002/072598, WO 2003/015771, WO 2003/099821, WO 2004/00752, WO 2004/048349, WO 2005/009387, WO 2005/082925, US 2005/0054634, WO 2007/052843, WO 2007/070796, WO 2007/076260, WO 2007/092751, WO 2007/095174, WO 2007/140174, WO 2007/140183, US 2007/0142340, WO 2008/000643, WO 2008/002573, WO 2008/025539, WO 2008/025540, WO 2008/051942, WO 2008/073825, WO 2008/157270, US 2008/0299118, US 2008/0300235, WO 2009/005998, WO 2009/012125, WO 2009/027264, WO 2009/062874, WO 2009/127321, WO 2009/149795, US 2009/0131409, US 2009/0137554, US 2009/0163474, US 2009/0163552, US 2009/0215748, WO 2010/043513, WO 2011/020615, WO 2011/117163, WO 2012/087519, WO 2012/087520, WO 2012/087521, WO 2013/007387, WO 2013/037482, WO 2013/166176, WO 2013/192097, WO 2014/184271, US 2014/0186438, US 2014/0187633, WO 2015/017813, WO 2015/069666, WO 2016/116054, WO 2016/103037, WO 2016/096116, WO 2016/096115, WO 2016/097933, WO 2016/081918, WO 2016/127924, CN 106632294, CN 106588804, US 2017/0196893, WO 2017/062763, WO 2017/053826, CN 106518708, CN 106518946, CN 106478759, CN 106478447, CN 106478453, WO 2017/027396, WO 2017/049172, WO 2017/049173, WO 2017/049176, WO 2017/049177, WO 2017/118294, WO 2017/128896, WO 2017/133521, and WO 2017/156024. Further small molecule FXR modulators have been recently reviewed (R. C. Buijsman, et al., *Curr. Med. Chem.* 2005, 12(9), 1017-1075; Crawley, M. L. *Expert Opin. Ther. Patents* 2010, 20(8), 1047-1057; V. Sepe, et al., *Expert Opin. Ther. Patents* 2015, 25(8), 885-896; Xu, Y., *J. Med. Chem.* DOI: 10.1021/acs.jmedchem.5b00342).

There is a need for development of FXR modulators for the treatment and prevention of diseases. The present invention has identified a series of isoxazole compounds containing a urea moiety as FXR agonists, and methods of using these compounds to treat disease.

SUMMARY OF THE INVENTION

In one aspect, the invention provides compounds represented by Formula (I), and pharmaceutically acceptable salts, stereoisomer, solvate, hydrate or combination thereof:

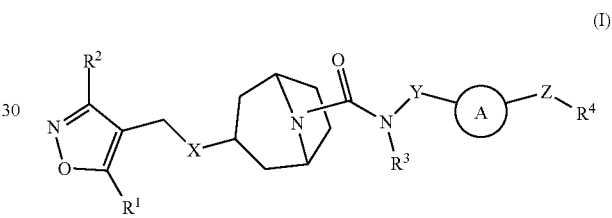

(I)

wherein:
R$^1$ is hydrogen, halogen, cyano, optionally substituted —C$_1$-C$_6$ alkyl, optionally substituted —C$_2$-C$_6$ alkenyl, optionally substituted —C$_2$-C$_6$ alkynyl, optionally substituted —C$_3$-C$_6$ cycloalkyl or optionally substituted 3- to 6-membered heterocycloalkyl. Preferably, R$^1$ is isopropyl, tert-butyl, or cyclopropyl.

R$^2$ is an optionally substituted aryl, optionally substituted heteroaryl, substituted arylalkyl, optionally substituted heteroarylalkyl, optionally substituted —C$_3$-C$_{12}$ cycloalkyl, or optionally substituted 3- to 12-membered heterocycloalkyl.

X is O or NR$^3$.

Each R$^3$ is independently selected from the group consisting of hydrogen, optionally substituted —C$_1$-C$_6$ alkyl, and optionally substituted —C$_3$-C$_6$ cycloalkyl.

Y, Y', and Z are independently selected from absent and optionally substituted —C$_1$-C$_6$ alkyl.

Ⓐ is optionally substituted —C$_5$-C$_{14}$ cycloalkyl; optionally substituted —C$_5$-C$_{14}$ cycloalkenyl; optionally substituted aryl, optionally substituted biaryl, optionally substituted 5- to 14-membered heterocyclic, optionally substituted heteroaryl or optionally substituted aryl-heterocyclic.

R$^4$ is hydrogen, hydroxy, tetrazolyl, cyano, —CHF$_2$, —CO$_2$R$^7$, —O—Y'—CO$_2$R$^7$, —NR$^5$—Y'—CO$_2$R$^7$, CONR$^5$R$^6$,

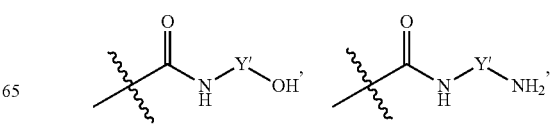

-continued

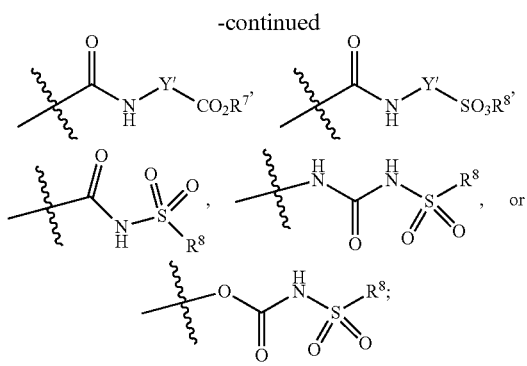

$R^5$ and $R^6$ are each independently selected from group consisting of:
1) Hydrogen;
2) Optionally substituted —$C_1$-$C_8$ alkyl;
3) Optionally substituted —$C_2$-$C_8$ alkenyl;
4) Optionally substituted —$C_2$-$C_8$ alkynyl; and
5) Optionally substituted —$C_3$-$C_8$ cycloalkyl; Alternatively, $R^5$ and $R^6$ are taken together with the nitrogen atom to which they are attached to form an optionally substituted 3- to 6-membered heterocycloalkyl.

$R^7$ is selected from the group consisting of:
1) Hydrogen;

2) 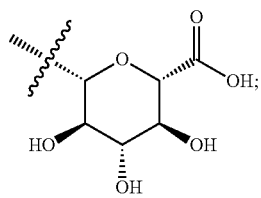

3) Optionally substituted —$C_1$-$C_8$ alkyl;
4) Optionally substituted —$C_2$-$C_8$ alkenyl;
5) Optionally substituted —$C_2$-$C_8$ alkynyl; and
6) Optionally substituted —$C_3$-$C_8$ cycloalkyl;

$R^8$ is selected from the group consisting of:
1) Optionally substituted —$C_1$-$C_8$ alkyl;
2) Optionally substituted —$C_2$-$C_8$ alkenyl;
3) Optionally substituted —$C_2$-$C_8$ alkynyl;
4) Optionally substituted —$C_3$-$C_8$ cycloalkyl;
5) Optionally substituted —$C_3$-$C_8$ cycloalkenyl;
6) Optionally substituted 3- to 8-membered heterocycloalkyl;
7) Optionally substituted 3- to 8-membered heterocycloalkenyl;
8) Optionally substituted aryl;
9) Optionally substituted aryl-$C_1$-$C_8$-alkyl;
10) Optionally substituted heteroaryl;
11) Optionally substituted heteroaryl-$C_1$-$C_8$-alkyl; and
12) $NR^5R^6$;

$R^5$ and $R^6$ are previously defined. Alternatively, $R^5$ and $R^6$ are taken together with the nitrogen atom to which they are attached to form an optionally substituted 3- to 6-membered heterocycloalkyl.

Alternatively, the moiety represented by —$N(R^3)$—Y is an optionally substituted 3- to 8-membered heterocycloalkyl which is fused to ⊙.

In another embodiment, the present invention provides a pharmaceutical composition comprising a therapeutically effective amount of a compound or combination of compounds of the present invention, or a pharmaceutically acceptable salt form, stereoisomer, solvate, hydrate or combination thereof, in combination with a pharmaceutically acceptable carrier or excipient.

In another embodiment, the present invention provides a method for the prevention or treatment of an FXR mediated disease or condition. The method comprises administering a therapeutically effective amount of a compound of Formula (I). The present invention also provides the use of a compound of Formula (I) for the preparation of a medicament for the prevention or treatment of an FXR mediated disease or condition.

DETAILED DESCRIPTION OF THE INVENTION

A first embodiment of the invention is a compound represented by Formula I as described above, or a pharmaceutically acceptable salt, ester, stereoisomer, tautomer, solvate, hydrate or combination thereof.

In certain embodiments, the present invention relates to compounds of Formula (I), and pharmaceutically acceptable salts thereof, wherein $R^1$ is optionally substituted isopropyl, cyclopropyl, or tert-butyl; preferably $R^1$ is cyclopropyl.

In certain embodiments, the present invention relates to compounds of Formula (I), and pharmaceutically acceptable salts thereof, wherein $R^2$ is optionally substituted phenyl.

In certain embodiments, the present invention relates to compounds of Formula (I), and pharmaceutically acceptable salts thereof, wherein $R^2$ is optionally substituted heteroaryl.

In certain embodiments, the present invention relates to compounds of Formula (I), and pharmaceutically acceptable salts thereof, wherein $R^2$ is selected from the groups set forth below:

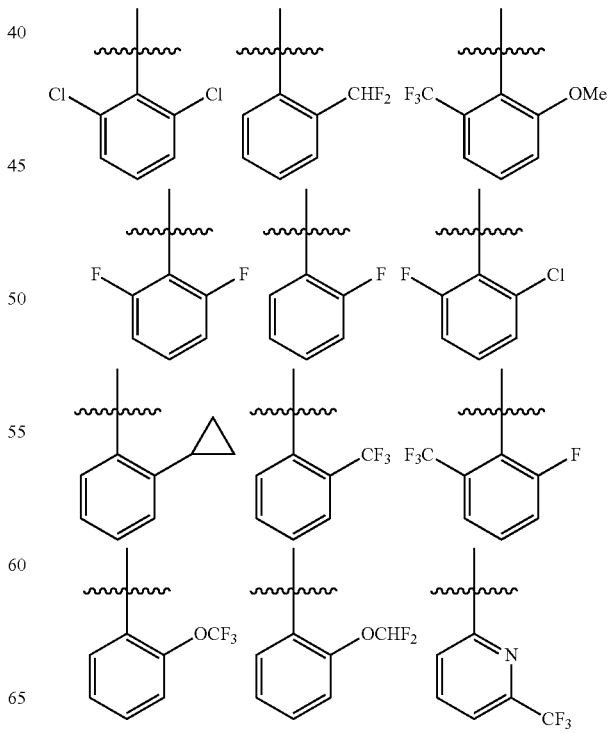

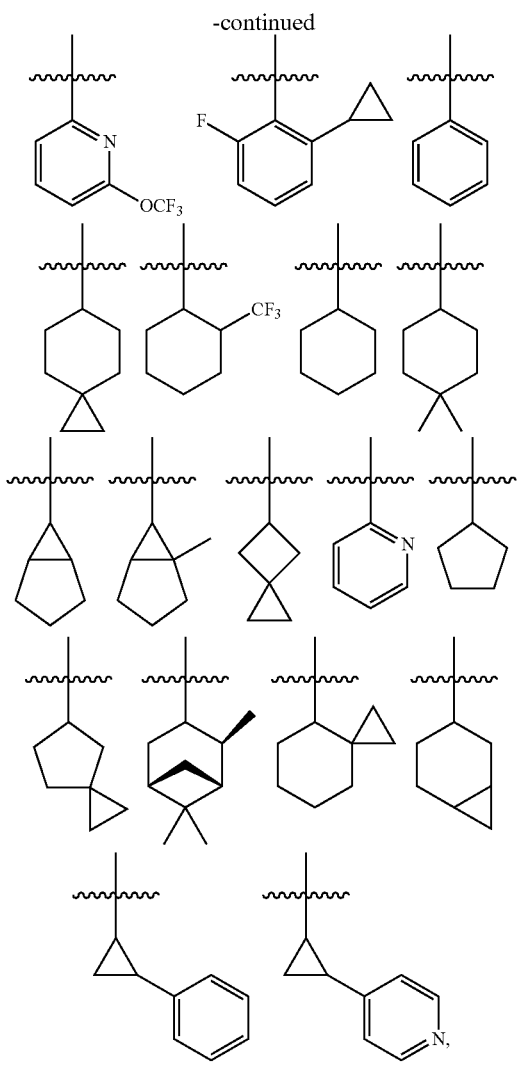

Each of above group can be optionally further substituted. The preferred substituents are halogen, optionally substituted $C_1$-$C_6$ alkyl, optionally substituted $C_1$-$C_6$ alkoxy, optionally substituted $C_3$-$C_6$ cycloalkyl, optionally substituted $C_3$-$C_6$ cycloalkenyl, optionally substituted aryl, and optionally substituted heteroaryl.

In certain embodiments, the present invention relates to compounds of Formula (I), and pharmaceutically acceptable salts thereof, wherein Ⓒ is optionally substituted and selected from phenyl, pyridyl, pyrimidinyl, pyrazolyl, thienyl, thiazolyl, triazolyl, isothiazolyl, pyrrolyl, pyrazolyl, oxazolyl, oxadiazolyl, imidazolyl, furanyl, indolyl, benzothienyl, naphthyl, quinolyl, naphthyridyl, quinoxalyl, pyridopyrazolyl, pyridooxazolyl, pyridothiazolyl, isoquinolyl, pyridofuranyl, indazolyl, benzisoxazolyl, benzofuranyl, benzotriazolyl, and benzothiazolyl. Preferred substituents include halogen, hydroxyl, —CN, —$NO_2$, —$NH_2$, —C(O)$R^7$, —S(O)$_n$$NR^5R^6$, —S(O)$_n$$R^8$, optionally substituted $C_1$-$C_6$ alkyl, $C_2$-$C_6$ alkenyl, $C_2$-$C_6$ alkynyl, optionally substituted $C_1$-$C_6$ alkoxy, optionally substituted $C_3$-$C_6$ cycloalkyl, optionally substituted $C_3$-$C_6$ cycloalkenyl, $C_3$-$C_6$ cycloalkenyl, optionally substituted aryl, optionally substituted heteroaryl, and optionally substituted —O—$C_1$-$C_2$ alkylphenyl, wherein n is 0, 1, or 2; $R^5$, $R^6$, $R^7$ and $R^8$ are defined previously.

In certain embodiments, the present invention relates to compounds of Formula (I), and pharmaceutically acceptable salts thereof, wherein Ⓒ is an optionally substituted biaryl group, such as, but not limited to, optionally substituted biphenyl, pyridylphenyl, pyrimidylphenyl, pyrimidylpyridyl, pyrimidyloxadiazolyl.

In certain embodiments, the present invention relates to compounds of Formula (I), and pharmaceutically acceptable salts thereof, wherein Ⓒ is selected from the groups set forth below:

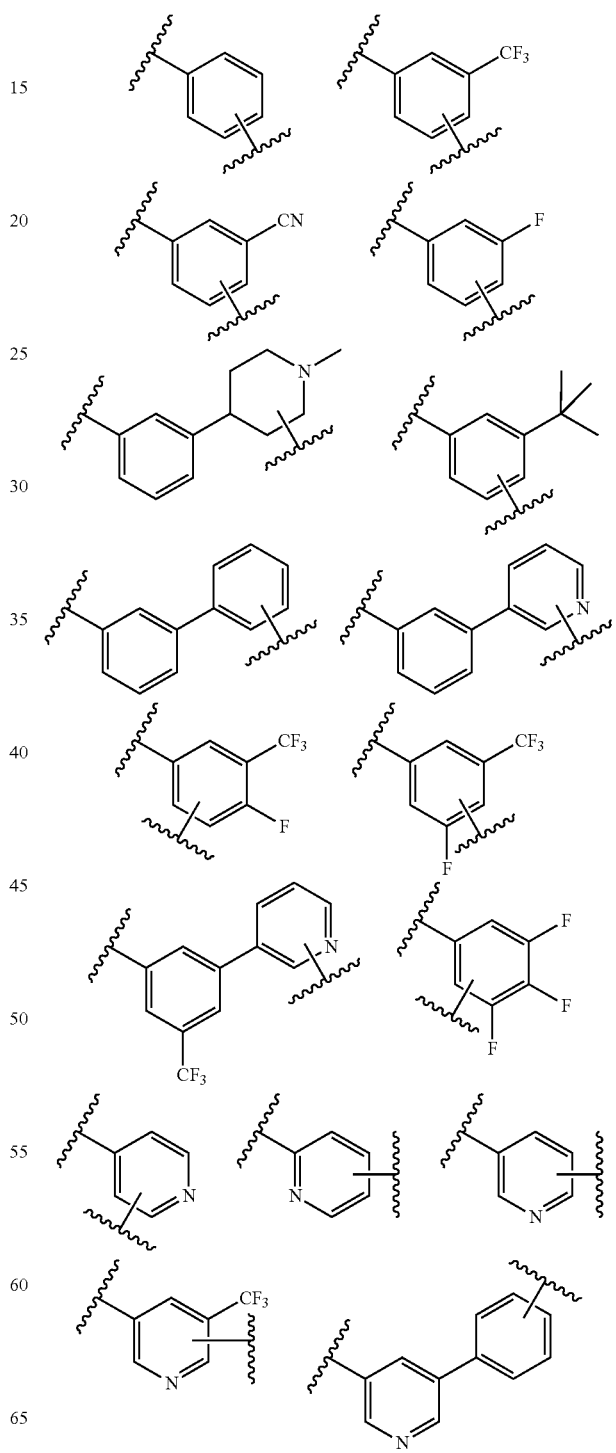

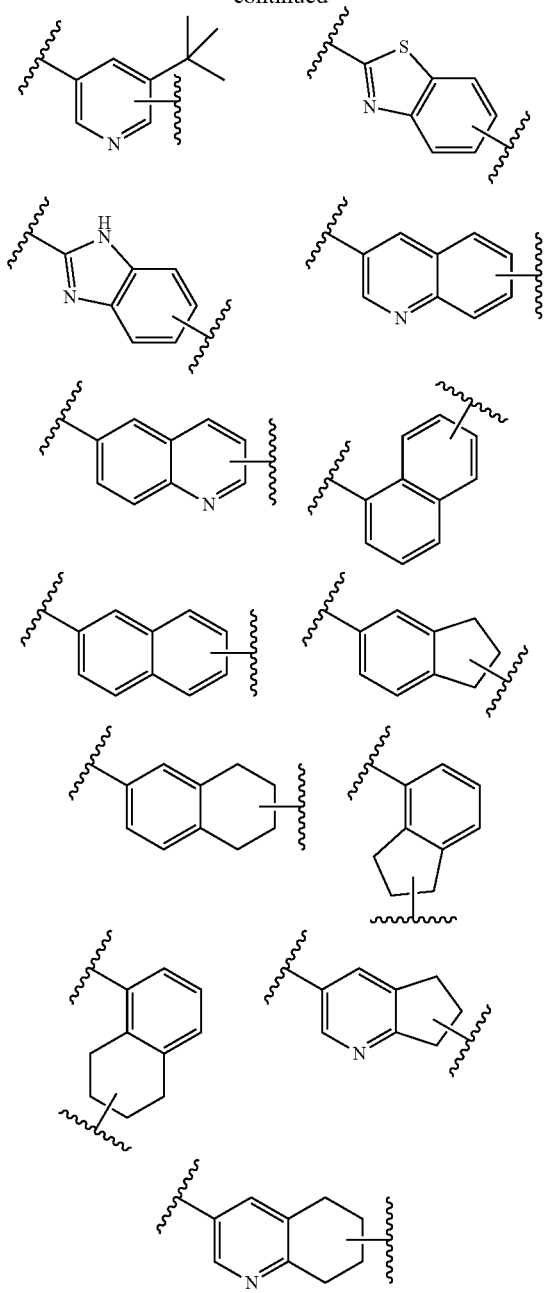

each of the above groups can be optionally further substituted.

In another embodiment, the compound of Formula (I) is represented by Formula (IIa) or Formula (IIb) or a pharmaceutically acceptable salt thereof:

(IIa)

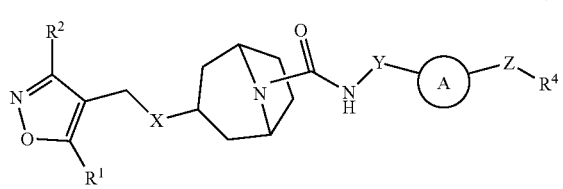

(IIb)

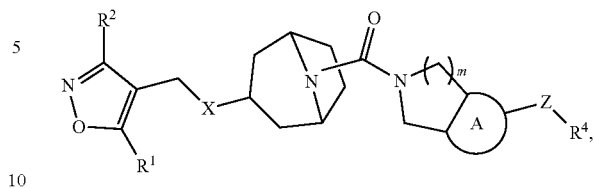

wherein $R^1$, $R^2$, $R^4$, X, Y, Z and ⊙ are previously defined and m is 0, 1, 2, or 3. Preferably, m is 1 or 2.

In another embodiment, the compound of Formula (I) is represented by Formula (IIIa) or Formula (IIIb) or a pharmaceutically acceptable salt thereof:

(IIIa)

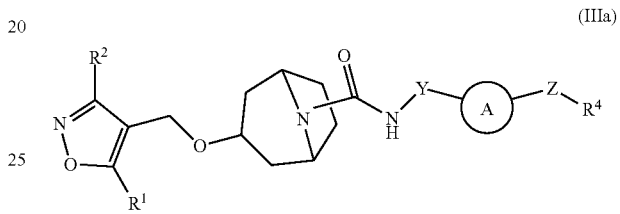

(IIIb)

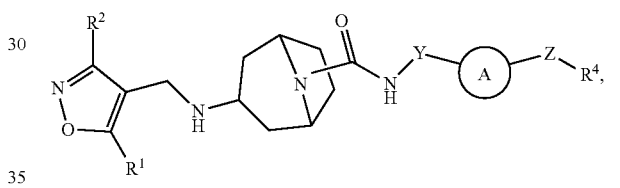

wherein $R^1$, $R^2$, $R^4$, Y, Z and ⊙ are previously defined.

In another embodiment, the compound of Formula (I) is represented by Formula (IVa) or Formula (IVb) or a pharmaceutically acceptable salt thereof:

(IVa)

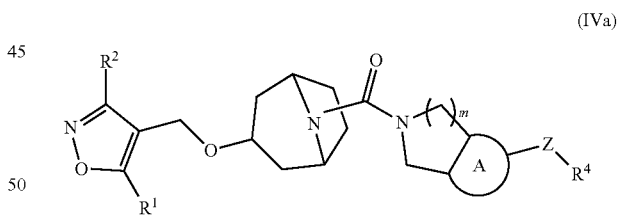

(IVb)

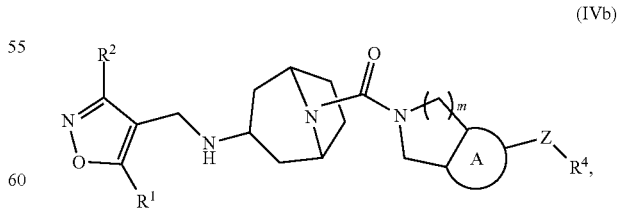

wherein $R^1$, $R^2$, $R^4$, m, Z and ⊙ are previously defined.

In another embodiment, when Y is absent and $R^4$ is hydrogen, the compound of Formula (I) is represented by Formula (V) or a pharmaceutically acceptable salt thereof:

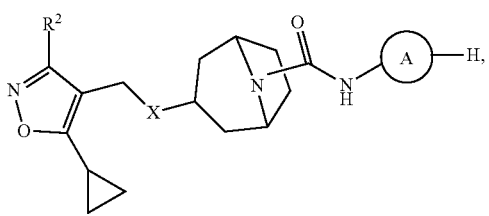

wherein $R^2$, X, and Ⓐ are previously defined.

Representative compounds of the invention include, but are not limited to, the following compounds (example 1 to example 180 in Table 1) according to Formula (V), wherein $R^2$, X, and Ⓐ are delineated for each example in Table 1.

TABLE 1

| Example | $R^2$ | X | Ⓐ |
|---|---|---|---|
| 1 | 2,6-diClPh | O | 3-F-Ph |
| 2 | 2,6-diClPh | O | 3-CF₃-Ph |
| 3 | 2,6-diClPh | O | 3-CN-Ph |
| 4 | 2,6-diClPh | O | 3-tBu-Ph |
| 5 | 2,6-diClPh | O | 3-(1-methylpiperidin-4-yl)-Ph |
| 6 | 2,6-diClPh | O | 2-CF₃-Ph |
| 7 | 2,6-diClPh | O | 2-F-Ph |
| 8 | 2,6-diClPh | O | 4-CF₃-Ph |
| 9 | 2,6-diClPh | O | 4-CN-Ph |
| 10 | 2,6-diClPh | O | 3,4,5-triF-Ph |
| 11 | 2,6-diClPh | O | 3-CF₃-5-F-Ph |
| 12 | 2,6-diClPh | O | 3-(pyridin-3-yl)-Ph |
| 13 | 2,6-diClPh | O | 3-(1-methylpyrazol-4-yl)-Ph |
| 14 | 2,6-diClPh | O | 3-CF₃-5-(pyridin-3-yl)-Ph |

TABLE 1-continued

| Example | R² | X | Ⓐ |
|---|---|---|---|
| 15 | 2,6-diCl-phenyl | O | pyridin-3-yl |
| 16 | 2,6-diCl-phenyl | O | pyridin-2-yl |
| 17 | 2,6-diCl-phenyl | O | pyridin-4-yl |
| 18 | 2,6-diCl-phenyl | O | 5-CF₃-pyridin-3-yl |
| 19 | 2,6-diCl-phenyl | O | naphthalen-1-yl |
| 20 | 2,6-diCl-phenyl | O | naphthalen-2-yl |
| 21 | 2,6-diCl-phenyl | O | quinolin-3-yl |
| 22 | 2,6-diCl-phenyl | O | quinolin-6-yl |
| 23 | 2,6-diCl-phenyl | O | benzothiazol-2-yl |
| 24 | 2,6-diCl-phenyl | O | 3-(SO₂NH₂)-phenyl |
| 25 | 2,6-diCl-phenyl | O | 3-(SO₂NMe₂)-phenyl |
| 26 | 2,6-diCl-phenyl | O | 3-(SO₂-cyclopropyl)-phenyl |
| 27 | 2,6-diCl-phenyl | O | 3-(CF₂-pyridin-3-yl)-phenyl |
| 28 | 2,6-diCl-phenyl | O | 5,6,7,8-tetrahydronaphthalen-2-yl |
| 29 | 2,6-diCl-phenyl | O | 5,6,7,8-tetrahydroquinolin-3-yl |
| 30 | 2,6-diCl-phenyl | O | cyclohexyl |
| 31 | 2-OCF₃-phenyl | O | 3-CF₃-phenyl |

TABLE 1-continued

| Example | R² | X | Ⓐ |
|---|---|---|---|
| 32 | F₃CO-phenyl | O | 3-F-phenyl |
| 33 | F₃CO-phenyl | O | 3-CN-phenyl |
| 34 | F₃CO-phenyl | O | 3-tBu-phenyl |
| 35 | F₃CO-phenyl | O | 3-(1-methylpiperidin-4-yl)phenyl |
| 36 | F₃CO-phenyl | O | 2-CF₃-phenyl |
| 37 | F₃CO-phenyl | O | 2-F-phenyl |
| 38 | F₃CO-phenyl | O | 4-CF₃-phenyl |
| 39 | F₃CO-phenyl | O | 4-CN-phenyl |
| 40 | F₃CO-phenyl | O | 3,4,5-trifluorophenyl |
| 41 | F₃CO-phenyl | O | 3-CF₃-5-F-phenyl |
| 42 | F₃CO-phenyl | O | 3-(pyridin-3-yl)phenyl |
| 43 | F₃CO-phenyl | O | 3-(1-methyl-1H-pyrazol-4-yl)phenyl |
| 44 | F₃CO-phenyl | O | 3-CF₃-5-(pyridin-3-yl)phenyl |
| 45 | F₃CO-phenyl | O | pyridin-3-yl |
| 46 | F₃CO-phenyl | O | pyridin-2-yl |
| 47 | F₃CO-phenyl | O | pyridin-4-yl |
| 48 | F₃CO-phenyl | O | 5-CF₃-pyridin-3-yl |
| 49 | F₃CO-phenyl | O | naphthalen-1-yl |

TABLE 1-continued

| Example | R² | X | Ⓐ |
|---|---|---|---|
| 50 | F₃CO-phenyl (2-) | O | naphthalen-2-yl |
| 51 | F₃CO-phenyl (2-) | O | quinolin-3-yl |
| 52 | F₃CO-phenyl (2-) | O | quinolin-6-yl |
| 53 | F₃CO-phenyl (2-) | O | benzothiazol-2-yl |
| 54 | F₃CO-phenyl (2-) | O | 3-(SO₂NH₂)-phenyl |
| 55 | F₃CO-phenyl (2-) | O | 3-(SO₂NMe₂)-phenyl |
| 56 | F₃CO-phenyl (2-) | O | 3-(SO₂-cyclopropyl)-phenyl |
| 57 | F₃CO-phenyl (2-) | O | 3-(CF₂-pyridin-3-yl)-phenyl |
| 58 | F₃CO-phenyl (2-) | O | 5,6,7,8-tetrahydronaphthalen-2-yl |
| 59 | F₃CO-phenyl (2-) | O | 5,6,7,8-tetrahydroquinolin-3-yl |
| 60 | F₃CO-phenyl (2-) | O | cyclohexyl |
| 61 | spiro[2.5]octan-6-yl | O | 3-CF₃-phenyl |
| 62 | spiro[2.5]octan-6-yl | O | 3-F-phenyl |
| 63 | spiro[2.5]octan-6-yl | O | 3-CN-phenyl |
| 64 | spiro[2.5]octan-6-yl | O | 3-tBu-phenyl |
| 65 | spiro[2.5]octan-6-yl | O | 3-(1-methylpiperidin-4-yl)-phenyl |
| 66 | spiro[2.5]octan-6-yl | O | 2-CF₃-phenyl |
| 67 | spiro[2.5]octan-6-yl | O | 2-F-phenyl |
| 68 | spiro[2.5]octan-6-yl | O | 4-CF₃-phenyl |

TABLE 1-continued

| Example | R² | X | Ⓐ |
|---|---|---|---|
| 69 | spiro[2.5]octane | O | 4-cyanophenyl |
| 70 | spiro[2.5]octane | O | 3,4,5-trifluorophenyl |
| 71 | spiro[2.5]octane | O | 3-CF₃-5-F-phenyl |
| 72 | spiro[2.5]octane | O | 3-(pyridin-3-yl)phenyl |
| 73 | spiro[2.5]octane | O | 3-(1-methyl-1H-pyrazol-4-yl)phenyl |
| 74 | spiro[2.5]octane | O | 3-CF₃-5-(pyridin-3-yl)phenyl |
| 75 | spiro[2.5]octane | O | pyridin-3-yl |
| 76 | spiro[2.5]octane | O | pyridin-2-yl |
| 77 | spiro[2.5]octane | O | pyridin-4-yl |
| 78 | spiro[2.5]octane | O | 5-CF₃-pyridin-3-yl |
| 79 | spiro[2.5]octane | O | naphthalen-1-yl |
| 80 | spiro[2.5]octane | O | naphthalen-2-yl |
| 81 | spiro[2.5]octane | O | quinolin-3-yl |
| 82 | spiro[2.5]octane | O | quinolin-6-yl |
| 83 | spiro[2.5]octane | O | benzo[d]thiazol-2-yl |
| 84 | spiro[2.5]octane | O | 3-sulfamoylphenyl |
| 85 | spiro[2.5]octane | O | 3-(N,N-dimethylsulfamoyl)phenyl |
| 86 | spiro[2.5]octane | O | 3-(cyclopropylsulfonyl)phenyl |
| 87 | spiro[2.5]octane | O | 3-(difluoro(pyridin-3-yl)methyl)phenyl |

TABLE 1-continued

| Example | R² | X | Ⓐ |
|---|---|---|---|
| 88 | spiro[2.5]octyl | O | tetrahydronaphthalenyl |
| 89 | spiro[2.5]octyl | O | 5,6,7,8-tetrahydroquinolinyl |
| 90 | spiro[2.5]octyl | O | cyclohexyl |
| 91 | 2,6-dichlorophenyl | NH | 3-fluorophenyl |
| 92 | 2,6-dichlorophenyl | NH | 3-(trifluoromethyl)phenyl |
| 93 | 2,6-dichlorophenyl | NH | 3-cyanophenyl |
| 94 | 2,6-dichlorophenyl | NH | 3-tert-butylphenyl |
| 95 | 2,6-dichlorophenyl | NH | 1-methylpiperidin-4-yl (attached to phenyl) |
| 96 | 2,6-dichlorophenyl | NH | 2-(trifluoromethyl)phenyl |
| 97 | 2,6-dichlorophenyl | NH | 2-fluorophenyl |
| 98 | 2,6-dichlorophenyl | NH | 4-(trifluoromethyl)phenyl |
| 99 | 2,6-dichlorophenyl | NH | 4-cyanophenyl |
| 100 | 2,6-dichlorophenyl | NH | 3,4,5-trifluorophenyl |
| 101 | 2,6-dichlorophenyl | NH | 3-fluoro-5-(trifluoromethyl)phenyl |
| 102 | 2,6-dichlorophenyl | NH | 3-(pyridin-3-yl)phenyl |
| 103 | 2,6-dichlorophenyl | NH | 3-(1-methyl-1H-pyrazol-4-yl)phenyl |
| 104 | 2,6-dichlorophenyl | NH | 3-(pyridin-3-yl)-5-(trifluoromethyl)phenyl |

TABLE 1-continued

| Example | R² | X | Ⓐ |
|---|---|---|---|
| 105 | 2,6-diCl-phenyl | NH | pyridin-3-yl |
| 106 | 2,6-diCl-phenyl | NH | pyridin-2-yl |
| 107 | 2,6-diCl-phenyl | NH | pyridin-4-yl |
| 108 | 2,6-diCl-phenyl | NH | 5-CF₃-pyridin-3-yl |
| 109 | 2,6-diCl-phenyl | NH | naphthalen-1-yl |
| 110 | 2,6-diCl-phenyl | NH | naphthalen-2-yl |
| 111 | 2,6-diCl-phenyl | NH | quinolin-3-yl |
| 112 | 2,6-diCl-phenyl | NH | quinolin-6-yl |
| 113 | 2,6-diCl-phenyl | NH | benzothiazol-2-yl |
| 114 | 2,6-diCl-phenyl | NH | 3-(SO₂NH₂)-phenyl |
| 115 | 2,6-diCl-phenyl | NH | 3-(SO₂NMe₂)-phenyl |
| 116 | 2,6-diCl-phenyl | NH | 3-(SO₂-cyclopropyl)-phenyl |
| 117 | 2,6-diCl-phenyl | NH | 3-(CF₂-pyridin-3-yl)-phenyl |
| 118 | 2,6-diCl-phenyl | NH | 5,6,7,8-tetrahydronaphthalen-2-yl |
| 119 | 2,6-diCl-phenyl | NH | 5,6,7,8-tetrahydroquinolin-3-yl |
| 120 | 2,6-diCl-phenyl | NH | cyclohexyl |
| 121 | 2-(F₃CO)-phenyl | NH | 3-CF₃-phenyl |

TABLE 1-continued

| Example | R² | X | Ⓐ |
|---|---|---|---|
| 122 | F₃CO (2-) phenyl | NH | 3-F phenyl |
| 123 | F₃CO (2-) phenyl | NH | 3-CN phenyl |
| 124 | F₃CO (2-) phenyl | NH | 3-tBu phenyl |
| 125 | F₃CO (2-) phenyl | NH | 3-(1-methylpiperidin-4-yl)phenyl |
| 126 | F₃CO (2-) phenyl | NH | 2-CF₃ phenyl |
| 127 | F₃CO (2-) phenyl | NH | 2-F phenyl |
| 128 | F₃CO (2-) phenyl | NH | 4-CF₃ phenyl |
| 129 | F₃CO (2-) phenyl | NH | 4-CN phenyl |
| 130 | F₃CO (2-) phenyl | NH | 3,4,5-triF phenyl |
| 131 | F₃CO (2-) phenyl | NH | 3-CF₃-5-F phenyl |
| 132 | F₃CO (2-) phenyl | NH | 3-(pyridin-3-yl)phenyl |
| 133 | F₃CO (2-) phenyl | NH | 3-(1-methyl-1H-pyrazol-4-yl)phenyl |
| 134 | F₃CO (2-) phenyl | NH | 3-CF₃-5-(pyridin-3-yl)phenyl |
| 135 | F₃CO (2-) phenyl | NH | pyridin-3-yl |
| 136 | F₃CO (2-) phenyl | NH | pyridin-2-yl |
| 137 | F₃CO (2-) phenyl | NH | pyridin-4-yl |
| 138 | F₃CO (2-) phenyl | NH | 5-CF₃-pyridin-3-yl |
| 139 | F₃CO (2-) phenyl | NH | naphthalen-1-yl |

TABLE 1-continued

| Example | R² | X | Ⓐ |
|---|---|---|---|
| 140 | F₃CO-phenyl | NH | naphthalen-2-yl |
| 141 | F₃CO-phenyl | NH | quinolin-3-yl |
| 142 | F₃CO-phenyl | NH | quinolin-6-yl |
| 143 | F₃CO-phenyl | NH | benzothiazol-2-yl |
| 144 | F₃CO-phenyl | NH | 3-(sulfamoyl)phenyl |
| 145 | F₃CO-phenyl | NH | 3-(N,N-dimethylsulfamoyl)phenyl |
| 146 | F₃CO-phenyl | NH | 3-(cyclopropylsulfonyl)phenyl |
| 147 | F₃CO-phenyl | NH | 3-(difluoro(pyridin-3-yl)methyl)phenyl |
| 148 | F₃CO-phenyl | NH | 5,6,7,8-tetrahydronaphthalen-2-yl |
| 149 | F₃CO-phenyl | NH | 5,6,7,8-tetrahydroquinolin-3-yl |
| 150 | F₃CO-phenyl | NH | cyclohexyl |
| 151 | spiro[2.5]octan-6-yl | NH | 3-(CF₃)phenyl |
| 152 | spiro[2.5]octan-6-yl | NH | 3-F-phenyl |
| 153 | spiro[2.5]octan-6-yl | NH | 3-CN-phenyl |
| 154 | spiro[2.5]octan-6-yl | NH | 3-tBu-phenyl |
| 155 | spiro[2.5]octan-6-yl | NH | 3-(1-methylpiperidin-4-yl)phenyl |
| 156 | spiro[2.5]octan-6-yl | NH | 2-(CF₃)phenyl |
| 157 | spiro[2.5]octan-6-yl | NH | 2-F-phenyl |
| 158 | spiro[2.5]octan-6-yl | NH | 4-(CF₃)phenyl |

TABLE 1-continued

| Example | R² | X | Ⓐ |
|---|---|---|---|
| 159 | spiro[2.5]octyl | NH | 4-cyanophenyl |
| 160 | spiro[2.5]octyl | NH | 3,4,5-trifluorophenyl |
| 161 | spiro[2.5]octyl | NH | 3-CF₃-5-F-phenyl |
| 162 | spiro[2.5]octyl | NH | 3-(pyridin-3-yl)phenyl |
| 163 | spiro[2.5]octyl | NH | 3-(1-methyl-1H-pyrazol-4-yl)phenyl |
| 164 | spiro[2.5]octyl | NH | 3-CF₃-5-(pyridin-3-yl)phenyl |
| 165 | spiro[2.5]octyl | NH | pyridin-3-yl |
| 166 | spiro[2.5]octyl | NH | pyridin-2-yl |
| 167 | spiro[2.5]octyl | NH | pyridin-4-yl |
| 168 | spiro[2.5]octyl | NH | 5-CF₃-pyridin-3-yl |
| 169 | spiro[2.5]octyl | NH | naphthalen-1-yl |
| 170 | spiro[2.5]octyl | NH | naphthalen-2-yl |
| 171 | spiro[2.5]octyl | NH | quinolin-3-yl |
| 172 | spiro[2.5]octyl | NH | quinolin-6-yl |
| 173 | spiro[2.5]octyl | NH | benzothiazol-2-yl |
| 174 | spiro[2.5]octyl | NH | 3-sulfamoylphenyl |
| 175 | spiro[2.5]octyl | NH | 3-(N,N-dimethylsulfamoyl)phenyl |
| 176 | spiro[2.5]octyl | NH | 3-(cyclopropylsulfonyl)phenyl |
| 177 | spiro[2.5]octyl | NH | 3-(difluoro(pyridin-3-yl)methyl)phenyl |

TABLE 1-continued

| Example | R² | X | Ⓐ |
|---|---|---|---|
| 178 | spiro[2.5]octyl | NH | tetrahydronaphthyl |
| 179 | spiro[2.5]octyl | NH | tetrahydroquinolinyl |
| 180 | spiro[2.5]octyl | NH | cyclohexyl |

In another embodiment, the compound of Formula (I) is represented by Formula (VI) or a pharmaceutically acceptable salt thereof:

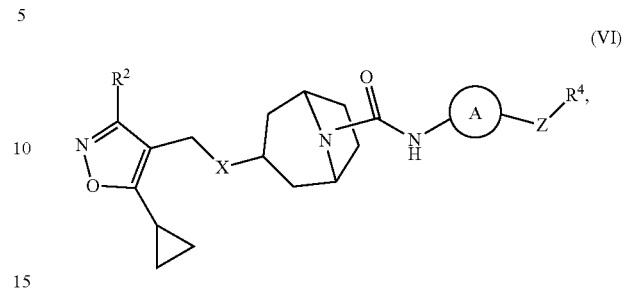

(VI)

wherein R², R⁴, X, Z, and Ⓐ are previously defined.

Representative compounds of the invention include, but are not limited to, the following compounds (example 181 to example 456 in Table 2) according to Formula (VI), wherein R², X, and Ⓐ-Z-R⁴ are delineated for each example in Table 2.

TABLE 2

| Example | R² | X | Ⓐ-Z-R⁴ |
|---|---|---|---|
| 181 | 2,6-dichlorophenyl | O | 3-(CO₂Et)phenyl |
| 182 | 2,6-dichlorophenyl | O | 4-(CO₂Et)phenyl |
| 183 | 2,6-dichlorophenyl | O | 3-(CO₂H)phenyl |
| 184 | 2,6-dichlorophenyl | O | 4-(CO₂H)phenyl |
| 185 | 2,6-dichlorophenyl | O | 3-(tetrazol-5-yl)phenyl |

TABLE 2-continued
| Example | R² | X | 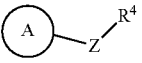 |
|---|---|---|---|
| 186 | 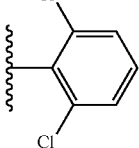 2,6-diCl-phenyl | O | 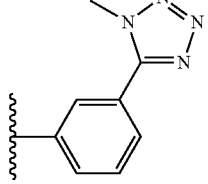 3-(1-methyltetrazol-5-yl)phenyl |
| 187 | 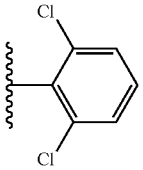 [SMILES: *c1c(Cl)cccc1Cl] 2,6-diCl-phenyl | O | 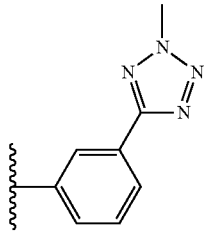 [SMILES: *c1cccc(-c2nnn(C)n2)c1] 3-(2-methyltetrazol-5-yl)phenyl |
| 188 | 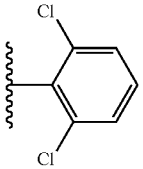 [SMILES: *c1c(Cl)cccc1Cl] 2,6-diCl-phenyl | O | 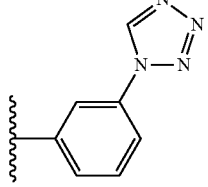 3-(tetrazol-1-yl)phenyl |
| 189 | 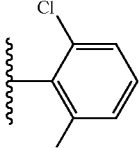 2,6-diCl-phenyl | O | 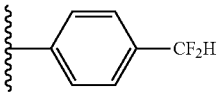 [SMILES: *c1ccc(C(F)F)cc1] 4-CF₂H-phenyl |
| 190 | 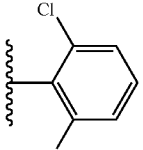 2,6-diCl-phenyl | O | 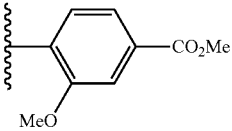 [SMILES: *c1ccc(C(=O)OC)cc1OC] 2-MeO-4-CO₂Me-phenyl |
| 191 | 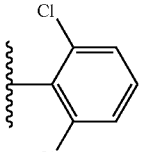 2,6-diCl-phenyl | O | 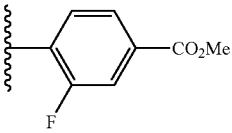 [SMILES: *c1ccc(C(=O)OC)cc1F] 2-F-4-CO₂Me-phenyl |
| 192 | 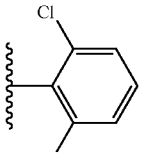 2,6-diCl-phenyl | O | 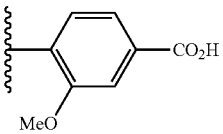 [SMILES: *c1ccc(C(=O)O)cc1OC] 2-MeO-4-CO₂H-phenyl |
| 193 | 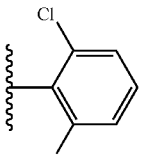 2,6-diCl-phenyl | O | 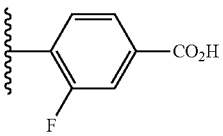 2-F-4-CO₂H-phenyl |

TABLE 2-continued

| Example | R² | X | (A)–Z–R⁴ |
|---|---|---|---|
| 194 | 2,6-diCl-phenyl | O | 4-(CO₂Me)-3-(CF₃)-phenyl |
| 195 | 2,6-diCl-phenyl | O | 4-(CO₂H)-3-(CF₃)-phenyl |
| 196 | 2,6-diCl-phenyl | O | 4-(CO₂Me)-3-F-phenyl |
| 197 | 2,6-diCl-phenyl | O | 4-(CO₂H)-3-F-phenyl |
| 198 | 2,6-diCl-phenyl | O | 4-(CO₂Me)-3,5-diF-phenyl |
| 199 | 2,6-diCl-phenyl | O | 4-(CO₂H)-3,5-diF-phenyl |
| 200 | 2,6-diCl-phenyl | O | 4-(CO₂Me)-3-phenyl-phenyl |
| 201 | 2,6-diCl-phenyl | O | 4-(CO₂H)-3-phenyl-phenyl |

TABLE 2-continued
| Example | R² | X | 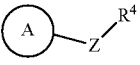 |
|---|---|---|---|
| 202 | 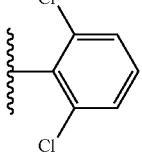 | O | 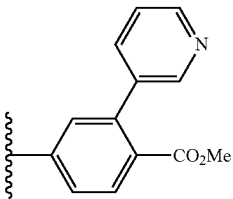 |
| 203 | 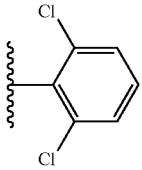 | O | 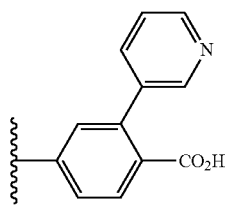 [SMILES: *c1ccc(C(=O)O)c(-c2cccnc2)c1] |
| 204 | 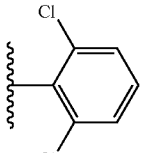 | O | 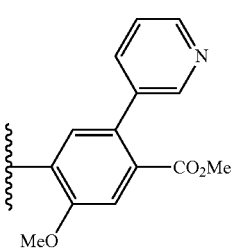 [SMILES: *c1cc(-c2cccnc2)c(C(=O)OC)cc1OC] |
| 205 | 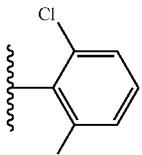 | O | 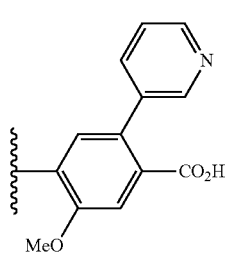 [SMILES: *c1cc(-c2cccnc2)c(C(=O)O)cc1OC] |
| 206 | 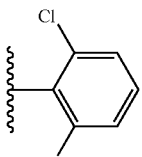 | O | 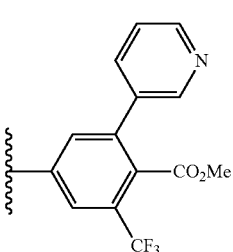 |
| 207 | 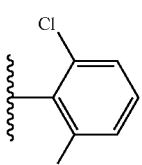 | O | 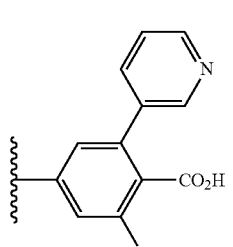 |

TABLE 2-continued
| Example | R² | X | ![A-Z-R⁴] |
|---|---|---|---|
| 208 | 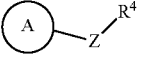 | O | 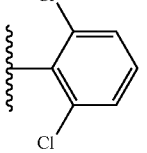 |
| 209 | 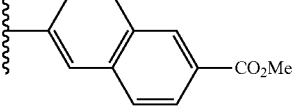 | O | 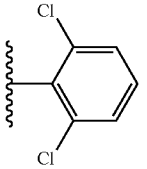 |
| 210 | 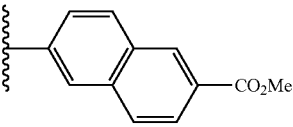 [SMILES: *c1ccc2cc(C(=O)OC)ccc2c1] | O | 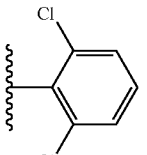 |
| 211 | 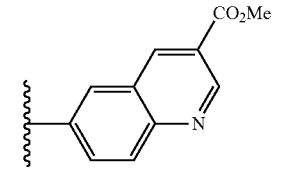 [SMILES: *c1ccc2ncc(C(=O)OC)cc2c1] | O | 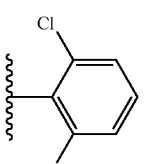 |
| 212 | 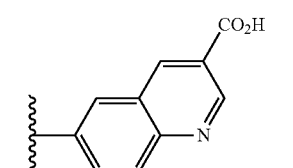 | O | 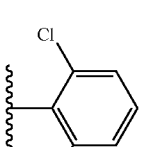 |
| 213 | 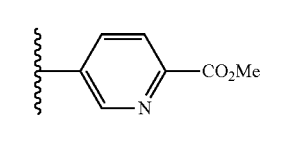 | O | 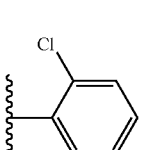 |
| 214 | 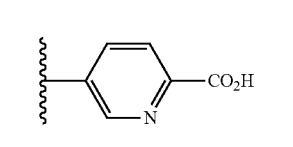 | O | 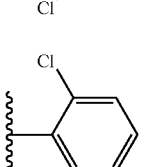 |
| 215 | 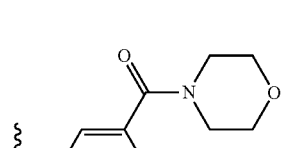 | O | 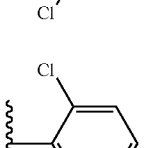 |

TABLE 2-continued

| Example | R² | X | A-Z-R⁴ |
|---|---|---|---|
| 216 | 2,6-diCl-phenyl | O | 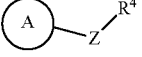 3-(methylsulfonylaminocarbonyl)phenyl |
| 217 | 2,6-diCl-phenyl | O | 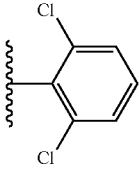 [SMILES: *c1c(Cl)cccc1Cl] 3-((4-tert-butylphenylsulfonyl)aminocarbonyl)phenyl |
| 218 | 2,6-diCl-phenyl | O | 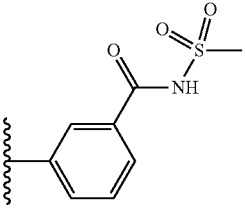 [SMILES: *c1cccc(C(=O)NS(C)(=O)=O)c1] 3-(cyclopropylsulfonylaminocarbonyl)phenyl |
| 219 | 2,6-diCl-phenyl | O | 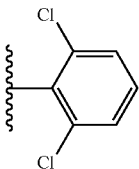 3-((N,N-dimethylaminosulfonyl)aminocarbonyl)phenyl |
| 220 | 2,6-diCl-phenyl | O | 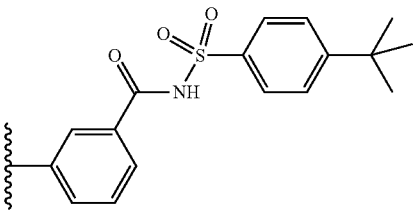 [SMILES: *c1cccc(C(=O)NS(=O)(=O)c2ccc(C(C)(C)C)cc2)c1] trans-4-carboxycyclohexyl |
| 221 | 2,6-diCl-phenyl | O | 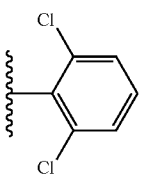 4-(carboxymethylaminocarbonyl)phenyl |
| 222 | 2,6-diCl-phenyl | O | 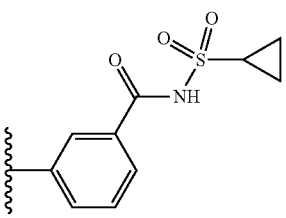 [SMILES: *c1cccc(C(=O)NS(=O)(=O)C2CC2)c1] 4-((2-sulfoethyl)aminocarbonyl)phenyl |

TABLE 2-continued

| Example | R² | X | A-Z-R⁴ |
|---|---|---|---|
| 223 | 2,6-diCl-phenyl | O | 3-(cyclopropanesulfonylaminocarbonylamino)phenyl 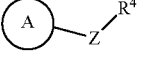 |
| 224 | 2,6-diCl-phenyl | O | 3-(N,N-dimethylsulfamoylaminocarbonylamino)phenyl 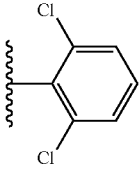 [SMILES: *c1c(Cl)cccc1Cl] |
| 225 | 2,6-diCl-phenyl | O | 3-(cyclopropanesulfonylaminocarbonyloxy)phenyl 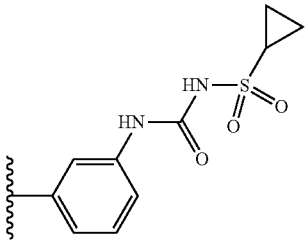 [SMILES: *c1cccc(NC(=O)NS(=O)(=O)C2CC2)c1] |
| 226 | 2,6-diCl-phenyl | O | 3-(N,N-dimethylsulfamoylaminocarbonyloxy)phenyl 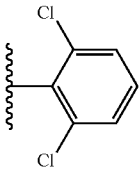 [SMILES: *c1c(Cl)cccc1Cl] |
| 227 | 2-F₃CO-phenyl | O | 3-CO₂Et-phenyl 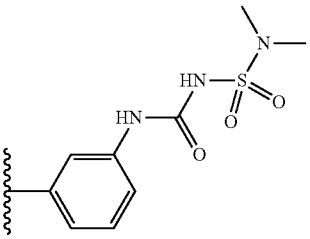 [SMILES: *c1cccc(NC(=O)NS(=O)(=O)N(C)C)c1] |
| 228 | 2-F₃CO-phenyl | O | 4-CO₂Et-phenyl 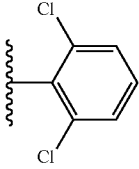 [SMILES: *c1c(Cl)cccc1Cl] |
| 229 | 2-F₃CO-phenyl | O | 3-CO₂H-phenyl 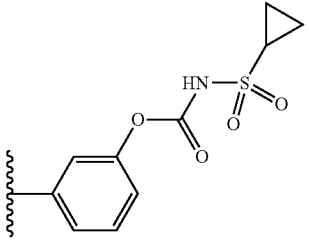 [SMILES: *c1cccc(OC(=O)NS(=O)(=O)C2CC2)c1] |

TABLE 2-continued

| Example | R² | X | A-Z-R⁴ |
|---|---|---|---|
| 230 | F₃CO- (phenyl) | O | -C₆H₄-CO₂H (para) |
| 231 | F₃CO- (phenyl) | O | -C₆H₄-(1H-tetrazol-5-yl) (meta) |
| 232 | F₃CO- (phenyl) | O | -C₆H₄-(1-methyl-1H-tetrazol-5-yl) (meta) |
| 233 | F₃CO- (phenyl) | O | -C₆H₄-(2-methyl-2H-tetrazol-5-yl) (meta) |
| 234 | F₃CO- (phenyl) | O | -C₆H₄-(1H-tetrazol-1-yl) (meta) |
| 235 | F₃CO- (phenyl) | O | -C₆H₄-CF₂H (para) |
| 236 | F₃CO- (phenyl) | O | 3-MeO-4-(-)-C₆H₃-CO₂Me |
| 237 | F₃CO- (phenyl) | O | 3-F-4-(-)-C₆H₃-CO₂Me |

TABLE 2-continued
| Example | R² | X | 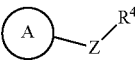 |
|---|---|---|---|
| 238 | 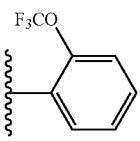 [SMILES: *c1ccccc1OC(F)(F)F] F₃CO- | O | 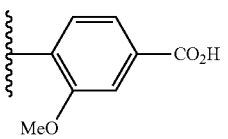 [SMILES: *c1ccc(C(=O)O)cc1OC] -CO₂H, MeO |
| 239 | 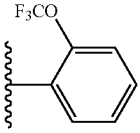 [SMILES: *c1ccccc1OC(F)(F)F] F₃CO- | O | 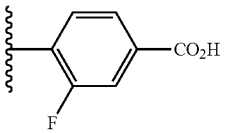 [SMILES: *c1ccc(C(=O)O)cc1F] -CO₂H, F |
| 240 | 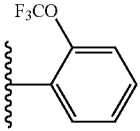 [SMILES: *c1ccccc1OC(F)(F)F] F₃CO- | O | 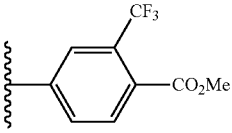 CF₃, -CO₂Me |
| 241 | 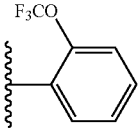 [SMILES: *c1ccccc1OC(F)(F)F] F₃CO- | O | 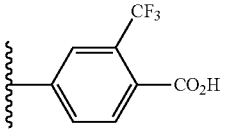 CF₃, -CO₂H |
| 242 | 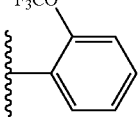 F₃CO- | O | 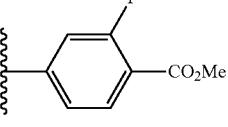 F, -CO₂Me |
| 243 | 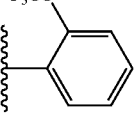 F₃CO- | O | 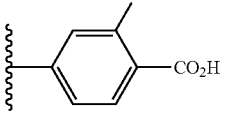 F, -CO₂H |
| 244 | 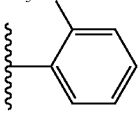 F₃CO- | O | 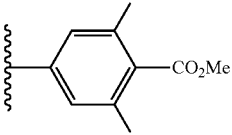 F, -CO₂Me, F |
| 245 | 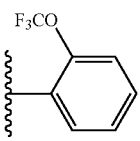 [SMILES: *c1ccccc1OC(F)(F)F] F₃CO- | O | 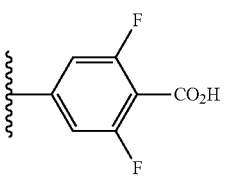 [SMILES: *c1cc(F)c(C(=O)O)c(F)c1] F, -CO₂H, F |
| 246 | 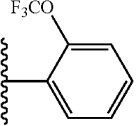 [SMILES: *c1ccccc1OC(F)(F)F] F₃CO- | O | 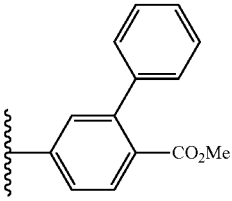 -CO₂Me |

TABLE 2-continued
| Example | R² | X | 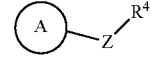 |
|---|---|---|---|
| 247 | 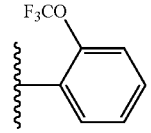 F₃CO- | O | 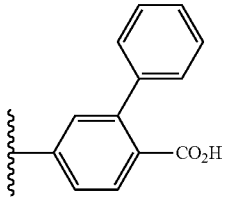 [SMILES: *c1ccc(C(=O)O)c(-c2ccccc2)c1] |
| 248 | F₃CO- | O | 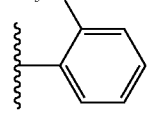 |
| 249 | F₃CO- | O | 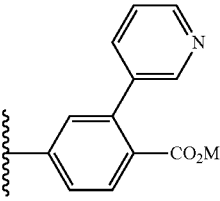 |
| 250 | F₃CO- | O | 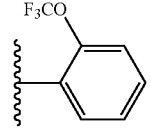 |
| 251 | F₃CO- | O | 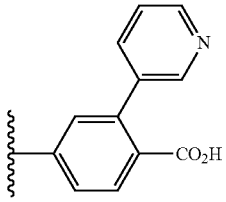 [SMILES: *c1ccc(C(=O)O)c(-c2cccnc2)c1] |
| 252 | F₃CO- | O | 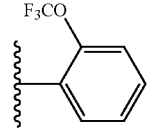 |

TABLE 2-continued

| Example | R² | X | (A)–Z–R⁴ |
|---|---|---|---|
| 253 | F₃CO-phenyl | O | pyridin-3-yl substituted phenyl with CO₂H and CF₃ |
| 254 | F₃CO-phenyl | O | naphthyl-CO₂Me |
| 255 | F₃CO-phenyl | O | naphthyl-CO₂H |
| 256 | F₃CO-phenyl | O | quinolinyl-CO₂Me |
| 257 | F₃CO-phenyl | O | quinolinyl-CO₂H |
| 258 | F₃CO-phenyl | O | pyridinyl-CO₂Me |
| 259 | F₃CO-phenyl | O | pyridinyl-CO₂H |
| 260 | F₃CO-phenyl | O | phenyl-C(O)-morpholine |
| 261 | F₃CO-phenyl | O | phenyl-C(O)-N(Me)₂ |

TABLE 2-continued
| Example | R² | X | (A)-Z-R⁴ |
|---|---|---|---|
| 262 | F₃CO-phenyl | O | 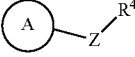 |
| 263 | F₃CO-phenyl | O | 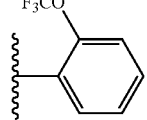 |
| 264 | F₃CO-phenyl | O | 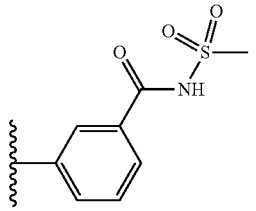 [SMILES: *c1cccc(C(=O)NS(C)(=O)=O)c1] |
| 265 | F₃CO-phenyl | O | 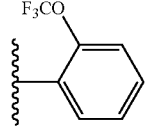 [SMILES: *c1ccccc1OC(F)(F)F] |
| 266 | F₃CO-phenyl | O | 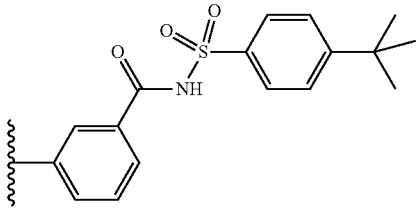 [SMILES: *c1cccc(C(=O)NS(=O)(=O)c2ccc(C(C)(C)C)cc2)c1] |
| 267 | F₃CO-phenyl | O | 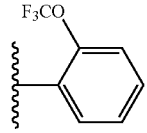 |
| 268 | F₃CO-phenyl | O | 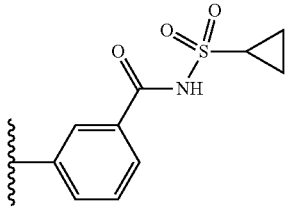 [SMILES: *c1cccc(C(=O)NS(=O)(=O)C2CC2)c1] |

TABLE 2-continued
| Example | R² | X | (A)−Z−R⁴ |
|---|---|---|---|
| 269 | 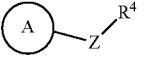 | O | 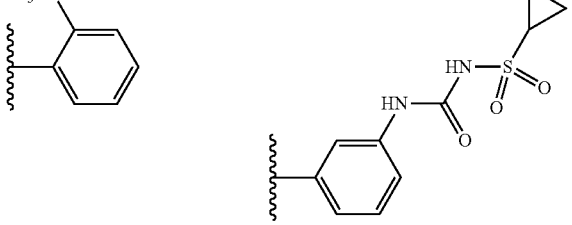 |
| 270 |  | O |  |
| 271 |  | O | 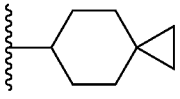 [SMILES: *C1CCC2(CC1)CC2] |
| 272 | 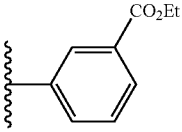 [SMILES: *c1cccc(C(=O)OCC)c1] | O | 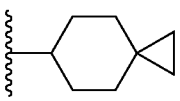 |
| 273 | 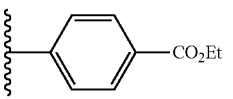 [SMILES: *c1ccc(C(=O)OCC)cc1] | O | 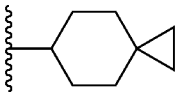 |
| 274 | 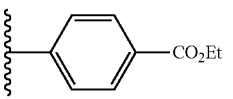 [SMILES: *c1ccc(C(=O)OCC)cc1] | O | 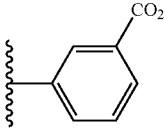 |
| 275 | 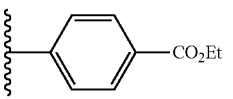 [SMILES: *c1ccc(C(=O)OCC)cc1] | O | 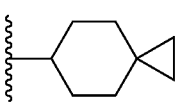 |
| 276 | 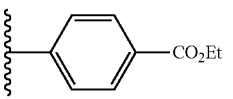 [SMILES: *c1ccc(C(=O)OCC)cc1] | O | 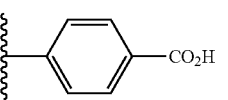 |

TABLE 2-continued
| Example | R² | X | ⟨A⟩–Z–R⁴ |
|---|---|---|---|
| 277 | 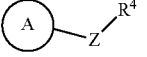 | O | 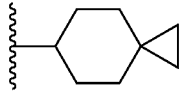 |
| 278 | 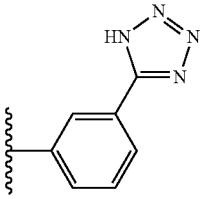 [SMILES: *c1cccc(-c2nnn[nH]2)c1] | O | 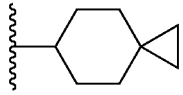 [SMILES: *C1CCC2(CC1)CC2] |
| 279 | 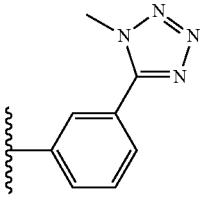 [SMILES: *c1cccc(-c2nnnn2C)c1] | O | 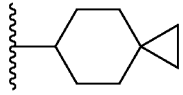 [SMILES: *C1CCC2(CC1)CC2] |
| 280 | 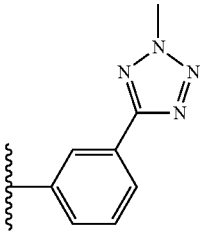 [SMILES: *c1cccc(-c2nnn(C)n2)c1] | O | 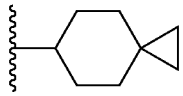 |
| 281 | 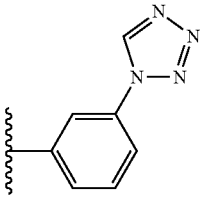 [SMILES: *c1cccc(-n2cnnn2)c1] | O | 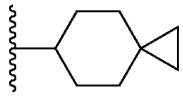 |
| 282 | 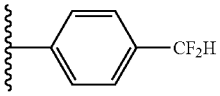 | O | 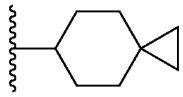 [SMILES: *C1CCC2(CC1)CC2] |
| 283 | 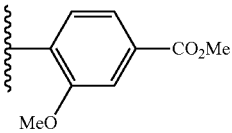 [SMILES: *c1ccc(C(=O)OC)cc1OC] | O | 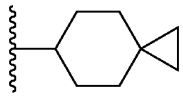 |
| 284 | 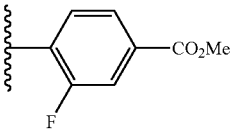 [SMILES: *c1ccc(C(=O)OC)cc1F] | O | 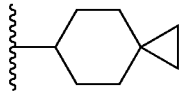 [SMILES: *C1CCC2(CC1)CC2] |
| 285 | 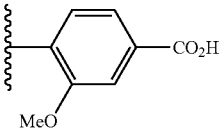 [SMILES: *c1ccc(C(=O)O)cc1OC] | O | 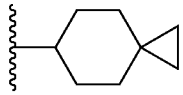 [SMILES: *C1CCC2(CC1)CC2] |

TABLE 2-continued
| Example | R² | X | (A)—Z—R⁴ |
|---|---|---|---|
| 286 | 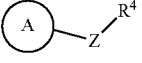 | O | 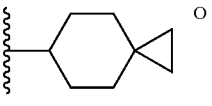 |
| 287 | 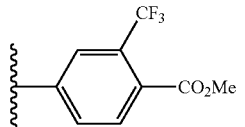 | O | 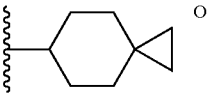 |
| 288 | 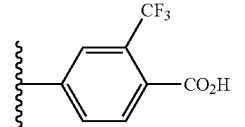 | O | 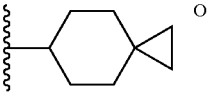 |
| 289 | 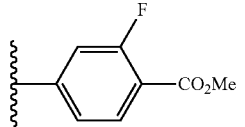 [SMILES: *c1ccc(C(=O)OC)c(F)c1] | O | 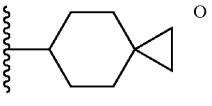 |
| 290 |  | O | 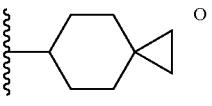 |
| 291 | 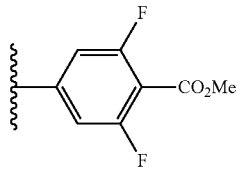 [SMILES: *c1cc(F)c(C(=O)OC)c(F)c1] | O | 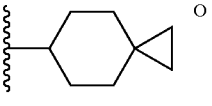 |
| 292 | 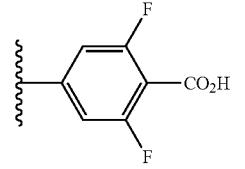 [SMILES: *c1cc(F)c(C(=O)O)c(F)c1] | O | 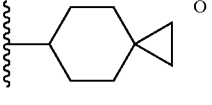 |
| 293 | 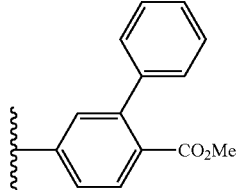 | O | 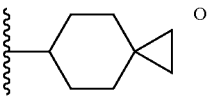 |

TABLE 2-continued
| Example | R² | X | A-Z-R⁴ |
|---|---|---|---|
| 294 | 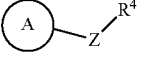 | O | 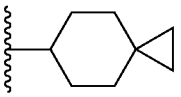 |
| 295 | 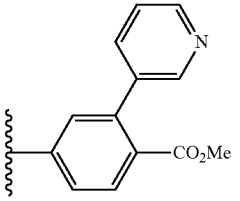 | O | 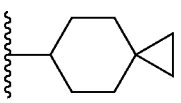 |
| 296 | 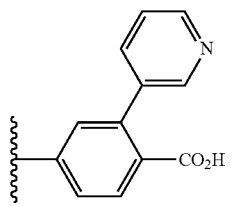 | O | 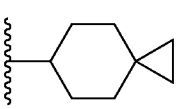 |
| 297 | 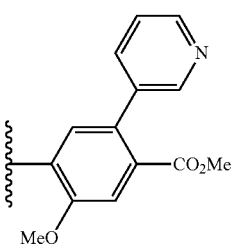 [SMILES: *c1cc(-c2cccnc2)c(C(=O)OC)cc1OC] | O | 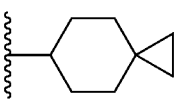 |
| 298 | 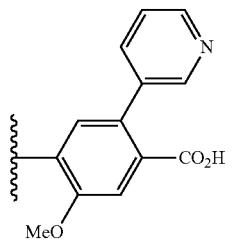 [SMILES: *c1cc(-c2cccnc2)c(C(=O)O)cc1OC] | O | 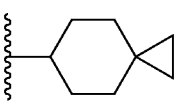 |
| 299 | 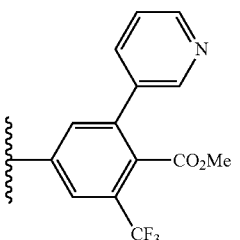 | O | 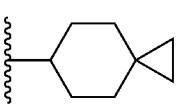 |
| 300 | 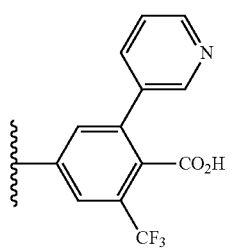 | O | 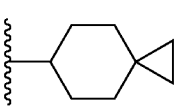 [SMILES: *C1CCC2(CC1)CC2] |

TABLE 2-continued
| Example | R² | X | (A)-Z-R⁴ |
|---|---|---|---|
| 301 | 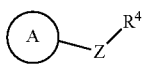 | O | 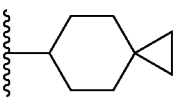 |
| 302 | 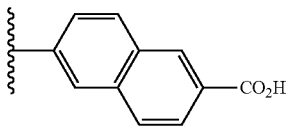 [SMILES: *c1ccc2cc(C(=O)O)ccc2c1] | O | 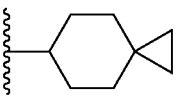 |
| 303 | 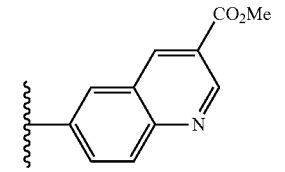 [SMILES: *c1ccc2ncc(C(=O)OC)cc2c1] | O |  |
| 304 | 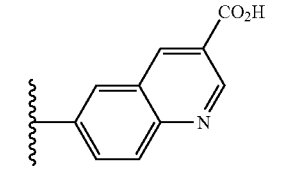 [SMILES: *c1ccc2ncc(C(=O)O)cc2c1] | O |  |
| 305 | 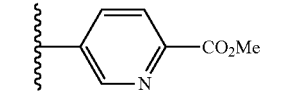 | O |  |
| 306 | 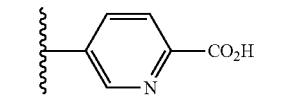 | O |  |
| 307 | 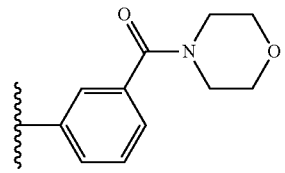 [SMILES: *c1cccc(C(=O)N2CCOCC2)c1] | O |  |
| 308 | 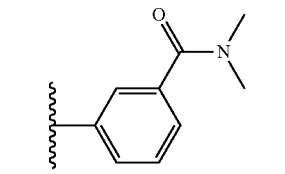 [SMILES: *c1cccc(C(=O)N(C)C)c1] | O |  |
| 309 | 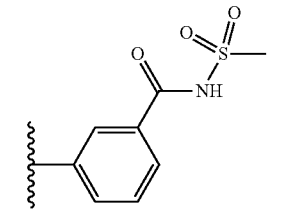 [SMILES: *c1cccc(C(=O)NS(C)(=O)=O)c1] | O |  |

TABLE 2-continued
| Example | R² | X | A-Z-R⁴ |
|---|---|---|---|
| 310 | 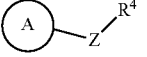 | O | 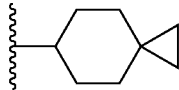 |
| 311 | 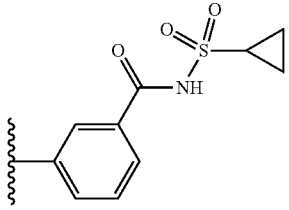 [SMILES: *c1cccc(C(=O)NS(=O)(=O)C2CC2)c1] | O | 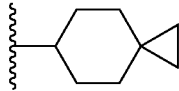 |
| 312 | 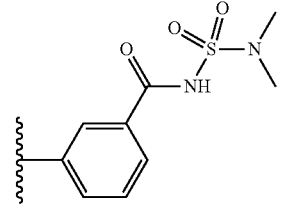 [SMILES: *c1cccc(C(=O)NS(=O)(=O)N(C)C)c1] | O | 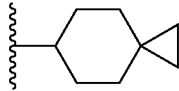 |
| 313 |  | O | 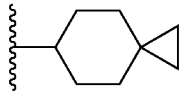 |
| 314 | 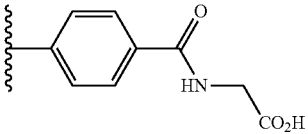 | O | 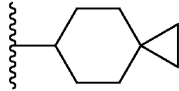 |
| 315 | 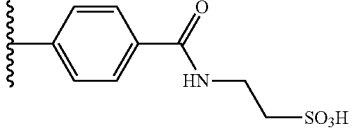 | O | 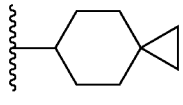 |
| 316 | 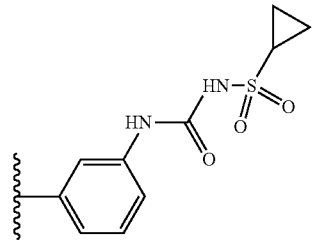 [SMILES: *c1cccc(NC(=O)NS(=O)(=O)C2CC2)c1] | O | 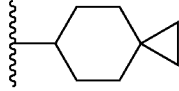 |

TABLE 2-continued
| Example | R² | X | (A)–Z–R⁴ |
|---|---|---|---|
| 317 | 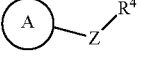 | O | 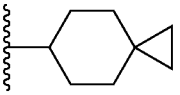 |
| 318 | 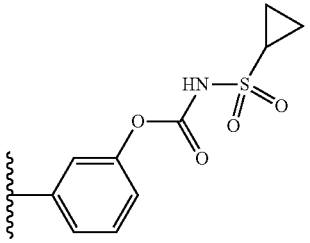 [SMILES: *c1cccc(OC(=O)NS(=O)(=O)C2CC2)c1] | O | 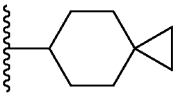 [SMILES: *C1CCC2(CC1)CC2] |
| 319 | 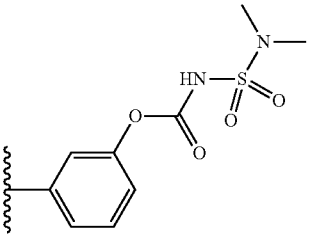 [SMILES: *c1cccc(OC(=O)NS(=O)(=O)N(C)C)c1] | NH | 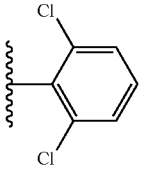 |
| 320 | 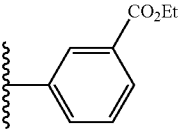 | NH | 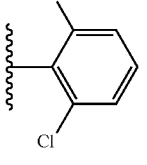 |
| 321 | 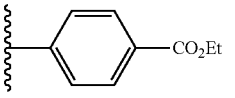 | NH | 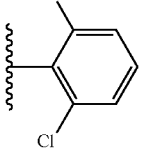 |
| 322 | 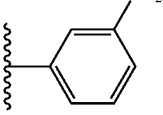 | NH | 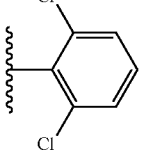 |
| 323 | 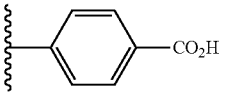 [SMILES: *c1ccc(C(=O)O)cc1] | NH | 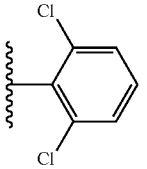 [SMILES: *c1c(Cl)cccc1Cl] |

TABLE 2-continued

| Example | R² | X | (A)–Z–R⁴ |
|---|---|---|---|
| 324 | 2,6-diCl-phenyl | NH | 3-(1-methyl-1H-tetrazol-5-yl)phenyl |
| 325 | 2,6-diCl-phenyl | NH | 3-(2-methyl-2H-tetrazol-5-yl)phenyl |
| 326 | 2,6-diCl-phenyl | NH | 3-(1H-tetrazol-1-yl)phenyl |
| 327 | 2,6-diCl-phenyl | NH | 4-(CF₂H)phenyl |
| 328 | 2,6-diCl-phenyl | NH | 3-MeO-4-(CO₂Me)phenyl |
| 329 | 2,6-diCl-phenyl | NH | 3-F-4-(CO₂Me)phenyl |
| 330 | 2,6-diCl-phenyl | NH | 3-MeO-4-(CO₂H)phenyl |
| 331 | 2,6-diCl-phenyl | NH | 3-F-4-(CO₂H)phenyl |

TABLE 2-continued

| Example | R² | X | (A)–Z–R⁴ |
|---|---|---|---|
| 332 | 2,6-diCl-phenyl | NH | 4-(CO₂Me)-3-(CF₃)-phenyl |
| 333 | 2,6-diCl-phenyl | NH | 4-(CO₂H)-3-(CF₃)-phenyl |
| 334 | 2,6-diCl-phenyl | NH | 4-(CO₂Me)-3-F-phenyl |
| 335 | 2,6-diCl-phenyl | NH | 4-(CO₂H)-3-F-phenyl |
| 336 | 2,6-diCl-phenyl | NH | 4-(CO₂Me)-3,5-diF-phenyl |
| 337 | 2,6-diCl-phenyl | NH | 4-(CO₂H)-3,5-diF-phenyl |
| 338 | 2,6-diCl-phenyl | NH | 4-(CO₂Me)-3-phenyl-phenyl |
| 339 | 2,6-diCl-phenyl | NH | 4-(CO₂H)-3-phenyl-phenyl |

TABLE 2-continued
| Example | R² | X | 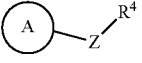 |
|---|---|---|---|
| 340 | 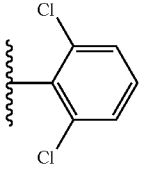 | NH | 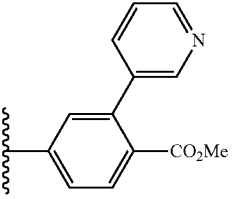 [SMILES: *c1ccc(C(=O)OC)c(-c2cccnc2)c1] |
| 341 | 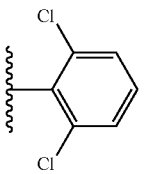 [SMILES: *c1c(Cl)cccc1Cl] | NH | 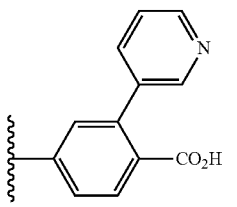 [SMILES: *c1ccc(C(=O)O)c(-c2cccnc2)c1] |
| 342 | 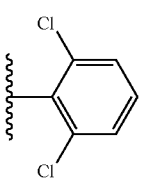 | NH | 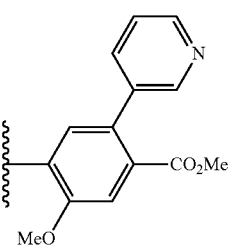 [SMILES: *c1cc(-c2cccnc2)c(C(=O)OC)cc1OC] |
| 343 | 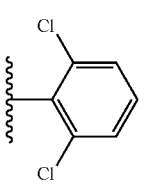 [SMILES: *c1c(Cl)cccc1Cl] | NH | 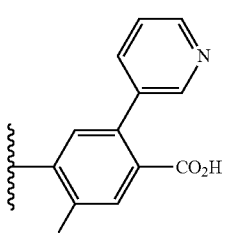 |
| 344 | 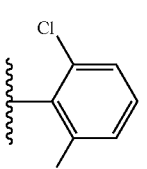 | NH | 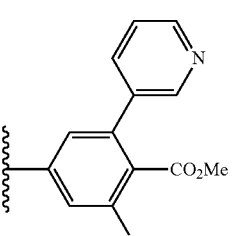 |
| 345 | 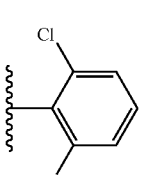 | NH | 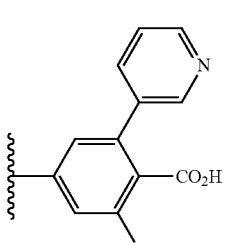 |

TABLE 2-continued

| Example | R² | X | A-Z-R⁴ |
|---|---|---|---|
| 346 | 2,6-diCl-phenyl | NH | 6-(methoxycarbonyl)naphthalen-2-yl (CO₂Me) |
| 347 | 2,6-diCl-phenyl | NH | 6-carboxynaphthalen-2-yl (CO₂H) |
| 348 | 2,6-diCl-phenyl | NH | 3-(methoxycarbonyl)quinolin-6-yl (CO₂Me) |
| 349 | 2,6-diCl-phenyl | NH | 3-carboxyquinolin-6-yl (CO₂H) |
| 350 | 2,6-diCl-phenyl | NH | 6-(methoxycarbonyl)pyridin-3-yl (CO₂Me) |
| 351 | 2,6-diCl-phenyl | NH | 6-carboxypyridin-3-yl (CO₂H) |
| 352 | 2,6-diCl-phenyl | NH | 3-(morpholine-4-carbonyl)phenyl |
| 353 | 2,6-diCl-phenyl | NH | 3-(N,N-dimethylcarbamoyl)phenyl |

TABLE 2-continued
| Example | R² | X | ⟨A⟩–Z–R⁴ |
|---|---|---|---|
| 354 | 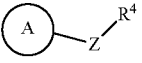 | NH | 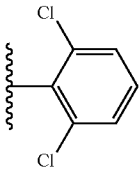 |
| 355 | 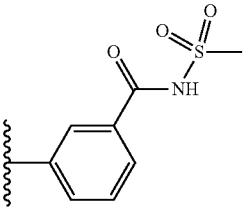 [SMILES: *c1cccc(C(=O)NS(C)(=O)=O)c1] | NH | 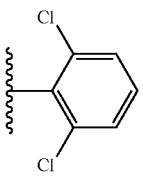 |
| 356 | 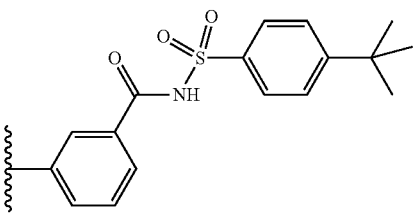 [SMILES: *c1cccc(C(=O)NS(=O)(=O)c2ccc(C(C)(C)C)cc2)c1] | NH | 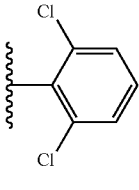 |
| 357 | 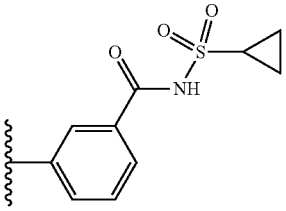 [SMILES: *c1cccc(C(=O)NS(=O)(=O)C2CC2)c1] | NH | 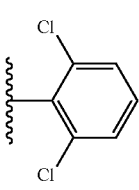 [SMILES: *c1c(Cl)cccc1Cl] |
| 358 | 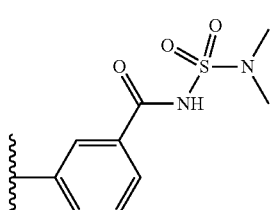 | NH | 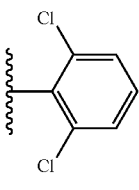 [SMILES: *c1c(Cl)cccc1Cl] |
| 359 | 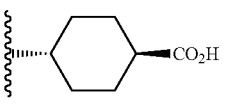 | NH | 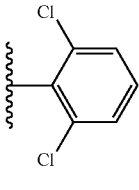 |
| 360 | 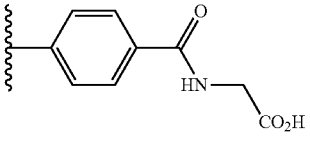 | NH | 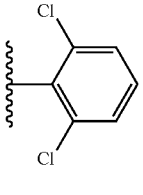 |

TABLE 2-continued
| Example | R² | X | A-Z-R⁴ |
|---|---|---|---|
| 361 | 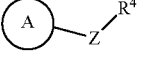 | NH | 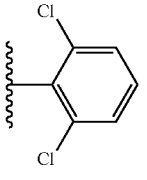 [SMILES: *c1c(Cl)cccc1Cl] |
| 362 | 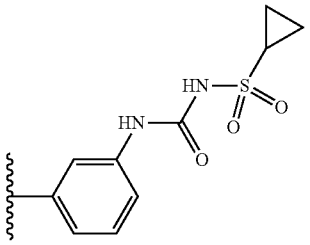 [SMILES: *c1cccc(NC(=O)NS(=O)(=O)C2CC2)c1] | NH | 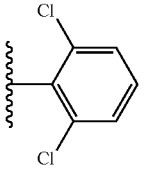 [SMILES: *c1c(Cl)cccc1Cl] |
| 363 | 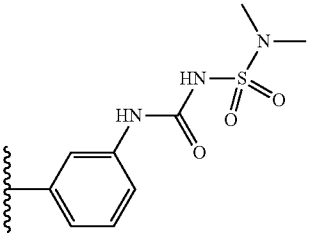 [SMILES: *c1cccc(NC(=O)NS(=O)(=O)N(C)C)c1] | NH | 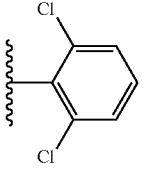 [SMILES: *c1c(Cl)cccc1Cl] |
| 364 | 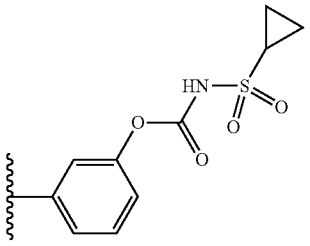 [SMILES: *c1cccc(OC(=O)NS(=O)(=O)C2CC2)c1] | NH | 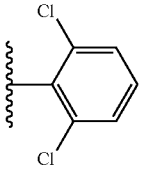 [SMILES: *c1c(Cl)cccc1Cl] |
| 365 | 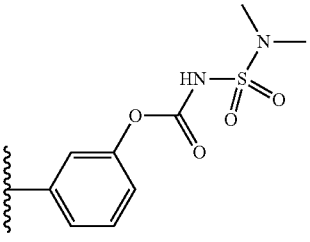 [SMILES: *c1cccc(OC(=O)NS(=O)(=O)N(C)C)c1] | NH | 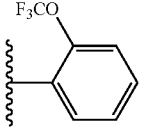 [SMILES: *c1ccccc1OC(F)(F)F] |
| 366 | 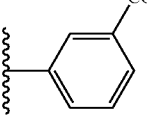 | NH | 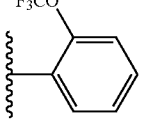 |
| 367 | 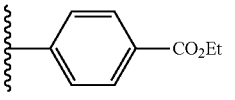 | NH | 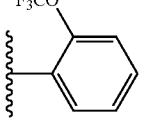 |

TABLE 2-continued

| Example | R² | X | A-Z-R⁴ |
|---|---|---|---|
| 368 | F₃CO-phenyl | NH | phenyl-CO₂H (para) |
| 369 | F₃CO-phenyl | NH | phenyl-(1H-tetrazol-5-yl) (meta) |
| 370 | F₃CO-phenyl | NH | phenyl-(1-methyl-tetrazol-5-yl) (meta) |
| 371 | F₃CO-phenyl | NH | phenyl-(2-methyl-tetrazol-5-yl) (meta) |
| 372 | F₃CO-phenyl | NH | phenyl-(tetrazol-1-yl) (meta) |
| 373 | F₃CO-phenyl | NH | phenyl-CF₂H (para) |
| 374 | F₃CO-phenyl | NH | phenyl-CO₂Me with MeO |
| 375 | F₃CO-phenyl | NH | phenyl-CO₂Me with F |

TABLE 2-continued

| Example | R² | X | A-Z-R⁴ |
|---------|-----|-----|--------|
| 376 | F₃CO- (2-position on phenyl) | NH | phenyl with CO₂H and MeO substituents |
| 377 | F₃CO- (2-position on phenyl) | NH | phenyl with CO₂H and F substituents |
| 378 | F₃CO- (2-position on phenyl) | NH | phenyl with CF₃ and CO₂Me substituents |
| 379 | F₃CO- (2-position on phenyl) | NH | phenyl with CF₃ and CO₂H substituents |
| 380 | F₃CO- (2-position on phenyl) | NH | phenyl with F and CO₂Me substituents |
| 381 | F₃CO- (2-position on phenyl) | NH | phenyl with F and CO₂H substituents |
| 382 | F₃CO- (2-position on phenyl) | NH | phenyl with two F and CO₂Me substituents |
| 383 | F₃CO- (2-position on phenyl) | NH | phenyl with two F and CO₂H substituents |
| 384 | F₃CO- (2-position on phenyl) | NH | biphenyl with CO₂Me substituent |

TABLE 2-continued
| Example | R² | X | 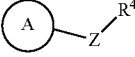 |
|---|---|---|---|
| 385 | 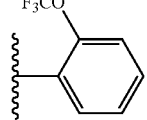 F₃CO | NH | 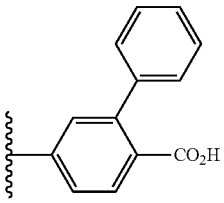 [SMILES: *c1ccc(C(=O)O)c(-c2ccccc2)c1] |
| 386 | 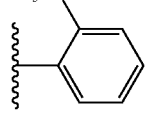 F₃CO | NH | 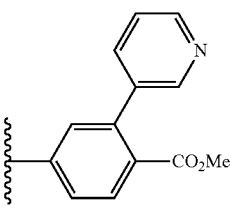 [SMILES: *c1ccc(C(=O)OC)c(-c2cccnc2)c1] |
| 387 | 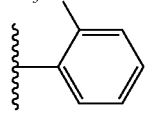 F₃CO | NH | 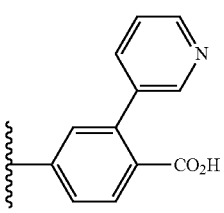 [SMILES: *c1ccc(C(=O)O)c(-c2cccnc2)c1] |
| 388 | 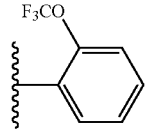 F₃CO | NH | 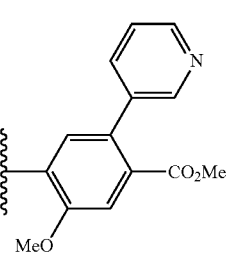 [SMILES: *c1cc(-c2cccnc2)c(C(=O)OC)cc1OC] |
| 389 | 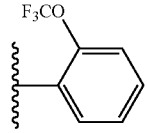 F₃CO | NH | 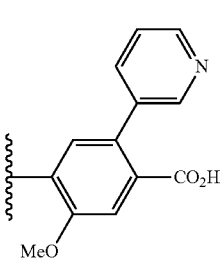 [SMILES: *c1cc(-c2cccnc2)c(C(=O)O)cc1OC] |
| 390 | 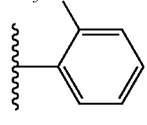 F₃CO | NH | 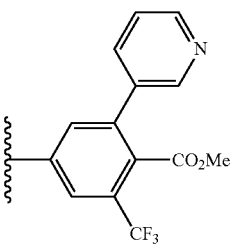 [SMILES: *c1cc(-c2cccnc2)c(C(=O)OC)c(C(F)(F)F)c1] |

TABLE 2-continued

| Example | R² | X | (A)–Z–R⁴ |
|---|---|---|---|
| 391 | F₃CO– (2-substituted phenyl) | NH | 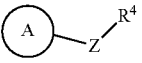 pyridin-3-yl substituted phenyl with CO₂H and CF₃ |
| 392 | F₃CO– (2-substituted phenyl) | NH | 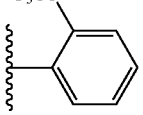 naphthalene-CO₂Me |
| 393 | F₃CO– (2-substituted phenyl) | NH | 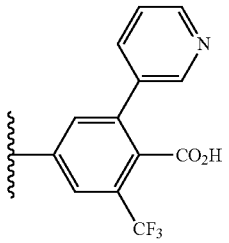 naphthalene-CO₂H |
| 394 | F₃CO– (2-substituted phenyl) | NH | 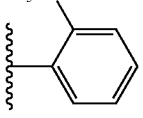 quinoline-CO₂Me |
| 395 | F₃CO– (2-substituted phenyl) | NH | 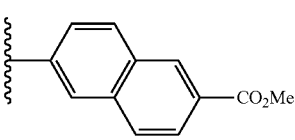 [SMILES: *c1ccc2cc(C(=O)OC)ccc2c1] quinoline-CO₂H |
| 396 | F₃CO– (2-substituted phenyl) | NH | 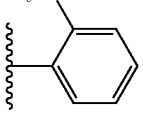 pyridine-CO₂Me |
| 397 | F₃CO– (2-substituted phenyl) | NH | 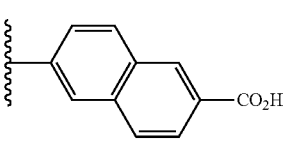 pyridine-CO₂H |
| 398 | F₃CO– (2-substituted phenyl) | NH | 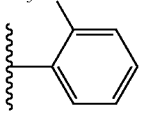 phenyl-C(O)-morpholine |
| 399 | F₃CO– (2-substituted phenyl) | NH | 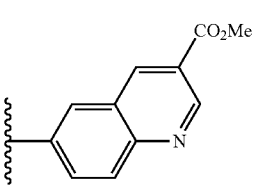 [SMILES: *c1ccc2ncc(C(=O)OC)cc2c1] phenyl-C(O)-N(Me)₂ |

TABLE 2-continued
| Example | R² | X | (A)–Z–R⁴ |
|---|---|---|---|
| 400 | F₃CO- (o-phenyl) | NH | 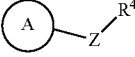 |
| 401 | F₃CO- (o-phenyl) | NH | 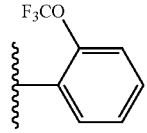 |
| 402 | F₃CO- (o-phenyl) | NH | 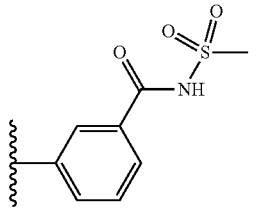 [SMILES: *c1cccc(C(=O)NS(C)(=O)=O)c1] |
| 403 | F₃CO- (o-phenyl) | NH | 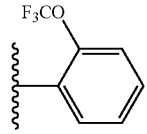 [SMILES: *c1ccccc1OC(F)(F)F] |
| 404 | F₃CO- (o-phenyl) | NH | 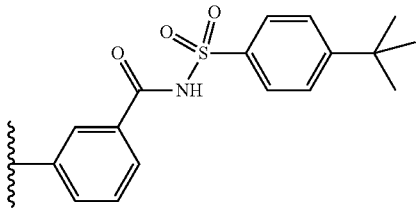 [SMILES: *c1cccc(C(=O)NS(=O)(=O)c2ccc(C(C)(C)C)cc2)c1] |
| 405 | F₃CO- (o-phenyl) | NH | 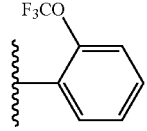 |
| 406 | F₃CO- (o-phenyl) | NH | 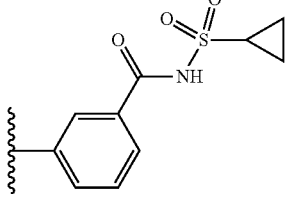 |

US 10,597,391 B2
TABLE 2-continued
| Example | R² | X | (A)–Z–R⁴ |
|---|---|---|---|
| 407 | 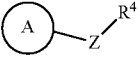 F₃CO- | NH | 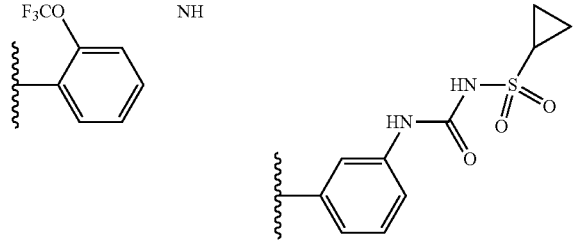 |
| 408 | 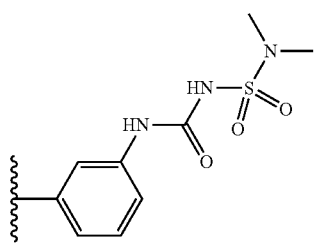 F₃CO- | NH | 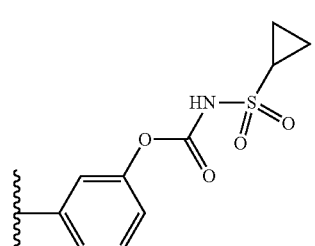 |
| 409 | 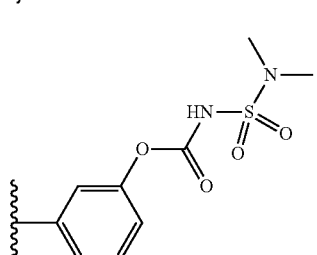 F₃CO- | NH | 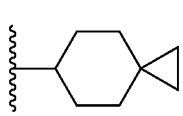 [SMILES: *C1CCC2(CC1)CC2] |
| 410 | 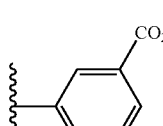 F₃CO- | NH | 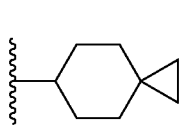 |
| 411 | 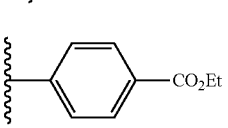 | NH | 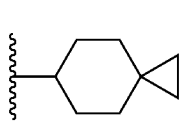 CO₂Et |
| 412 | 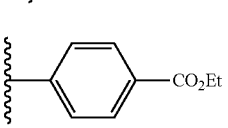 | NH | 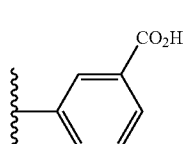 CO₂Et |
| 413 | 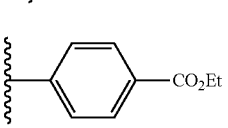 | NH | 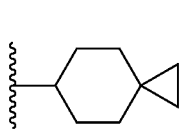 CO₂H |
| 414 | 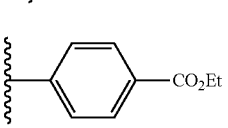 | NH | 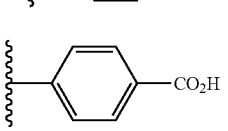 CO₂H |

TABLE 2-continued
| Example | R² | X | (A)—Z—R⁴ |
|---|---|---|---|
| 415 | 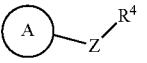 | NH | 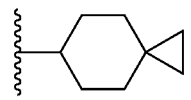 |
| 416 | 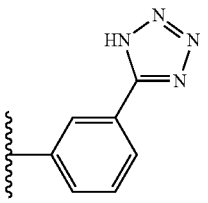 [SMILES: *c1cccc(-c2nnn[nH]2)c1] | NH | 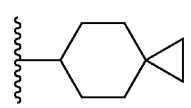 |
| 417 | 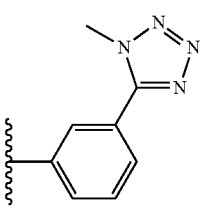 [SMILES: *c1cccc(-c2nnnn2C)c1] | NH | 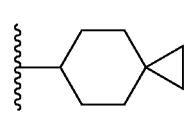 [SMILES: *C1CCC2(CC1)CC2] |
| 418 | 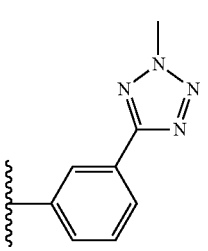 [SMILES: *c1cccc(-c2nnn(C)n2)c1] | NH | 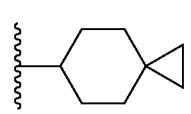 |
| 419 | 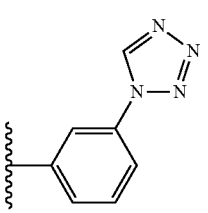 [SMILES: *c1cccc(-n2cnnn2)c1] | NH | 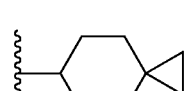 |
| 420 | 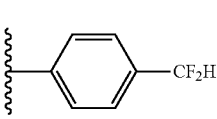 | NH | 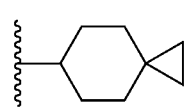 [SMILES: *C1CCC2(CC1)CC2] |
| 421 | 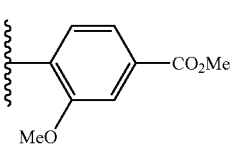 [SMILES: *c1ccc(C(=O)OC)cc1OC] | NH | 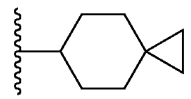 |
| 422 | 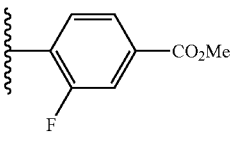 [SMILES: *c1ccc(C(=O)OC)cc1F] | NH | 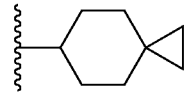 [SMILES: *C1CCC2(CC1)CC2] |
| 423 | 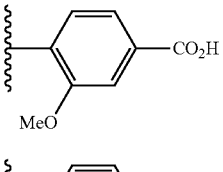 | NH | 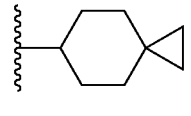 |

TABLE 2-continued
| Example | R² | X | 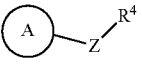 |
|---|---|---|---|
| 424 |  | NH | 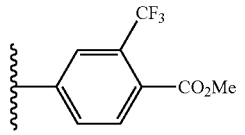 [SMILES: *c1ccc(C(=O)OC)c(C(F)(F)F)c1] |
| 425 | 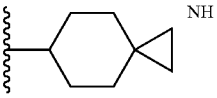 | NH | 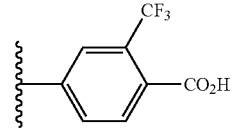 |
| 426 | 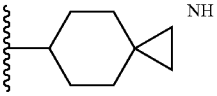 | NH | 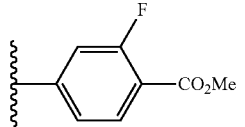 [SMILES: *c1ccc(C(=O)OC)c(F)c1] |
| 427 | 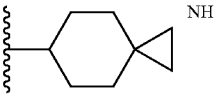 | NH |  |
| 428 | 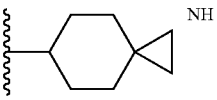 | NH | 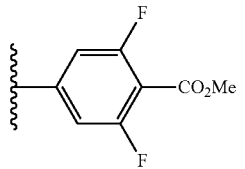 [SMILES: *c1cc(F)c(C(=O)OC)c(F)c1] |
| 429 | 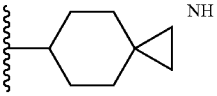 | NH | 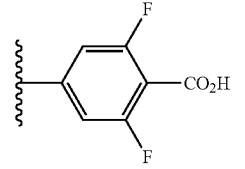 [SMILES: *c1cc(F)c(C(=O)O)c(F)c1] |
| 430 | 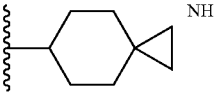 | NH | 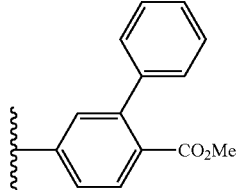 |
| 431 | 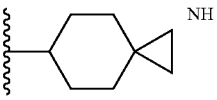 | NH | 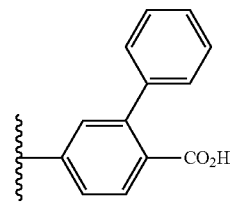 [SMILES: *c1ccc(C(=O)O)c(-c2ccccc2)c1] |

TABLE 2-continued
| Example | R² | X | (A-Z-R⁴) |
|---|---|---|---|
| 432 | 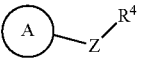 | NH | 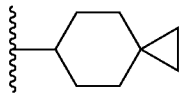 |
| 433 | 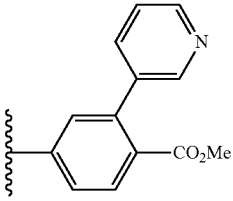 | NH | 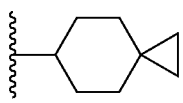 |
| 434 | 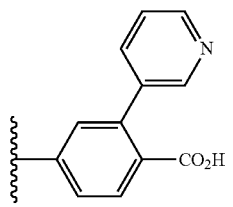 | NH | 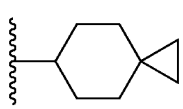 |
| 435 | 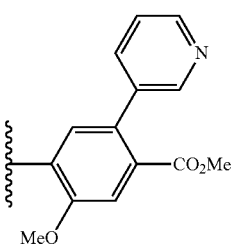 [SMILES: *c1cc(-c2cccnc2)c(C(=O)OC)cc1OC] | NH | 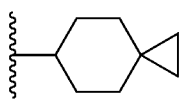 |
| 436 | 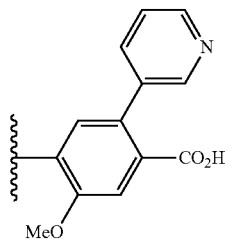 [SMILES: *c1cc(-c2cccnc2)c(C(=O)O)cc1OC] | NH | 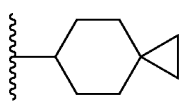 |
| 437 | 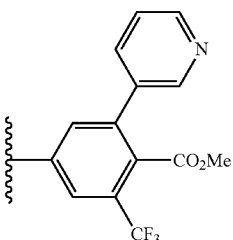 | NH | 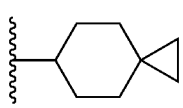 |
| 438 | 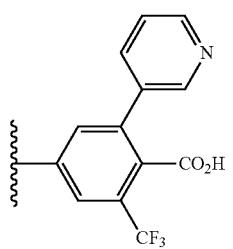 | NH | 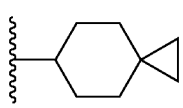 [SMILES: *C1CCC2(CC1)CC2] |

TABLE 2-continued

| Example | R² | X | ![A-Z-R⁴ structure] |
|---------|----|----|---------------------|
| 439 | spiro[2.5]octyl | NH | naphthalene-2-CO₂H |
| 440 | spiro[2.5]octyl | NH | quinoline-3-CO₂Me |
| 441 | spiro[2.5]octyl | NH | quinoline-3-CO₂H |
| 442 | spiro[2.5]octyl | NH | pyridine-2-CO₂Me |
| 443 | spiro[2.5]octyl | NH | pyridine-2-CO₂H |
| 444 | spiro[2.5]octyl | NH | 3-(morpholine-4-carbonyl)phenyl |
| 445 | spiro[2.5]octyl | NH | 3-(N,N-dimethylcarbamoyl)phenyl |
| 446 | spiro[2.5]octyl | NH | 3-(methylsulfonylaminocarbonyl)phenyl |
| 447 | spiro[2.5]octyl | NH | 3-((4-tert-butylphenylsulfonyl)aminocarbonyl)phenyl |

TABLE 2-continued
| Example | R² | X | (A)–Z–R⁴ |
|---|---|---|---|
| 448 | 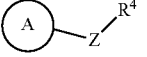 | NH |  |
| 449 | 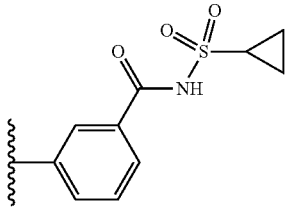 [SMILES: *c1cccc(C(=O)NS(=O)(=O)C2CC2)c1] | NH |  |
| 450 | 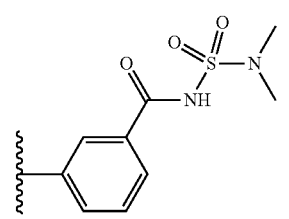 [SMILES: *c1cccc(C(=O)NS(=O)(=O)N(C)C)c1] | NH | 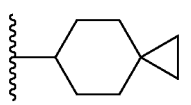 [SMILES: *C1CCC2(CC1)CC2] |
| 451 |  | NH |  |
| 452 | 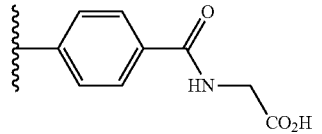 | NH |  |
| 453 | 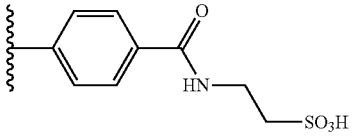 | NH |  |
| 454 | 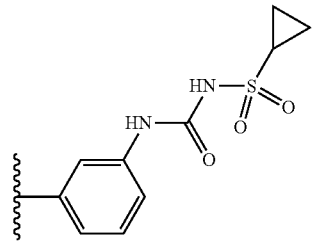 [SMILES: *c1cccc(NC(=O)NS(=O)(=O)C2CC2)c1] | NH |  |

TABLE 2-continued

| Example | R² | X | 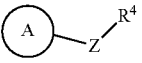 |
|---|---|---|---|
| 455 | 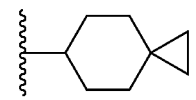 | NH | 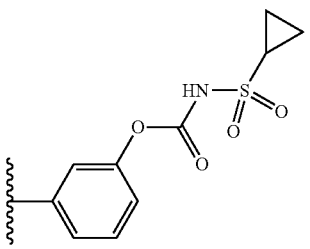 [SMILES: *c1cccc(OC(=O)NS(=O)(=O)C2CC2)c1] |
| 456 | 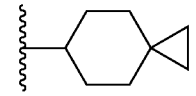 | NH | 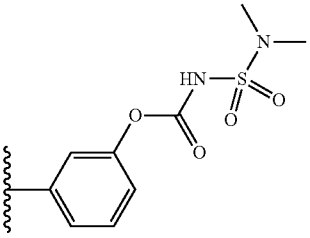 [SMILES: *c1cccc(OC(=O)NS(=O)(=O)N(C)C)c1] |

In another embodiment, when Y is absent and R⁴ is hydrogen, the compound of Formula (I) is represented by Formula (VII) or a pharmaceutically acceptable salt thereof:

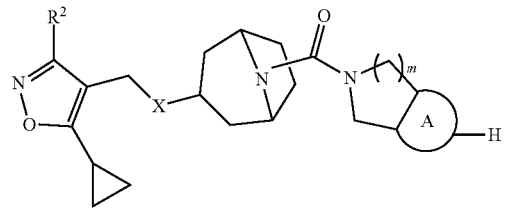

(VII)

wherein R², X, m and Ⓐ are previously defined.

Representative compounds of the invention include, but are not limited to, the following compounds (example 457 to example 552 in Table 3) according to Formula (VII), wherein R², X, and

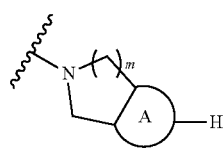

are delineated for each compound in Table 3.

TABLE 3

| Example | R² | X | 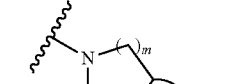 |
|---|---|---|---|
| 457 | 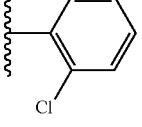 | O | 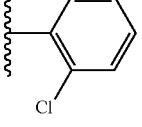 |
| 458 | 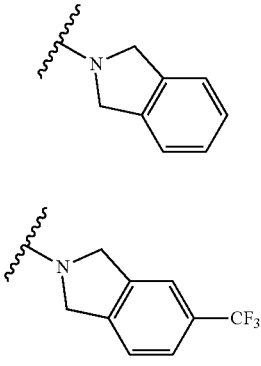 | O | 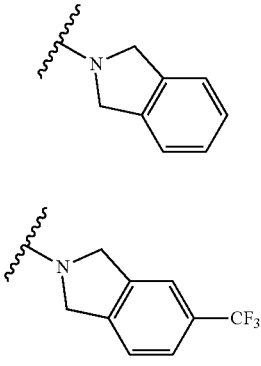 |
| 459 | 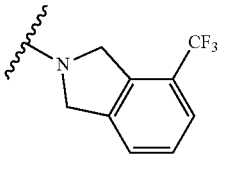 [SMILES: *N1Cc2cccc(C(F)(F)F)c2C1] | O | 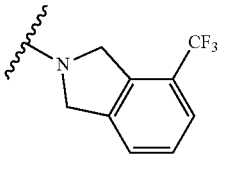 [SMILES: *N1Cc2cccc(C(F)(F)F)c2C1] |
| 460 | 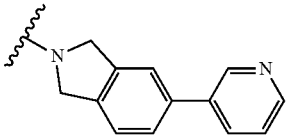 [SMILES: *N1Cc2ccc(-c3cccnc3)cc2C1] | O | 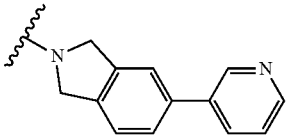 [SMILES: *N1Cc2ccc(-c3cccnc3)cc2C1] |

TABLE 3-continued

| Example | R² | X | (structure) |
|---|---|---|---|
| 461 | 2,6-diCl-phenyl | O | 4-(pyridin-3-yl)isoindoline |
| 462 | 2,6-diCl-phenyl | O | 5-CF₃-6-F-isoindoline |
| 463 | 2,6-diCl-phenyl | O | 4-F-5-CF₃-isoindoline |
| 464 | 2,6-diCl-phenyl | O | 5-tBu-isoindoline |
| 465 | 2,6-diCl-phenyl | O | 4-tBu-isoindoline |
| 466 | 2,6-diCl-phenyl | O | 2,3-dihydro-1H-pyrrolo[3,4-c]pyridine |
| 467 | 2,6-diCl-phenyl | O | 6-CF₃-2,3-dihydro-1H-pyrrolo[3,4-c]pyridine |
| 468 | 2,6-diCl-phenyl | O | 7-CF₃-2,3-dihydro-1H-pyrrolo[3,4-c]pyridine |
| 469 | 2,6-diCl-phenyl | O | 1,2,3,4-tetrahydroisoquinoline |
| 470 | 2,6-diCl-phenyl | O | 1,2,3,4-tetrahydroquinoline |
| 471 | 2,6-diCl-phenyl | O | 1,2,3,4-tetrahydro-2,7-naphthyridine |
| 472 | 2,6-diCl-phenyl | O | 1,2,3,4-tetrahydro-1,8-naphthyridine |
| 473 | 2-OCF₃-phenyl | O | isoindoline |
| 474 | 2-OCF₃-phenyl | O | 5-CF₃-isoindoline |
| 475 | 2-OCF₃-phenyl | O | 4-CF₃-isoindoline |

TABLE 3-continued

| Example | R² | X | (structure) |
|---|---|---|---|
| 476 | F₃CO-phenyl | O | 2-(pyridin-3-yl)isoindoline |
| 477 | F₃CO-phenyl | O | 4-(pyridin-3-yl)isoindoline |
| 478 | F₃CO-phenyl | O | 5-CF₃-6-F-isoindoline |
| 479 | F₃CO-phenyl | O | 4-F-5-CF₃-isoindoline |
| 480 | F₃CO-phenyl | O | 5-tert-butyl-isoindoline |
| 481 | F₃CO-phenyl | O | 4-tert-butyl-isoindoline |
| 482 | F₃CO-phenyl | O | 5-aza-isoindoline |
| 483 | F₃CO-phenyl | O | 6-CF₃-5-aza-isoindoline |
| 484 | F₃CO-phenyl | O | 4-CF₃-5-aza-isoindoline |
| 485 | F₃CO-phenyl | O | 1,2,3,4-tetrahydroisoquinoline |
| 486 | F₃CO-phenyl | O | 1,2,3,4-tetrahydroquinoline |
| 487 | F₃CO-phenyl | O | 1,2,3,4-tetrahydro-2,7-naphthyridine |
| 488 | F₃CO-phenyl | O | 1,2,3,4-tetrahydro-1,8-naphthyridine |
| 489 | spiro[2.5]octane | O | isoindoline |
| 490 | spiro[2.5]octane | O | 5-CF₃-isoindoline |
| 491 | spiro[2.5]octane | O | 4-CF₃-isoindoline |

TABLE 3-continued
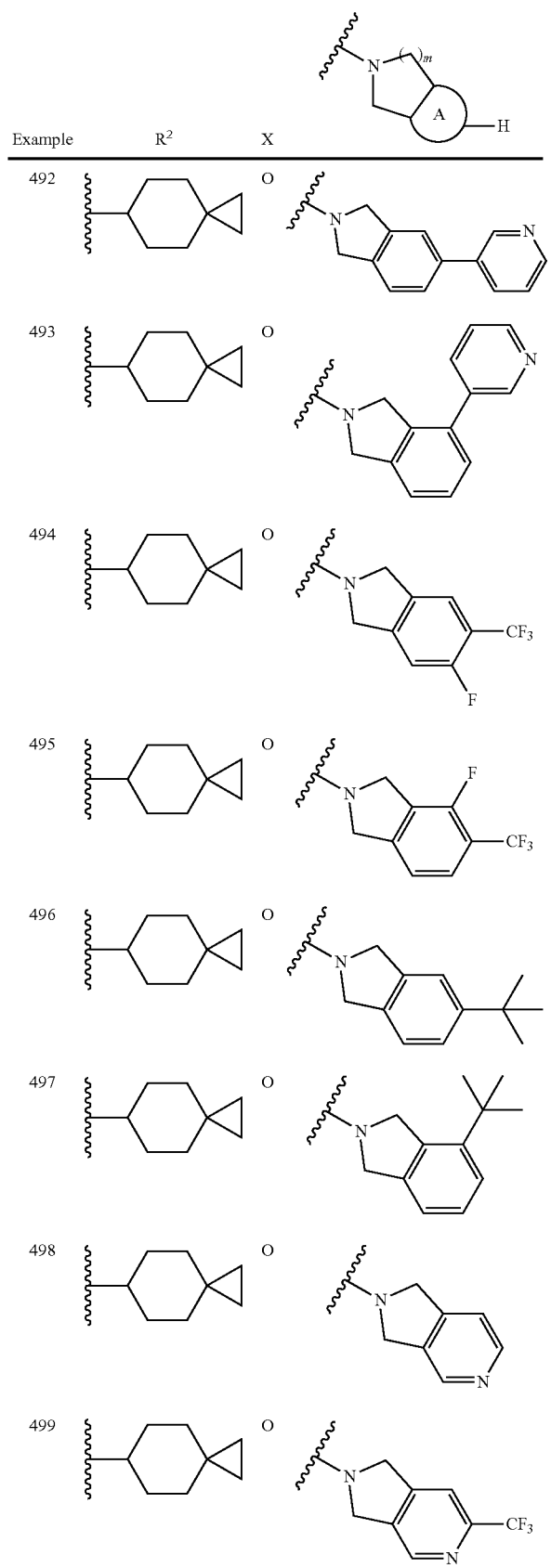
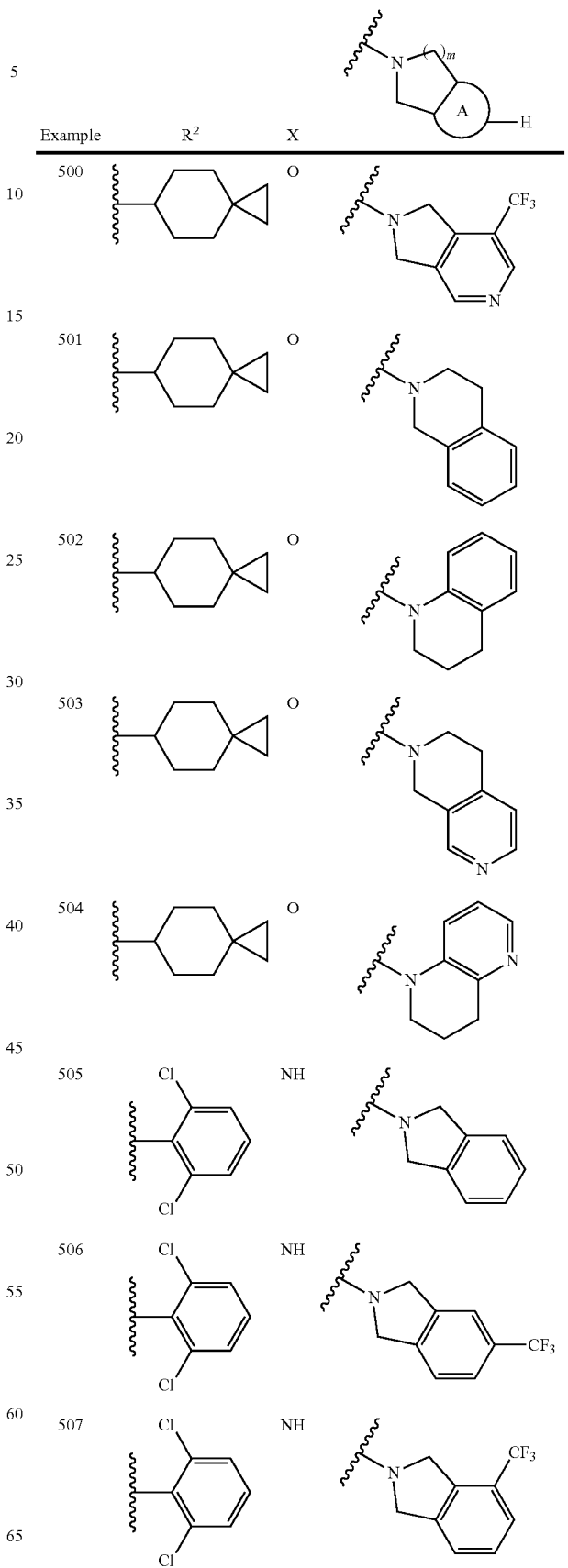

TABLE 3-continued

| Example | R² | X | |
|---|---|---|---|
| 508 | 2,6-diCl-phenyl | NH | 5-(pyridin-3-yl)isoindolin-2-yl |
| 509 | 2,6-diCl-phenyl | NH | 4-(pyridin-3-yl)isoindolin-2-yl |
| 510 | 2,6-diCl-phenyl | NH | 5-CF3, 6-F isoindolin-2-yl |
| 511 | 2,6-diCl-phenyl | NH | 4-F, 5-CF3 isoindolin-2-yl |
| 512 | 2,6-diCl-phenyl | NH | 5-tert-butyl isoindolin-2-yl |
| 513 | 2,6-diCl-phenyl | NH | 4-tert-butyl isoindolin-2-yl |
| 514 | 2,6-diCl-phenyl | NH | 2,3-dihydro-1H-pyrrolo[3,4-c]pyridin-2-yl |
| 515 | 2,6-diCl-phenyl | NH | 6-CF3-2,3-dihydro-1H-pyrrolo[3,4-c]pyridin-2-yl |
| 516 | 2,6-diCl-phenyl | NH | 4-CF3-2,3-dihydro-1H-pyrrolo[3,4-c]pyridin-2-yl |
| 517 | 2,6-diCl-phenyl | NH | 1,2,3,4-tetrahydroisoquinolin-2-yl |
| 518 | 2,6-diCl-phenyl | NH | 1,2,3,4-tetrahydroquinolin-1-yl |
| 519 | 2,6-diCl-phenyl | NH | 5,6,7,8-tetrahydro-2,7-naphthyridin-7-yl |
| 520 | 2,6-diCl-phenyl | NH | 1,2,3,4-tetrahydro-1,8-naphthyridin-1-yl |
| 521 | 2-F3CO-phenyl | NH | isoindolin-2-yl |

TABLE 3-continued

| Example | R² | X | (structure) |
|---|---|---|---|
| 522 | F₃CO-phenyl | NH | 5-CF₃-isoindoline |
| 523 | F₃CO-phenyl | NH | 4-CF₃-isoindoline |
| 524 | F₃CO-phenyl | NH | 5-(pyridin-3-yl)-isoindoline |
| 525 | F₃CO-phenyl | NH | 4-(pyridin-3-yl)-isoindoline |
| 526 | F₃CO-phenyl | NH | 5-CF₃-6-F-isoindoline |
| 527 | F₃CO-phenyl | NH | 4-F-5-CF₃-isoindoline |
| 528 | F₃CO-phenyl | NH | 5-tert-butyl-isoindoline |
| 529 | F₃CO-phenyl | NH | 4-tert-butyl-isoindoline |
| 530 | F₃CO-phenyl | NH | pyrrolo[3,4-c]pyridine |
| 531 | F₃CO-phenyl | NH | CF₃-pyrrolo[3,4-c]pyridine |
| 532 | F₃CO-phenyl | NH | CF₃-pyrrolo[3,4-c]pyridine (isomer) |
| 533 | F₃CO-phenyl | NH | 1,2,3,4-tetrahydroisoquinoline |
| 534 | F₃CO-phenyl | NH | 1,2,3,4-tetrahydroquinoline |
| 535 | F₃CO-phenyl | NH | tetrahydro-2,7-naphthyridine |
| 536 | F₃CO-phenyl | NH | 1,2,3,4-tetrahydro-1,8-naphthyridine |
| 537 | spiro[2.5]octyl | NH | isoindoline |

TABLE 3-continued

In another embodiment, the compound of Formula (I) is represented by Formula (VIII) or a pharmaceutically acceptable salt thereof:

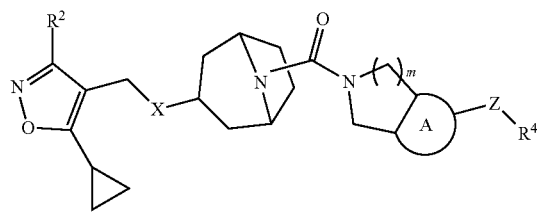

(VIII)

wherein R², R⁴, X, Z, m and are ⊙ previously defined.

Representative compounds of the invention include, but are not limited to, the following compounds (example 553 to example 690 in Table 4) according to Formula (VIII), wherein R², R⁴, X, Z, m and

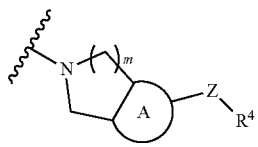

are delineated for each example in Table 4.

TABLE 4

| Example | R² | X | (structure) |
|---|---|---|---|
| 553 | 2,6-diCl-phenyl | O | tetrahydroisoquinoline-6-CO₂Me |
| 554 | 2,6-diCl-phenyl | O | tetrahydroisoquinoline-6-CO₂H |
| 555 | 2,6-diCl-phenyl | O | tetrahydroisoquinoline-6-CO₂H, 7-CF₃ |
| 556 | 2,6-diCl-phenyl | O | tetrahydroisoquinoline-6-CO₂H, 8-CF₃ |
| 557 | 2,6-diCl-phenyl | O | tetrahydroisoquinoline-6-CO₂H, 7-(pyridin-3-yl) |

TABLE 4-continued

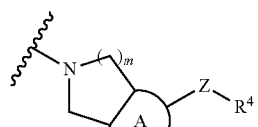

| Example | R² | X | |
|---|---|---|---|
| 558 | 2,6-diCl-phenyl | O | tetrahydroisoquinoline-6-C(O)NH-S(O)₂-(1-methylcyclopropyl) |
| 559 | 2,6-diCl-phenyl | O | tetrahydroisoquinoline-6-C(O)NH-S(O)₂-phenyl |
| 560 | 2,6-diCl-phenyl | O | tetrahydroisoquinoline-6-C(O)NH-S(O)₂-N(CH₃)₂ |
| 561 | 2,6-diCl-phenyl | O | tetrahydroisoquinoline-6-NH-C(O)-NH-S(O)₂-(1-methylcyclopropyl) |
| 562 | 2,6-diCl-phenyl | O | tetrahydroisoquinoline-6-O-C(O)-NH-S(O)₂-(1-methylcyclopropyl) |
| 563 | 2,6-diCl-phenyl | O | tetrahydroisoquinoline-6-(1H-tetrazol-5-yl) |
| 564 | 2,6-diCl-phenyl | O | tetrahydroisoquinoline-6-C(O)NH-CH₂-CO₂H |

TABLE 4-continued
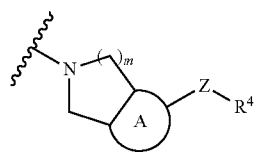
| Example | R² | X | |
|---|---|---|---|
| 565 | 2,6-diCl-phenyl | O | tetrahydroisoquinoline-6-C(O)NH-CH₂CH₂-SO₃H |
| 566 | 2,6-diCl-phenyl | O | indoline-6-CO₂Me |
| 567 | 2,6-diCl-phenyl | O | indoline-6-CO₂H |
| 568 | 2,6-diCl-phenyl | O | indoline-5-CO₂Et |
| 569 | 2,6-diCl-phenyl | O | indoline-5-CO₂H |
| 570 | 2,6-diCl-phenyl | O | 1,2,3,4-tetrahydroquinoline-6-CO₂Et |
| 571 | 2,6-diCl-phenyl | O | 1,2,3,4-tetrahydroquinoline-6-CO₂H |

TABLE 4-continued
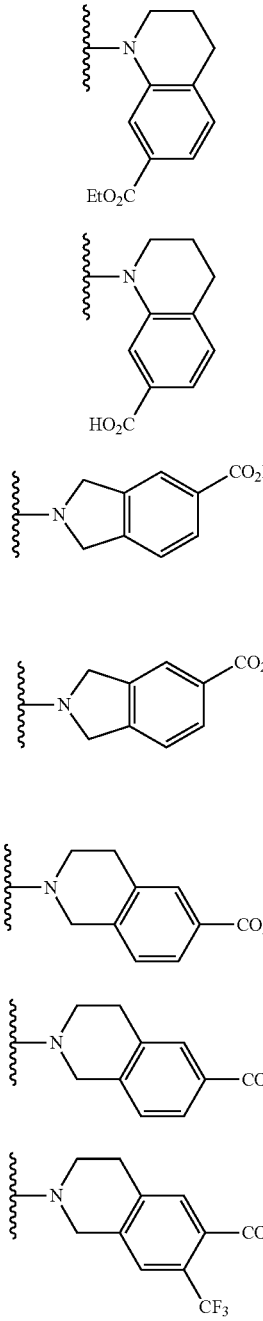
| Example | R² | X | |
|---|---|---|---|
| 572 | 2,6-diCl-phenyl | O | 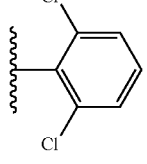 |
| 573 | 2,6-diCl-phenyl | O | 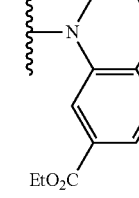 |
| 574 | 2,6-diCl-phenyl | O | 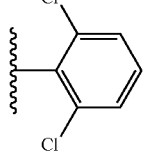 |
| 575 | 2,6-diCl-phenyl | O | 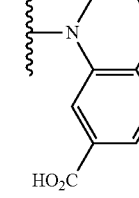 |
| 576 | 2-F₃CO-phenyl | O | 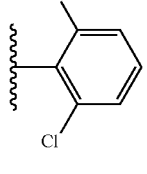 |
| 577 | 2-F₃CO-phenyl | O | 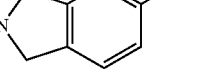 |
| 578 | 2-F₃CO-phenyl | O | 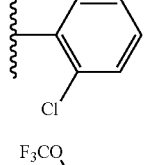 |
| 579 | 2-F₃CO-phenyl | O | 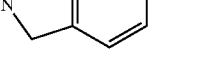 |

TABLE 4-continued

| Example | R² | X | (structure) |
|---|---|---|---|
| 580 | F₃CO-phenyl | O | tetrahydroisoquinoline-6-(3-pyridyl)-7-CO₂H |
| 581 | F₃CO-phenyl | O | tetrahydroisoquinoline-6-C(O)NH-S(O)₂-(1-methylcyclopropyl) |
| 582 | F₃CO-phenyl | O | tetrahydroisoquinoline-6-C(O)NH-S(O)₂-phenyl |
| 583 | F₃CO-phenyl | O | tetrahydroisoquinoline-6-C(O)NH-S(O)₂-N(CH₃)₂ |
| 584 | F₃CO-phenyl | O | tetrahydroisoquinoline-6-NH-C(O)NH-S(O)₂-(1-methylcyclopropyl) |
| 585 | F₃CO-phenyl | O | tetrahydroisoquinoline-6-O-C(O)NH-S(O)₂-(1-methylcyclopropyl) |

TABLE 4-continued

| Example | R² | X | (structure) |
|---|---|---|---|
| 586 | F₃CO-phenyl | O | tetrahydroisoquinoline-tetrazole |
| 587 | F₃CO-phenyl | O | tetrahydroisoquinoline-C(O)NH-CH₂-CO₂H |
| 588 | F₃CO-phenyl | O | tetrahydroisoquinoline-C(O)NH-CH₂CH₂-SO₃H |
| 589 | F₃CO-phenyl | O | indoline-6-CO₂Me |
| 590 | F₃CO-phenyl | O | indoline-6-CO₂H |
| 591 | F₃CO-phenyl | O | indoline-5-CO₂Et |
| 592 | F₃CO-phenyl | O | indoline-5-CO₂H |

TABLE 4-continued

| Example | R² | X | (structure) |
|---|---|---|---|
| 593 | F₃CO-phenyl | O | tetrahydroquinoline-6-CO₂Et |
| 594 | F₃CO-phenyl | O | tetrahydroquinoline-6-CO₂H |
| 595 | F₃CO-phenyl | O | tetrahydroquinoline-7-CO₂Et |
| 596 | F₃CO-phenyl | O | tetrahydroquinoline-7-CO₂H |
| 597 | F₃CO-phenyl | O | isoindoline-5-CO₂Me |
| 598 | F₃CO-phenyl | O | isoindoline-5-CO₂H |
| 599 | spiro[2.5]octane | O | tetrahydroisoquinoline-6-CO₂Me |
| 600 | spiro[2.5]octane | O | tetrahydroisoquinoline-6-CO₂H |

TABLE 4-continued

| Example | R² | X | (structure) |
|---|---|---|---|
| 601 | spiro[2.5]octyl | O | 1,2,3,4-tetrahydroisoquinoline-6-carboxylic acid, 7-CF₃ |
| 602 | spiro[2.5]octyl | O | 1,2,3,4-tetrahydroisoquinoline-6-carboxylic acid, 8-CF₃ |
| 603 | spiro[2.5]octyl | O | 1,2,3,4-tetrahydroisoquinoline-6-carboxylic acid, 7-(pyridin-3-yl) |
| 604 | spiro[2.5]octyl | O | N-(1-methylcyclopropylsulfonyl)-1,2,3,4-tetrahydroisoquinoline-6-carboxamide |
| 605 | spiro[2.5]octyl | O | N-(phenylsulfonyl)-1,2,3,4-tetrahydroisoquinoline-6-carboxamide |
| 606 | spiro[2.5]octyl | O | N-(N,N-dimethylsulfamoyl)-1,2,3,4-tetrahydroisoquinoline-6-carboxamide |

TABLE 4-continued

| Example | R² | X | |
|---|---|---|---|
| 607 | spiro[5.2]cyclohexane | O | tetrahydroisoquinoline-6-NH-C(O)-NH-S(O)₂-(1-methylcyclopropyl) |
| 608 | spiro[5.2]cyclohexane | O | tetrahydroisoquinoline-6-O-C(O)-NH-S(O)₂-(1-methylcyclopropyl) |
| 609 | spiro[5.2]cyclohexane | O | tetrahydroisoquinoline-6-(1H-tetrazol-5-yl) |
| 610 | spiro[5.2]cyclohexane | O | tetrahydroisoquinoline-6-C(O)-NH-CH₂-CO₂H |
| 611 | spiro[5.2]cyclohexane | O | tetrahydroisoquinoline-6-C(O)-NH-CH₂CH₂-SO₃H |
| 612 | spiro[5.2]cyclohexane | O | 6-MeO₂C-indoline-1-yl |
| 613 | spiro[5.2]cyclohexane | O | 6-HO₂C-indoline-1-yl |

TABLE 4-continued

| Example | R² | X | (structure with N, A, Z, R⁴) |
|---|---|---|---|
| 614 | spiro[5.2]cyclohexane-cyclopropane | O | 2,3-dihydroindole-5-CO₂Et (N-linked) |
| 615 | spiro[5.2]cyclohexane-cyclopropane | O | 2,3-dihydroindole-5-CO₂H (N-linked) |
| 616 | spiro[5.2]cyclohexane-cyclopropane | O | 1,2,3,4-tetrahydroquinoline-6-CO₂Et (N-linked) |
| 617 | spiro[5.2]cyclohexane-cyclopropane | O | 1,2,3,4-tetrahydroquinoline-6-CO₂H (N-linked) |
| 618 | spiro[5.2]cyclohexane-cyclopropane | O | 1,2,3,4-tetrahydroquinoline-7-CO₂Et (N-linked) |
| 619 | spiro[5.2]cyclohexane-cyclopropane | O | 1,2,3,4-tetrahydroquinoline-7-CO₂H (N-linked) |
| 620 | spiro[5.2]cyclohexane-cyclopropane | O | isoindoline-5-CO₂Me (N-linked) |

TABLE 4-continued

| Example | R² | X | (structure) |
|---|---|---|---|
| 621 | spiro[2.5]octyl | O | isoindoline-5-carboxylic acid |
| 622 | 2,6-dichlorophenyl | NH | 1,2,3,4-tetrahydroisoquinoline-6-CO₂Me |
| 623 | 2,6-dichlorophenyl | NH | 1,2,3,4-tetrahydroisoquinoline-6-CO₂H |
| 624 | 2,6-dichlorophenyl | NH | 7-CF₃-1,2,3,4-tetrahydroisoquinoline-6-CO₂H |
| 625 | 2,6-dichlorophenyl | NH | 8-CF₃-1,2,3,4-tetrahydroisoquinoline-6-CO₂H |
| 626 | 2,6-dichlorophenyl | NH | 7-(pyridin-3-yl)-1,2,3,4-tetrahydroisoquinoline-6-CO₂H |
| 627 | 2,6-dichlorophenyl | NH | 1,2,3,4-tetrahydroisoquinoline-6-C(O)NHS(O)₂-(1-methylcyclopropyl) |

TABLE 4-continued

| Example | R² | X | (structure with N-(CH₂)ₘ ring fused to A with Z-R⁴) |
|---|---|---|---|
| 628 | 2,6-dichlorophenyl | NH | tetrahydroisoquinoline-6-C(O)NH-SO₂-phenyl |
| 629 | 2,6-dichlorophenyl | NH | tetrahydroisoquinoline-6-C(O)NH-SO₂-N(CH₃)₂ |
| 630 | 2,6-dichlorophenyl | NH | tetrahydroisoquinoline-6-NH-C(O)NH-SO₂-(1-methylcyclopropyl) |
| 631 | 2,6-dichlorophenyl | NH | tetrahydroisoquinoline-6-O-C(O)NH-SO₂-(1-methylcyclopropyl) |
| 632 | 2,6-dichlorophenyl | NH | tetrahydroisoquinoline-6-(1H-tetrazol-5-yl) |
| 633 | 2,6-dichlorophenyl | NH | tetrahydroisoquinoline-6-C(O)NH-CH₂-CO₂H |
| 634 | 2,6-dichlorophenyl | NH | tetrahydroisoquinoline-6-C(O)NH-CH₂CH₂-SO₃H |

TABLE 4-continued

| Example | R² | X | (structure shown in header) |
|---|---|---|---|
| 635 | 2,6-diCl-phenyl | NH | 6-(MeO₂C)-indolin-1-yl |
| 636 | 2,6-diCl-phenyl | NH | 6-(HO₂C)-indolin-1-yl |
| 637 | 2,6-diCl-phenyl | NH | 5-(CO₂Et)-indolin-1-yl |
| 638 | 2,6-diCl-phenyl | NH | 5-(CO₂H)-indolin-1-yl |
| 639 | 2,6-diCl-phenyl | NH | 6-(CO₂Et)-1,2,3,4-tetrahydroquinolin-1-yl |
| 640 | 2,6-diCl-phenyl | NH | 6-(CO₂H)-1,2,3,4-tetrahydroquinolin-1-yl |
| 641 | 2,6-diCl-phenyl | NH | 7-(CO₂Et)-1,2,3,4-tetrahydroquinolin-1-yl |

TABLE 4-continued
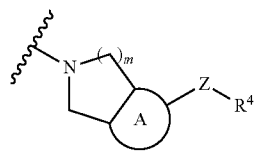
| Example | R² | X | |
|---|---|---|---|
| 642 | 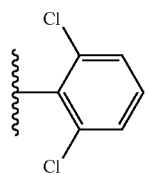 [SMILES: *c1c(Cl)cccc1Cl] | NH | 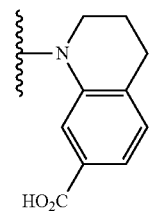 |
| 643 | 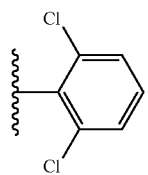 [SMILES: *c1c(Cl)cccc1Cl] | NH | 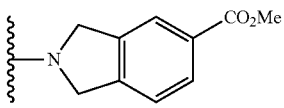 [SMILES: *N1Cc2ccc(C(=O)OC)cc2C1] |
| 644 | 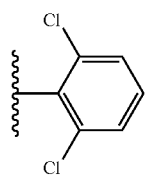 [SMILES: *c1c(Cl)cccc1Cl] | NH | 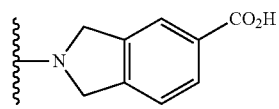 [SMILES: *N1Cc2ccc(C(=O)O)cc2C1] |
| 645 | 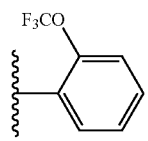 [SMILES: *c1ccccc1OC(F)(F)F] | NH | 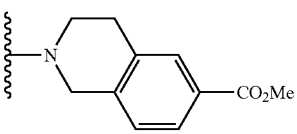 [SMILES: *N1CCc2cc(C(=O)OC)ccc2C1] |
| 646 | 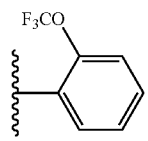 [SMILES: *c1ccccc1OC(F)(F)F] | NH | 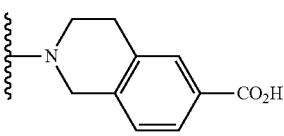 [SMILES: *N1CCc2cc(C(=O)O)ccc2C1] |
| 647 | 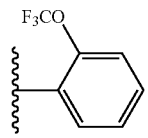 [SMILES: *c1ccccc1OC(F)(F)F] | NH | 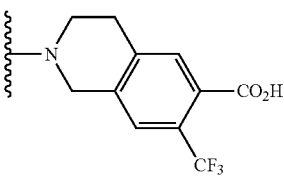 [SMILES: *N1CCc2cc(C(=O)O)c(C(F)(F)F)cc2C1] |
| 648 | 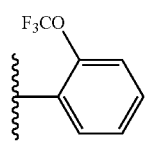 [SMILES: *c1ccccc1OC(F)(F)F] | NH | 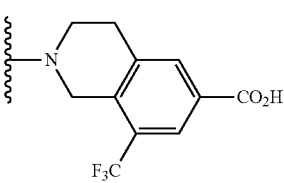 [SMILES: *N1CCc2cc(C(=O)O)cc(C(F)(F)F)c2C1] |

TABLE 4-continued
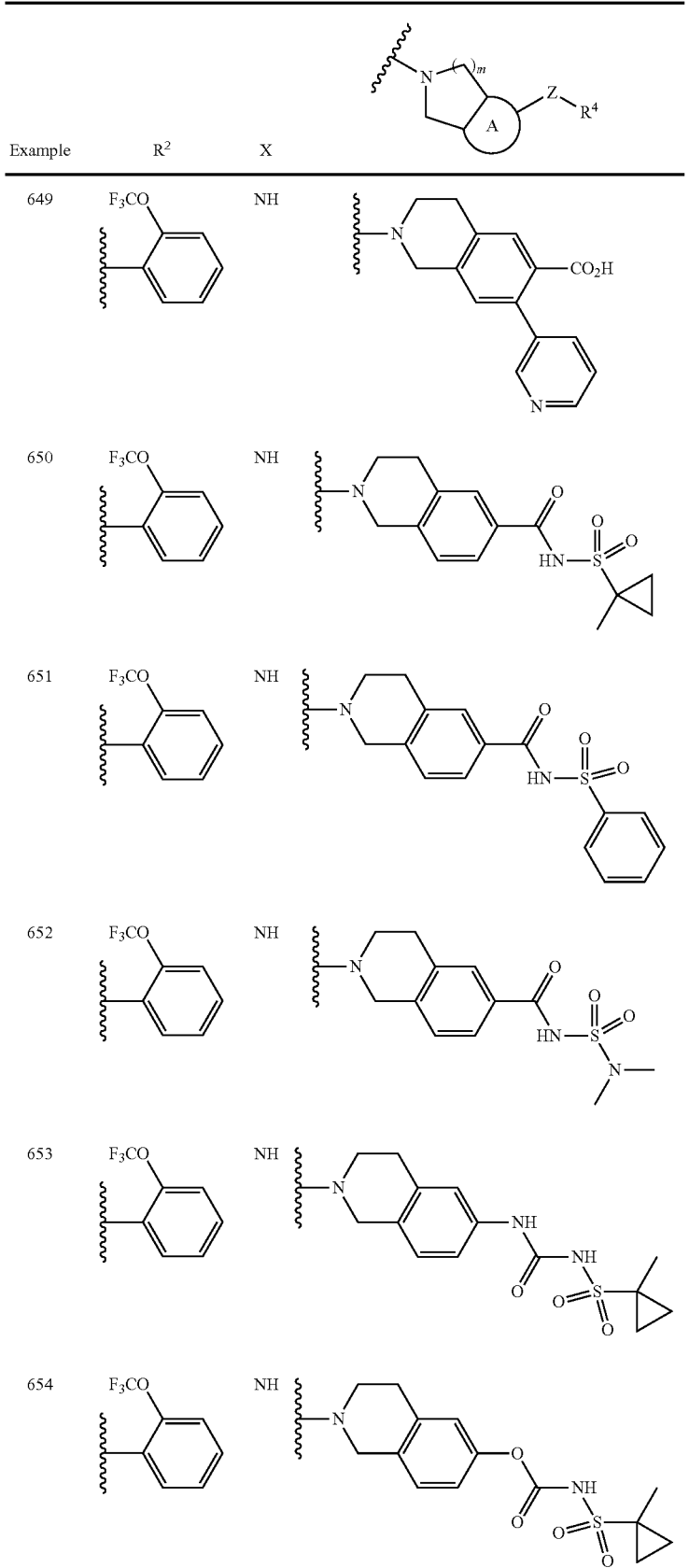

TABLE 4-continued

| Example | R² | X | (structure) |
|---|---|---|---|
| 655 | F₃CO-phenyl | NH | tetrahydroisoquinoline-6-yl-tetrazole |
| 656 | F₃CO-phenyl | NH | tetrahydroisoquinoline-6-C(O)NH-CH₂-CO₂H |
| 657 | F₃CO-phenyl | NH | tetrahydroisoquinoline-6-C(O)NH-CH₂CH₂-SO₃H |
| 658 | F₃CO-phenyl | NH | indoline-6-CO₂Me |
| 659 | F₃CO-phenyl | NH | indoline-6-CO₂H |
| 660 | F₃CO-phenyl | NH | indoline-5-CO₂Et |
| 661 | F₃CO-phenyl | NH | indoline-5-CO₂H |

TABLE 4-continued
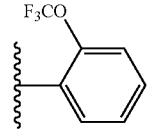 [SMILES: *c1ccccc1OC(F)(F)F]
| Example | R² | X | |
|---|---|---|---|
| 662 | F₃CO— 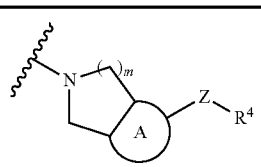 | NH | 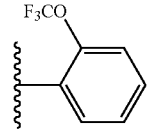 [SMILES: *c1ccccc1OC(F)(F)F] (CO₂Et) |
| 663 | F₃CO— 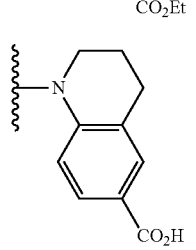 | NH | 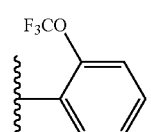 (CO₂H) |
| 664 | F₃CO— 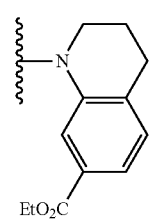 | NH | 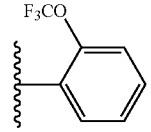 [SMILES: *c1ccccc1OC(F)(F)F] (EtO₂C) |
| 665 | F₃CO— 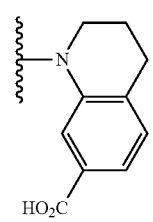 | NH | 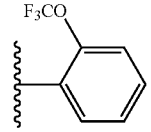 [SMILES: *c1ccccc1OC(F)(F)F] (HO₂C) |
| 666 | F₃CO— 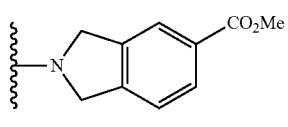 [SMILES: *N1Cc2ccc(C(=O)OC)cc2C1] | NH | 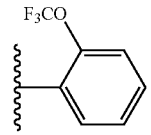 [SMILES: *c1ccccc1OC(F)(F)F] (CO₂Me) |
| 667 | F₃CO— 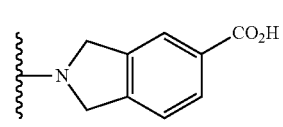 | NH | 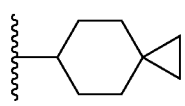 (CO₂H) |
| 668 | 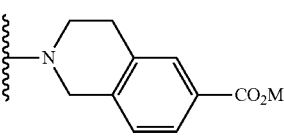 | NH | 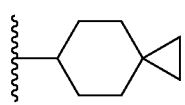 [SMILES: *C1CCC2(CC1)CC2] (CO₂Me) |
| 669 | 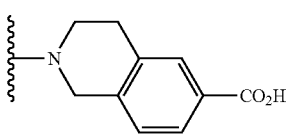 | NH | (CO₂H) |

TABLE 4-continued

| Example | R² | X | |
|---|---|---|---|
| 670 | spiro[2.5]octyl | NH | 1,2,3,4-tetrahydroisoquinoline-6-CO₂H, 7-CF₃ |
| 671 | spiro[2.5]octyl | NH | 1,2,3,4-tetrahydroisoquinoline-6-CO₂H, 8-CF₃ |
| 672 | spiro[2.5]octyl | NH | 1,2,3,4-tetrahydroisoquinoline-6-CO₂H, 7-(pyridin-3-yl) |
| 673 | spiro[2.5]octyl | NH | 1,2,3,4-tetrahydroisoquinoline-6-C(O)NHS(O)₂-(1-methylcyclopropyl) |
| 674 | spiro[2.5]octyl | NH | 1,2,3,4-tetrahydroisoquinoline-6-C(O)NHS(O)₂-phenyl |
| 675 | spiro[2.5]octyl | NH | 1,2,3,4-tetrahydroisoquinoline-6-C(O)NHS(O)₂-N(CH₃)₂ |

TABLE 4-continued

| Example | R² | X | (structure with N-(CH₂)ₘ-A-Z-R⁴) |
|---|---|---|---|
| 676 | spiro[5.2]cyclohexane-cyclopropane | NH | tetrahydroisoquinoline-6-NHC(O)NHS(O)₂-(1-methylcyclopropyl) |
| 677 | spiro[5.2]cyclohexane-cyclopropane | NH | tetrahydroisoquinolin-6-yl OC(O)NHS(O)₂-(1-methylcyclopropyl) |
| 678 | spiro[5.2]cyclohexane-cyclopropane | NH | 6-(1H-tetrazol-5-yl)-tetrahydroisoquinoline |
| 679 | spiro[5.2]cyclohexane-cyclopropane | NH | tetrahydroisoquinoline-6-C(O)NH-CH₂-CO₂H |
| 680 | spiro[5.2]cyclohexane-cyclopropane | NH | tetrahydroisoquinoline-6-C(O)NH-CH₂CH₂-SO₃H |
| 681 | spiro[5.2]cyclohexane-cyclopropane | NH | 6-MeO₂C-indoline |
| 682 | spiro[5.2]cyclohexane-cyclopropane | NH | 6-HO₂C-indoline |

TABLE 4-continued

| Example | R² | X | (structure) |
|---|---|---|---|
| 683 | spiro[5.2]cyclohexane-cyclopropane | NH | 2,3-dihydroindole-5-CO₂Et (N-linked) |
| 684 | spiro[5.2]cyclohexane-cyclopropane | NH | 2,3-dihydroindole-5-CO₂H (N-linked) |
| 685 | spiro[5.2]cyclohexane-cyclopropane | NH | 1,2,3,4-tetrahydroquinoline-6-CO₂Et (N-linked) |
| 686 | spiro[5.2]cyclohexane-cyclopropane | NH | 1,2,3,4-tetrahydroquinoline-6-CO₂H (N-linked) |
| 687 | spiro[5.2]cyclohexane-cyclopropane | NH | 1,2,3,4-tetrahydroquinoline-7-CO₂Et (N-linked) |
| 688 | spiro[5.2]cyclohexane-cyclopropane | NH | 1,2,3,4-tetrahydroquinoline-7-CO₂H (N-linked) |
| 689 | spiro[5.2]cyclohexane-cyclopropane | NH | 2,3-dihydroisoindole-5-CO₂Me (N-linked) |

TABLE 4-continued

| Example | R² | X | (structure with N-(—)ₘ, A ring, Z-R⁴) |
|---|---|---|---|
| 690 | (spiro cyclohexane-cyclopropane) | NH | (isoindoline-CO₂H) |

In certain embodiments, the present invention provides a method for the prevention or treatment of an FXR mediated disease or condition. The method comprises administering a therapeutically effective amount of a compound of Formula (I). The present invention also provides the use of a compound of Formula (I) for the preparation of a medicament for the prevention or treatment of an FXR mediated disease or condition.

In certain embodiments, the FXR-mediated disease or condition is cardiovascular disease, atherosclerosis, arteriosclerosis, hypercholesterolemia, or hyperlipidemia chronic liver disease, gastrointestinal disease, fibrotic diseases such as primary biliary cirrhosis, primary sclerosing cholangitis, pulmonary fibrosis, renal fibrosis, liver fibrosis, renal disease, metabolic disease, cancer (i.e., colorectal cancer), or neurological indications such as stroke.

In certain embodiments, the chronic liver disease is primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, or alpha 1-antitrypsin deficiency. In certain embodiments, the gastrointestinal disease is inflammatory bowel disease (IBD) (including Crohn's disease and ulcerative colitis), irritable bowel syndrome (IBS), bacterial overgrowth, malabsorption, post-radiation colitis, or microscopic colitis.

In certain embodiments, the renal disease is diabetic nephropathy, focal segmental glomerulosclerosis (FSGS), hypertensive nephrosclerosis, chronic glomerulonephritis, chronic transplant glomerulopathy, chronic interstitial nephritis, or polycystic kidney disease.

In certain embodiments, the cardiovascular disease is atherosclerosis, arteriosclerosis, dyslipidemia, hypercholesterolemia, or hypertriglyceridemia.

In certain embodiments, the metabolic disease is insulin resistance, Type I and Type II diabetes, or obesity.

In one aspect, the compound is a selective FXR agonist over TGR5 activator.

Yet a further aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group.

The term "alkyl", as used herein, refers to a saturated, monovalent straight- or branched-chain hydrocarbon group. Preferred alkyl radicals include $C_1$-$C_6$ alkyl and $C_1$-$C_8$ alkyl radicals. Examples of $C_1$-$C_6$ alkyl groups include, but are not limited to, methyl, ethyl, propyl, isopropyl, n-butyl, tert-butyl, neopentyl, n-hexyl groups; and examples of $C_1$-$C_8$ alkyl groups include, but are not limited to, methyl, ethyl, propyl, isopropyl, n-butyl, tert-butyl, neopentyl, n-hexyl, heptyl, and octyl groups.

The term "alkenyl", as used herein, denote a monovalent group derived from a hydrocarbon moiety by the removal of a single hydrogen atom wherein the hydrocarbon moiety has at least one carbon-carbon double bond. Preferred alkenyl groups include $C_2$-$C_6$ alkenyl and $C_2$-$C_8$ alkenyl groups. Alkenyl groups include, but are not limited to, for example, ethenyl, propenyl, butenyl, 1-methyl-2-buten-1-yl, heptenyl, octenyl and the like.

The term "alkynyl", as used herein, denotes a monovalent group derived from a hydrocarbon moiety by the removal of a single hydrogen atom wherein the hydrocarbon moiety has at least one carbon-carbon triple bond. Preferred alkynyl groups include $C_2$-$C_6$ alkynyl and $C_2$-$C_8$ alkynyl groups. Representative alkynyl groups include, but are not limited to, for example, ethynyl, 1-propynyl, 1-butynyl, heptynyl, octynyl and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic double bond. Preferred cycloalkyl groups include $C_3$-$C_8$ cycloalkyl and $C_3$-$C_{12}$ cycloalkyl groups. Examples of $C_3$-$C_{12}$-cycloalkyl include, but are not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, cyclooctyl, bicyclo[2.2.1]heptyl, bicyclo[2.2.2]octyl, spiro[2.5]octyl, 3-methylenebicyclo[3.2.1]octyl, spiro[4.4]nonanyl, bicycle[3.1.0]hexanyl, spiro[2.3]hexanyl, bicycle[3.1.1]heptanyl, spiro[2.5]octanyl, bicycle[4.1.0]heptanyl, bicycle[3.1.0]hexan-6-yl, spiro[2.3]hexan-5-yl, bicycle[3.1.1]heptan-3-yl, spiro[2.5]octan-4-yl, and bicycle[4.1.0]heptan-3-yl and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic double bond. Preferred cycloalkenyl groups include $C_3$-$C_8$ cycloalkenyl and $C_3$-$C_{12}$ cycloalkenyl groups. Examples of $C_3$-$C_{12}$-cycloalkenyl include, but are not limited to, cyclopropenyl, cyclobutenyl, cyclopentenyl, cyclohexenyl, cycloheptenyl, cyclooctenyl, and the like; and examples of $C_3$-$C_{12}$-cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-1-enyl, bicyclo[4.2.1]non-3-en-9-yl, and the like.

The terms "heterocyclic" or "heterocycloalkyl" can be used interchangeably and referred to a non-aromatic ring or a bi- or tri-cyclic group fused, bridged or spiro system, wherein (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic double bond. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl, 2-azabicyclo[2.2.1]-heptyl, 8-azabicyclo[3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

The term "aryl," as used herein, refers to a mono- or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "arylalkyl," as used herein, refers to a functional group wherein an alkylene chain is attached to an aryl group, e.g., —$CH_2CH_2$-phenyl. The term "substituted arylalkyl" means an arylalkyl functional group in which the aryl group is substituted. Examples include, but are not limited to, benzyl, phenethyl and the like. Preferred arylalkyl groups include aryl-$C_1$-$C_8$-alkyl groups.

The term "heteroaryl," as used herein, refers to a mono-, bi-, or tri-cyclic group comprising at least one 5- or 6-membered aromatic ring comprising at least one ring atom selected from S, O and N. Preferred heteroaryl groups are monocyclic or bicyclic. Heteroaryl groups include monocyclic groups having 5 or 6 ring atoms and fused bicyclic groups comprising 8 to 10 ring atoms. Heteroaryl groups include, but are not limited to, pyridinyl, pyrazolyl, pyrazinyl, pyrimidinyl, pyrrolyl, pyrazolyl, imidazolyl, thiazolyl, thienyl, triazolyl, isothiazolyl, oxazolyl, isoxazolyl, thiadiazolyl, oxadiazolyl, thiophenyl, furanyl, quinolinyl, isoquinolinyl, benzimidazolyl, benzooxazolyl, benzothienyl, quinoxalyl, indolyl, indazolyl, benzisoxazolyl, benzofuranyl, benzotriazolyl, benzothiazolyl, and the like.

The term "heteroarylalkyl," as used herein, refers to an alkylene chain is attached to a heteroaryl group. The term "substituted heteroarylalkyl" means a heteroarylalkyl functional group in which the heteroaryl group is substituted. Examples include, but are not limited to, pyridinylmethyl, pyrimidinylethyl and the like. Preferred heteroarylalkyl groups include heteroaryl-$C_1$-$C_8$-alkyl groups.

The term "biaryl", as used herein, refers to a moiety consisting of two aryl groups, two heteroaryl groups or an aryl group and a heteroaryl group, wherein the two groups are connected by a single bond. A substituted biaryl group is a biaryl moiety in which at least one of the connected groups has at least one non-hydrogen substituent. Examples of biaryl groups include biphenyl, pyridylphenyl, pyrimidylphenyl, pyrimidypyridyl, and pyrimidyloxadizolyl groups.

The term "aryl-heterocyclyl" refers to a bicyclic group comprising a monocyclic aryl or heteroaryl group connected to a heterocyclic group by a single bond. Examples of aryl-heterocyclyl groups include phenyl-piperidinyl and pyridyl-piperidinyl groups.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

The term "substituted" refers to substitution by independent replacement of one, two, or three or more of the hydrogen atoms with substituents including, but not limited to, —F, —Cl, —Br, —I, —OH, $C_1$-$C_{12}$-alkyl; $C_2$-$C_{12}$-alkenyl, $C_2$-$C_{12}$-alkynyl, protected hydroxy, —$NO_2$, —$N_3$, —CN, —$NH_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH— heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O— heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_5$-alkenyl, —$OCO_2$—$C_2$-$C_5$-alkynyl, —$OCO_2$—$C_3$-$C_{12}$-cycloalkyl, —$OCO_2$-aryl, —$OCO_2$-heteroaryl, —$OCO_2$-heterocycloalkyl, —$CO_2$—$C_1$-$C_{12}$ alkyl, —$CO_2$—$C_2$-$C_8$ alkenyl, —$CO_2$—$C_2$-$C_5$ alkynyl, $CO_2$—$C_3$-$C_{12}$-cycloalkyl, —$CO_2$-aryl, $CO_2$-heteroaryl, $CO_2$-heterocyloalkyl, —$OCONH_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocyclo-alkyl, —NHC(O)H, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_8$-alkenyl, —$NHCO_2$—$C_2$-$C_8$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —$NHC(O)NH_2$, —NHC(O)NH—$C_1$-$C_2$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, $NHC(S)NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH— heterocycloalkyl, —$NHC(NH)NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, —$SO_2NH_2$, —$SO_2$NH—$C_1$-$C_{12}$-alkyl, —$SO_2$NH—$C_2$-$C_8$-alkenyl, —$SO_2$NH—$C_2$-$C_8$-alkynyl, —$SO_2$NH—$C_3$-$C_{12}$-cycloalkyl, —$SO_2$NH-aryl, —$SO_2$NH-heteroaryl, —$SO_2$NH-heterocycloalkyl, —$NHSO_2$—$C_1$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S— heteroaryl, —S-heterocycloalkyl, or methylthiomethyl. It is understood that the alkenyls, alkynyls, aryls, heteroaryls, alkyls, heterocycloalkyl, cycloalkyls and the like can be further substituted. In some cases, each substituent in a substituted moiety is additionally optionally substituted with one or more groups, each group being independently selected from $C_1$-$C_6$-alkyl, $CF_3$, —F, —Cl, —Br, —I, —OH, —$NO_2$, —CN, and —$NH_2$.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl and cycloalkenyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl, alkenyl, alkynyl, alkylene, alkenylene, and alkynylene groups described herein.

The term "alicyclic," as used herein, denotes a monovalent group derived from a monocyclic or polycyclic saturated carbocyclic ring compound by the removal of a single hydrogen atom. Examples include, but are not limited to, cyclopropyl, cyclobutyl, cyclopentyl, cyclohexyl, bicyclo[2.2.1]heptyl, and bicyclo[2.2.2]octyl. Such alicyclic groups may be further substituted.

It will be apparent that in various embodiments of the invention, the substituted or unsubstituted alkyl, alkenyl, alkynyl, cycloalkyl, cycloalkenyl, cycloalkynyl, arylalkyl, heteroarylalkyl, and heterocycloalkyl are intended to be monovalent or divalent. Thus, alkylene, alkenylene, and alkynylene, cycloaklylene, cycloalkenylene, cycloalkynylene, arylalkylene, heteroarylalkylene and heterocycloalkylene groups are to be included in the above definitions, and are applicable to provide the Formulas herein with proper valency.

The terms "halo" and "halogen," as used herein, refer to an atom selected from fluorine, chlorine, bromine and iodine.

The term "hydrogen" includes hydrogen and deuterium. In addition, the recitation of an atom includes other isotopes of that atom so long as the resulting compound is pharmaceutically acceptable.

In certain embodiments, the compounds of each formula herein are defined to include isotopically labelled compounds. An "isotopically labelled compound" is a compound in which at least one atomic position is enriched in a specific isotope of the designated element to a level which is significantly greater than the natural abundance of that isotope. For example, one or more hydrogen atom positions in a compound can be enriched with deuterium to a level which is significantly greater than the natural abundance of deuterium, for example, enrichment to a level of at least 1%, preferably at least 20% or at least 50%. Such a deuterated compound may, for example, be metabolized more slowly than its non-deuterated analog, and therefore exhibit a longer half-life when administered to a subject. Such compounds can synthesize using methods known in the art, for example by employing deuterated starting materials. Unless stated to the contrary, isotopically labelled compounds are pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis*, 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992) and in "Prodrugs of Alcohols and Phenols" by S. S. Dhareshwar and V. J. Stella, in *Prodrugs Challenges and Rewards Part*-2, (Biotechnology: Pharmaceutical Aspects), edited by V. J. Stella, et al, Springer and AAPSPress, 2007, pp 31-99.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis*, 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "amino acid" refers to naturally occurring and synthetic α, β, γ, or δ amino acids, and includes but is not limited to, amino acids found in proteins or intermediates in metabolism of amino acids or proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, citrulline, arginine and histidine. In certain embodiments, the amino acid is in the L-configuration. In certain embodiments, the amino acid is in the D-configuration. In certain embodiments, the amino acid is provided as a substituent of a compound described herein, wherein the amino acid is a residue selected from the group consisting of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, fβ-phenylalaninyl, β-tryptophanyl, (β-methioninyl, β-glycinyl, β-serinyl, β-threoninyl, β-cysteinyl, β-tyrosinyl, β-asparaginyl, β-glutaminyl, β-aspartoyl, β-glutaroyl, (β-lysinyl, β-argininyl and β-histidinyl.

The term "amino acid derivative" refers to a group derivable from a naturally or non-naturally occurring amino acid, as described and exemplified herein. Amino acid derivatives are apparent to those of skill in the art and include, but are not limited to, ester, amino alcohol, amino aldehyde, amino lactone, and N-methyl derivatives of naturally and non-naturally occurring amino acids. In an embodiment, an amino acid derivative is provided as a substituent of a compound described herein, wherein the substituent is —NR$^u$-G(S$_c$)—C(O)-Q$^1$, wherein Q$^1$ is —SR$^v$, —NR$^v$R$^v$ or alkoxyl, R$^v$ is hydrogen or alkyl, S$_c$ is a side-chain of a naturally occurring or non-naturally occurring amino acid, G is C$_1$-C$_2$ alkyl, and R$^u$ is hydrogen; or R$^u$ and S$_c$ are taken together with the atoms to which they are attached to form a five-membered heterocyclic ring. In an embodiment, an amino acid derivative is provided as a substituent of a compound described herein, wherein the substituent is —O—C(O)-G(S$_c$)—NH-Q$^2$, wherein Q$^2$ is hydrogen or alkoxyl, S$_c$ is a side-chain of a naturally occurring or non-naturally occurring amino acid and G is C$_1$-C$_2$ alkyl. In certain embodiments, Q$^2$ and S$_c$ are taken together with the atoms to which they are attached to form a five-membered heterocyclic ring. In certain embodiments, G is an optionally substituted methylene and S$_c$ is selected from the group consisting of hydrogen, alkyl, arylalkyl, heterocycloalkyl, carboxylalkyl, heteroarylalkyl, aminoalkyl, hydroxylalkyl, aminoiminoaminoalkyl, aminocarbonylalkyl, sulfanylalkyl, carbamoylalkyl, alkylsulfanylalkyl and hydroxylarylalkyl. In an embodiment, an amino acid derivative is provided as a substituent of a compound described herein, wherein the amino acid derivative is in the D-configuration. In an embodiment, an amino acid derivative is provided as a substituent of a compound described herein, wherein the amino acid derivative is in the L-configuration.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

When the compounds described herein contain one or more asymmetric centers they give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques, which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus, a carbon-carbon double bond depicted arbitrarily herein as trans may be cis, trans, or a mixture of the two in any proportion.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art.

Berge, et al. describes pharmaceutically acceptable salts in detail in J. Pharmaceutical Sciences, 66: 1-19 (1977). The salts can be prepared in situ during the final isolation and purification of the compounds of the invention, or separately by reaction of the free base function with a suitable organic acid. Examples of pharmaceutically acceptable salts include, but are not limited to, nontoxic acid addition salts e.g., salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethyl succinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the Formulae of the instant invention. Various forms of prodrugs are known in the art, for example, as discussed in Bundgaard, (ed.), *Design of Prodrugs*, Elsevier (1985); Widder, et al. (ed.), *Methods in Enzymology*, Vol. 4, Academic Press (1985); Krogsgaard-Larsen, et al., (ed). "Design and Application of Prodrugs, *Textbook of Drug Design and Development*, Chapter 5, 113-191 (1991); Bundgaard, et al., *Journal of Drug Deliver Reviews*, 8:1-38 (1992); Bundgaard, J. of *Pharmaceutical Sciences*, 77:285 et seq. (1988); Higuchi and Stella (eds.) Prodrugs as Novel Drug Delivery Systems, *American Chemical Society* (1975); and Bernard Testa & Joachim Mayer, "Hydrolysis In Drug And Prodrug Metabolism: Chemistry, Biochemistry And Enzymology," John Wiley and Sons, Ltd. (2002).

The term "treating", as used herein, means relieving, lessening, reducing, eliminating, modulating, or ameliorating, i.e. causing regression of the disease state or condition. Treating can also include inhibiting, i.e. arresting the development, of an existing disease state or condition, and relieving or ameliorating, i.e. causing regression of an existing disease state or condition, for example when the disease state or condition may already be present.

The term "preventing", as used herein means, to completely or almost completely stop a disease state or condition, from occurring in a patient or subject, especially when the patient or subject is predisposed to such or at risk of contracting a disease state or condition.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired isoxazole products of the present invention. Synthetic chemistry transformations and protecting group methodologies (protection and deprotection) useful in synthesizing the compounds described herein include, for example, those described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention Formulated together with one or more pharmaceutically acceptable carriers. As used herein, the term "pharmaceutically acceptable carrier" means a non-toxic, inert solid, semi-solid or liquid filler, diluent, encapsulating material or Formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the Formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the Formulation may be adjusted with pharmaceutically acceptable acids, bases or buffers to enhance the stability of the Formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable Formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable Formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragées, capsules, pills, and granules can be prepared with coatings and shells such as enteric coatings, release controlling coatings and other coatings well known in the pharmaceutical Formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic Formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the schemes and the examples that follow are:
BOP-Cl for bis(2-oxo-3-oxazolidinyl)phosphinic chloride;
CDI for carbonyldiimidazole;
DBU for 1,8-diazabicycloundec-7-ene;
DCC for N,N-dicyclohexylcarbodiimide;
DCM for dichloromethane;
DMAP for N,N-dimethylaminopyridine;
DMF for N,N-dimethyl formamide;
DPPA for diphenylphosphoryl azide;
EDC for 1-(3-diethylaminopropyl)-3-ethylcarbodiimide hydrochloride;
Et$_3$N for triethylamine;
EtOAc for ethyl acetate;
HATU for 1-[bis(dimethylamino)methylene]-1H-1,2,3-triazolo[4,5-b]pyridinium 3-oxid hexafluorophosphate;
HCl for hydrochloric acid;
PyAOP for 7-azabenzotriazol-1-yloxy)tripyrrolidinophosphonium hexafluorophosphate;
PyBOP for benzotriazol-1-yl-oxytripyrrolidinophosphonium hexafluorophosphate;
TFFH for tetramethylfluoroformamidinium hexafluorophosphate;
THF for tetrahydrofuran.

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

Scheme 1

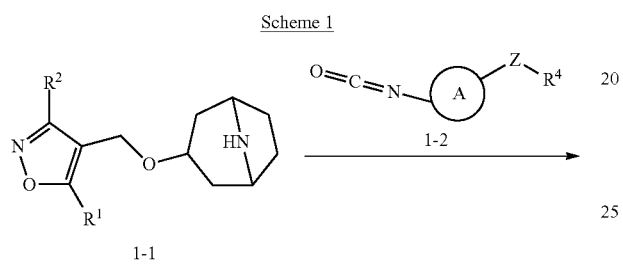

1-1

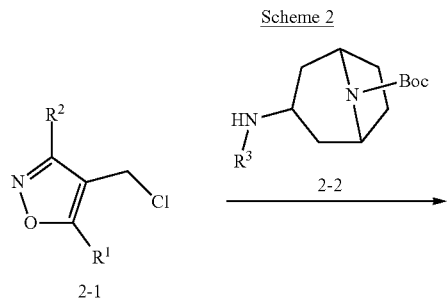

1-3

As shown in Scheme 1, novel isoxazole urea analogs of the compound of Formula (1-3) are prepared from the compound of Formula (1-1), wherein $R^1$, $R^2$, ⓒ, $R^4$ and Z are as previously defined. For the preparation of secondary amine of Formula (1-1), see WO 2012087519. The compound of Formula (1-1) is coupled with an isocyanate of Formula (1-2) to give the urea compound of Formula (1-3), wherein $R^1$, $R^2$, ⓒ, $R^4$ and Z are as previously defined. The reaction is carried out in an aprotic solvent such as, but not limited to, DCM, DMF or THF. The reaction temperature can vary from room temperature to about 50° C.

Scheme 2

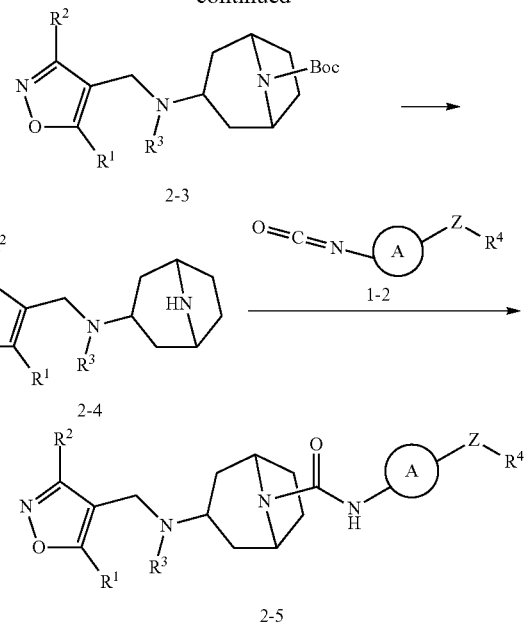

As shown in Scheme 2, novel isoxazole urea analogs of the compound of Formula (2-5) are prepared from the compound of Formula (2-1), wherein $R^1$, $R^2$, ⓒ, $R^3$, $R^4$ and Z are as previously defined. For the preparation of isoxazole chloride compound of Formula (2-1), see WO 2012087519 and WO 2012/087520. The compound of Formula (2-1) is coupled with amine compound of Formula (2-2) to give the compound of Formula (2-3). The Boc protecting group is removed under acidic condition to provide the secondary amine compound of Formula (2-4), which reacts with an isocyanate of Formula (1-2) to give the urea compound of Formula (2-5), wherein $R^1$, $R^2$, ⓒ, $R^3$, $R^4$ and Z are as previously defined.

Scheme 3

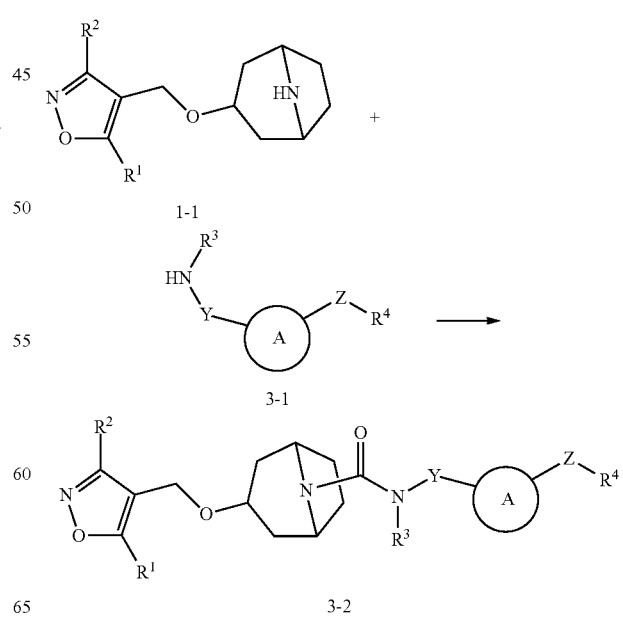

As shown in Scheme 3, novel isoxazole urea analogs of the compound of Formula (3-2) can be prepared from the compound of Formula (1-1), wherein Y, Z, $R^1$, $R^2$, ⊚, $R^3$, and $R^4$ are as previously defined. The compound of Formula (1-1) is coupled with nitrogen containing compound of Formula (3-1) to afford the urea compound of Formula (1-3) using a suitable coupling reagent such as, but not limited to, CDI, phosgene, or 4-nitrophenyl chloroformate. The reaction solvent can be, but not limited to, DCM, DMF and toluene. The reaction temperature is from room temperature to 80° C.

Scheme 4

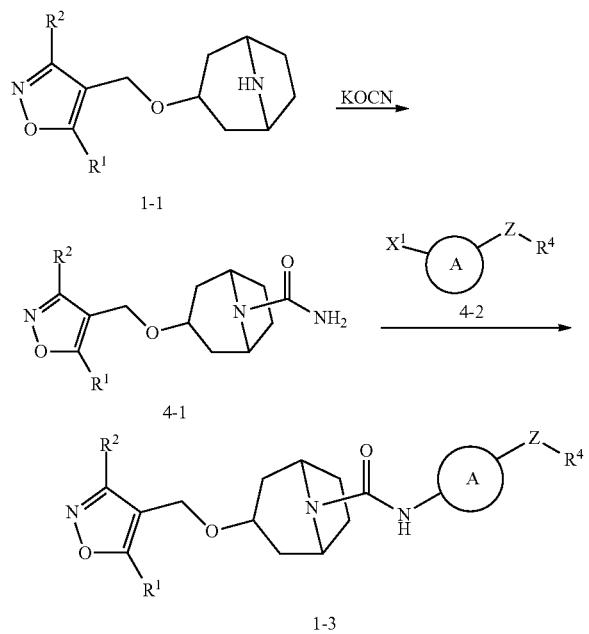

As shown in Scheme 4, novel isoxazole urea analogs of the compound of Formula (1-3) can also be alternatively prepared from the compound of Formula (1-1) in a two-step sequence, wherein $R^1$, $R^2$, ⊚, $R^4$ and Z are as previously defined. The compound of Formula (1-1) reacts with KOCN to afford primary urea compound of Formula (4-1), which then is coupled with aryl halides compound of Formula (4-2) to provide the desired urea compound of Formula (1-3) under a suitable C—N coupling condition. For representative C—N coupling conditions, see: 1) *Org. Lett.*, 2009, 11 (4), pp 947-950; 2) WO2002085838.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, Formulations and/or methods of the invention may be made without departing from the spirit of the invention and the scope of the appended claims.

Example 2

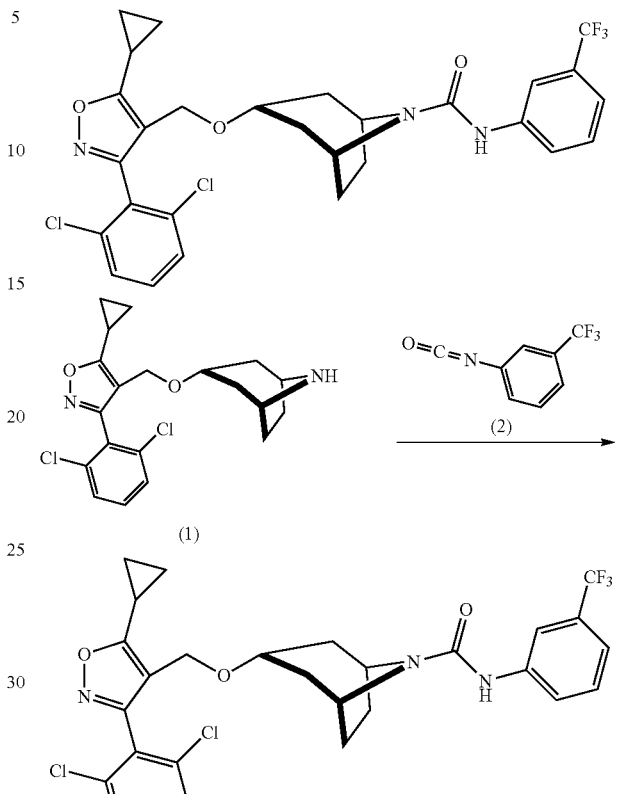

Example 2

For the preparation of secondary amine (1), see WO 2012087519. To a solution of secondary amine (1) (20.8 mg, 0.053 mmol) in DCM (0.264 mL) was added 1-isocyanato-3-(trifluoromethyl)benzene (2) (11.9 mg, 0.063 mmol). The mixture was allowed to stir at 23° C. for 2 hours. The reaction crude was then concentrated in vacuo. Purification of the residue on silica gel column with 0-30% of EtOAc/hexanes provided Example 2 (17.8 mg) as a white solid. LC/MS observed [M+H]$^+$: 580.14.

Example 185

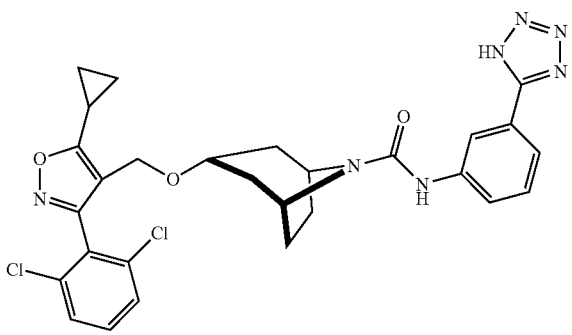

173
-continued

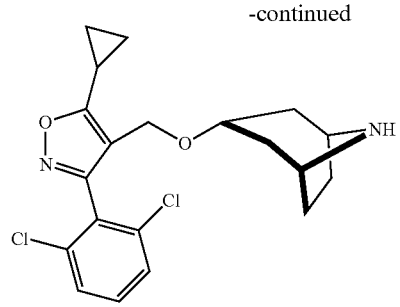
(1)

+

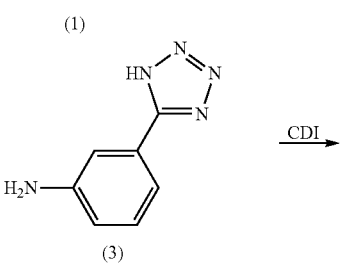
(3)

CDI →

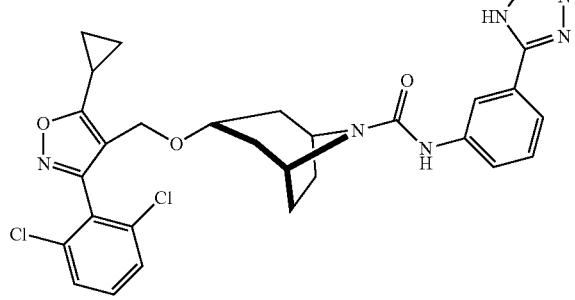
Example 185

To a suspension of aniline (3) (51.5 mg, 0.32 mmol) in DCM/DMF (1:1, 0.8 mL) was added CDI (62.2 mg, 0.383 mmol). The mixture was allowed to stir at 23° C. for 15 hours before addition of secondary amine (1) (62.8 mg, 0.16 mmol). Then the suspension was allowed to stir for additional 5 hours. The reaction was filtered to remove precipitate and concentrated in vacuo. Purification of the residue on silica gel column with 0-10% of MeOH/DCM provided Example 185 (50.8 mg) as a white solid. LC/MS observed [M+H]$^+$: 580.17.

Example 12

174
-continued

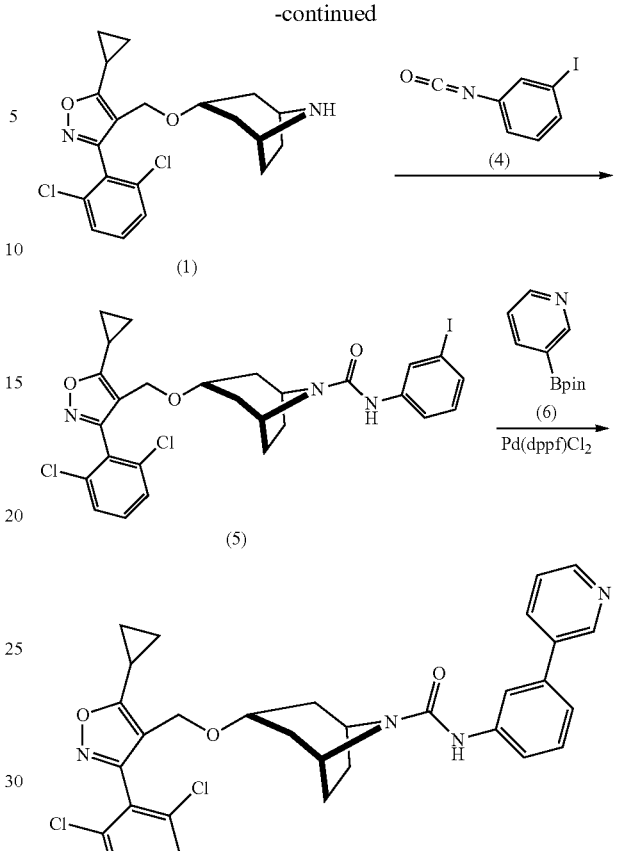

For the preparation of urea compound (5), see the representative method of Example 2. To a solution of urea compound (5) (58.6 mg, 0.092 mmol) in toluene (2.3 ml) and EtOH (1.4 mL) is added 3-pyridineboronic acid pinacol ester (24.5 mg, 0.119 mmol), [1,1'-bis(diphenylphosphino)ferrocene]palladium(II) dichloride (3.4 mg, 0.005 mmol) and 2.0 M K$_2$CO$_3$ aq. solution (0.482 mL). The mixture was allowed to stir at 110° C. for 2 hours, quenched with saturated NH$_4$Cl aq. solution at 23° C., and extracted with EtOAc (2×). The combined organic layers were washed by brine and dried over Na$_2$SO$_4$, and concentrated in vacuo. Purification of the residue on silica gel column with 0-100% EtOAc/hexanes provided Example 12 (35 mg) as a white solid. LC/MS observed [M+H]$^+$: 589.18.

Example 691

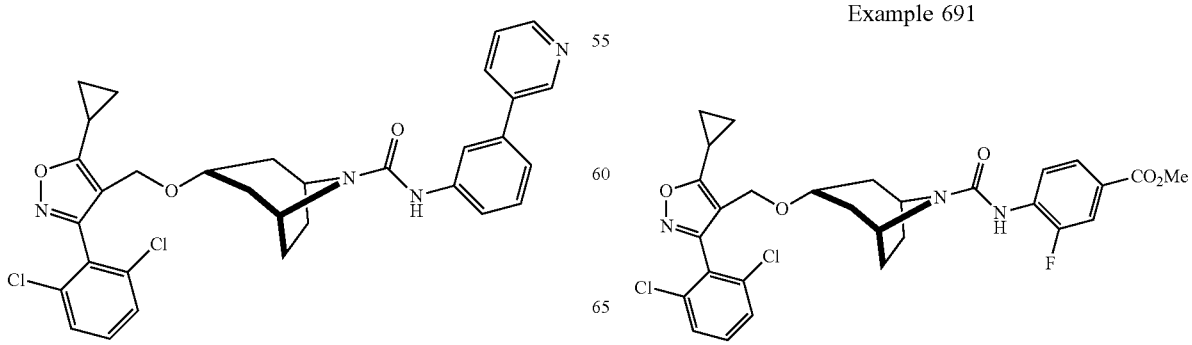

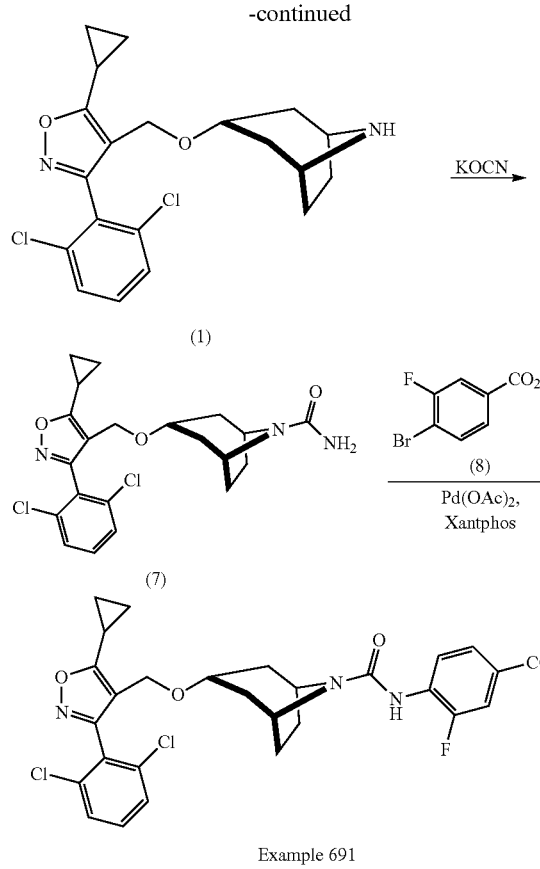

Example 691

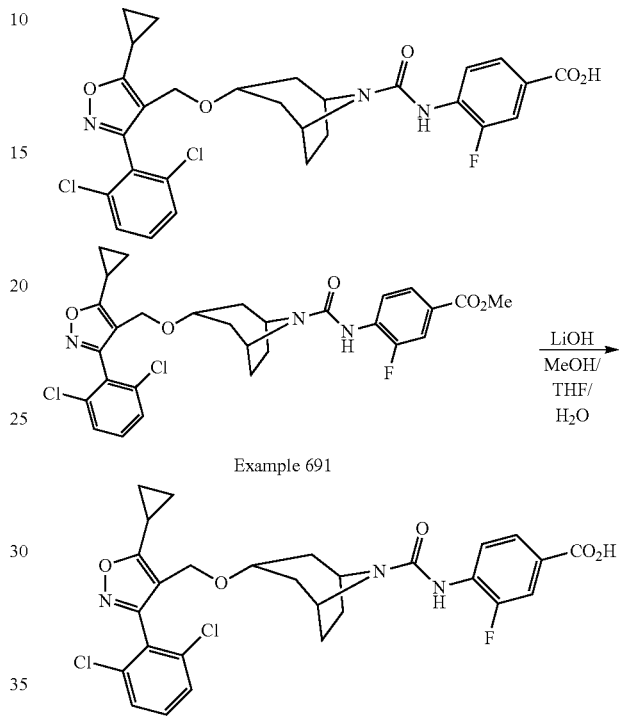

Example 691

Example 692

To a solution of secondary amine (1) (515.3 mg, 1.31 mmol) and KOCN (213 mg, 2.62 mmol) in dioxane (2.62 mL) and water (2.62 mL) was added acetic acid (0.15 mL, 2.62 mmol). The reaction was stirred at room temperature for 4 hours, quenched with water, and extracted with EtOAc (3×). The combined organic layers were washed with brine, dried over Na$_2$SO$_4$, and concentrated in vacuo to afford crude primary urea (7) as white solid (572 mg). LC/MS observed [M+H]$^+$: 436.12. Without any purification, this crude was directly used in the following transformation.

To a solution of primary urea compound (7) (102 mg, 0.234 mmol) in toluene (1.2 mL) was charged with methyl 4-bromo-2-fluorobenzoate (65.4 mg, 0.281 mmol), Pd(OAc)$_2$ (5.3 mg, 0.023 mmol), Xantphos (27.1 mg, 0.047 mmol) and cesium carbonate (152 mg, 0.468 mmol). The reaction was allowed to stir at 80° C. for 17 hours. Then the crude was quenched with water, and extracted with EtOAc (3×). The combined organic layers were washed with brine, dried over Na$_2$SO$_4$, and concentrated in vacuo. Purification of the residue on silica gel column with 0-50% EtOAc/hexanes provided Example 691 (53 mg) as a white solid. LC/MS observed [M+H]$^+$: 588.15.

Example 692

To a solution of Example 691 (29.5 mg, 0.05 mmol) in MeOH/THF/H$_2$O (1:1:1, 0.3 mL) was added LiOH (6.0 mg, 0.25 mmol). The reaction was allowed to stir at 60° C. for 1 hour. The reaction was then acidified by 1M aq. HCl solution and extracted with EtOAc (3×). The combined organic layers were washed by brine and dried over Na$_2$SO$_4$, and concentrated in vacuo. Purification of the residue on silica gel column with 0-100% acetone/hexanes provided Example 692 (28.7 mg) as a white solid. LC/MS observed [M+H]$^+$: 574.13.

Example 693

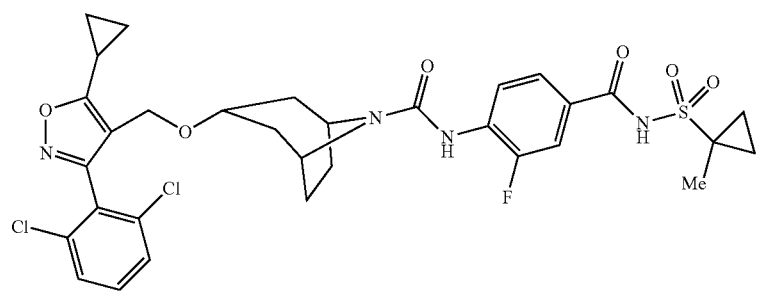

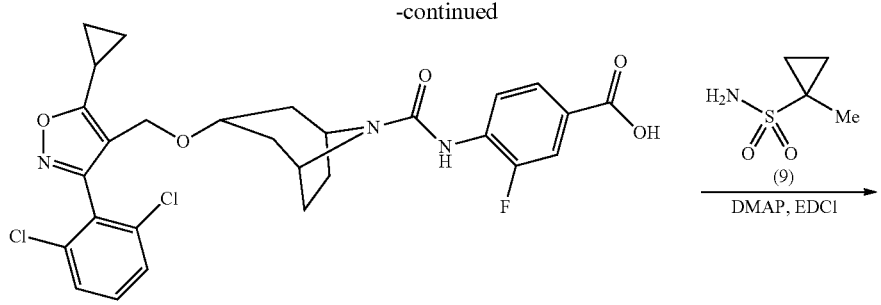
Example 692
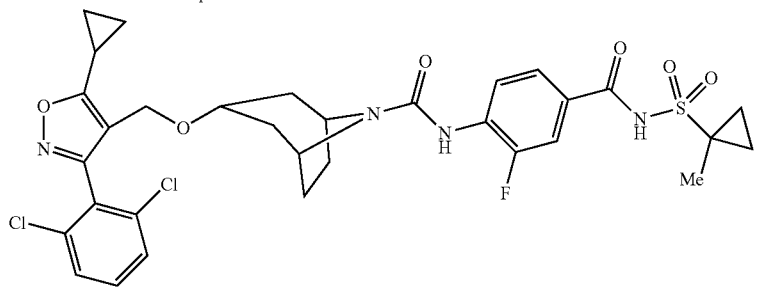
Example 693
To a solution of Example 692 (28.7 mg, 0.05 mmol) in CH₂Cl₂ (1 mL) was added sulfonamide (9), DMAP and EDCI. The reaction was stirred at room temperature for 12 hours. The reaction was then directly concentrated in vacuo. Purification of the residue on silica gel column with 0-100% acetone/hexanes provided Example 693 (28.9 mg) as a white solid. LC/MS observed [M+H]⁺: 691.16.
Example 694

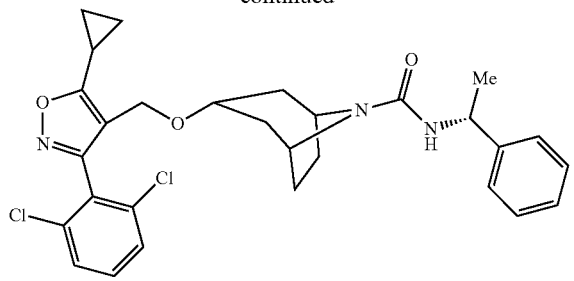

Example 694

To a solution of (R)-1-phenylethan-1-amine (10) (282 mg, 2.33 mmol) in DCM (7.8 mL) was added N,N-diisopropylethylamine (0.81 mL, 4.65 mmol) and 4-nitrophenyl chloroformate (11) (516 mg, 2.56 mmol) at 0° C. The reaction was allowed to stir at room temperature for 2 hours, quenched with saturated NH₄Cl aq.solution, and extracted with EtOAc (2×). The combined organic layers were washed by brine and dried over Na₂SO₄, and concentrated in vacuo. Purification of the residue on silica gel column with 0-20% EtOAc/hexanes provided carbamate compound (12) (480 mg) was white solid.

To a microwave reaction vessel was charged carbamate compound (12) (151 mg, 0.526 mmol) and secondary amine compound (1) (69 mg, 0.175 mmol) in acetonitrile (1 mL). The reaction was heated in microwave reactor at 180° C. for 60 min. The crude was concentrated and purified on silica gel column with 0-30% acetone/hexanes twice to afford Example 694 (25 mg) as a white solid. LC/MS observed [M+H]⁺: 540.18.

The compounds in table 5 below were synthesized using the general methods described above.

TABLE 5

| Example | Structure | ESMS: |
|---|---|---|
| 695 | 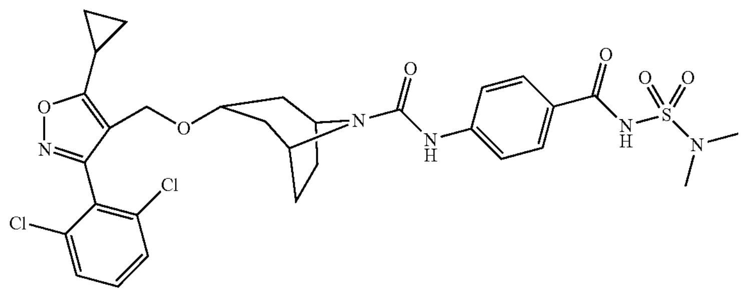 [SMILES: CN(C)S(=O)(=O)NC(=O)c1ccc(NC(=O)N2C3CCC2CC(OCc2c(-c4c(Cl)cccc4Cl)noc2C2CC2)C3)cc1] | M + 1: 660.14 |
| 181 | 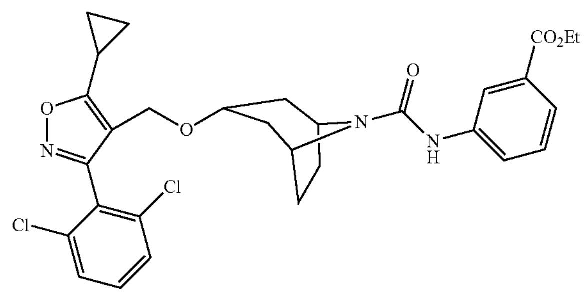 [SMILES: CCOC(=O)c1cccc(NC(=O)N2C3CCC2CC(OCc2c(-c4c(Cl)cccc4Cl)noc2C2CC2)C3)c1] | M + 1: 584.17 |
| 183 | 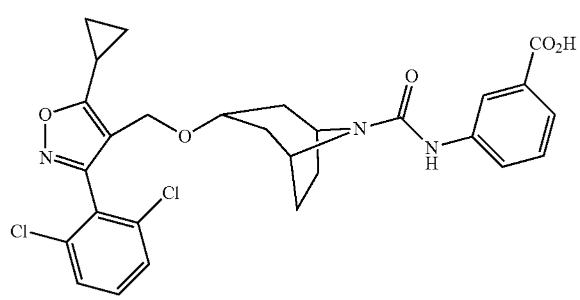 [SMILES: O=C(O)c1cccc(NC(=O)N2C3CCC2CC(OCc2c(-c4c(Cl)cccc4Cl)noc2C2CC2)C3)c1] | M + 1: 556.22 |

TABLE 5-continued

| Example | Structure | ESMS: |
|---------|-----------|-------|
| 219 | 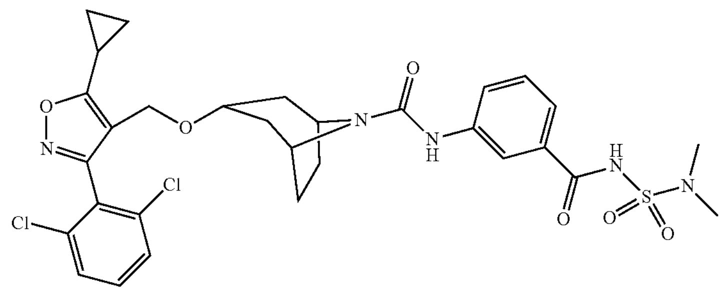 [SMILES: CN(C)S(=O)(=O)NC(=O)c1cccc(NC(=O)N2C3CCC2CC(OCc2c(-c4c(Cl)cccc4Cl)noc2C2CC2)C3)c1] | M + 1: 660.14 |
| 217 | 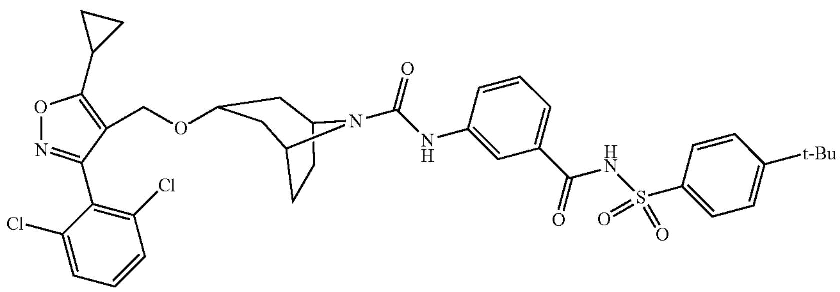 [SMILES: CC(C)(C)c1ccc(S(=O)(=O)NC(=O)c2cccc(NC(=O)N3C4CCC3CC(OCc3c(-c5c(Cl)cccc5Cl)noc3C3CC3)C4)c2)cc1] | M + 1: 749.20 |
| 216 | 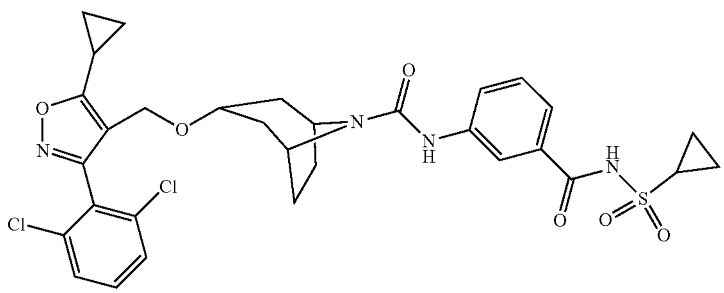 [SMILES: O=C(NS(=O)(=O)C1CC1)c1cccc(NC(=O)N2C3CCC2CC(OCc2c(-c4c(Cl)cccc4Cl)noc2C2CC2)C3)c1] | M + 1: 657.13 |
| 9 | 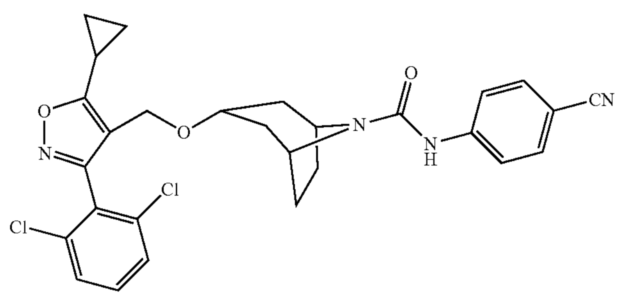 [SMILES: N#Cc1ccc(NC(=O)N2C3CCC2CC(OCc2c(-c4c(Cl)cccc4Cl)noc2C2CC2)C3)cc1] | M + 1: 537.15 |
| 696 | 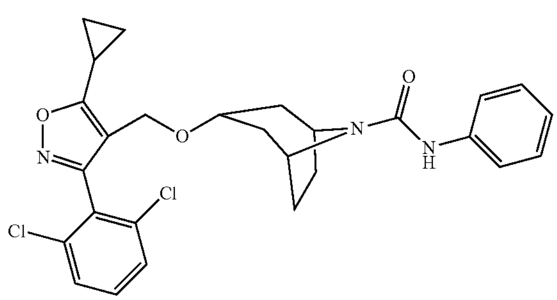 [SMILES: O=C(Nc1ccccc1)N1C2CCC1CC(OCc1c(-c3c(Cl)cccc3Cl)noc1C1CC1)C2] | M + 1: 512.15 |

TABLE 5-continued
| Example | Structure | ESMS: |
|---|---|---|
| 1 | 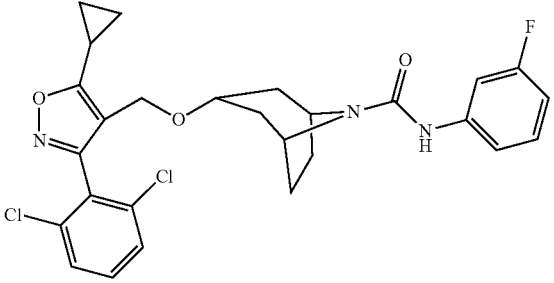 [SMILES: O=C(Nc1cccc(F)c1)N1C2CCC1CC(OCc1c(-c3c(Cl)cccc3Cl)noc1C1CC1)C2] | M + 1: 530.14 |
| 24 | 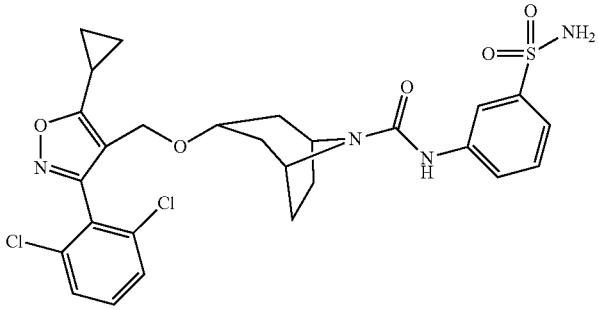 [SMILES: NS(=O)(=O)c1cccc(NC(=O)N2C3CCC2CC(OCc2c(-c4c(Cl)cccc4Cl)noc2C2CC2)C3)c1] | M + 1: 591.13 |
| 697 | 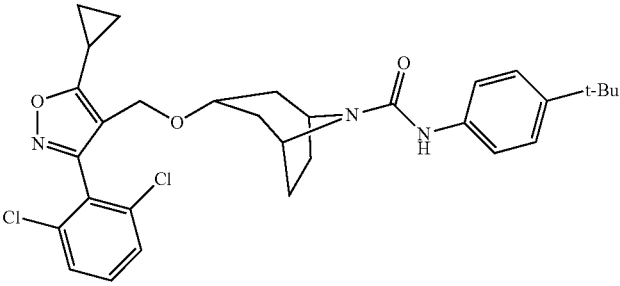 [SMILES: CC(C)(C)c1ccc(NC(=O)N2C3CCC2CC(OCc2c(-c4c(Cl)cccc4Cl)noc2C2CC2)C3)cc1] | M + 1: 568.21 |
| 698 | 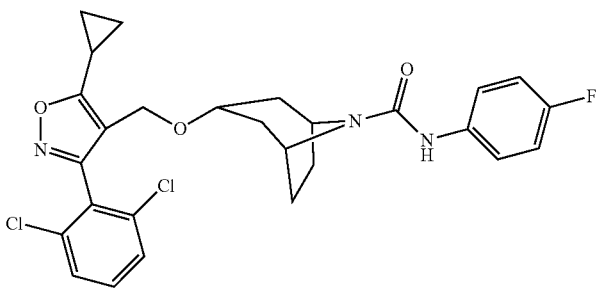 [SMILES: O=C(Nc1ccc(F)cc1)N1C2CCC1CC(OCc1c(-c3c(Cl)cccc3Cl)noc1C1CC1)C2] | M + 1: 530.14 |
| 8 | 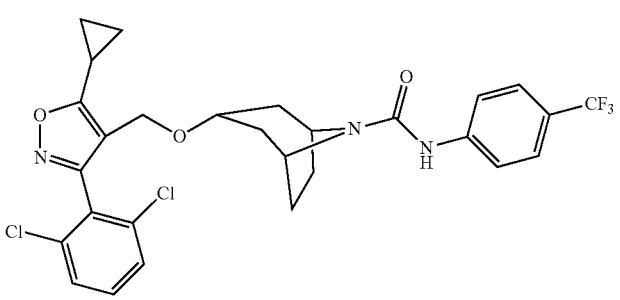 [SMILES: O=C(Nc1ccc(C(F)(F)F)cc1)N1C2CCC1CC(OCc1c(-c3c(Cl)cccc3Cl)noc1C1CC1)C2] | M + 1: 580.14 |

TABLE 5-continued
| Example | Structure | ESMS: |
|---|---|---|
| 19 | 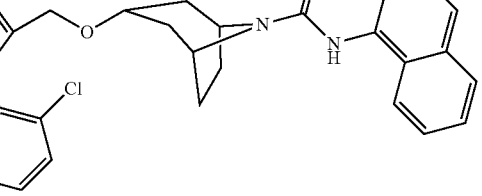 | M + 1: 562.17 |
| 6 | 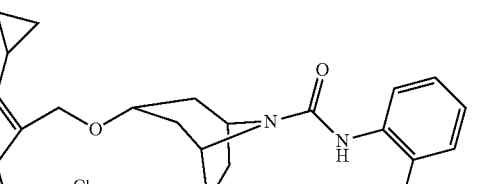 | M + 1: 580.14 |
| 10 | 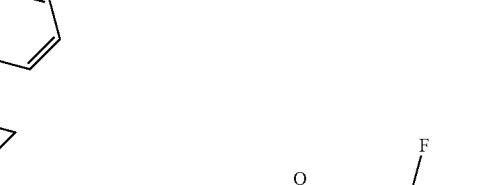 | M + 1: 566.12 |
| 3 | 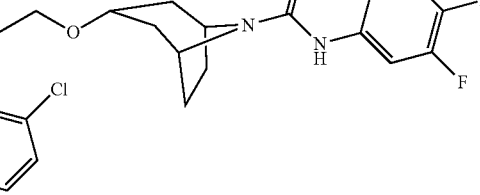 | M + 1: 537.15 |
| 15 | 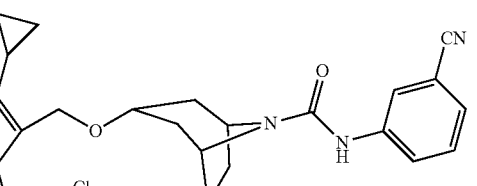 | M + 1: 513.15 |

TABLE 5-continued
| Example | Structure | ESMS: |
|---|---|---|
| 13 | 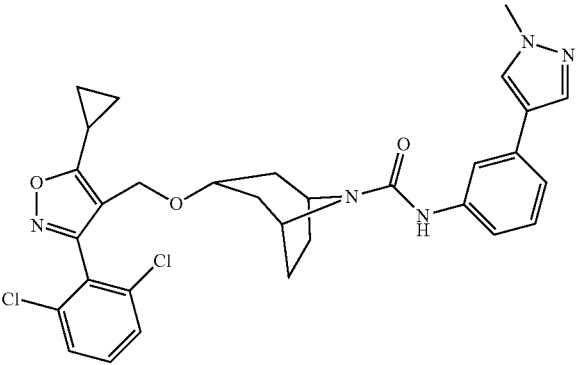 [SMILES: Cn1cc(-c2cccc(NC(=O)N3C4CCC3CC(OCc3c(-c5c(Cl)cccc5Cl)noc3C3CC3)C4)c2)cn1] | M + 1: 592.19 |
| 7 | 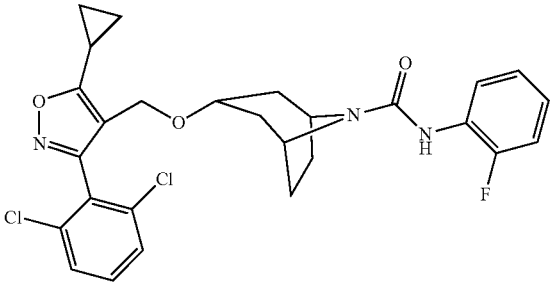 [SMILES: O=C(Nc1ccccc1F)N1C2CCC1CC(OCc1c(-c3c(Cl)cccc3Cl)noc1C1CC1)C2] | M + 1: 530.14 |
| 699 | 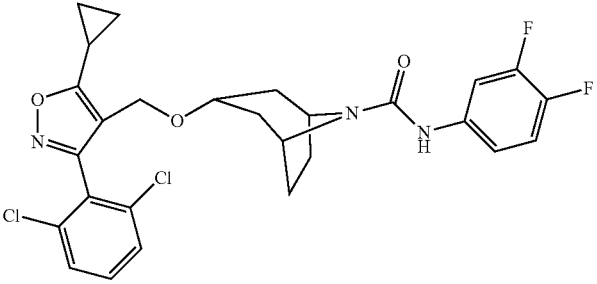 [SMILES: O=C(Nc1ccc(F)c(F)c1)N1C2CCC1CC(OCc1c(-c3c(Cl)cccc3Cl)noc1C1CC1)C2] | M + 1: 548.13 |
| 700 | 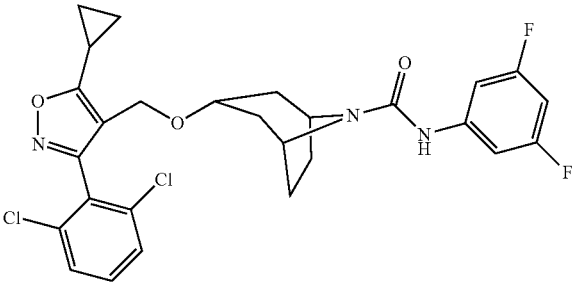 [SMILES: O=C(Nc1cc(F)cc(F)c1)N1C2CCC1CC(OCc1c(-c3c(Cl)cccc3Cl)noc1C1CC1)C2] | M + 1: 548.13 |
| 701 | 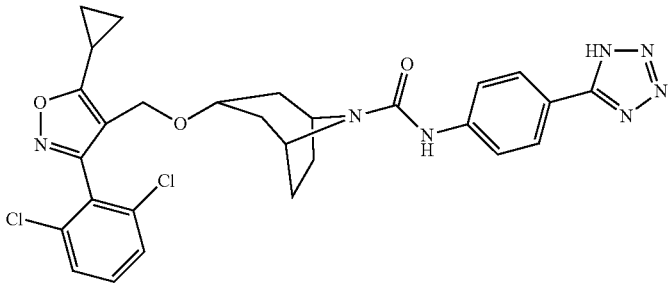 [SMILES: O=C(Nc1ccc(-c2nnn[nH]2)cc1)N1C2CCC1CC(OCc1c(-c3c(Cl)cccc3Cl)noc1C1CC1)C2] | M + 1: 580.17 |

TABLE 5-continued

| Example | Structure | ESMS: |
|---|---|---|
| 702 | 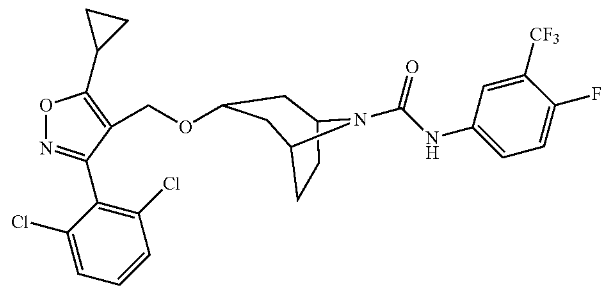 [SMILES: O=C(Nc1ccc(F)c(C(F)(F)F)c1)N1C2CCC1CC(OCc1c(-c3c(Cl)cccc3Cl)noc1C1CC1)C2] | M + 1: 598.13 |
| 20 | 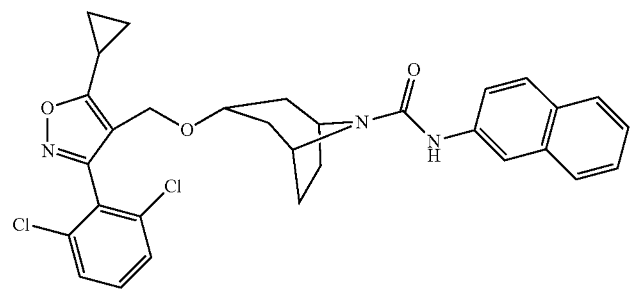 [SMILES: O=C(Nc1ccc2ccccc2c1)N1C2CCC1CC(OCc1c(-c3c(Cl)cccc3Cl)noc1C1CC1)C2] | M + 1: 562.17 |
| 835 | 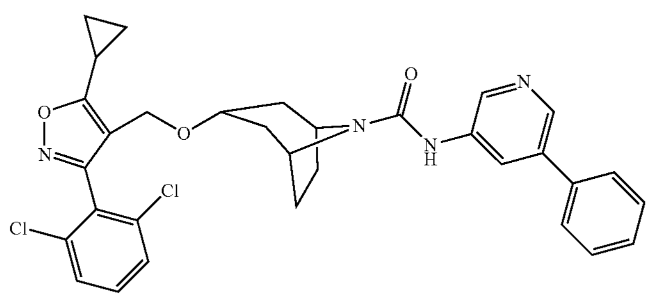 [SMILES: O=C(Nc1cncc(-c2ccccc2)c1)N1C2CCC1CC(OCc1c(-c3c(Cl)cccc3Cl)noc1C1CC1)C2] | M + 1: 589.04 |
| 18 | 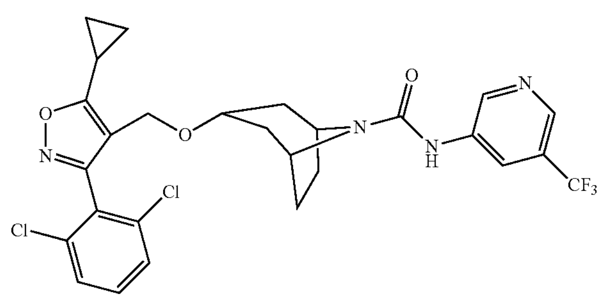 [SMILES: O=C(Nc1cncc(C(F)(F)F)c1)N1C2CCC1CC(OCc1c(-c3c(Cl)cccc3Cl)noc1C1CC1)C2] | M + 1: 581.13 |
| 703 | 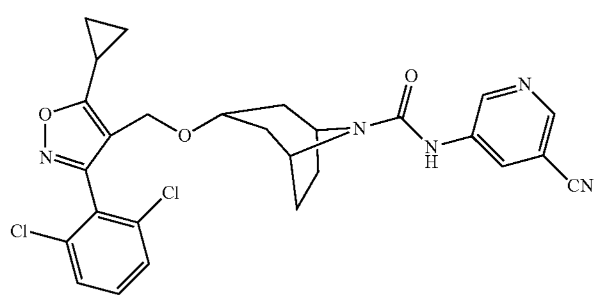 [SMILES: N#Cc1cncc(NC(=O)N2C3CCC2CC(OCc2c(-c4c(Cl)cccc4Cl)noc2C2CC2)C3)c1] | M + 1: 538.14 |

TABLE 5-continued
| Example | Structure | ESMS: |
|---|---|---|
| 11 | 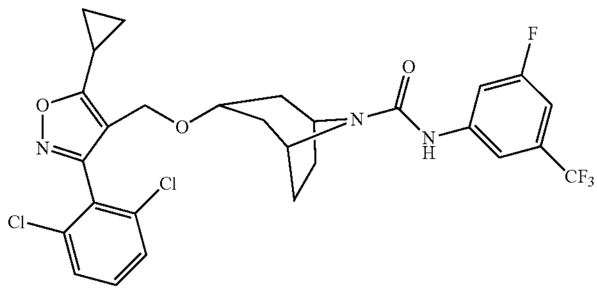 [SMILES: O=C(Nc1cc(F)cc(C(F)(F)F)c1)N1C2CCC1CC(OCc1c(-c3c(Cl)cccc3Cl)noc1C1CC1)C2] | M + 1: 598.13 |
| 704 | 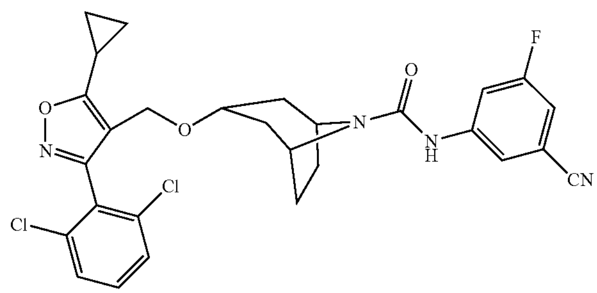 [SMILES: N#Cc1cc(F)cc(NC(=O)N2C3CCC2CC(OCc2c(-c4c(Cl)cccc4Cl)noc2C2CC2)C3)c1] | M + 1: 555.14 |
| 182 | 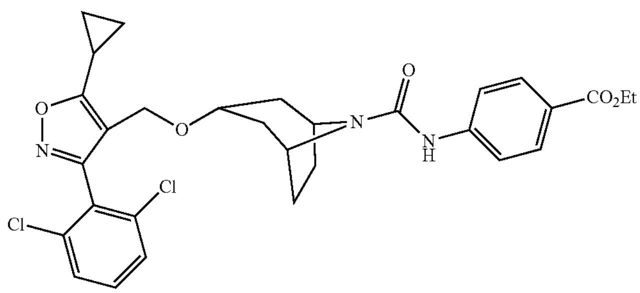 [SMILES: CCOC(=O)c1ccc(NC(=O)N2C3CCC2CC(OCc2c(-c4c(Cl)cccc4Cl)noc2C2CC2)C3)cc1] | M + 1: 584.18 |
| 184 | 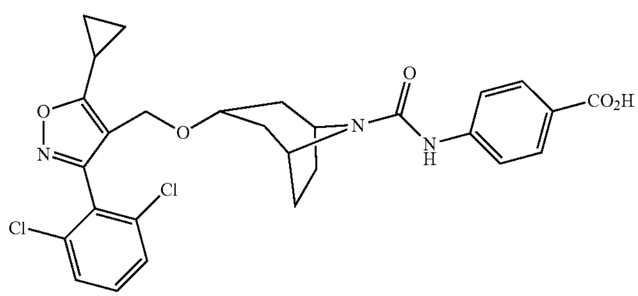 [SMILES: O=C(O)c1ccc(NC(=O)N2C3CCC2CC(OCc2c(-c4c(Cl)cccc4Cl)noc2C2CC2)C3)cc1] | M + 1: 556.21 |
| 16 | 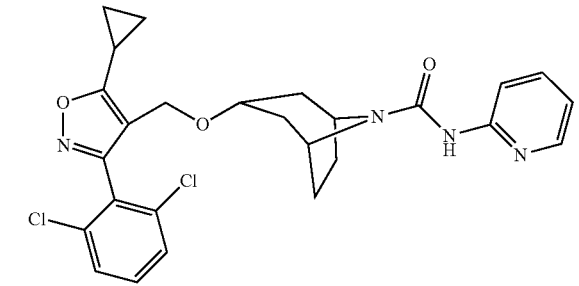 | M + 1: 513.15 |

TABLE 5-continued
| Example | Structure | ESMS: |
|---|---|---|
| 17 | 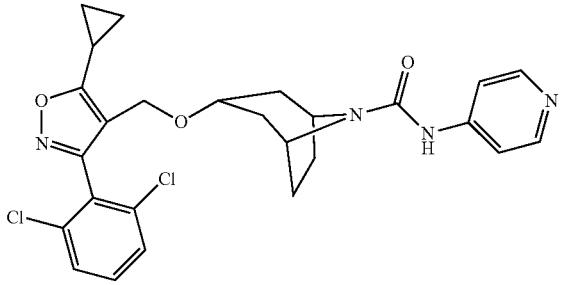 [SMILES: O=C(Nc1ccncc1)N1C2CCC1CC(OCc1c(-c3c(Cl)cccc3Cl)noc1C1CC1)C2] | M + 1: 513.15 |
| 21 | 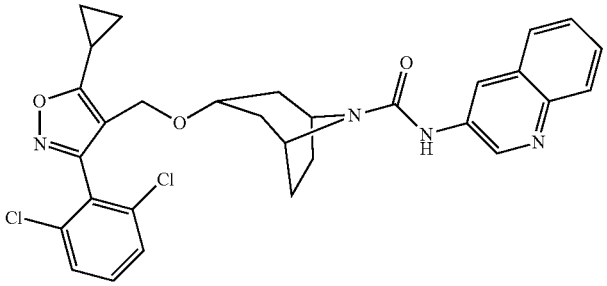 [SMILES: O=C(Nc1cnc2ccccc2c1)N1C2CCC1CC(OCc1c(-c3c(Cl)cccc3Cl)noc1C1CC1)C2] | M + 1: 563.16 |
| 14 | 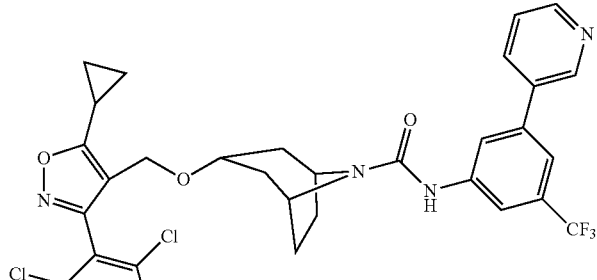 | M + 1: 657.17 |
| 30 | 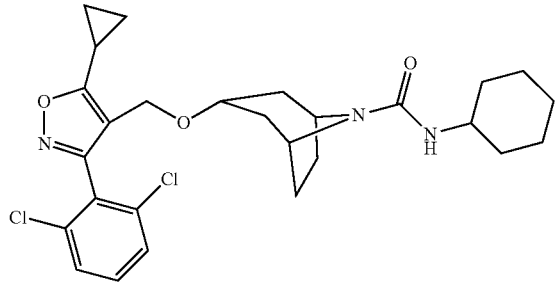 [SMILES: O=C(NC1CCCCC1)N1C2CCC1CC(OCc1c(-c3c(Cl)cccc3Cl)noc1C1CC1)C2] | M + 1: 518.20 |
| 186 | 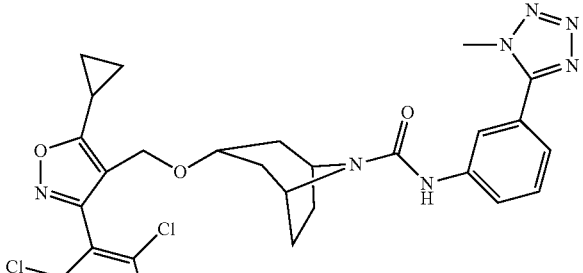 | M + 1: 594.18 |

TABLE 5-continued
| Example | Structure | ESMS: |
|---|---|---|
| 187 | 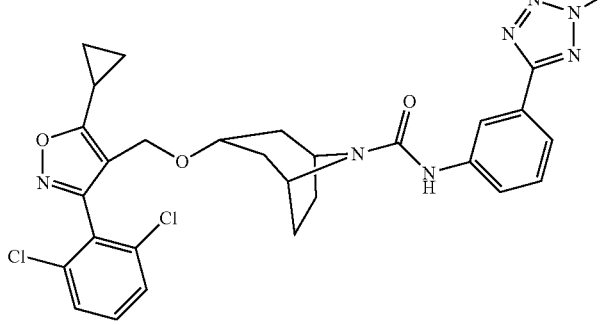 | M + 1: 594.18 |
| 705 | 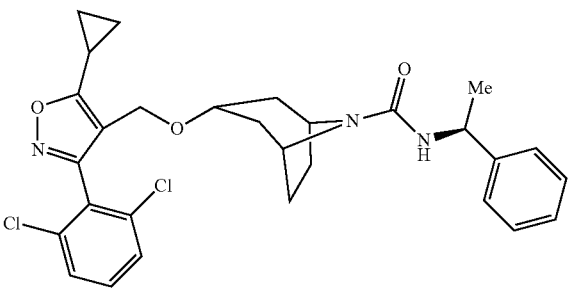 [SMILES: C[C@H](NC(=O)N1C2CCC1CC(OCc1c(-c3c(Cl)cccc3Cl)noc1C1CC1)C2)c1ccccc1] | M + 1: 540.18 |
| 706 | 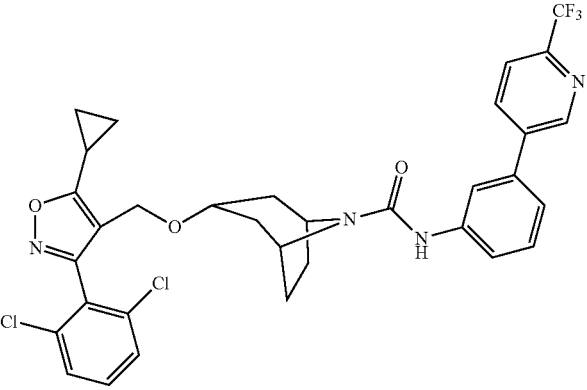 [SMILES: O=C(Nc1cccc(-c2ccc(C(F)(F)F)nc2)c1)N1C2CCC1CC(OCc1c(-c3c(Cl)cccc3Cl)noc1C1CC1)C2] | M + 1: 657.18 |
| 707 | 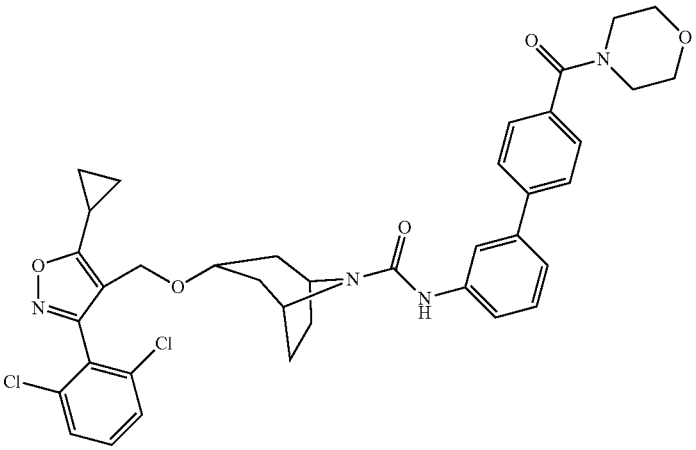 [SMILES: O=C(c1ccc(-c2cccc(NC(=O)N3C4CCC3CC(OCc3c(-c5c(Cl)cccc5Cl)noc3C3CC3)C4)c2)cc1)N1CCOCC1] | M + 1: 701.24 |

TABLE 5-continued

| Example | Structure | ESMS: |
|---|---|---|
| 708 | 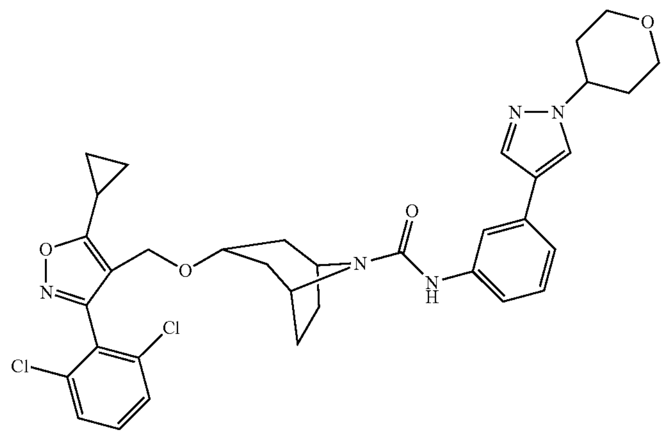 [SMILES: O=C(Nc1cccc(-c2cnn(C3CCOCC3)c2)c1)N1C2CCC1CC(OCc1c(-c3c(Cl)cccc3Cl)noc1C1CC1)C2] | M + 1: 662.24 |
| 194 | 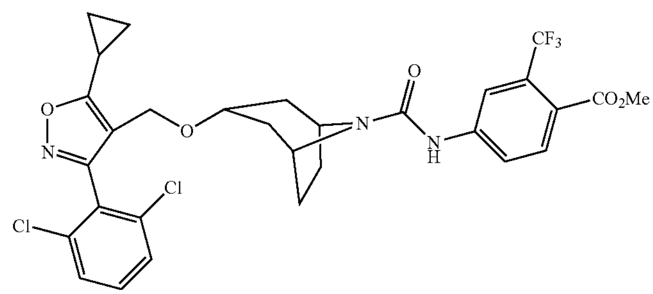 [SMILES: COC(=O)c1ccc(NC(=O)N2C3CCC2CC(OCc2c(-c4c(Cl)cccc4Cl)noc2C2CC2)C3)cc1C(F)(F)F] | M + 1: 638.15 |
| 195 | 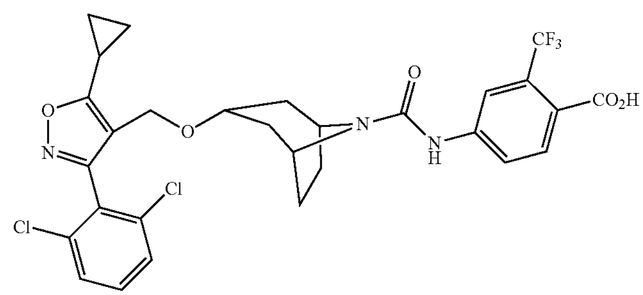 [SMILES: O=C(O)c1ccc(NC(=O)N2C3CCC2CC(OCc2c(-c4c(Cl)cccc4Cl)noc2C2CC2)C3)cc1C(F)(F)F] | M + 1: 624.14 |
| 196 | 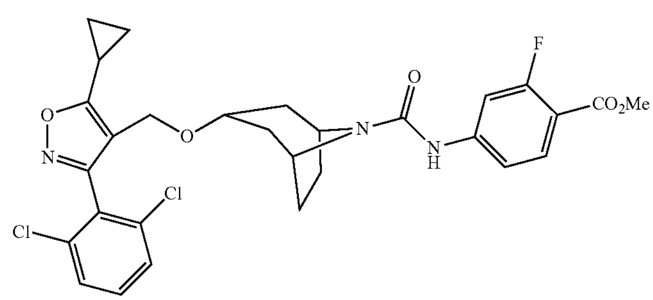 [SMILES: COC(=O)c1ccc(NC(=O)N2C3CCC2CC(OCc2c(-c4c(Cl)cccc4Cl)noc2C2CC2)C3)cc1F] | M + 1: 588.15 |
| 198 | 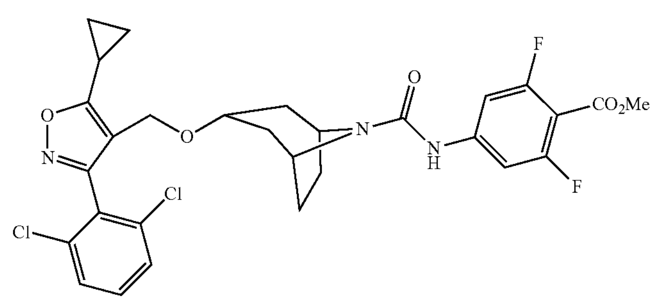 [SMILES: COC(=O)c1c(F)cc(NC(=O)N2C3CCC2CC(OCc2c(-c4c(Cl)cccc4Cl)noc2C2CC2)C3)cc1F] | M + 1: 606.14 |

TABLE 5-continued

| Example | Structure | ESMS: |
|---------|-----------|-------|
| 709 | 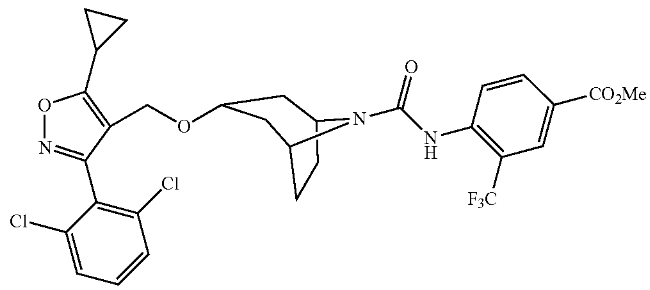 [SMILES: COC(=O)c1ccc(NC(=O)N2C3CCC2CC(OCc2c(-c4c(Cl)cccc4Cl)noc2C2CC2)C3)c(C(F)(F)F)c1] | M + 1: 638.15 |
| 212 | 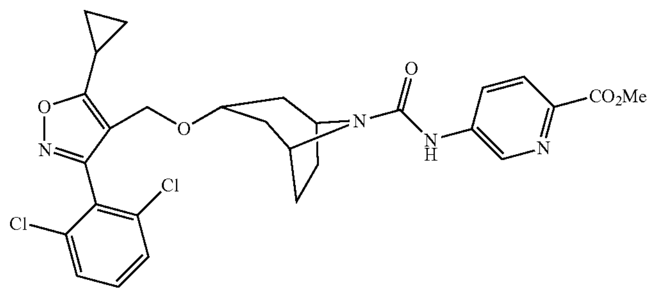 [SMILES: COC(=O)c1ccc(NC(=O)N2C3CCC2CC(OCc2c(-c4c(Cl)cccc4Cl)noc2C2CC2)C3)cn1] | M + 1: 571.15 |
| 197 | 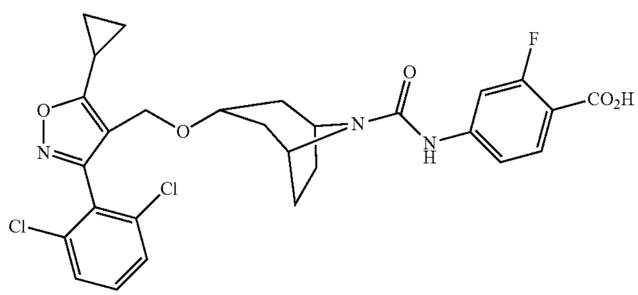 [SMILES: O=C(O)c1ccc(NC(=O)N2C3CCC2CC(OCc2c(-c4c(Cl)cccc4Cl)noc2C2CC2)C3)cc1F] | M + 1: 574.13 |
| 199 | 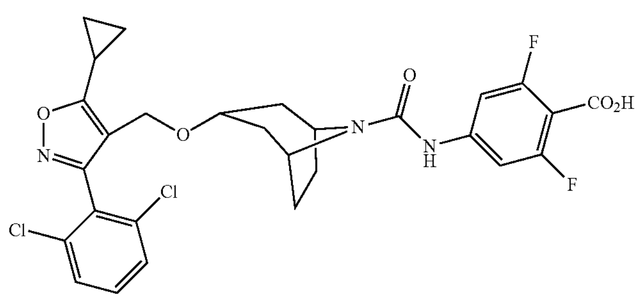 [SMILES: O=C(O)c1c(F)cc(NC(=O)N2C3CCC2CC(OCc2c(-c4c(Cl)cccc4Cl)noc2C2CC2)C3)cc1F] | M + 1: 592.13 |
| 710 | 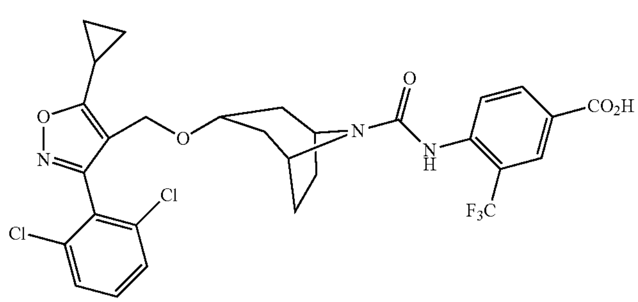 [SMILES: O=C(O)c1ccc(NC(=O)N2C3CCC2CC(OCc2c(-c4c(Cl)cccc4Cl)noc2C2CC2)C3)c(C(F)(F)F)c1] | M + 1: 624.14 |

TABLE 5-continued

| Example | Structure | ESMS: |
|---|---|---|
| 213 | 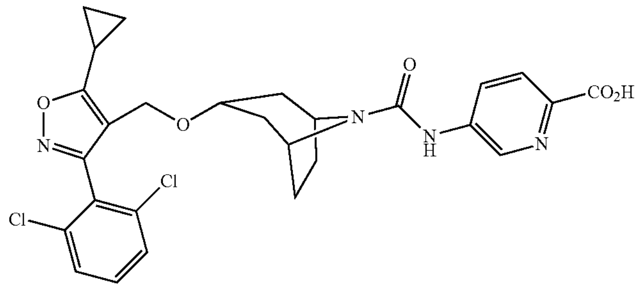 [SMILES: O=C(O)c1ccc(NC(=O)N2C3CCC2CC(OCc2c(-c4c(Cl)cccc4Cl)noc2C2CC2)C3)cn1] | M + 1: 557.14 |
| 189 | 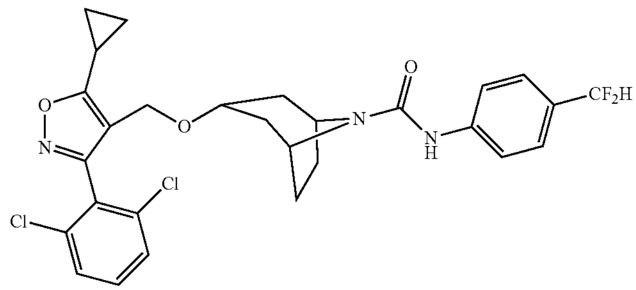 [SMILES: O=C(Nc1ccc(C(F)F)cc1)N1C2CCC1CC(OCc1c(-c3c(Cl)cccc3Cl)noc1C1CC1)C2] | M + 1: 562.15 |
| 215 | 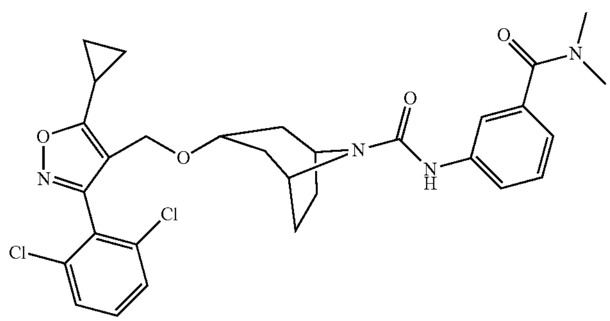 [SMILES: CN(C)C(=O)c1cccc(NC(=O)N2C3CCC2CC(OCc2c(-c4c(Cl)cccc4Cl)noc2C2CC2)C3)c1] | M + 1: 583.19 |
| 214 | 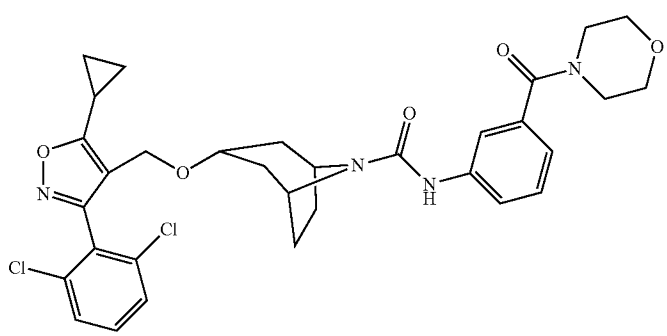 [SMILES: O=C(c1cccc(NC(=O)N2C3CCC2CC(OCc2c(-c4c(Cl)cccc4Cl)noc2C2CC2)C3)c1)N1CCOCC1] | M + 1: 625.21 |
| 25 | 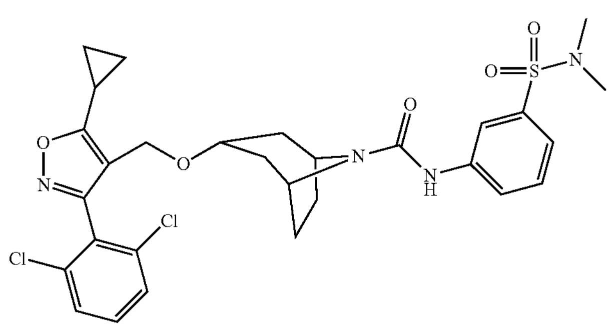 [SMILES: CN(C)S(=O)(=O)c1cccc(NC(=O)N2C3CCC2CC(OCc2c(-c4c(Cl)cccc4Cl)noc2C2CC2)C3)c1] | M + 1: 619.16 |

TABLE 5-continued
| Example | Structure | ESMS: |
|---|---|---|
| 711 | 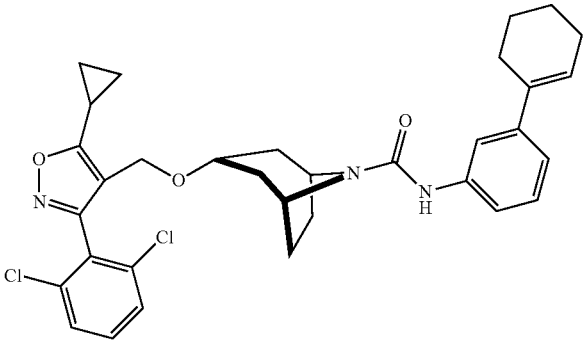 | M + 1: 592.22 |
| 712 | 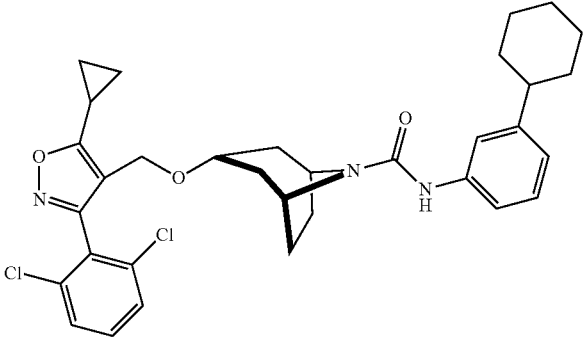 | M + 1: 594.23 |
| 713 | 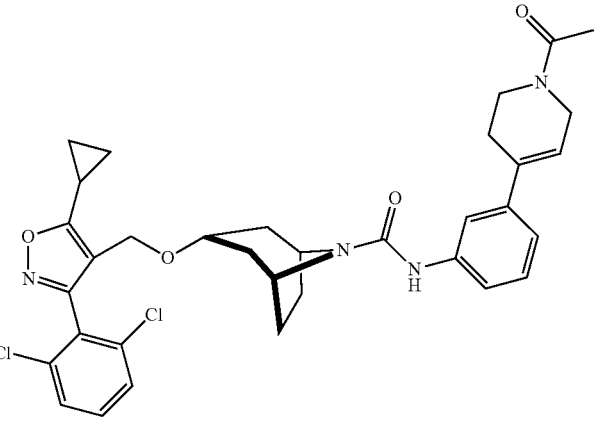 | M + 1: 635.23 |
| 714 | 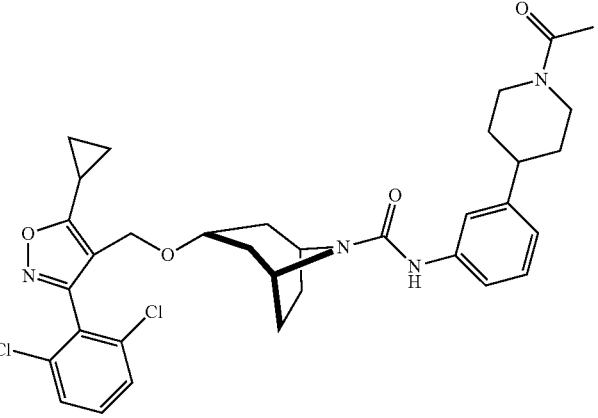 | M + 1: 637.24 |

TABLE 5-continued

| Example | Structure | ESMS: |
|---|---|---|
| 715 | 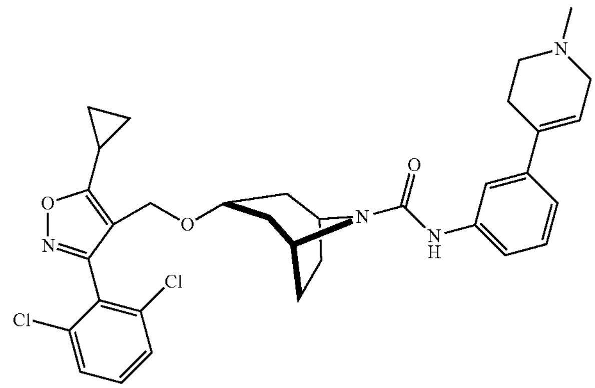 | M + 1: 607.23 |
| 5 | 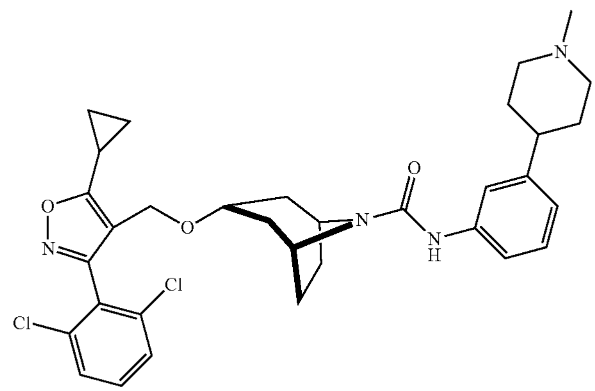 | M + 1: 609.25 |
| 716 | 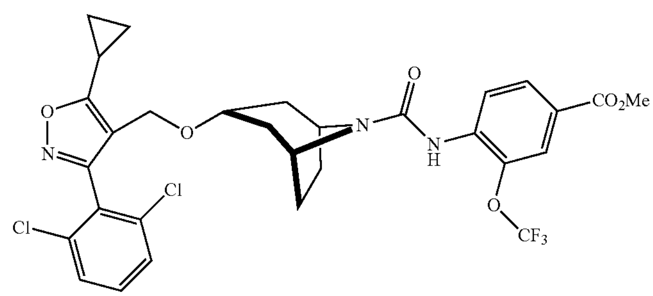 | M + 1: 654.14 |
| 717 | 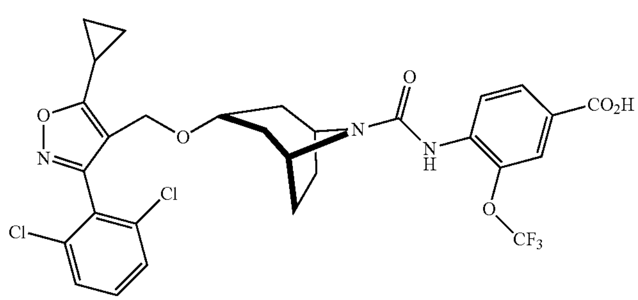 | M + 1: 640.12 |

TABLE 5-continued
| Example | Structure | ESMS: |
|---|---|---|
| 718 | 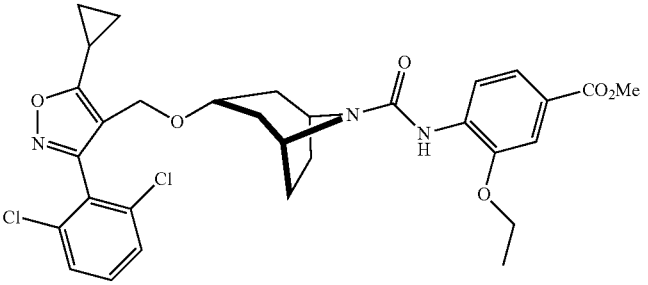 | M + 1: 614.18 |
| 719 | 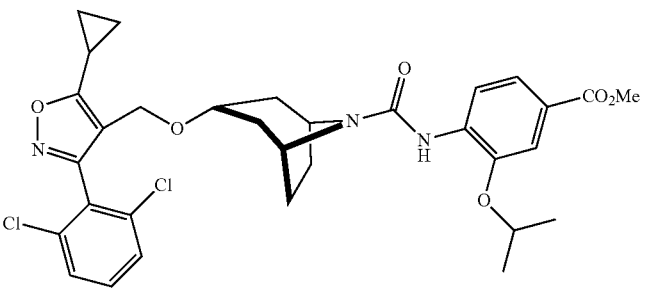 | M + 1: 628.20 |
| 720 | 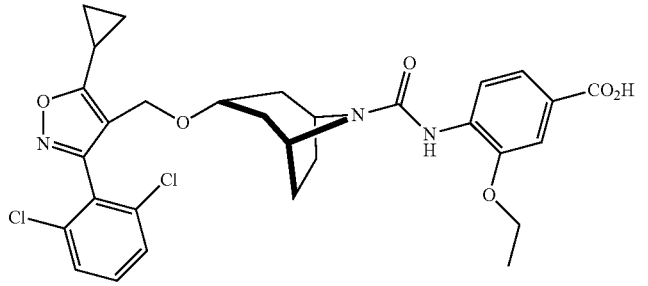 | M + 1: 600.16 |
| 721 | 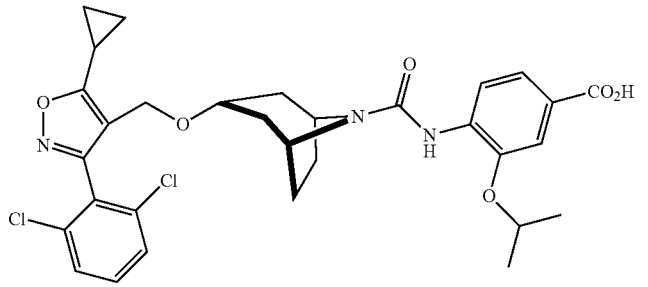 | M + 1: 614.18 |
| 722 | 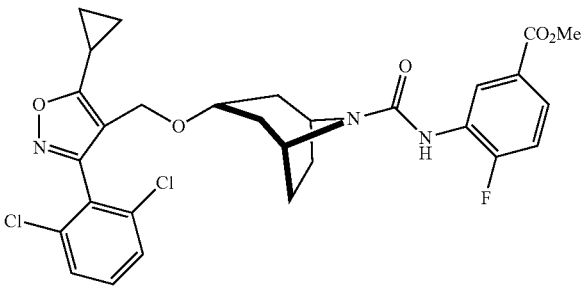 | M + 1: 588.15 |

TABLE 5-continued

| Example | Structure | ESMS: |
|---------|-----------|-------|
| 723 | 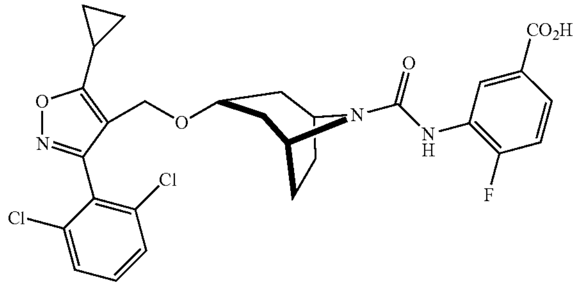 | M + 1: 574.13 |
| 724 | 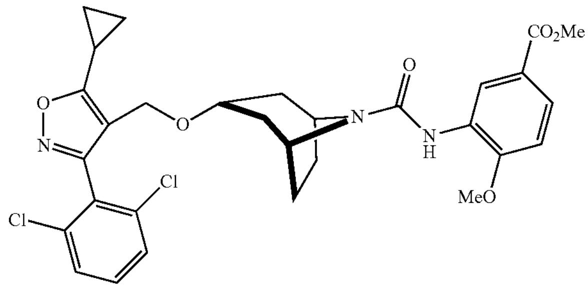 | M + 1: 600.17 |
| 725 | 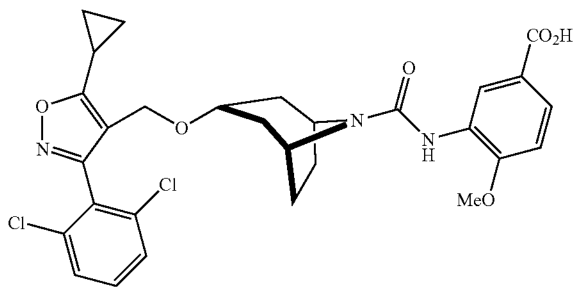 | M + 1: 586.16 |
| 200 | 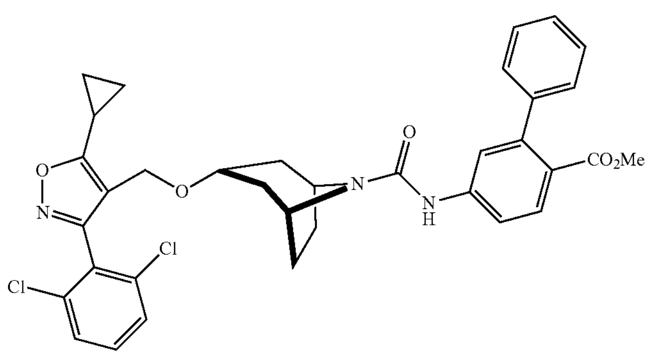 | M + 1: 646.19 |
| 201 | 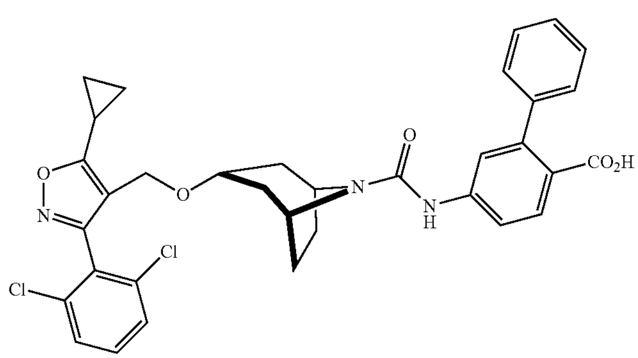 | M − 1: 630.16 |

TABLE 5-continued
| Example | Structure | ESMS: |
|---------|-----------|-------|
| 726 | 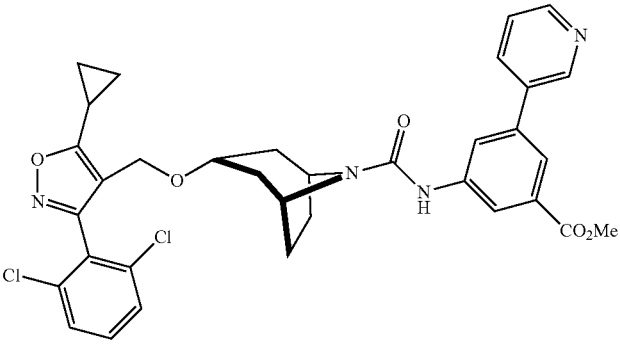 | M + 1: 647.19 |
| 727 | 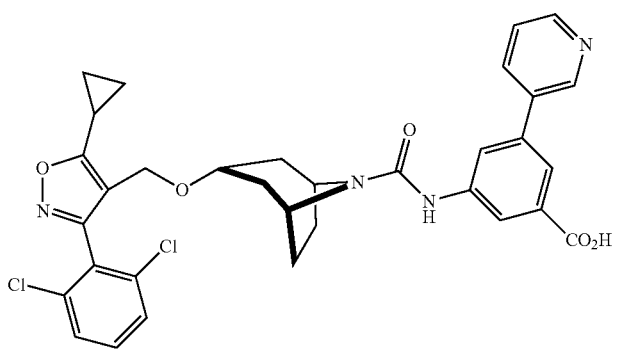 | M + 1: 633.19 |
| 728 | 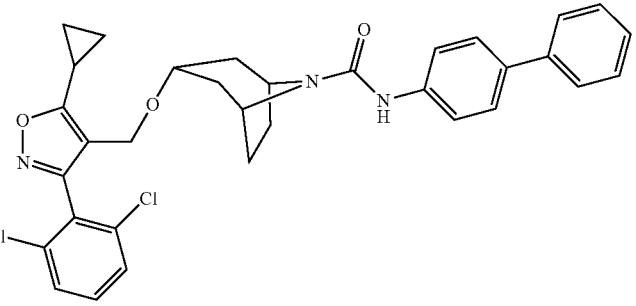 | M + 1: 588.18 |
| 729 | 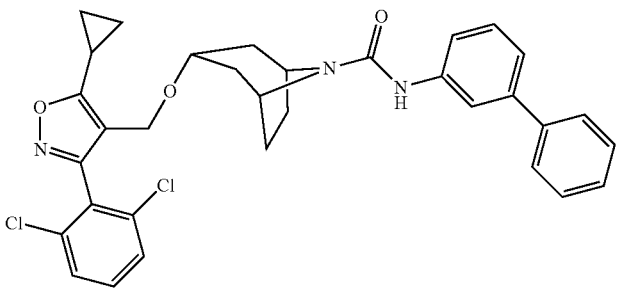 [SMILES: O=C(Nc1cccc(-c2ccccc2)c1)N1C2CCC1CC(OCc1c(-c3c(Cl)cccc3Cl)noc1C1CC1)C2] | M + 1: 588.18 |

TABLE 5-continued
| Example | Structure | ESMS: |
|---|---|---|
| 22 | 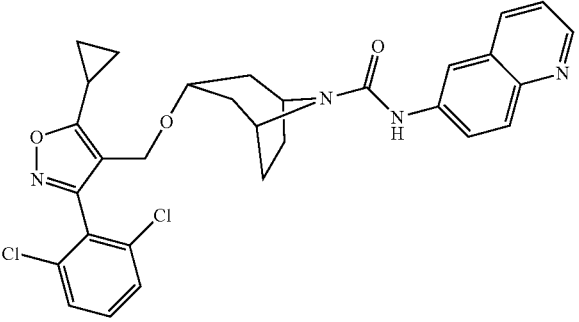 [SMILES: O=C(Nc1ccc2ncccc2c1)N1C2CCC1CC(OCc1c(-c3c(Cl)cccc3Cl)noc1C1CC1)C2] | M + 1: 563.16 |
| 4 | 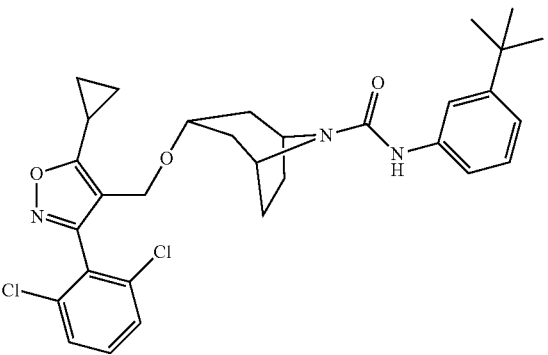 [SMILES: CC(C)(C)c1cccc(NC(=O)N2C3CCC2CC(OCc2c(-c4c(Cl)cccc4Cl)noc2C2CC2)C3)c1] | M + 1: 568.21 |
| 23 | 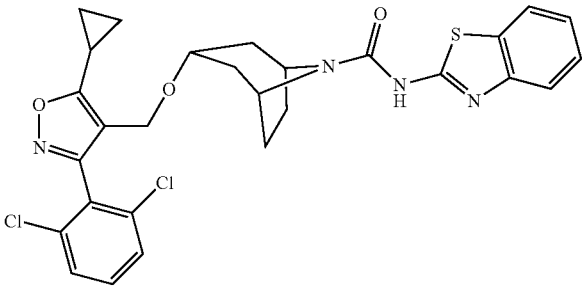 [SMILES: O=C(Nc1nc2ccccc2s1)N1C2CCC1CC(OCc1c(-c3c(Cl)cccc3Cl)noc1C1CC1)C2] | M + 1: 569.12 |
| 730 | 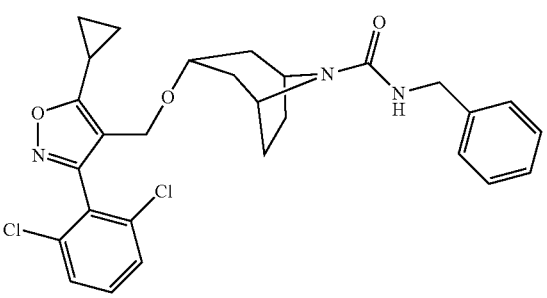 [SMILES: O=C(NCc1ccccc1)N1C2CCC1CC(OCc1c(-c3c(Cl)cccc3Cl)noc1C1CC1)C2] | M + 1: 526.16 |
| 190 | 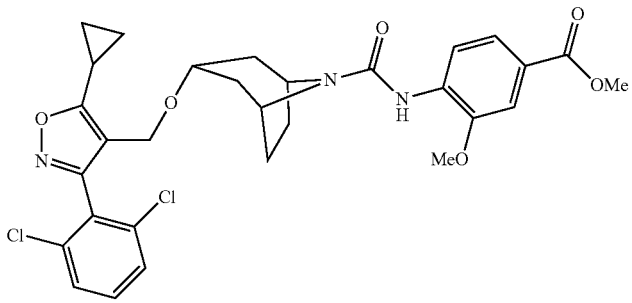 [SMILES: COC(=O)c1ccc(NC(=O)N2C3CCC2CC(OCc2c(-c4c(Cl)cccc4Cl)noc2C2CC2)C3)c(OC)c1] | M + 1: 600.17 |

TABLE 5-continued

| Example | Structure | ESMS: |
|---|---|---|
| 192 | 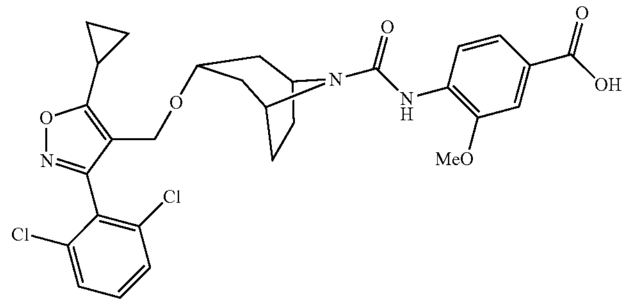 [SMILES: COc1cc(C(=O)O)ccc1NC(=O)N1C2CCC1CC(OCc1c(-c3c(Cl)cccc3Cl)noc1C1CC1)C2] | M + 1: 586.15 |
| 731 | 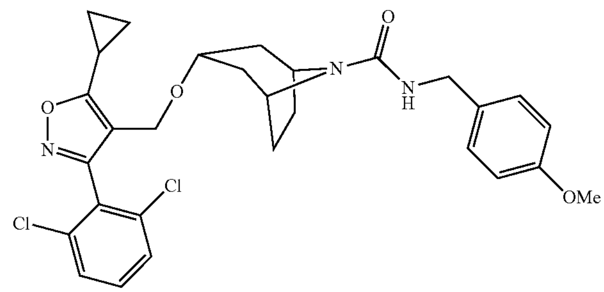 [SMILES: COc1ccc(CNC(=O)N2C3CCC2CC(OCc2c(-c4c(Cl)cccc4Cl)noc2C2CC2)C3)cc1] | M + 1: 556.18 |
| 732 | 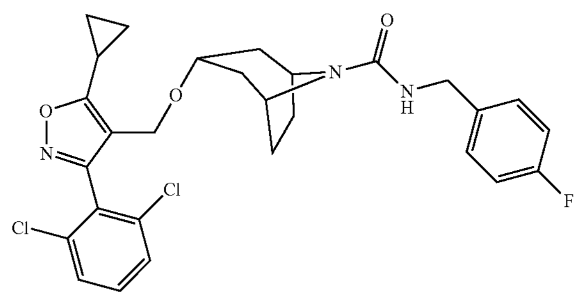 [SMILES: O=C(NCc1ccc(F)cc1)N1C2CCC1CC(OCc1c(-c3c(Cl)cccc3Cl)noc1C1CC1)C2] | M + 1: 546.15 |
| 733 | 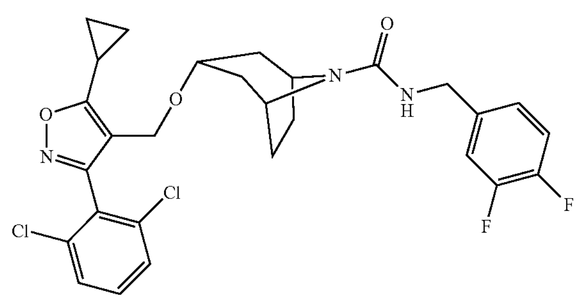 [SMILES: O=C(NCc1ccc(F)c(F)c1)N1C2CCC1CC(OCc1c(-c3c(Cl)cccc3Cl)noc1C1CC1)C2] | M + 1: 562.15 |
| 734 | 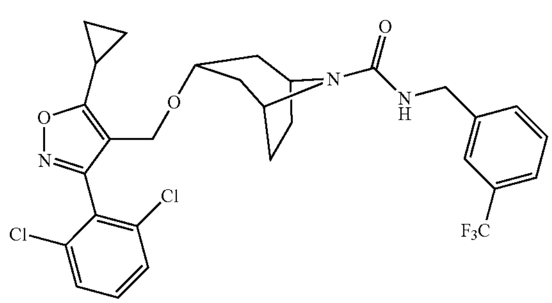 [SMILES: O=C(NCc1cccc(C(F)(F)F)c1)N1C2CCC1CC(OCc1c(-c3c(Cl)cccc3Cl)noc1C1CC1)C2] | M + 1: 594.16 |

TABLE 5-continued

| Example | Structure | ESMS: |
|---------|-----------|-------|
| 836 | 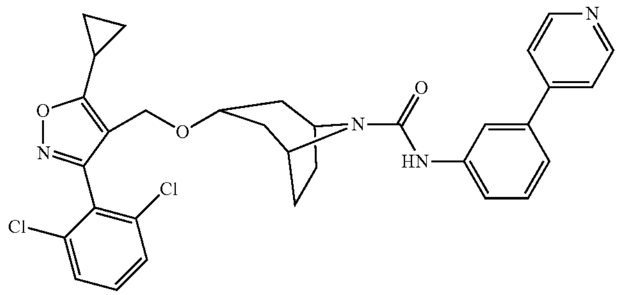 [SMILES: O=C(Nc1cccc(-c2ccncc2)c1)N1C2CCC1CC(OCc1c(-c3c(Cl)cccc3Cl)noc1C1CC1)C2] | M + 1: 589.18 |
| 735 | 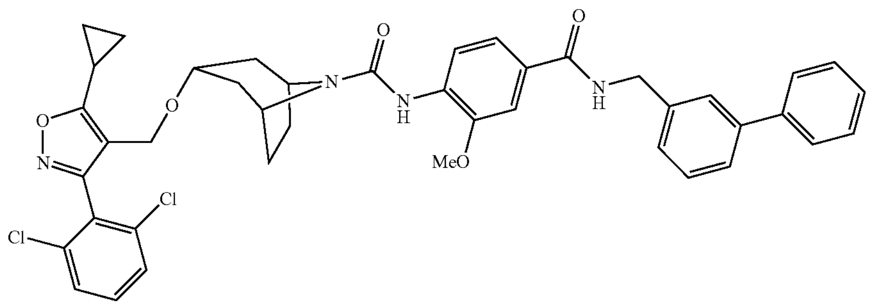 [SMILES: COc1cc(C(=O)NCc2cccc(-c3ccccc3)c2)ccc1NC(=O)N1C2CCC1CC(OCc1c(-c3c(Cl)cccc3Cl)noc1C1CC1)C2] | M + 1: 602.20 |
| 736 | 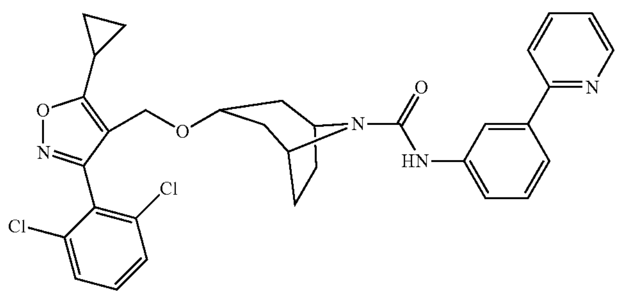 [SMILES: O=C(Nc1cccc(-c2ccccn2)c1)N1C2CCC1CC(OCc1c(-c3c(Cl)cccc3Cl)noc1C1CC1)C2] | M + 1: 589.19 |
| 737 | 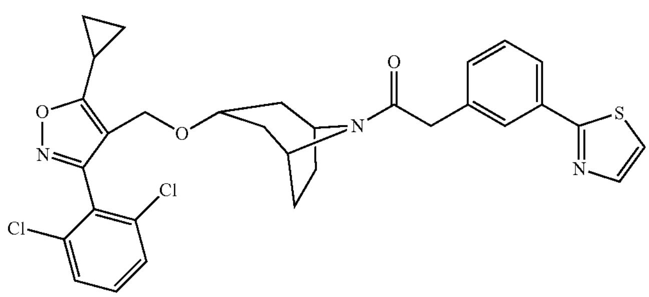 [SMILES: O=C(Cc1cccc(-c2nccs2)c1)N1C2CCC1CC(OCc1c(-c3c(Cl)cccc3Cl)noc1C1CC1)C2] | M + 1: 595.14 |
| 738 | 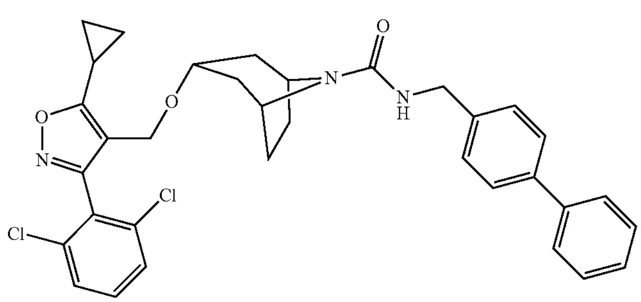 [SMILES: O=C(NCc1ccc(-c2ccccc2)cc1)N1C2CCC1CC(OCc1c(-c3c(Cl)cccc3Cl)noc1C1CC1)C2] | M + 1: 602.20 |

TABLE 5-continued

| Example | Structure | ESMS: |
|---------|-----------|-------|
| 739 | 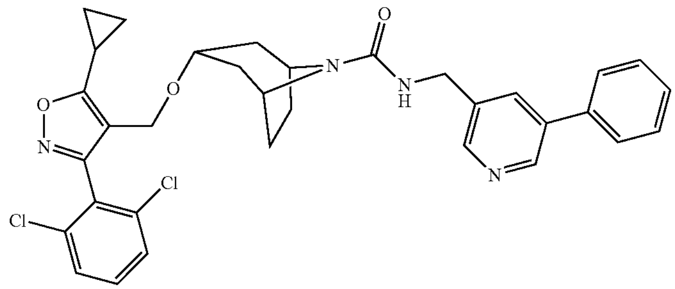 [SMILES: O=C(NCc1cncc(-c2ccccc2)c1)N1C2CCC1CC(OCc1c(-c3c(Cl)cccc3Cl)noc1C1CC1)C2] | M + 1: 603.20 |
| 740 | 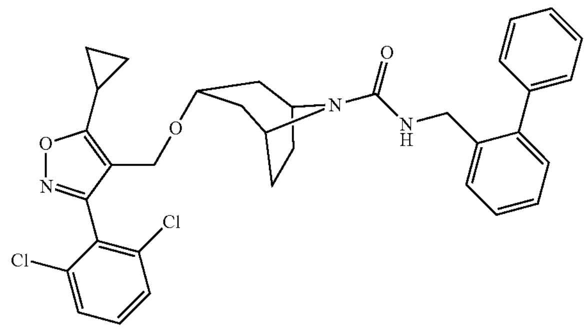 [SMILES: O=C(NCc1ccccc1-c1ccccc1)N1C2CCC1CC(OCc1c(-c3c(Cl)cccc3Cl)noc1C1CC1)C2] | M + 1: 602.20 |
| 741 | 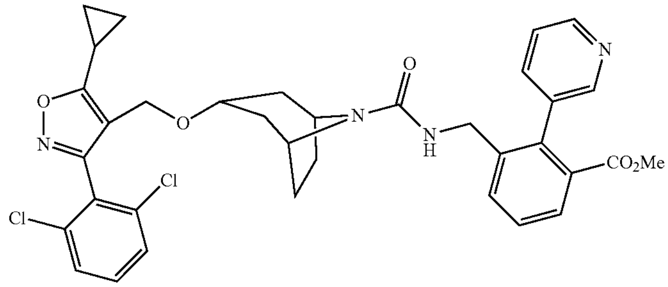 [SMILES: COC(=O)c1cccc(CNC(=O)N2C3CCC2CC(OCc2c(-c4c(Cl)cccc4Cl)noc2C2CC2)C3)c1-c1cccnc1] | M + 1: 647.19 |
| 742 | 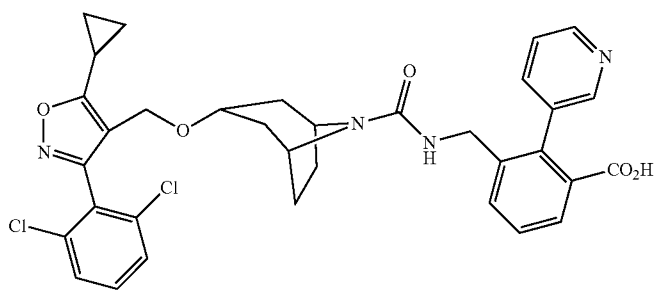 [SMILES: O=C(O)c1cccc(CNC(=O)N2C3CCC2CC(OCc2c(-c4c(Cl)cccc4Cl)noc2C2CC2)C3)c1-c1cccnc1] | M + 1: 633.19 |
| 774 | 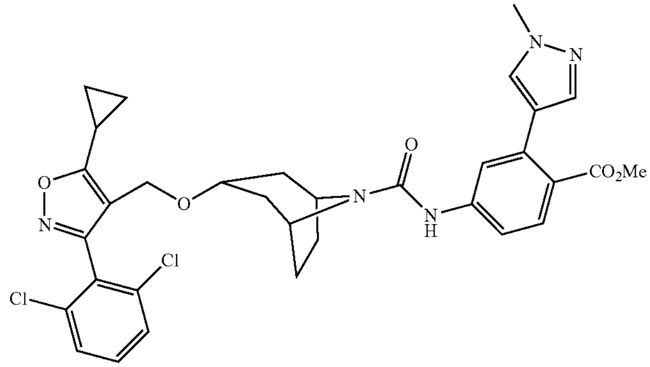 [SMILES: COC(=O)c1ccc(NC(=O)N2C3CCC2CC(OCc2c(-c4c(Cl)cccc4Cl)noc2C2CC2)C3)cc1-c1cnn(C)c1] | M + 1: 650.24 |

TABLE 5-continued

| Example | Structure | ESMS: |
|---|---|---|
| 775 | 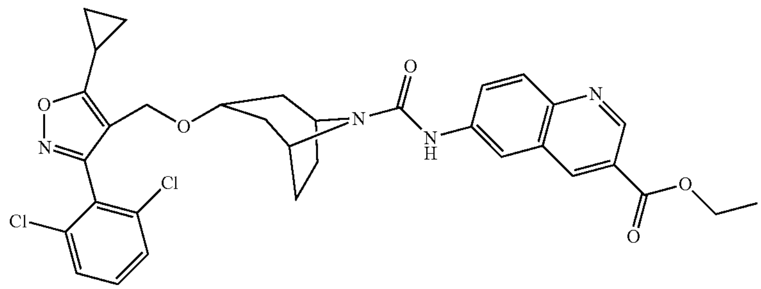 [SMILES: CCOC(=O)c1cnc2ccc(NC(=O)N3C4CCC3CC(OCc3c(-c5c(Cl)cccc5Cl)noc3C3CC3)C4)cc2c1] | M + 1: 635.22 |
| 776 | 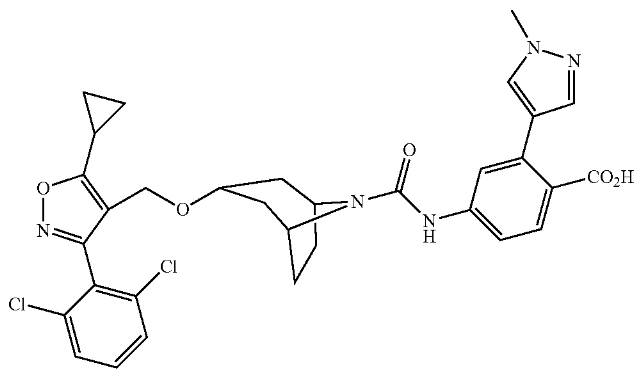 [SMILES: Cn1cc(-c2cc(NC(=O)N3C4CCC3CC(OCc3c(-c5c(Cl)cccc5Cl)noc3C3CC3)C4)ccc2C(=O)O)cn1] | M + 1: 636.18 |
| 211 | 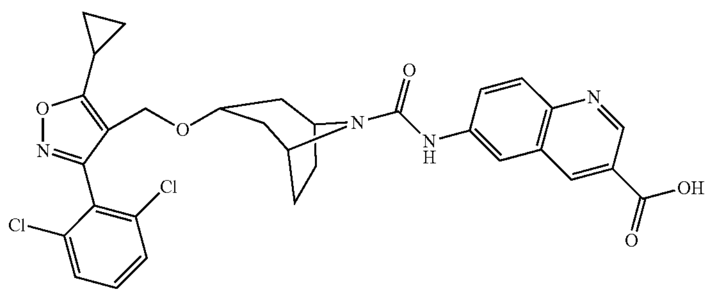 [SMILES: O=C(O)c1cnc2ccc(NC(=O)N3C4CCC3CC(OCc3c(-c5c(Cl)cccc5Cl)noc3C3CC3)C4)cc2c1] | M + 1: 607.15 |
| 777 | 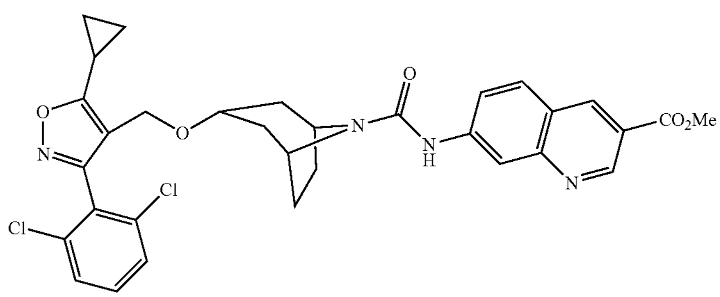 [SMILES: COC(=O)c1cnc2cc(NC(=O)N3C4CCC3CC(OCc3c(-c5c(Cl)cccc5Cl)noc3C3CC3)C4)ccc2c1] | M + 1: 621.17 |
| 778 | 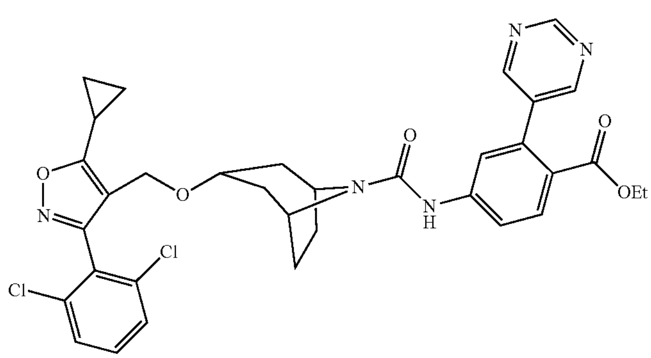 [SMILES: CCOC(=O)c1ccc(NC(=O)N2C3CCC2CC(OCc2c(-c4c(Cl)cccc4Cl)noc2C2CC2)C3)cc1-c1cncnc1] | M + 1: 662.20 |

TABLE 5-continued

| Example | Structure | ESMS: |
|---------|-----------|-------|
| 779 | 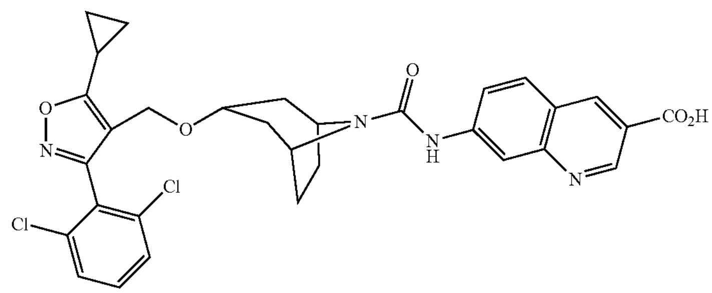 [SMILES: O=C(O)c1cnc2cc(NC(=O)N3C4CCC3CC(OCc3c(-c5c(Cl)cccc5Cl)noc3C3CC3)C4)ccc2c1] | M + 1: 607.15 |
| 780 | 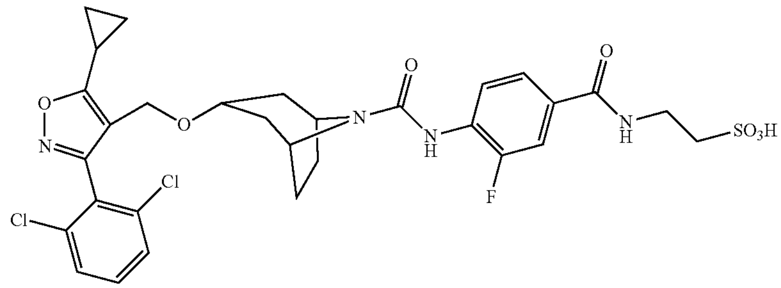 [SMILES: O=C(NCCS(=O)(=O)O)c1ccc(NC(=O)N2C3CCC2CC(OCc2c(-c4c(Cl)cccc4Cl)noc2C2CC2)C3)c(F)c1] | M + 1: 681.14 |
| 781 | 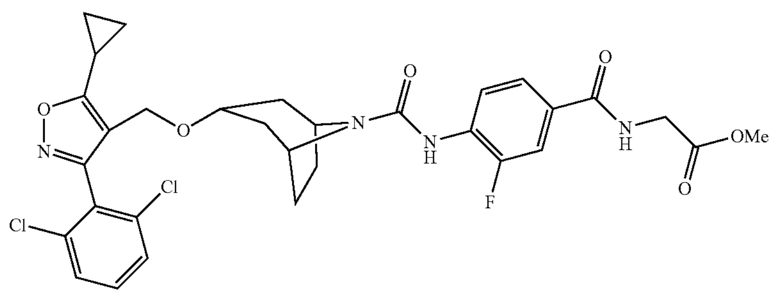 [SMILES: COC(=O)CNC(=O)c1ccc(NC(=O)N2C3CCC2CC(OCc2c(-c4c(Cl)cccc4Cl)noc2C2CC2)C3)c(F)c1] | M + 1: 645.17 |
| 782 | 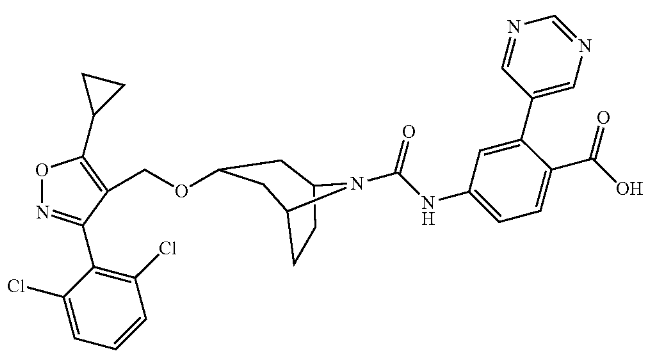 [SMILES: O=C(O)c1ccc(NC(=O)N2C3CCC2CC(OCc2c(-c4c(Cl)cccc4Cl)noc2C2CC2)C3)cc1-c1cncnc1] | M + 1: 634.16 |
| 783 | 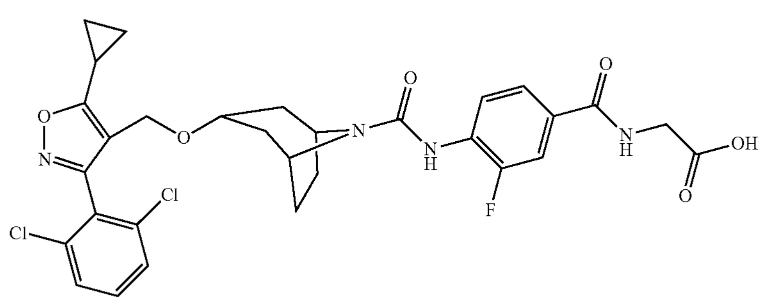 [SMILES: O=C(O)CNC(=O)c1ccc(NC(=O)N2C3CCC2CC(OCc2c(-c4c(Cl)cccc4Cl)noc2C2CC2)C3)c(F)c1] | M + 1: 631.15 |

TABLE 5-continued

| Example | Structure | ESMS: |
|---|---|---|
| 784 | 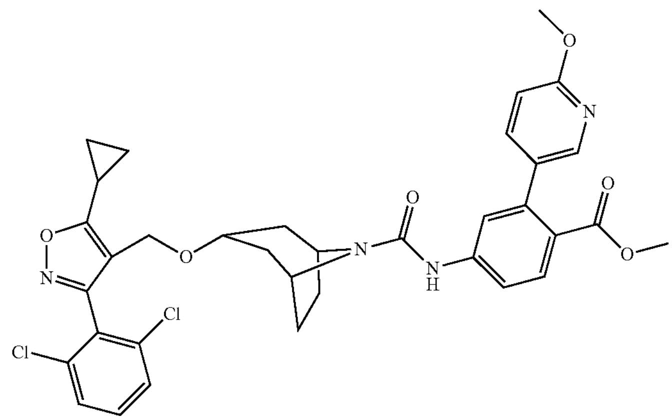 [SMILES: COC(=O)c1ccc(NC(=O)N2C3CCC2CC(OCc2c(-c4c(Cl)cccc4Cl)noc2C2CC2)C3)cc1-c1ccc(OC)nc1] | M + 1: 677.20 |
| 785 | 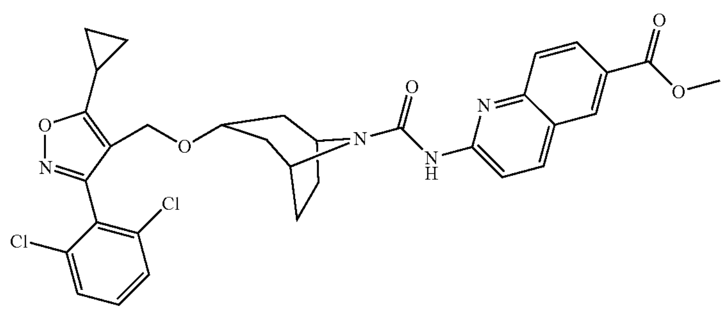 [SMILES: COC(=O)c1ccc2nc(NC(=O)N3C4CCC3CC(OCc3c(-c5c(Cl)cccc5Cl)noc3C3CC3)C4)ccc2c1] | M + 1: 621.17 |
| 786 | 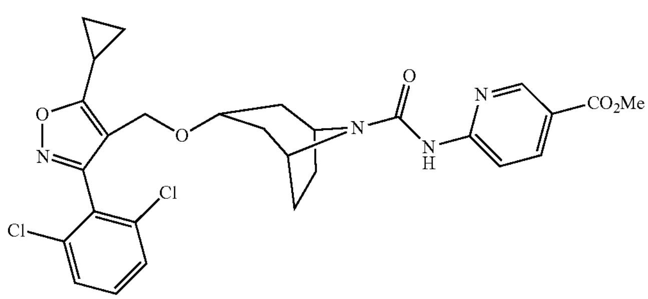 [SMILES: COC(=O)c1ccc(NC(=O)N2C3CCC2CC(OCc2c(-c4c(Cl)cccc4Cl)noc2C2CC2)C3)nc1] | M + 1: 573.15 |
| 787 | 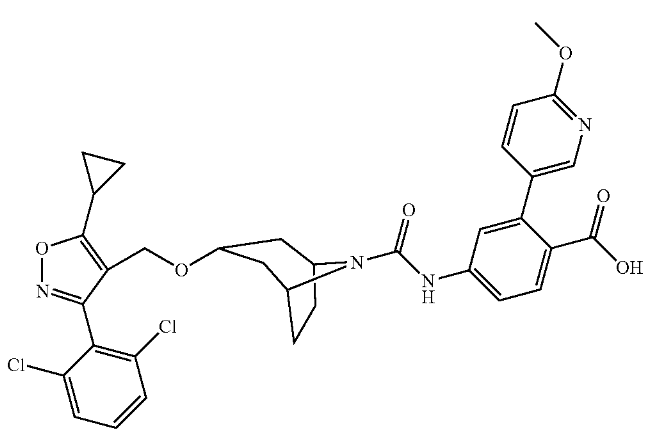 [SMILES: COc1ccc(-c2cc(NC(=O)N3C4CCC3CC(OCc3c(-c5c(Cl)cccc5Cl)noc3C3CC3)C4)ccc2C(=O)O)cn1] | M + 1: 663.18 |

TABLE 5-continued

| Example | Structure | ESMS: |
|---|---|---|
| 788 | 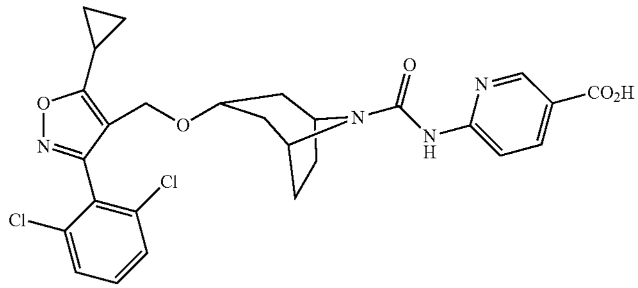 [SMILES: O=C(O)c1ccc(NC(=O)N2C3CCC2CC(OCc2c(-c4c(Cl)cccc4Cl)noc2C2CC2)C3)nc1] | M + 1: 557.14 |
| 789 | 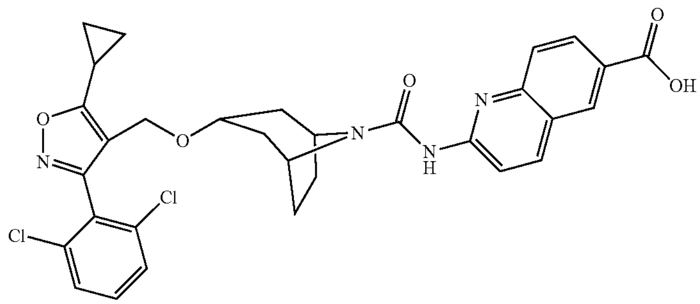 [SMILES: O=C(O)c1ccc2nc(NC(=O)N3C4CCC3CC(OCc3c(-c5c(Cl)cccc5Cl)noc3C3CC3)C4)ccc2c1] | M + 1: 607.15 |
| 790 | 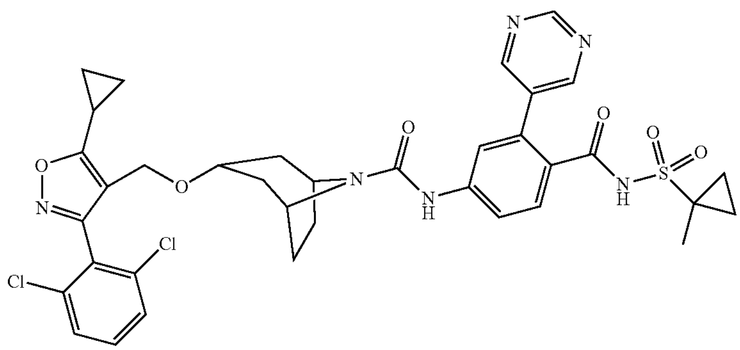 [SMILES: CC1(S(=O)(=O)NC(=O)c2ccc(NC(=O)N3C4CCC3CC(OCc3c(-c5c(Cl)cccc5Cl)noc3C3CC3)C4)cc2-c2cncnc2)CC1] | M + 1: 751.19 |
| 791 | 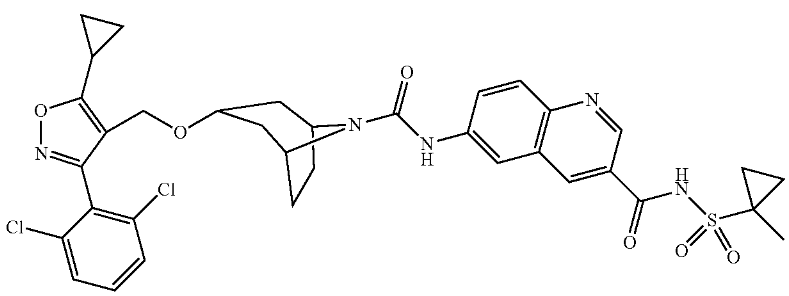 [SMILES: CC1(S(=O)(=O)NC(=O)c2cnc3ccc(NC(=O)N4C5CCC4CC(OCc4c(-c6c(Cl)cccc6Cl)noc4C4CC4)C5)cc3c2)CC1] | M + 1: 724.16 |
| 792 | 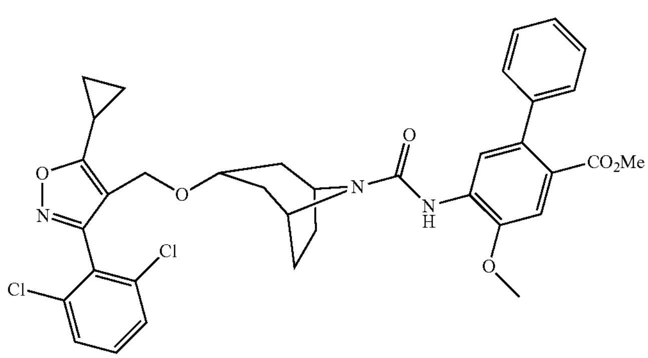 [SMILES: COC(=O)c1cc(OC)c(NC(=O)N2C3CCC2CC(OCc2c(-c4c(Cl)cccc4Cl)noc2C2CC2)C3)cc1-c1ccccc1] | M + 1: 676.20 |

TABLE 5-continued

| Example | Structure | ESMS: |
|---|---|---|
| 793 | 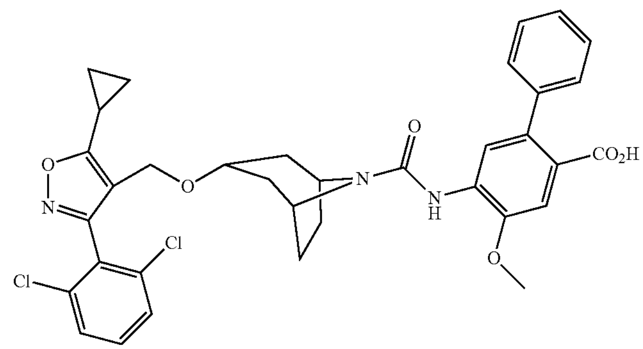 [SMILES: COc1cc(C(=O)O)c(-c2ccccc2)cc1NC(=O)N1C2CCC1CC(OCc1c(-c3c(Cl)cccc3Cl)noc1C1CC1)C2] | M + 1: 662.18 |
| 794 | 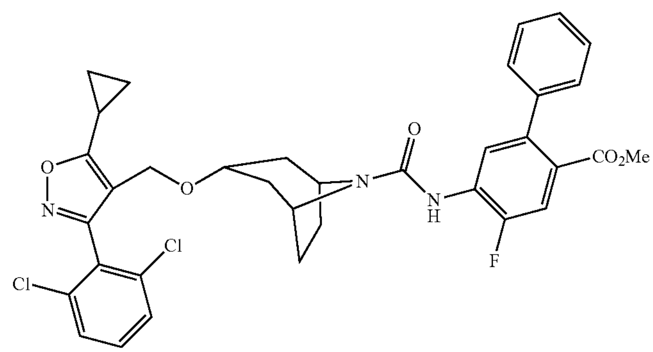 [SMILES: COC(=O)c1cc(F)c(NC(=O)N2C3CCC2CC(OCc2c(-c4c(Cl)cccc4Cl)noc2C2CC2)C3)cc1-c1ccccc1] | M + 1: 664.18 |
| 795 | 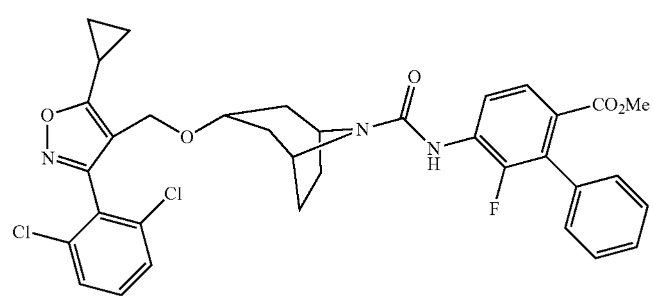 [SMILES: COC(=O)c1ccc(NC(=O)N2C3CCC2CC(OCc2c(-c4c(Cl)cccc4Cl)noc2C2CC2)C3)c(F)c1-c1ccccc1] | M + 1: 664.18 |
| 796 | 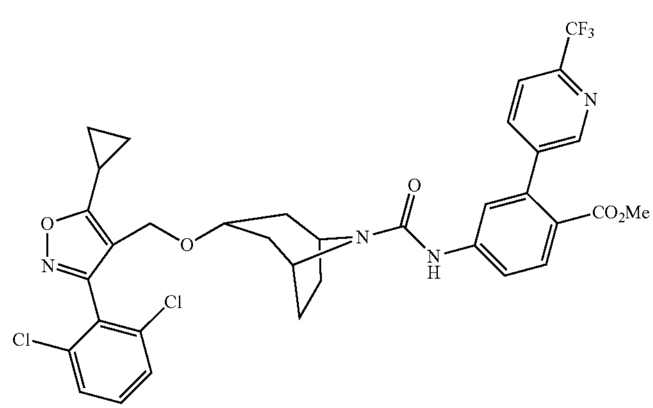 [SMILES: COC(=O)c1ccc(NC(=O)N2C3CCC2CC(OCc2c(-c4c(Cl)cccc4Cl)noc2C2CC2)C3)cc1-c1ccc(C(F)(F)F)nc1] | M + 1: 715.17 |

TABLE 5-continued

| Example | Structure | ESMS: |
|---|---|---|
| 797 | 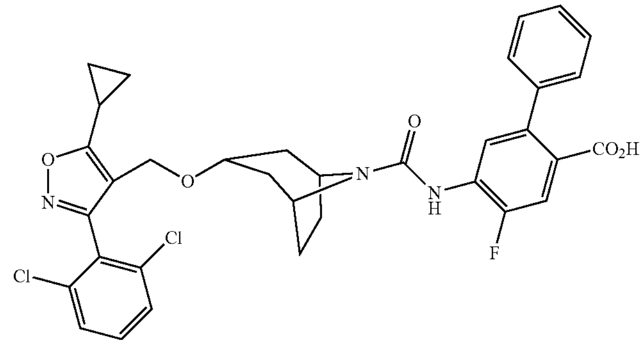 [SMILES: O=C(O)c1cc(F)c(NC(=O)N2C3CCC2CC(OCc2c(-c4c(Cl)cccc4Cl)noc2C2CC2)C3)cc1-c1ccccc1] | M + 1: 650.16 |
| 798 | 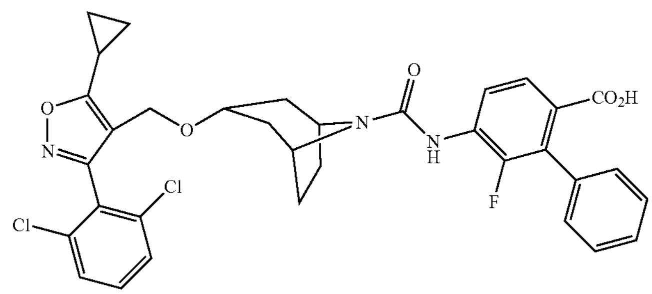 [SMILES: O=C(O)c1ccc(NC(=O)N2C3CCC2CC(OCc2c(-c4c(Cl)cccc4Cl)noc2C2CC2)C3)c(F)c1-c1ccccc1] | M + 1: 650.16 |
| 799 | 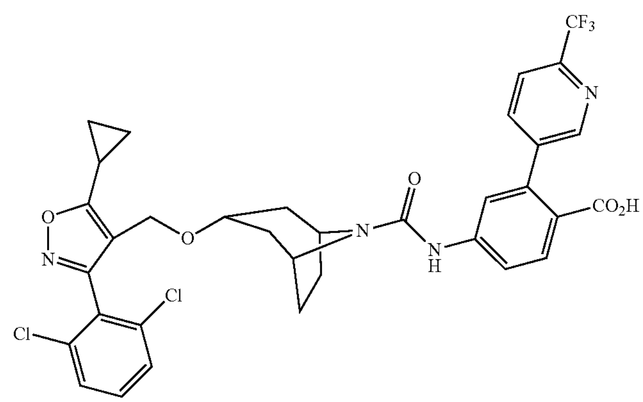 [SMILES: O=C(O)c1ccc(NC(=O)N2C3CCC2CC(OCc2c(-c4c(Cl)cccc4Cl)noc2C2CC2)C3)cc1-c1ccc(C(F)(F)F)nc1] | M + 1: 701.16 |
| 800 | 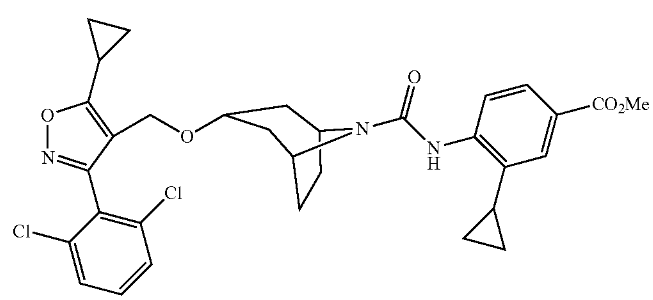 [SMILES: COC(=O)c1ccc(NC(=O)N2C3CCC2CC(OCc2c(-c4c(Cl)cccc4Cl)noc2C2CC2)C3)c(C2CC2)c1] | M + 1: 610.19 |

TABLE 5-continued

| Example | Structure | ESMS: |
|---|---|---|
| 801 | 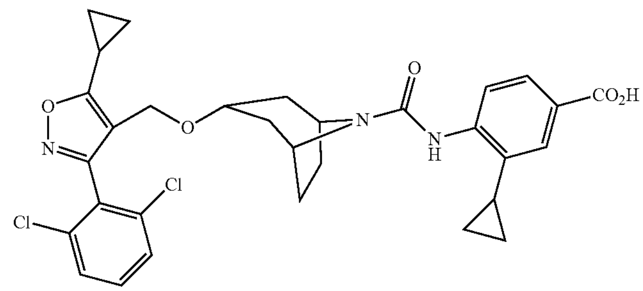 [SMILES: O=C(O)c1ccc(NC(=O)N2C3CCC2CC(OCc2c(-c4c(Cl)cccc4Cl)noc2C2CC2)C3)c(C2CC2)c1] | M + 1: 596.18 |
| 802 | 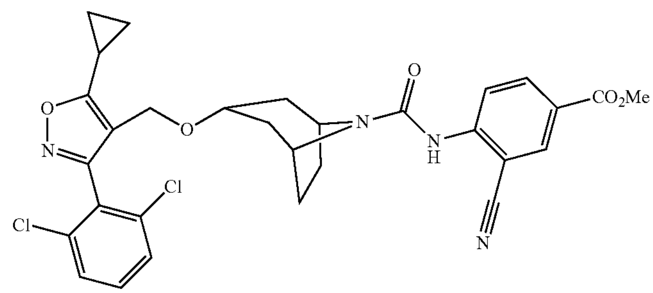 [SMILES: COC(=O)c1ccc(NC(=O)N2C3CCC2CC(OCc2c(-c4c(Cl)cccc4Cl)noc2C2CC2)C3)c(C#N)c1] | M + 1: 595.15 |
| 803 | 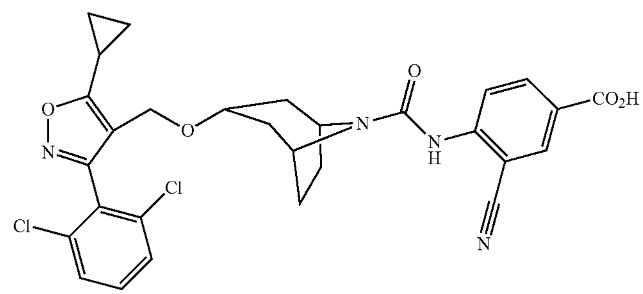 [SMILES: N#Cc1cc(C(=O)O)ccc1NC(=O)N1C2CCC1CC(OCc1c(-c3c(Cl)cccc3Cl)noc1C1CC1)C2] | M + 1: 599.15 |
| 804 | 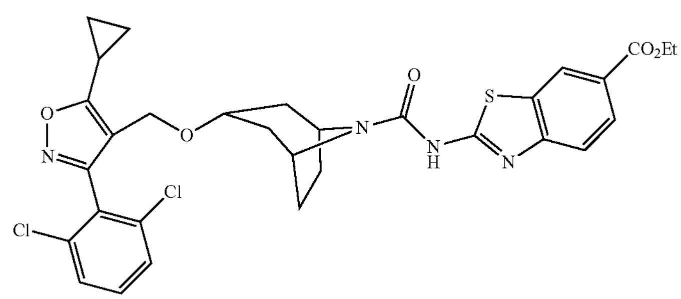 [SMILES: CCOC(=O)c1ccc2nc(NC(=O)N3C4CCC3CC(OCc3c(-c5c(Cl)cccc5Cl)noc3C3CC3)C4)sc2c1] | M + 1: 641.14 |
| 805 | 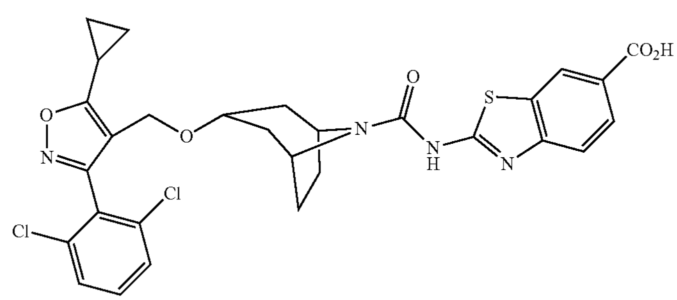 [SMILES: O=C(O)c1ccc2nc(NC(=O)N3C4CCC3CC(OCc3c(-c5c(Cl)cccc5Cl)noc3C3CC3)C4)sc2c1] | M + 1: 613.11 |

TABLE 5-continued

| Example | Structure | ESMS: |
|---|---|---|
| 806 | 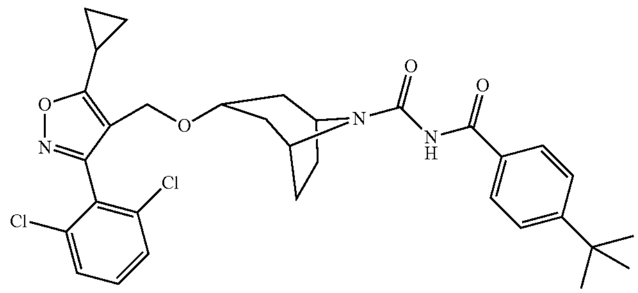 [SMILES: CC(C)(C)c1ccc(C(=O)NC(=O)N2C3CCC2CC(OCc2c(-c4c(Cl)cccc4Cl)noc2C2CC2)C3)cc1] | M + 1: 596.21 |

The compounds in Table 5a were synthesized using the general methods described above.

TABLE 5a

| Example | Structure | ESMS: |
|---|---|---|
| 807 | 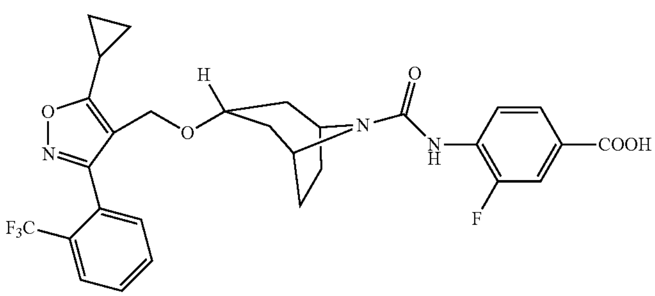 [SMILES: O=C(O)c1ccc(NC(=O)N2C3CCC2CC(OCc2c(-c4ccccc4C(F)(F)F)noc2C2CC2)C3)c(F)c1] | M + 1: 574.30 |
| 808 | 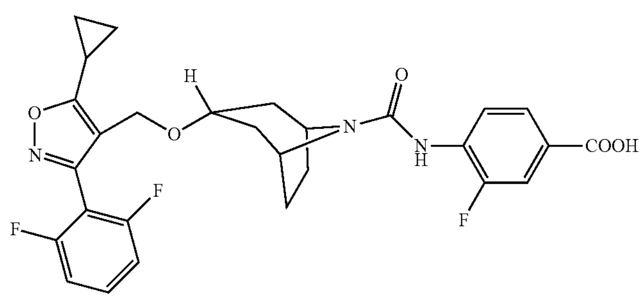 [SMILES: O=C(O)c1ccc(NC(=O)N2C3CCC2CC(OCc2c(-c4c(F)cccc4F)noc2C2CC2)C3)c(F)c1] | M + 1: 542.30 |
| 285 | 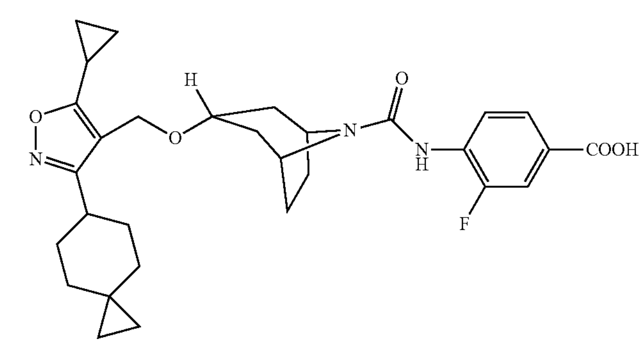 [SMILES: O=C(O)c1ccc(NC(=O)N2C3CCC2CC(OCc2c(C4CCC5(CC4)CC5)noc2C2CC2)C3)c(F)c1] | M + 1: 538.25 |

TABLE 5a-continued

| Example | Structure | ESMS: |
|---|---|---|
| 809 | 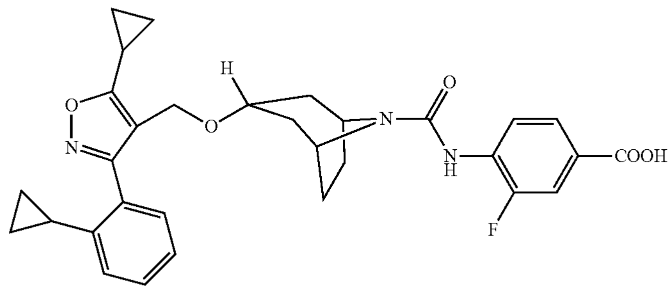 [SMILES: O=C(O)c1ccc(NC(=O)N2C3CCC2CC(OCc2c(-c4ccccc4C4CC4)noc2C2CC2)C3)c(F)c1] | M + 1: 546.20 |
| 810 | 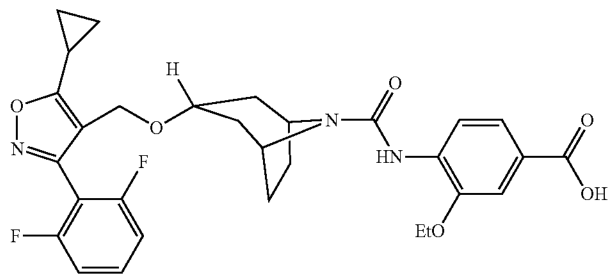 [SMILES: CCOc1cc(C(=O)O)ccc1NC(=O)N1C2CCC1CC(OCc1c(-c3c(F)cccc3F)noc1C1CC1)C2] | M + 1: 568.30 |
| 811 | 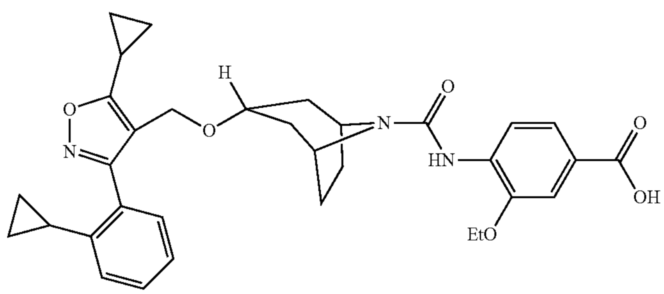 [SMILES: CCOc1cc(C(=O)O)ccc1NC(=O)N1C2CCC1CC(OCc1c(-c3ccccc3C3CC3)noc1C1CC1)C2] | M + 1: 572.25 |
| 812 | 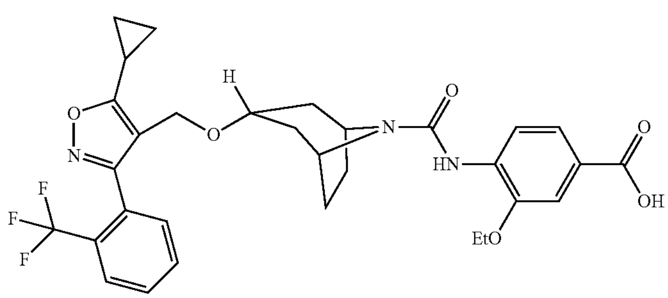 [SMILES: CCOc1cc(C(=O)O)ccc1NC(=O)N1C2CCC1CC(OCc1c(-c3ccccc3C(F)(F)F)noc1C1CC1)C2] | M + 1: 600.20 |
| 813 | 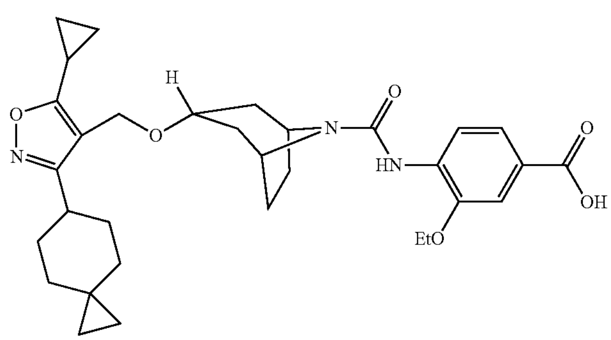 [SMILES: CCOc1cc(C(=O)O)ccc1NC(=O)N1C2CCC1CC(OCc1c(C3CCC4(CC3)CC4)noc1C1CC1)C2] | M − 1: 562.45 |

TABLE 5a-continued
| Example | Structure | ESMS: |
|---|---|---|
| 814 | 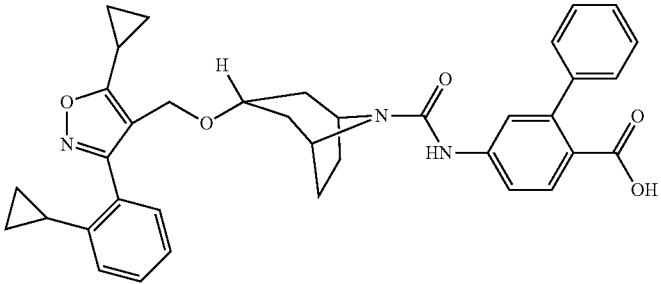 [SMILES: O=C(O)c1ccc(NC(=O)N2C3CCC2CC(OCc2c(-c4ccccc4C4CC4)noc2C2CC2)C3)cc1-c1ccccc1] | M − 1: 602.15 |
| 815 | 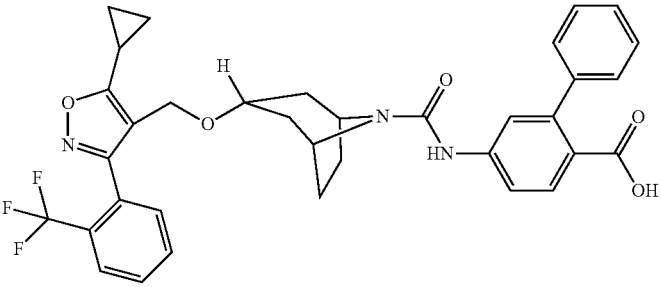 [SMILES: O=C(O)c1ccc(NC(=O)N2C3CCC2CC(OCc2c(-c4ccccc4C(F)(F)F)noc2C2CC2)C3)cc1-c1ccccc1] | M + 1: 632.50 |
| 816 | 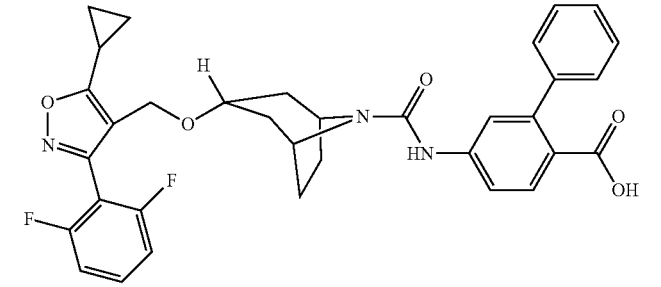 [SMILES: O=C(O)c1ccc(NC(=O)N2C3CCC2CC(OCc2c(-c4c(F)cccc4F)noc2C2CC2)C3)cc1-c1ccccc1] | M + 1: 600.45 |
| 293 | 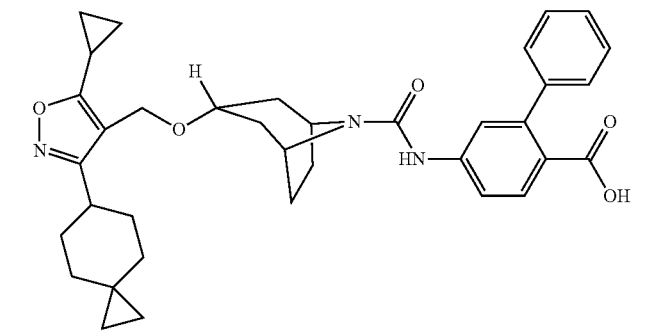 [SMILES: O=C(O)c1ccc(NC(=O)N2C3CCC2CC(OCc2c(C4CCC5(CC4)CC5)noc2C2CC2)C3)cc1-c1ccccc1] | M + 1: 596.55 |
| 817 | 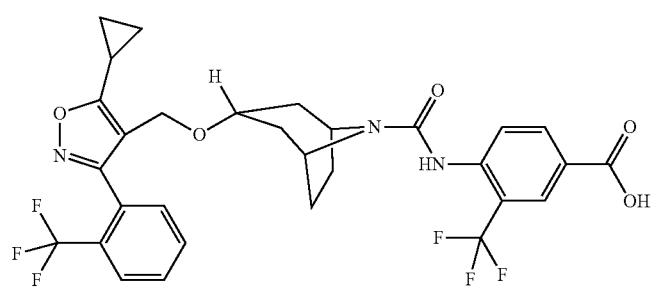 [SMILES: O=C(O)c1ccc(NC(=O)N2C3CCC2CC(OCc2c(-c4ccccc4C(F)(F)F)noc2C2CC2)C3)c(C(F)(F)F)c1] | M + 1: 624.45 |

TABLE 5a-continued

| Example | Structure | ESMS: |
|---------|-----------|-------|
| 818 | 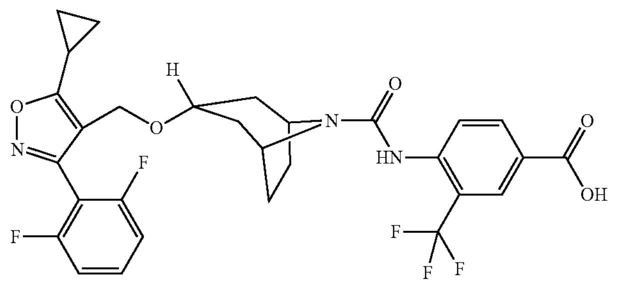 [SMILES: O=C(O)c1ccc(NC(=O)N2C3CCC2CC(OCc2c(-c4c(F)cccc4F)noc2C2CC2)C3)c(C(F)(F)F)c1] | M + 1: 592.45 |
| 819 | 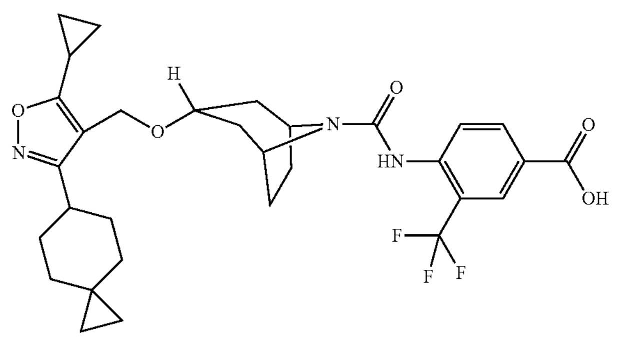 [SMILES: O=C(O)c1ccc(NC(=O)N2C3CCC2CC(OCc2c(C4CCC5(CC4)CC5)noc2C2CC2)C3)c(C(F)(F)F)c1] | M + 1: 588.50 |
| 820 | 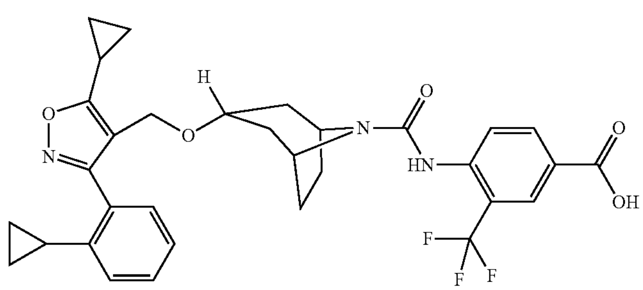 [SMILES: O=C(O)c1ccc(NC(=O)N2C3CCC2CC(OCc2c(-c4ccccc4C4CC4)noc2C2CC2)C3)c(C(F)(F)F)c1] | M + 1: 596.50 |

The compounds in Table 6 were synthesized using the general methods described above.

TABLE 6

| Example | Structure | ESMS: |
|---------|-----------|-------|
| 228 | 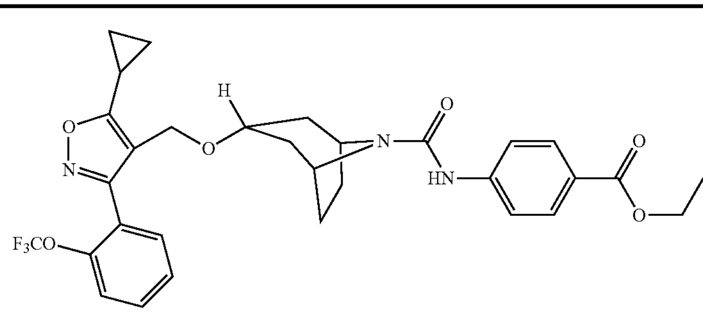 | M + 1: 600.27 |

TABLE 6-continued
| Example | Structure | ESMS: |
|---------|-----------|-------|
| 227 | 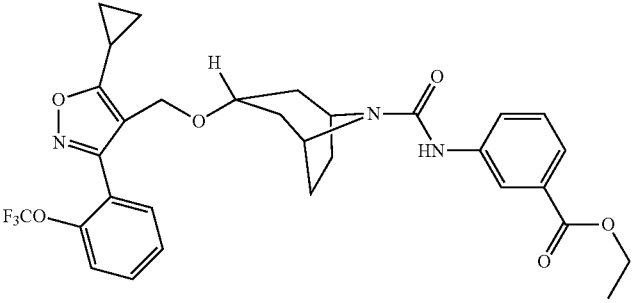 [SMILES: CCOC(=O)c1cccc(NC(=O)N2C3CCC2CC(OCc2c(-c4ccccc4OC(F)(F)F)noc2C2CC2)C3)c1] | M + 1: 600.27 |
| 229 | 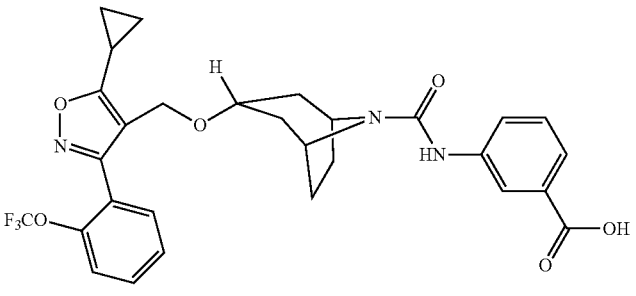 [SMILES: O=C(O)c1cccc(NC(=O)N2C3CCC2CC(OCc2c(-c4ccccc4OC(F)(F)F)noc2C2CC2)C3)c1] | M + 1: 572.45 |
| 743 | 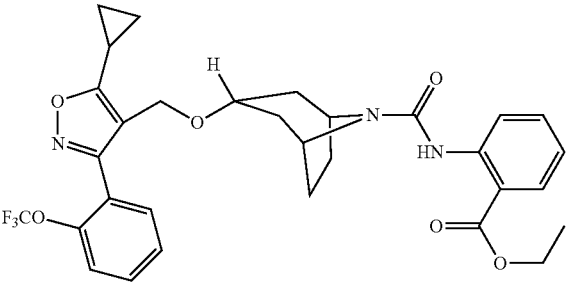 [SMILES: CCOC(=O)c1ccccc1NC(=O)N1C2CCC1CC(OCc1c(-c3ccccc3OC(F)(F)F)noc1C1CC1)C2] | M + 1: 600.27 |
| 744 | 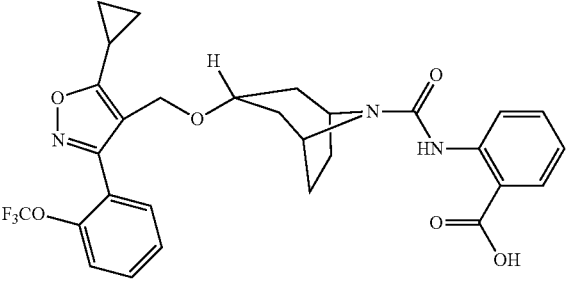 [SMILES: O=C(O)c1ccccc1NC(=O)N1C2CCC1CC(OCc1c(-c3ccccc3OC(F)(F)F)noc1C1CC1)C2] | M + 1: 572.45 |
| 230 | 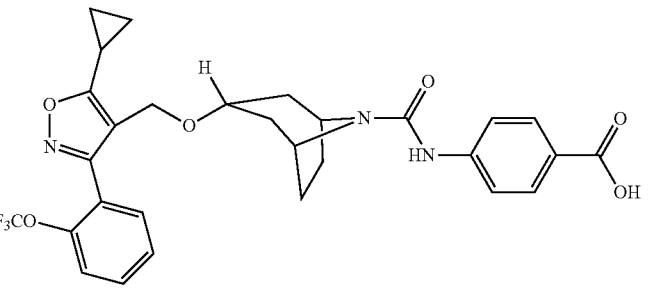 | M + 1: 572.40 |

TABLE 6-continued
| Example | Structure | ESMS: |
|---|---|---|
| 237 | 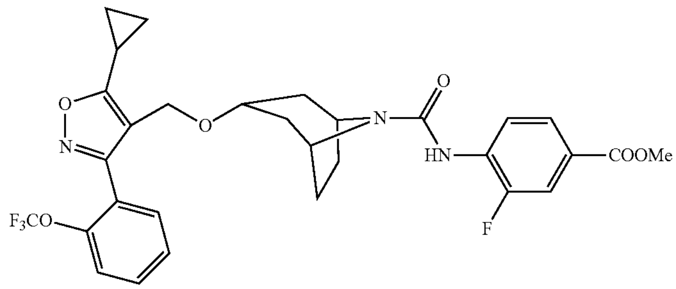 [SMILES: COC(=O)c1ccc(NC(=O)N2C3CCC2CC(OCc2c(-c4ccccc4OC(F)(F)F)noc2C2CC2)C3)c(F)c1] | M + 1: 604.45 |
| 239 | 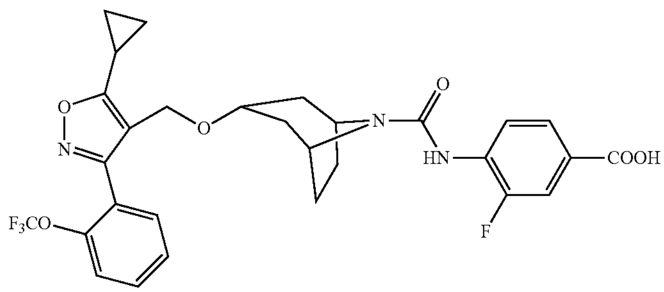 [SMILES: O=C(O)c1ccc(NC(=O)N2C3CCC2CC(OCc2c(-c4ccccc4OC(F)(F)F)noc2C2CC2)C3)c(F)c1] | M + 1: 590.45 |
| 745 | 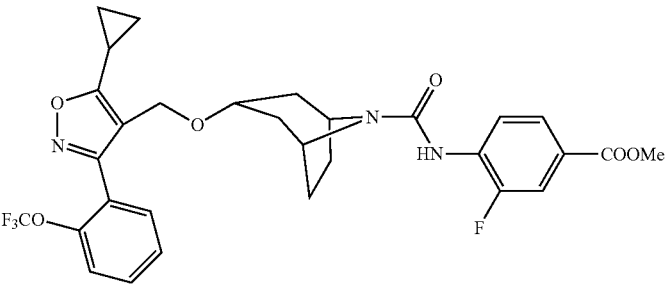 [SMILES: COC(=O)c1ccc(NC(=O)N2C3CCC2CC(OCc2c(-c4ccccc4OC(F)(F)F)noc2C2CC2)C3)c(F)c1] | M + 1: 604.45 |
| 746 | 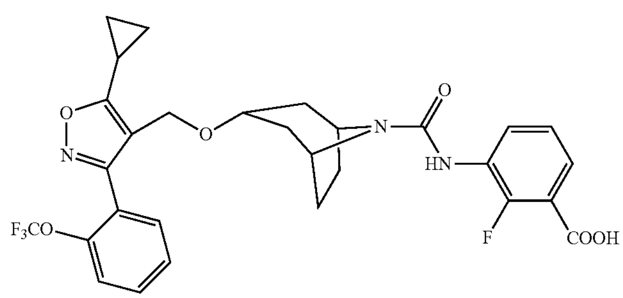 [SMILES: O=C(O)c1cccc(NC(=O)N2C3CCC2CC(OCc2c(-c4ccccc4OC(F)(F)F)noc2C2CC2)C3)c1F] | M + 1: 590.45 |
| 747 | 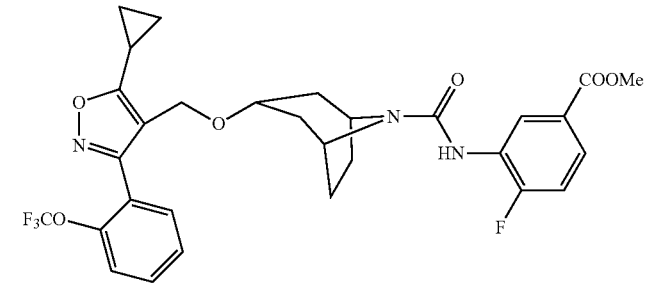 [SMILES: COC(=O)c1ccc(F)c(NC(=O)N2C3CCC2CC(OCc2c(-c4ccccc4OC(F)(F)F)noc2C2CC2)C3)c1] | M + 1: 604.45 |

TABLE 6-continued

| Example | Structure | ESMS: |
|---------|-----------|-------|
| 748 | 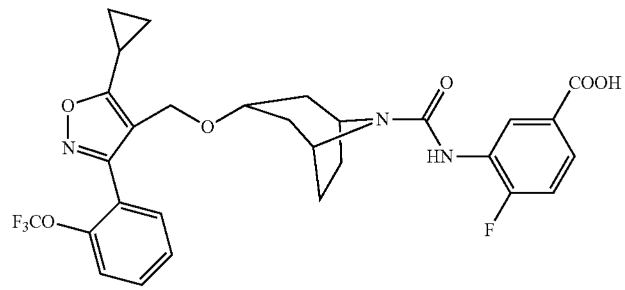 [SMILES: O=C(O)c1ccc(F)c(NC(=O)N2C3CCC2CC(OCc2c(-c4ccccc4OC(F)(F)F)noc2C2CC2)C3)c1] | M + 1: 590.45 |
| 236 | 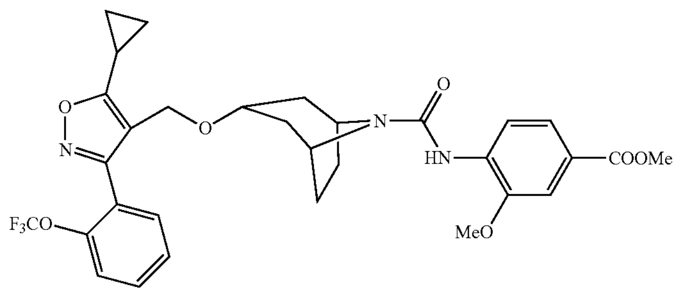 [SMILES: COC(=O)c1ccc(NC(=O)N2C3CCC2CC(OCc2c(-c4ccccc4OC(F)(F)F)noc2C2CC2)C3)c(OC)c1] | M + 1: 616.45 |
| 238 | 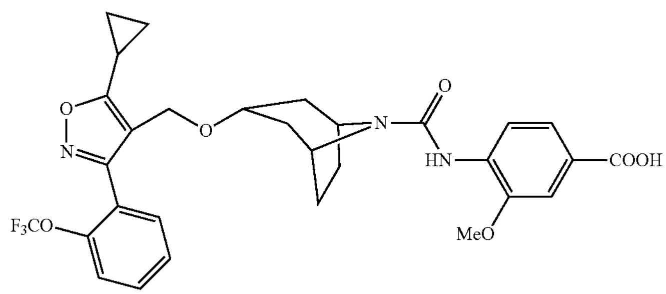 [SMILES: COc1cc(C(=O)O)ccc1NC(=O)N1C2CCC1CC(OCc1c(-c3ccccc3OC(F)(F)F)noc1C1CC1)C2] | M + 1: 602.50 |
| 749 | 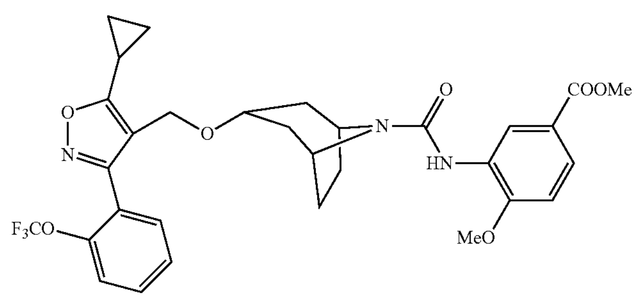 [SMILES: COC(=O)c1ccc(OC)c(NC(=O)N2C3CCC2CC(OCc2c(-c4ccccc4OC(F)(F)F)noc2C2CC2)C3)c1] | M + 1: 616.40 |
| 750 | 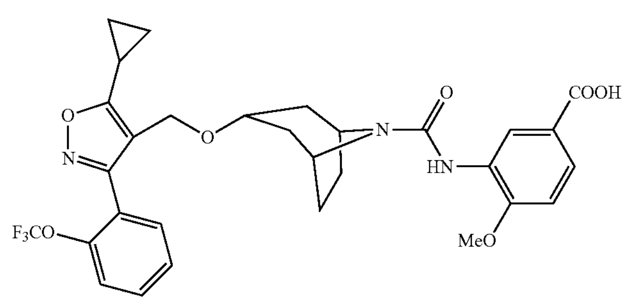 [SMILES: COc1ccc(C(=O)O)cc1NC(=O)N1C2CCC1CC(OCc1c(-c3ccccc3OC(F)(F)F)noc1C1CC1)C2] | M + 1: 602.45 |

TABLE 6-continued

| Example | Structure | ESMS: |
|---|---|---|
| 751 | 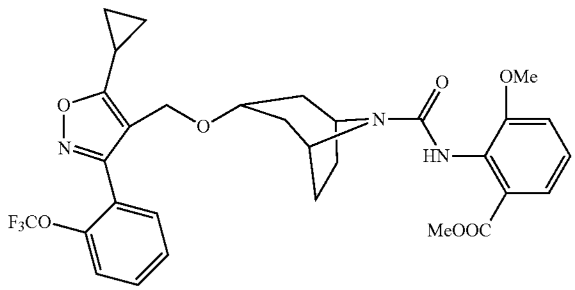 [SMILES: COC(=O)c1cccc(OC)c1NC(=O)N1C2CCC1CC(OCc1c(-c3ccccc3OC(F)(F)F)noc1C1CC1)C2] | M + 1: 616.45 |
| 266 | 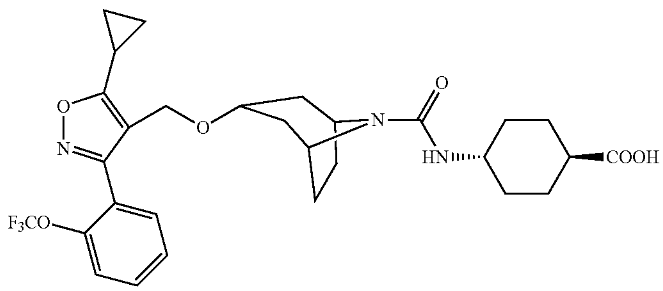 [SMILES: O=C(N[C@H]1CC[C@H](C(=O)O)CC1)N1C2CCC1CC(OCc1c(-c3ccccc3OC(F)(F)F)noc1C1CC1)C2] | M + 1: 578.10 |
| 752 | 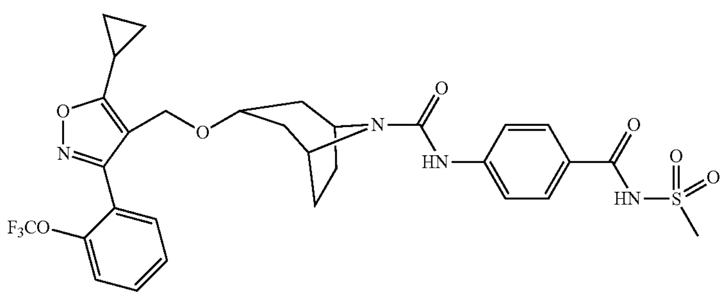 [SMILES: CS(=O)(=O)NC(=O)c1ccc(NC(=O)N2C3CCC2CC(OCc2c(-c4ccccc4OC(F)(F)F)noc2C2CC2)C3)cc1] | M + 1: 649.25 |
| 753 | 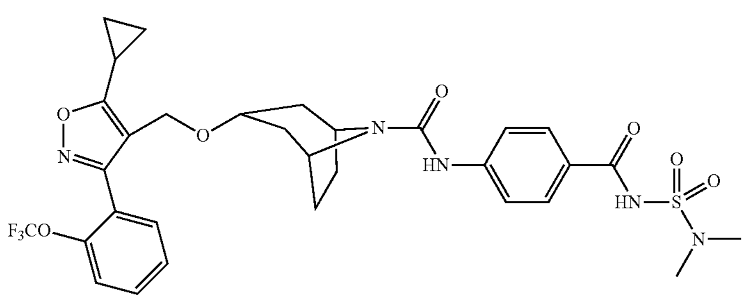 [SMILES: CN(C)S(=O)(=O)NC(=O)c1ccc(NC(=O)N2C3CCC2CC(OCc2c(-c4ccccc4OC(F)(F)F)noc2C2CC2)C3)cc1] | M + 1: 678.45 |
| 754 | 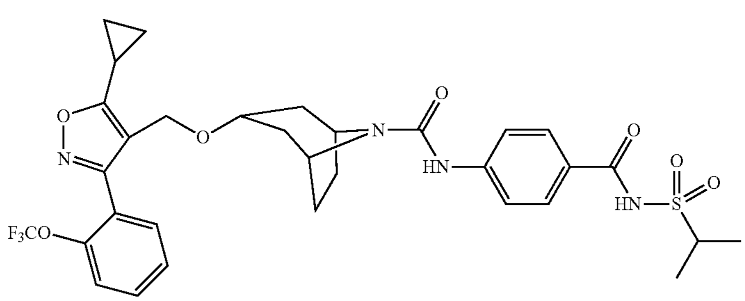 [SMILES: CC(C)S(=O)(=O)NC(=O)c1ccc(NC(=O)N2C3CCC2CC(OCc2c(-c4ccccc4OC(F)(F)F)noc2C2CC2)C3)cc1] | M + 1: 677.30 |

TABLE 6-continued

| Example | Structure | ESMS: |
|---|---|---|
| 755 | 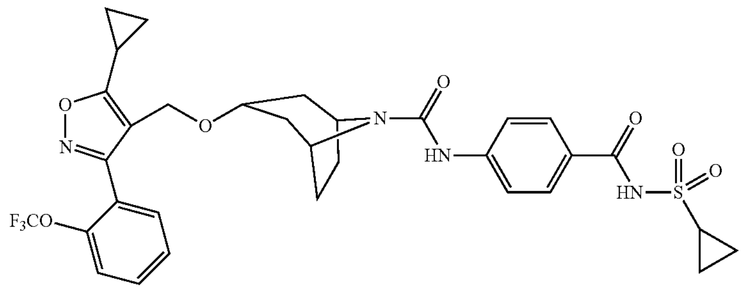 [SMILES: O=C(NS(=O)(=O)C1CC1)c1ccc(NC(=O)N2C3CCC2CC(OCc2c(-c4ccccc4OC(F)(F)F)noc2C2CC2)C3)cc1] | M + 1: 675.30 |
| 756 | 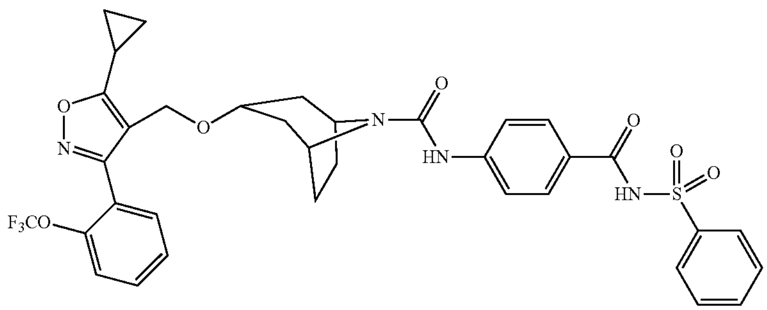 [SMILES: O=C(NS(=O)(=O)c1ccccc1)c1ccc(NC(=O)N2C3CCC2CC(OCc2c(-c4ccccc4OC(F)(F)F)noc2C2CC2)C3)cc1] | M + 1: 711.40 |
| 757 | 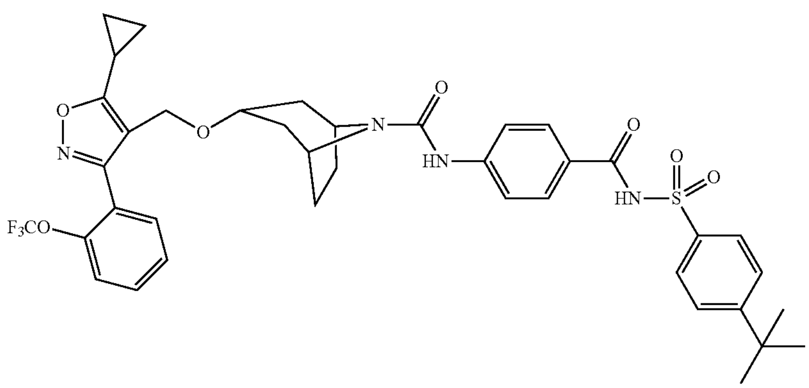 [SMILES: CC(C)(C)c1ccc(S(=O)(=O)NC(=O)c2ccc(NC(=O)N3C4CCC3CC(OCc3c(-c5ccccc5OC(F)(F)F)noc3C3CC3)C4)cc2)cc1] | M + 1: 767.45 |
| 262 | 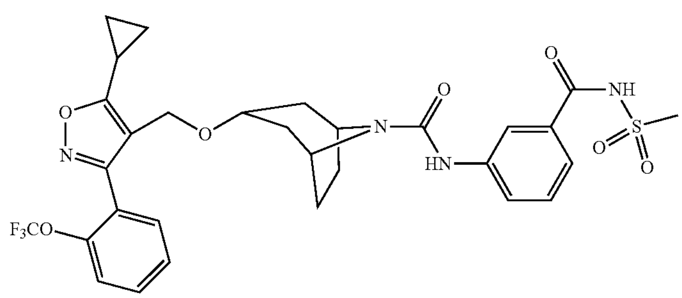 [SMILES: CS(=O)(=O)NC(=O)c1cccc(NC(=O)N2C3CCC2CC(OCc2c(-c4ccccc4OC(F)(F)F)noc2C2CC2)C3)c1] | M + 1: 649.45 |
| 265 | 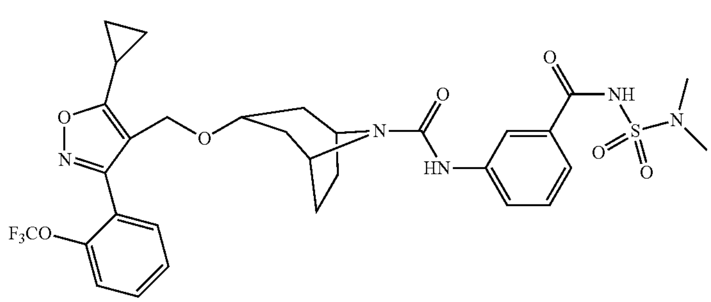 [SMILES: CN(C)S(=O)(=O)NC(=O)c1cccc(NC(=O)N2C3CCC2CC(OCc2c(-c4ccccc4OC(F)(F)F)noc2C2CC2)C3)c1] | M + 1: 678.45 |

TABLE 6-continued
| Example | Structure | ESMS: |
|---|---|---|
| 758 | 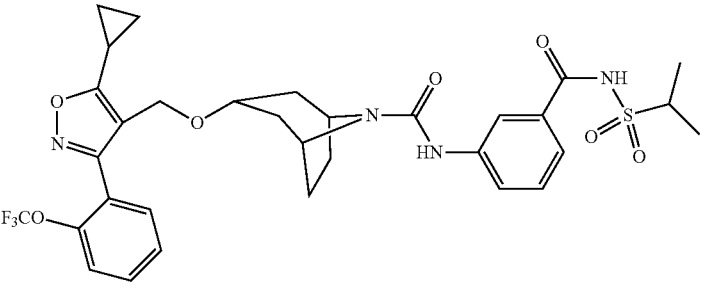 [SMILES: CC(C)S(=O)(=O)NC(=O)c1cccc(NC(=O)N2C3CCC2CC(OCc2c(-c4ccccc4OC(F)(F)F)noc2C2CC2)C3)c1] | M + 1: 677.45 |
| 264 | 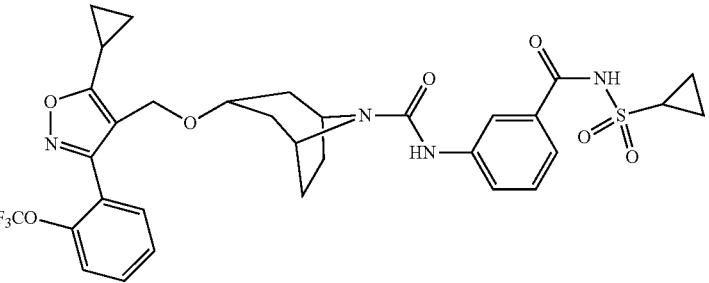 | M + 1: 675.45 |
| 759 | 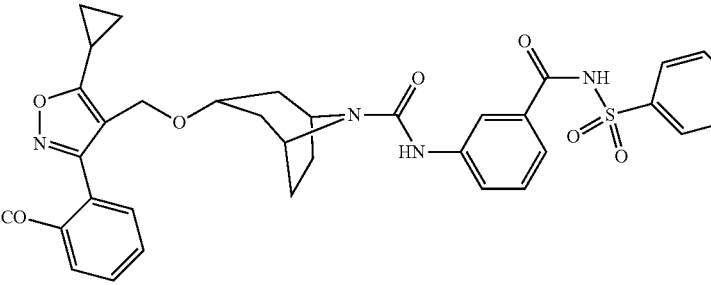 | M + 1: 711.40 |
| 263 | 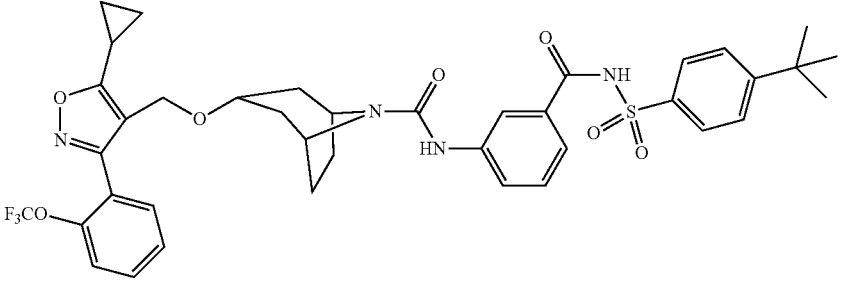 [SMILES: CC(C)(C)c1ccc(S(=O)(=O)NC(=O)c2cccc(NC(=O)N3C4CCC3CC(OCc3c(-c5ccccc5OC(F)(F)F)noc3C3CC3)C4)c2)cc1] | M + 1: 767.45 |
| 760 | 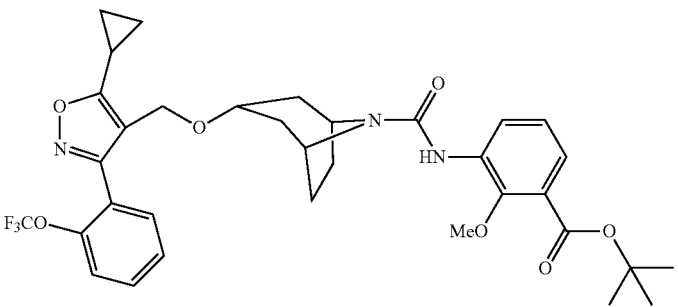 [SMILES: COc1c(NC(=O)N2C3CCC2CC(OCc2c(-c4ccccc4OC(F)(F)F)noc2C2CC2)C3)cccc1C(=O)OC(C)(C)C] | M + 1: 658.55 |

TABLE 6-continued
| Example | Structure | ESMS: |
|---|---|---|
| 761 | 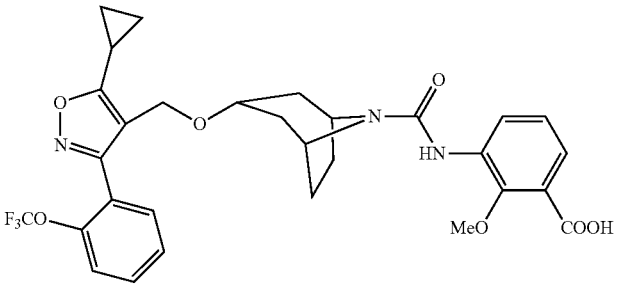 [SMILES: COc1c(NC(=O)N2C3CCC2CC(OCc2c(-c4ccccc4OC(F)(F)F)noc2C2CC2)C3)cccc1C(=O)O] | M + 1: 602.45 |
| 762 | 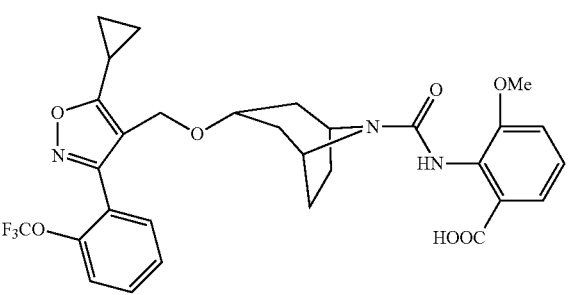 [SMILES: COc1cccc(C(=O)O)c1NC(=O)N1C2CCC1CC(OCc1c(-c3ccccc3OC(F)(F)F)noc1C1CC1)C2] | M + 1: 602.45 |
| 763 | 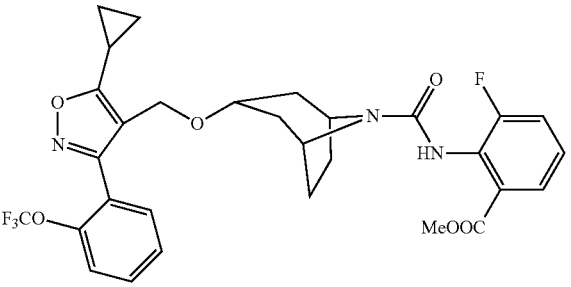 | M + 1: 604.45 |
| 764 | 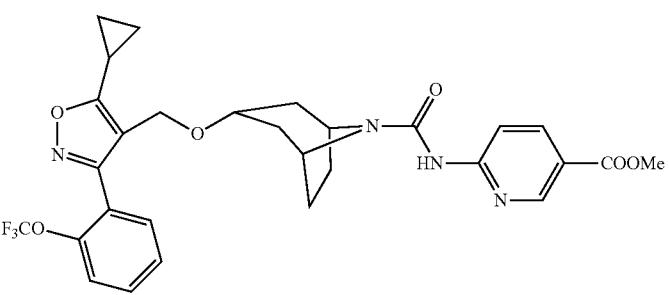 [SMILES: COC(=O)c1ccc(NC(=O)N2C3CCC2CC(OCc2c(-c4ccccc4OC(F)(F)F)noc2C2CC2)C3)nc1] | M + 1: 587.20 |
| 765 | 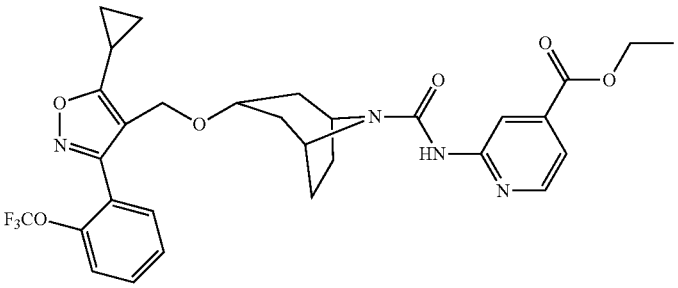 [SMILES: CCOC(=O)c1ccnc(NC(=O)N2C3CCC2CC(OCc2c(-c4ccccc4OC(F)(F)F)noc2C2CC2)C3)c1] | M + 1: 601.26 |

TABLE 6-continued
| Example | Structure | ESMS: |
|---|---|---|
| 766 | 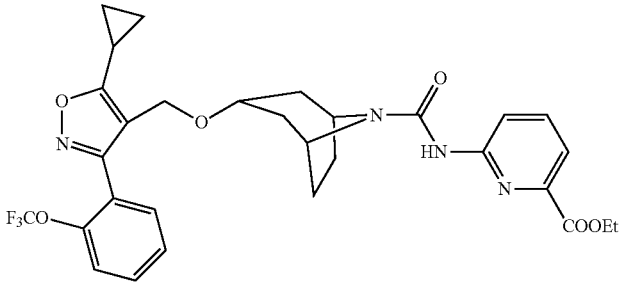 [SMILES: CCOC(=O)c1cccc(NC(=O)N2C3CCC2CC(OCc2c(-c4ccccc4OC(F)(F)F)noc2C2CC2)C3)n1] | M + 1: 601.20 |
| 767 | 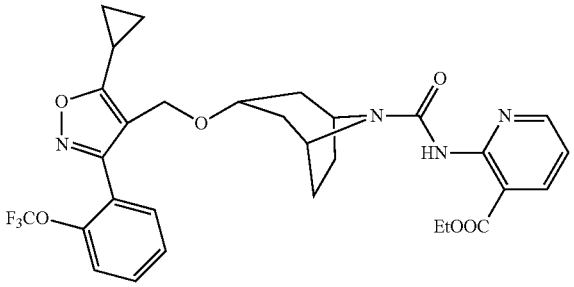 | M + 1: 601.20 |
| 768 | 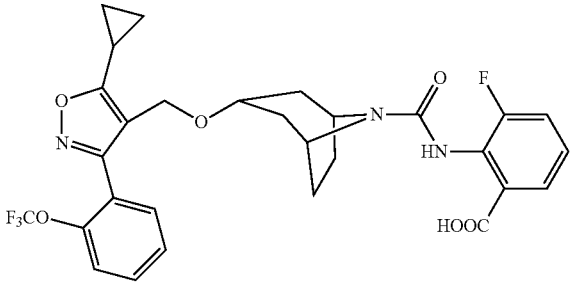 [SMILES: O=C(O)c1cccc(F)c1NC(=O)N1C2CCC1CC(OCc1c(-c3ccccc3OC(F)(F)F)noc1C1CC1)C2] | M + 1: 590.45 |
| 769 | 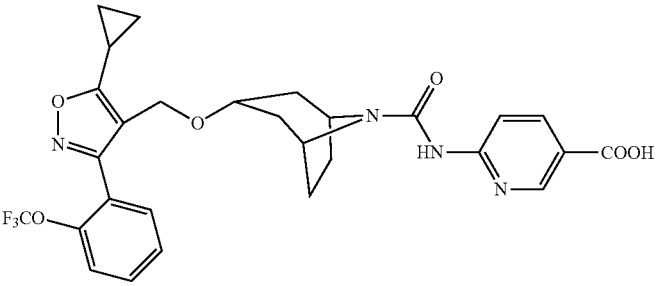 [SMILES: O=C(O)c1ccc(NC(=O)N2C3CCC2CC(OCc2c(-c4ccccc4OC(F)(F)F)noc2C2CC2)C3)nc1] | M + 1: 573.30 |
| 770 | 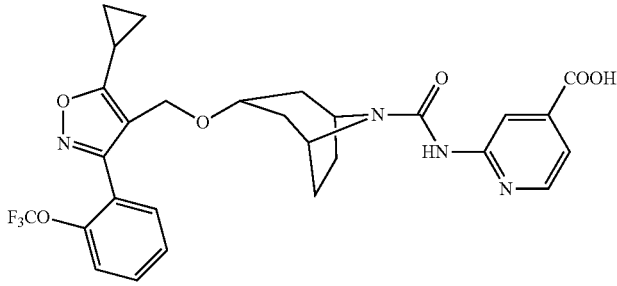 [SMILES: O=C(O)c1ccnc(NC(=O)N2C3CCC2CC(OCc2c(-c4ccccc4OC(F)(F)F)noc2C2CC2)C3)c1] | M + 1: 573.30 |

TABLE 6-continued
| Example | Structure | ESMS: |
|---|---|---|
| 771 | 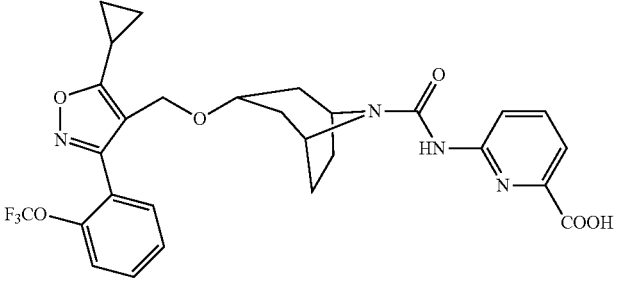 [SMILES: O=C(O)c1cccc(NC(=O)N2C3CCC2CC(OCc2c(-c4ccccc4OC(F)(F)F)noc2C2CC2)C3)n1] | M + 1: 573.30 |
| 772 | 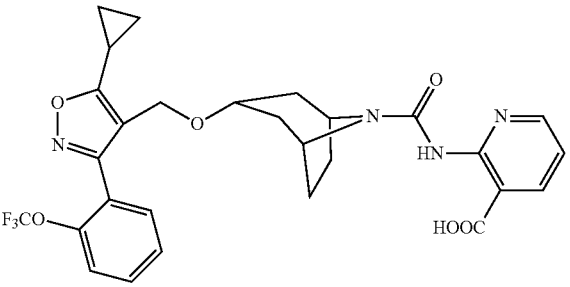 [SMILES: O=C(O)c1cccnc1NC(=O)N1C2CCC1CC(OCc1c(-c3ccccc3OC(F)(F)F)noc1C1CC1)C2] | M + 1: 573.30 |
| 821 | 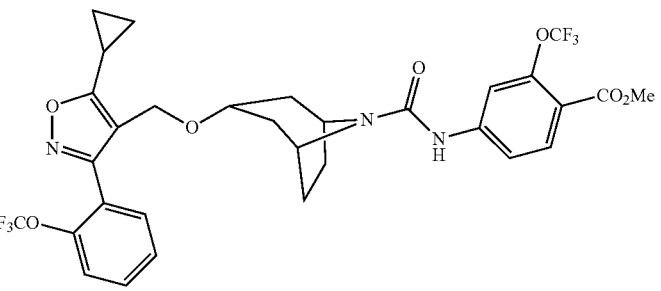 | M + 1: 670.20 |
| 822 | 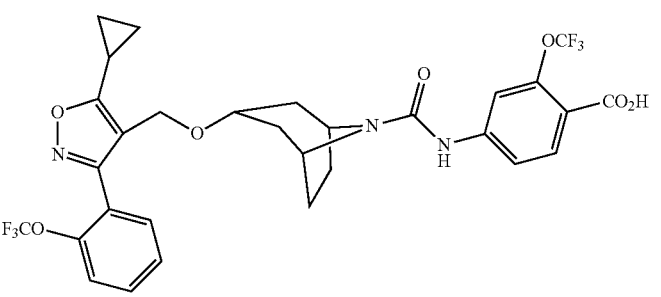 [SMILES: O=C(O)c1ccc(NC(=O)N2C3CCC2CC(OCc2c(-c4ccccc4OC(F)(F)F)noc2C2CC2)C3)cc1OC(F)(F)F] | M + 1: 655.18 |
| 823 | 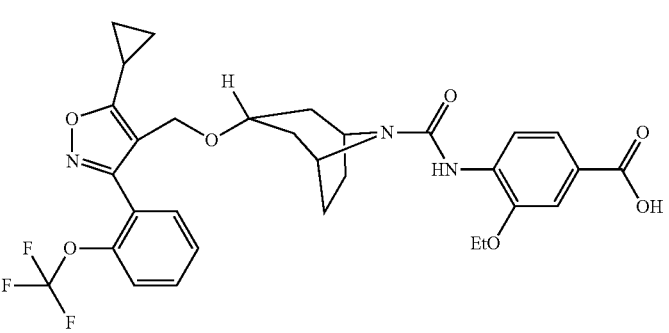 [SMILES: CCOc1cc(C(=O)O)ccc1NC(=O)N1C2CCC1CC(OCc1c(-c3ccccc3OC(F)(F)F)noc1C1CC1)C2] | M + 1: 616.55 |

TABLE 6-continued
| Example | Structure | ESMS: |
|---|---|---|
| 247 | 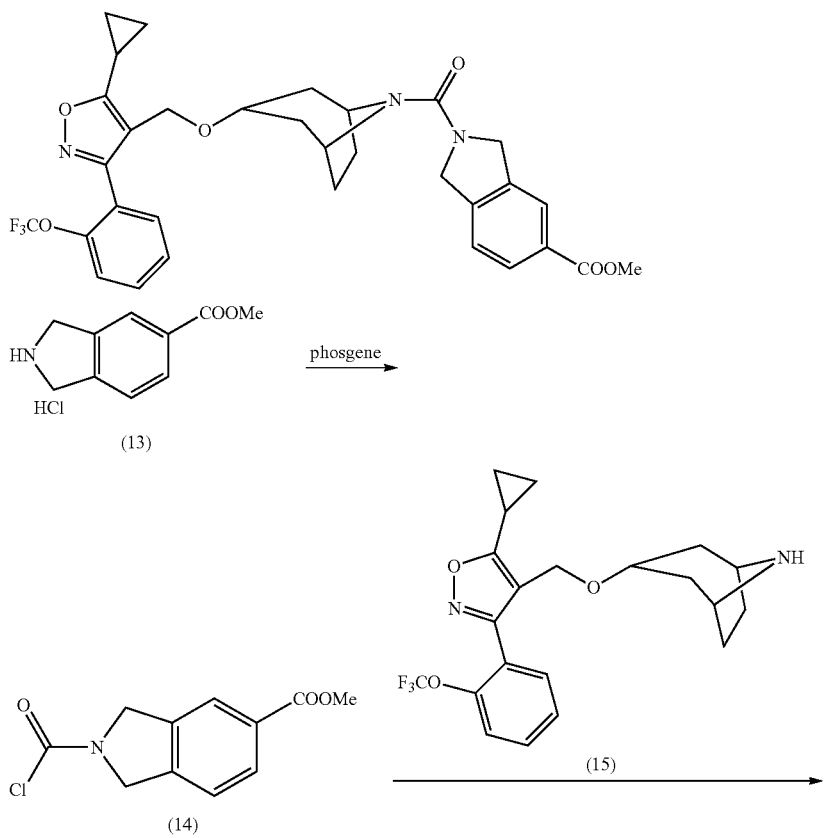 | M + 1: 648.50 |
| 824 | 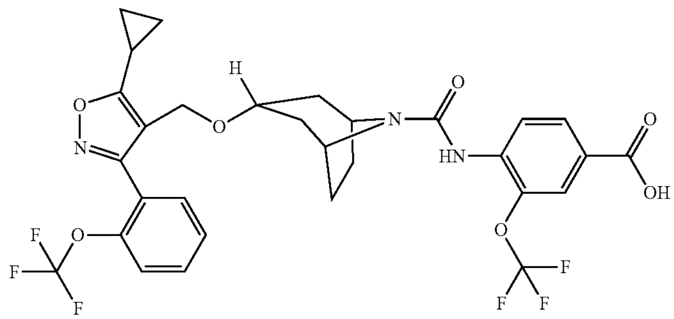 [SMILES: O=C(O)c1ccc(NC(=O)N2C3CCC2CC(OCc2c(-c4ccccc4OC(F)(F)F)noc2C2CC2)C3)c(OC(F)(F)F)c1] | M + 1: 640.40 |
Example 597

-continued

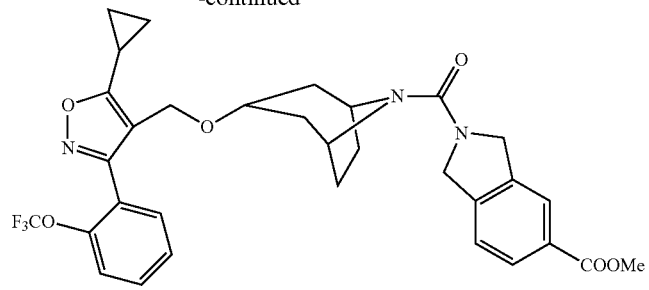

Example 597

To a solution of secondary amine HCl salt (13) (53 mg, 0.25 mmol) and Et₃N (75 mg, 0.74 mmol) in THF (2 mL) was slowly added a solution of phosgene (29 mg, 0.10 mmol) in THF (1.0 mL) at 0° C. The reaction was stirred at room temperature for 1 hour before addition of secondary amine (15). The resulting mixture was quenched 1 hour later with water (10 mL), extracted with EtOAc (3×), the combined organic layer was dried over Na₂SO₄, filtered and evaporated. The residue was purified by flash column chromatography (Column, C18; mobile layer, MeCN/H₂O, Detector, UV 254 nm) to give Example 597 (63 mg) as a white solid. LC/MS observed [M+H]⁺: 612.45.

The compounds in table 7 were synthesized using the general method of Example 597.

TABLE 7

| Example | Structure | ESMS: |
|---------|-----------|-------|
| 833 | 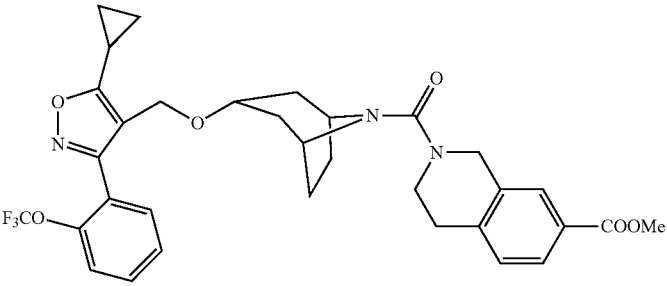 [SMILES: COC(=O)c1ccc2c(c1)CN(C(=O)N1C3CCC1CC(OCc1c(-c4ccccc4OC(F)(F)F)noc1C1CC1)C3)CC2] | M + 1: 626.50 |
| 834 | 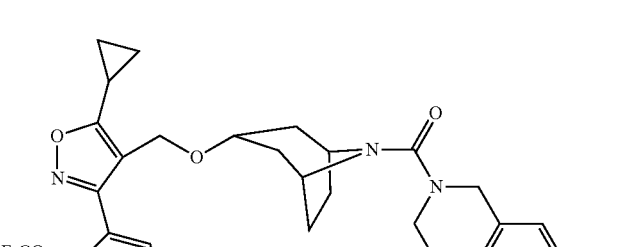 | M + 1: 612.50 |
| 589 | 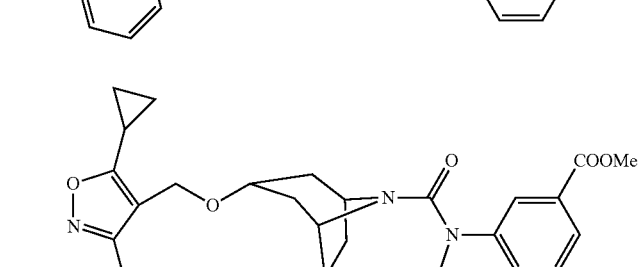 | M + 1: 612.45 |

TABLE 7-continued
| Example | Structure | ESMS: |
|---|---|---|
| 590 | 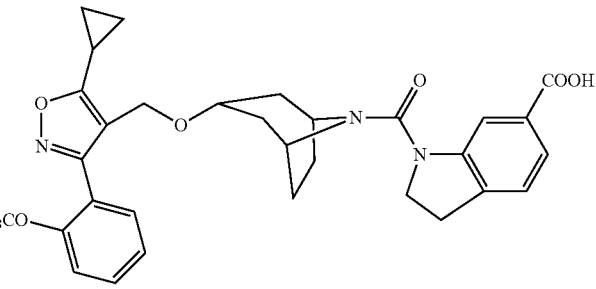 | M + 1: 598.45 |
| 591 | 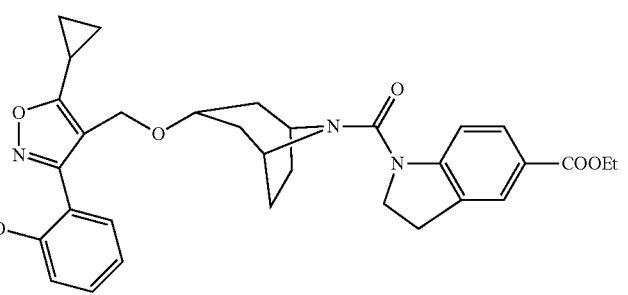 | M + Na: 648.50 |
| 592 | 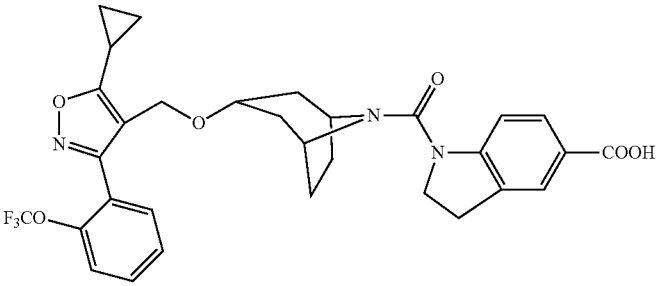 [SMILES: O=C(O)c1ccc2c(c1)CCN2C(=O)N1C2CCC1CC(OCc1c(-c3ccccc3OC(F)(F)F)noc1C1CC1)C2] | M + 1: 598.50 |
| 593 | 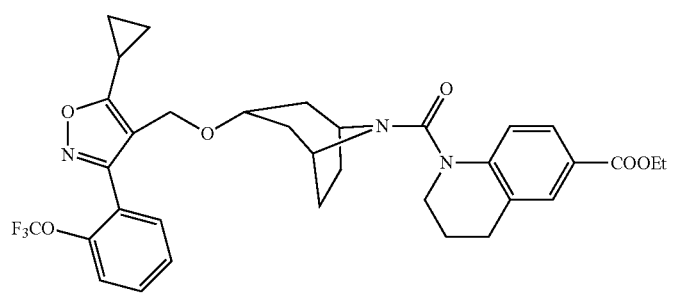 [SMILES: CCOC(=O)c1ccc2c(c1)CCCN2C(=O)N1C2CCC1CC(OCc1c(-c3ccccc3OC(F)(F)F)noc1C1CC1)C2] | M + 1: 640.50 |
| 594 | 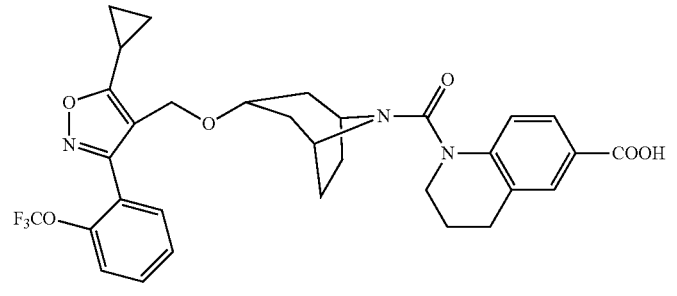 | M + 1: 612.50 |

TABLE 7-continued
| Example | Structure | ESMS: |
|---------|-----------|-------|
| 595 | 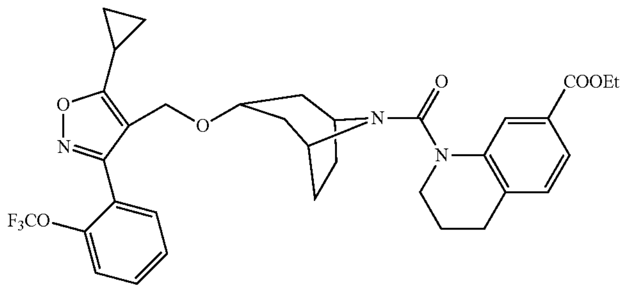 [SMILES: CCOC(=O)c1ccc2c(c1)N(C(=O)N1C3CCC1CC(OCc1c(-c4ccccc4OC(F)(F)F)noc1C1CC1)C3)CCC2] | M + Na: 662.50 |
| 596 | 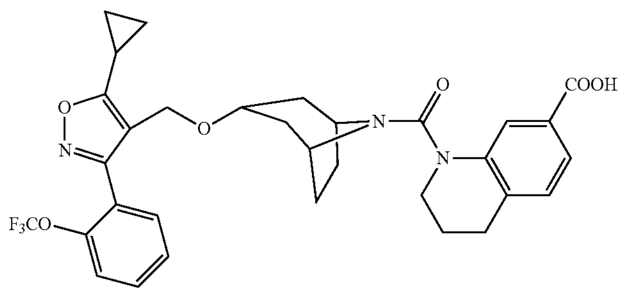 [SMILES: O=C(O)c1ccc2c(c1)N(C(=O)N1C3CCC1CC(OCc1c(-c4ccccc4OC(F)(F)F)noc1C1CC1)C3)CCC2] | M + 1: 612.50 |
| 598 | 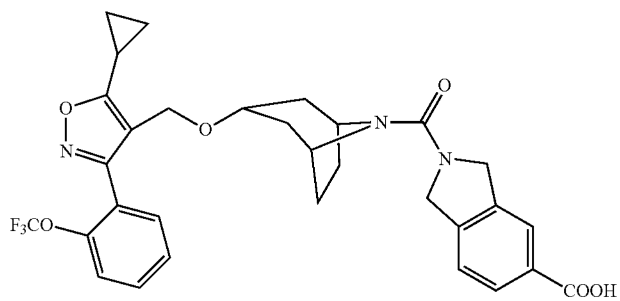 [SMILES: O=C(O)c1ccc2c(c1)CN(C(=O)N1C3CCC1CC(OCc1c(-c4ccccc4OC(F)(F)F)noc1C1CC1)C3)C2] | M + 1: 598.45 |
Example 773
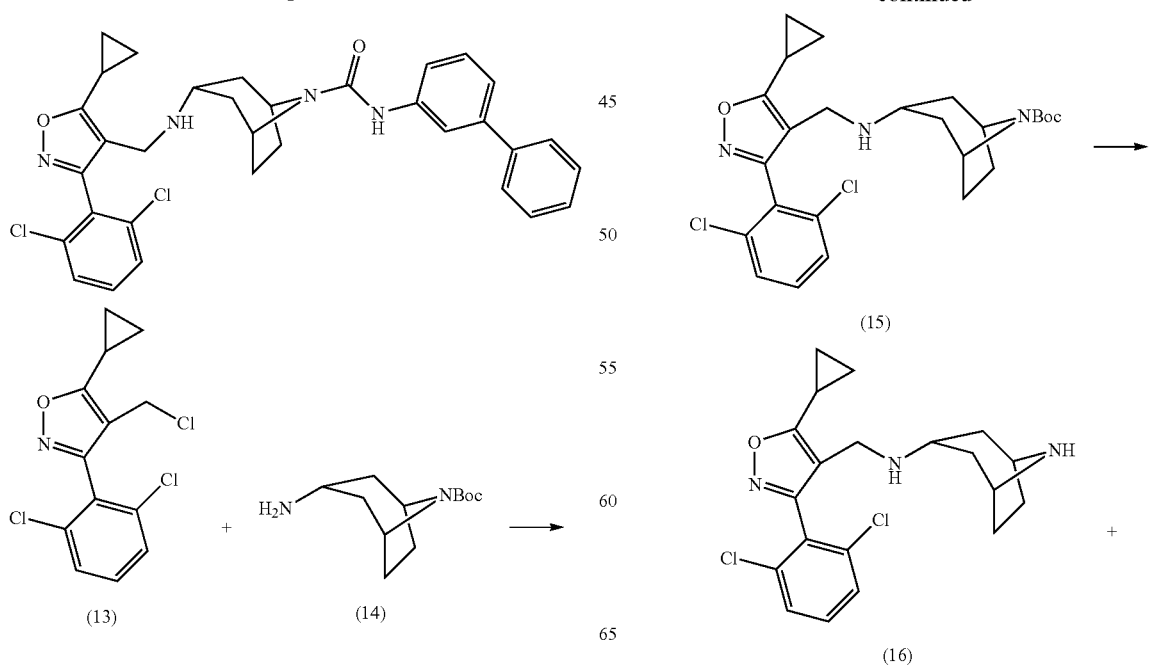

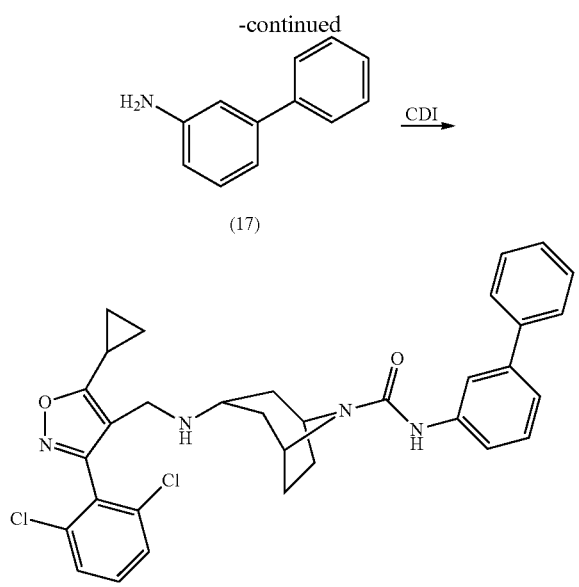

Example 773

To tert-butyl (1R,3R,5S)-3-amino-8-azabicyclo[3.2.1]octane-8-carboxylate (14) (5 g, 22.09 mmol) and 4-(chloromethyl)-5-cyclopropyl-3-(2,6-dichlorophenyl)isoxazole (13) (7.35 g, 24.30 mmol) in acetonitrile (50 ml) was added TBAI (0.816 g, 2.209 mmol) and cesium carbonate (18.00 g, 55.2 mmol). The resulting mixture was stirred at 65° C. for 16 h and then concentrated under vacuo to remove most of the solvents. The mixture was diluted with ethyl acetate, washed with water and brine, dried, filtered, and concentrated. The residue was chromatographed by CombiFlash eluting with 0 to 50% acetone in hexane to give tert-butyl (1R,3R,5 S)-3-(((5-cyclopropyl-3-(2,6-dichlorophenyl)isoxazol-4-yl)methyl)amino)-8-azabicyclo[3.2.1]octane-8-carboxylate (15) (4.12 g). LC/MS observed [M+H]$^+$: 492.19; 494.17.

To tert-butyl (1R,3R,5 S)-3-(((5-cyclopropyl-3-(2,6-dichlorophenyl)isoxazol-4-yl)methyl)amino)-8-azabicyclo [3.2.1]octane-8-carboxylate (15) (758 mg, 1.539 mmol) in DCM (4 ml) was added HCl (3.85 ml, 15.39 mmol, 4 M in dioxane) and the resulting mixture was stirred at room temperature for 3 h. The mixture was concentrated under vacuo and chased with DCM to afford (1R,3R,5S)—N-((5-cyclopropyl-3-(2,6-dichlorophenyl)isoxazol-4-yl)methyl)-8-azabicyclo[3.2.1]octan-3-amine (16) (785 mg) as HCl salt. LC/MS observed [M+H]$^+$: 392.13.

A solution of [1,1'-biphenyl]-3-amine (17) (39.5 mg, 0.233 mmol) and CDI (37.8 mg, 0.233 mmol) in DCM (0.58 mL) was allowed to stir at room temperature for 15 hours before addition of secondary amine HCl salt (16) (50 mg, 0.117 mmol) and N,N-diisopropylethylamine (61 μL, 0.35 mmol). The resulting mixture was allowed to stir at room temperature for additional 15 hours. The reaction was quenched with water and extracted with EtOAc (3×). The combined organic layer was dried and concentrated in vacuo. Purification of the residue on amine column (20 g) with 0-50% EtOAc/hexane provided Example 773 (12 mg) as a white solid. LC/MS observed [M+H]$^+$: 587.20.

The compounds in table 8 were synthesized using the general method of Example 773.

TABLE 8

| Example | Structure | ESMS: |
|---|---|---|
| 93 | 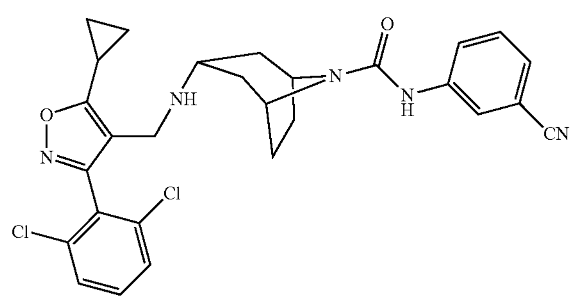 [SMILES: N#Cc1cccc(NC(=O)N2C3CCC2CC(NCc2c(-c4c(Cl)cccc4Cl)noc2C2CC2)C3)c1] | M + 1: 536.16 |
| 825 | 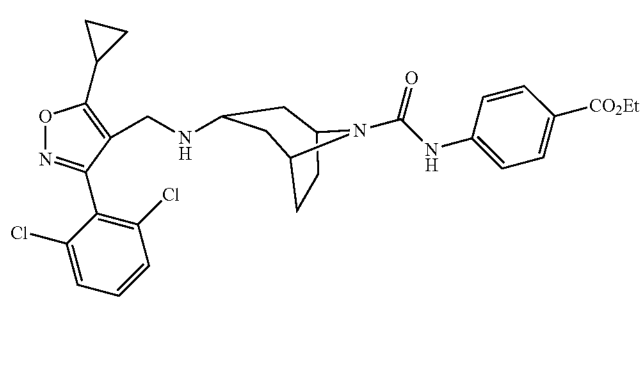 [SMILES: CCOC(=O)c1ccc(NC(=O)N2C3CCC2CC(NCc2c(-c4c(Cl)cccc4Cl)noc2C2CC2)C3)cc1] | M + 1: 583.19 |

TABLE 8-continued
| Example | Structure | ESMS: |
|---|---|---|
| 826 | 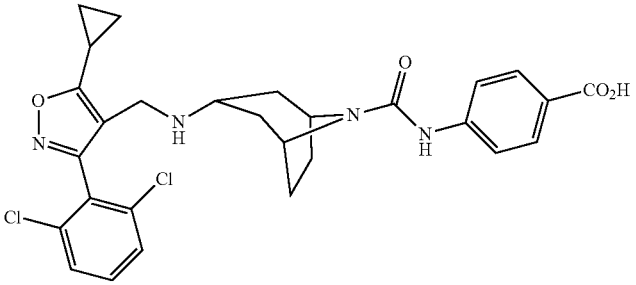 [SMILES: O=C(O)c1ccc(NC(=O)N2C3CCC2CC(NCc2c(-c4c(Cl)cccc4Cl)noc2C2CC2)C3)cc1] | M + 1: 555.16 |
| 827 | 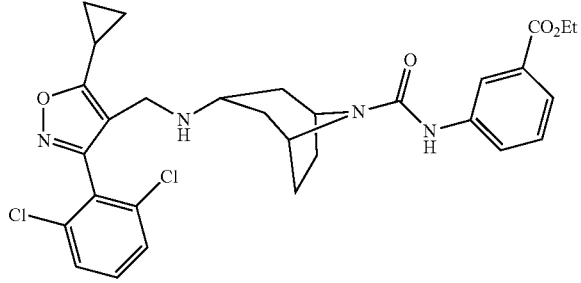 [SMILES: CCOC(=O)c1cccc(NC(=O)N2C3CCC2CC(NCc2c(-c4c(Cl)cccc4Cl)noc2C2CC2)C3)c1] | M + 1: 583.19 |
| 828 | 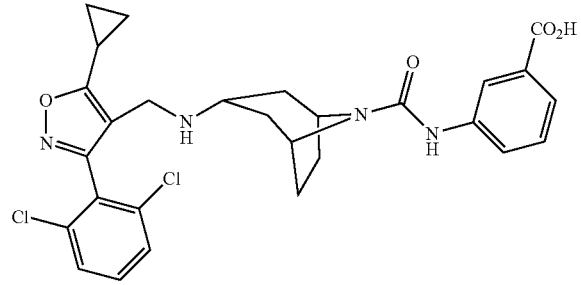 [SMILES: O=C(O)c1cccc(NC(=O)N2C3CCC2CC(NCc2c(-c4c(Cl)cccc4Cl)noc2C2CC2)C3)c1] | M + 1: 555.16 |
| 829 | 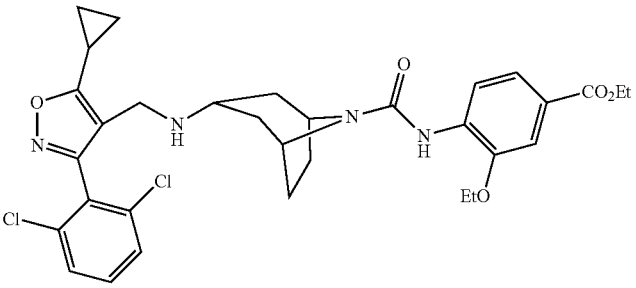 [SMILES: CCOC(=O)c1ccc(NC(=O)N2C3CCC2CC(NCc2c(-c4c(Cl)cccc4Cl)noc2C2CC2)C3)c(OCC)c1] | M + 1: 627.22 |
| 830 | 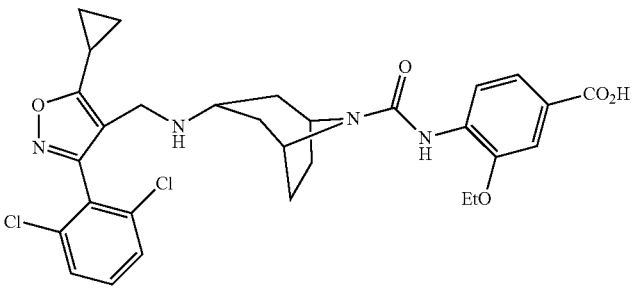 [SMILES: CCOc1cc(C(=O)O)ccc1NC(=O)N1C2CCC1CC(NCc1c(-c3c(Cl)cccc3Cl)noc1C1CC1)C2] | M + 1: 599.18 |

TABLE 8-continued

| Example | Structure | ESMS: |
|---|---|---|
| 831 | 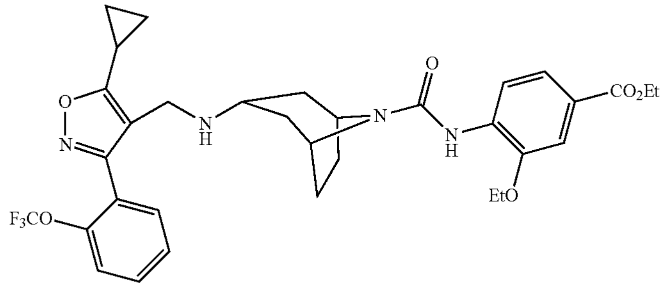 [SMILES: CCOC(=O)c1ccc(NC(=O)N2C3CCC2CC(NCc2c(-c4ccccc4OC(F)(F)F)noc2C2CC2)C3)c(OCC)c1] | M + 1: 643.28 |
| 832 | 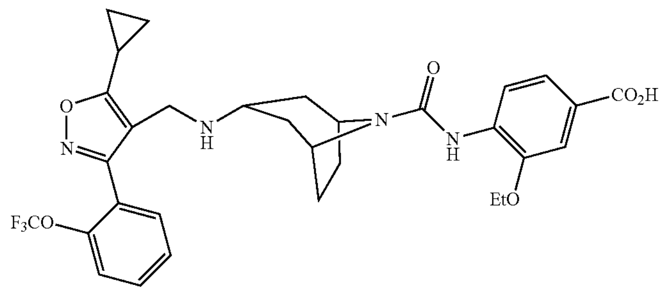 [SMILES: CCOc1cc(C(=O)O)ccc1NC(=O)N1C2CCC1CC(NCc1c(-c3ccccc3OC(F)(F)F)noc1C1CC1)C2] | M + 1: 615.25 |
| 121 | 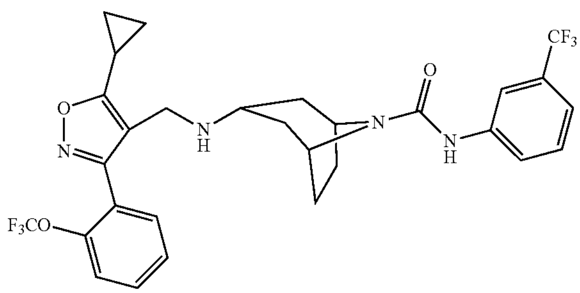 [SMILES: O=C(Nc1cccc(C(F)(F)F)c1)N1C2CCC1CC(NCc1c(-c3ccccc3OC(F)(F)F)noc1C1CC1)C2] | M + 1: 595.22 |

Assays

Human FXR (NR1H4) Assay

Determination of a ligand mediated Gal4 promoter driven transactivation to quantify ligand binding mediated activation of FXR. FXR Reporter Assay kit purchased from Indigo Bioscience (Catalogue number: IB00601) to determine the potency and efficacy of compounds that can induce FXR activation. The principle application of this reporter assay system is to quantify functional activity of human FXR. The assay utilizes non-human mammalian cells, CHO (Chinese hamster ovary) cells engineered to express human NR1H4 protein (referred to as FXR). Reporter cells also incorporate the cDNA encoding beetle luciferase which catalyzes the substrates and yields photon emission. Luminescence intensity of the reaction is quantified using a plate-reading luminometer, Envision. Reporter Cells include the luciferase reporter gene functionally linked to an FXR responsive promoter. Thus, quantifying changes in luciferase expression in the treated reporter cells provides a sensitive surrogate measure of the changes in FXR activity. $EC_{50}$ and efficacy (normalize to CDCA set as 100%) is determined by XLFit. The assay is according to the manufacturer's instructions. In brief, the assay was performed in white, 96 well plates using final volume of 100 ul containing cells with different doses of compounds. Retrieve Reporter Cells from −80° C. storage. Perform a rapid thaw of the frozen cells by transferring a 10 ml volume of 37° C. cell recovery medium into the tube of frozen cells. Recap the tube of Reporter Cells and immediately place it in a 37° C. water bath for 5-10 minutes. Retrieve the tube of Reporter Cell Suspension from the water bath. Sanitize the outside surface of the tube with a 70% alcohol swab, and then transfer it into the cell culture hood. Dispense 90 μl of cell suspension into each well of the 96-well Assay Plate. Transfer the plate into 37° C. incubator, allowing the cells adherent to the bottom of the well. Dilute compounds in Dilution Plate (DP), and administrate to cells at Assay Plate (AP). DMSO content of the samples was kept at 0.2%. Cells were incubated for additional 22 hours before luciferase activities were measured. Thirty minutes before intending to quantify FXR activity, remove Detection Substrate and Detection Buffer from the refrigerator and place them in a low-light area so that they may equilibrate to room temperature. Remove the plate's lid and discard all media contents by ejecting it into an appropriate waste container. Gently tap the inverted plate onto a clean absorbent paper towel to remove residual droplets. Cells will remain tightly adhered to well bottoms. Add 100 μl of luciferase detection reagent to each well of the assay plate. Allow the assay plate to rest at room temperature for at least 5 minutes following the addition of LDR. Set the instrument (Envision) to perform a single 5 second "plate shake" prior to reading the first assay well. Read time may be 0.5 second (500 mSec) per well. $EC_{50}$ and Efficacy (normalize to CDCA set as 100%) is determined by XLFit.

To assess the FXR agonistic potency of the example compounds as well as for the reference compound (1), potency ranges were determined in the Human FXR (NR1H4) Assay as listed below in Table 9. The efficacy was normalized to CDCA set as 100%. (A=EC50<10 nM; B=10 nM<EC50<0.1 µM; C=0.1 µM<EC50<1 µM; D=EC50>1 µM)

TABLE 9

| Example | EC50 | Efficacy (%) | Example | EC50 | Efficacy (%) |
|---|---|---|---|---|---|
| CDCA | D | 100 | 727 | A | 263 |
| 185 | C | 229 | 12 | A | 152 |
| 691 | B | 165 | 692 | A | 156 |
| 693 | C | 203 | 694 | C | 124 |
| 695 | B | 140 | 181 | A | 217 |
| 183 | C | 229 | 219 | C | 152 |
| 217 | D | 121 | 216 | C | 138 |
| 9 | B | 258 | 696 | A | 246 |
| 1 | A | 253 | 24 | C | 211 |
| 697 | C | 174 | 698 | B | 182 |
| 8 | C | 195 | 19 | B | 177 |
| 6 | C | 146 | 10 | B | 201 |
| 3 | A | 154 | 15 | A | 169 |
| 13 | A | 298 | 7 | B | 231 |
| 699 | B | 232 | 700 | A | 292 |
| 701 | C | 306 | 702 | A | 258 |
| 20 | B | 263 | 835 | A | 223 |
| 18 | A | 207 | 703 | A | 170 |
| 11 | A | 141 | 704 | A | 157 |
| 182 | B | 215 | 184 | A | 264 |
| 16 | C | 295 | 17 | B | 234 |
| 21 | B | 242 | 14 | A | 121 |
| 30 | B | 140 | 186 | B | 192 |
| 187 | B | 235 | 705 | A | 242 |
| 706 | B | 207 | 707 | B | 220 |
| 708 | A | 209 | 194 | A | 137 |
| 195 | B | 153 | 196 | A | 150 |
| 198 | A | 179 | 709 | C | 119 |
| 212 | A | 151 | 197 | B | 163 |
| 199 | C | 131 | 710 | B | 170 |
| 213 | C | 141 | 189 | B | 135 |
| 215 | A | 147 | 214 | B | 135 |
| 25 | A | 126 | 711 | A | 157 |
| 712 | B | 144 | 713 | A | 162 |
| 714 | B | 156 | 715 | B | 123 |
| 5 | B | 142 | 716 | C | 43 |
| 717 | C | 149 | 718 | B | 119 |
| 719 | C | 104 | 720 | A | 171 |
| 721 | B | 133 | 722 | A | 115 |
| 723 | C | 140 | 724 | B | 137 |
| 725 | C | 140 | 200 | A | 75 |
| 201 | A | 75 | 726 | A | 81 |
| 727 | B | 22 | 728 | B | 141 |
| 729 | A | 148 | 22 | A | 312 |
| 4 | B | 278 | 23 | B | 337 |
| 730 | A | 252 | 190 | B | 146 |
| 192 | A | 187 | 731 | A | 229 |
| 732 | A | 180 | 733 | A | 175 |
| 734 | B | 172 | 836 | A | 135 |
| 735 | C | 136 | 736 | A | 136 |
| 737 | A | 179 | 738 | C | 139 |
| 739 | B | 108 | 740 | A | 90 |
| 741 | A | 87 | 742 | B | 36 |
| 228 | C | 234 | 227 | B | 220 |
| 229 | C | 178 | 743 | D | 140 |
| 744 | D | 165 | 230 | B | 175 |
| 237 | C | 159 | 239 | B | 193 |
| 745 | C | 147 | 746 | D | 156 |
| 747 | C | 145 | 748 | B | 103 |
| 236 | B | 158 | 238 | A | 179 |
| 749 | B | 104 | 750 | C | 76 |
| 751 | C | 26 | 266 | C | 211 |
| 752 | D | 239 | 753 | B | 217 |
| 754 | C | 236 | 755 | C | 220 |
| 756 | C | 205 | 757 | C | 257 |
| 262 | D | 164 | 265 | C | 229 |
| 758 | C | 233 | 264 | D | 228 |
| 759 | D | 205 | 263 | D | 207 |

TABLE 9-continued

| Example | EC50 | Efficacy (%) | Example | EC50 | Efficacy (%) |
|---|---|---|---|---|---|
| 760 | D | 180 | 761 | D | 105 |
| 762 | C | 6 | 763 | C | 211 |
| 764 | C | 230 | 765 | B | 272 |
| 766 | D | 192 | 767 | C | 136 |
| 768 | D | 33 | 769 | C | 132 |
| 770 | D | 93 | 771 | D | 54 |
| 772 | D | 31 | 833 | D | 80 |
| 834 | C | 102 | 589 | D | 76 |
| 590 | D | 67 | 591 | D | 166 |
| 592 | D | 227 | 593 | D | 40 |
| 594 | C | 49 | 595 | D | 7 |
| 596 | D | 48 | 597 | C | 53 |
| 598 | B | 105 | 773 | B | 135 |
| 93 | B | 146 | 774 | A | 102 |
| 775 | A | 82 | 776 | C | 11 |
| 211 | C | 2 | 111 | A | 95 |
| 778 | A | 248 | 779 | B | 50 |
| 780 | C | 0 | 781 | B | 100 |
| 782 | B | 20 | 783 | C | 0 |
| 784 | A | 102 | 785 | B | 46 |
| 786 | B | 44 | 787 | A | 97 |
| 788 | B | 31 | 789 | B | 57 |
| 790 | B | 49 | 791 | C | 11 |
| 792 | A | 92 | 793 | A | 99 |
| 794 | A | 80 | 795 | B | 44 |
| 796 | A | 95 | 797 | A | 129 |
| 798 | B | 124 | 799 | A | 133 |
| 800 | A | 54 | 801 | B | 70 |
| 802 | C | 28 | 803 | C | 8 |
| 804 | B | 90 | 805 | B | 104 |
| 806 | B | 5 | 807 | B | 42 |
| 808 | B | 32 | 285 | B | 17 |
| 809 | B | 43 | 810 | B | 64 |
| 811 | B | 66 | 812 | B | 102 |
| 813 | B | 16 | 814 | B | 112 |
| 815 | B | 36 | 816 | B | 36 |
| 293 | B | 14 | 817 | B | 20 |
| 818 | B | 25 | 819 | B | 11 |
| 820 | B | 13 | 821 | B | 75 |
| 822 | A | 76 | 823 | B | 112 |
| 247 | A | 56 | 824 | B | 28 |
| 825 | B | 104 | 826 | B | 63 |
| 827 | A | 110 | 828 | B | 59 |
| 829 | B | 57 | 830 | A | 82 |
| 831 | B | 15 | 832 | B | 50 |
| 121 | B | 29 | | | |

While this invention has been particularly shown and described with references to preferred embodiments thereof, it will be understood by those skilled in the art that various changes in form and details may be made therein without departing from the scope of the invention encompassed by the appended claims.

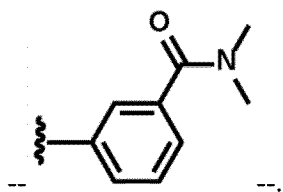
At Column 394
In Claim 16, at Example 521 2nd formula delete " 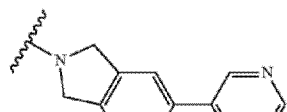 " and insert
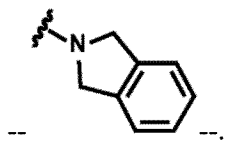
At Column 400
In Claim 16, at Example 546 2nd formula delete " 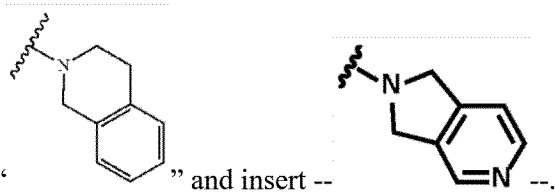 ".
At Column 436
In Claim 18, at Example 665 2nd formula delete " 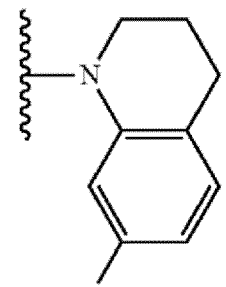 " and insert
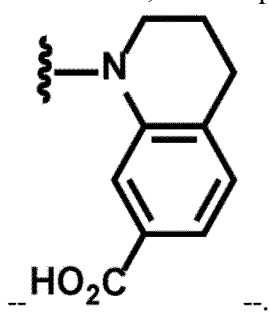

What is claimed is:

1. A compound represented by Formula I,

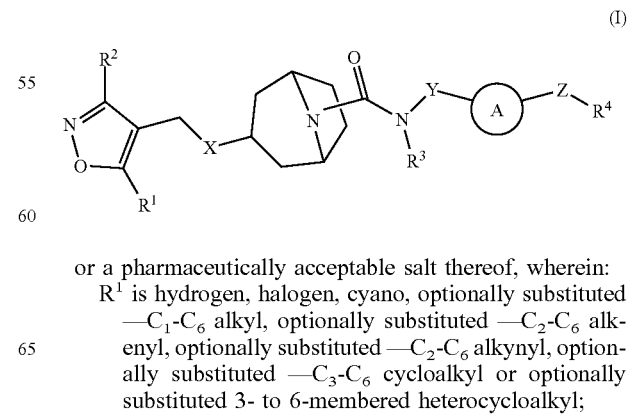

or a pharmaceutically acceptable salt thereof, wherein:
$R^1$ is hydrogen, halogen, cyano, optionally substituted —$C_1$-$C_6$ alkyl, optionally substituted —$C_2$-$C_6$ alkenyl, optionally substituted —$C_2$-$C_6$ alkynyl, optionally substituted —$C_3$-$C_6$ cycloalkyl or optionally substituted 3- to 6-membered heterocycloalkyl;

$R^2$ is an optionally substituted aryl, optionally substituted heteroaryl, substituted arylalkyl, optionally substituted heteroarylalkyl, optionally substituted —$C_3$-$C_{12}$ cycloalkyl, or optionally substituted 3- to 12-membered heterocycloalkyl;

X is O or $NR^3$;

Each $R^3$ is independently selected from the group consisting of hydrogen, optionally substituted —$C_1$-$C_6$ alkyl, and optionally substituted —$C_3$-$C_6$ cycloalkyl;

Y, Y' and Z are independently selected from absent and optionally substituted —$C_1$-$C_6$ alkyl;

(A) is optionally substituted —$C_5$-$C_{14}$ cycloalkyl, optionally substituted —$C_5$-$C_{14}$ cycloalkenyl, optionally substituted aryl, optionally substituted biaryl, optionally substituted 5- to 14-membered heterocycle or optionally substituted heteroaryl;

$R^4$ is hydrogen, hydroxy, tetrazolyl, cyano, —$CHF_2$, —$CO_2R^7$, —O—Y'—$CO_2R^7$, —$NR^5$—Y'—$CO_2R^7$, $CONR^5R^6$,

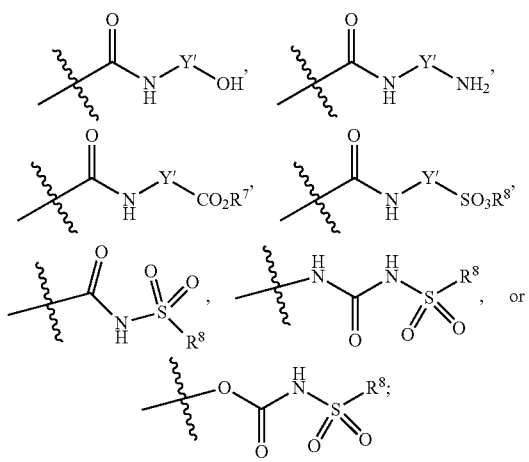

$R^5$ and $R^6$ are independently selected from group consisting of:
1) Hydrogen;
2) Optionally substituted —$C_1$-$C_8$ alkyl;
3) Optionally substituted —$C_2$-$C_8$ alkenyl;
4) Optionally substituted —$C_2$-$C_8$ alkynyl; and
5) Optionally substituted —$C_3$-$C_8$ cycloalkyl;

Alternatively, $R^5$ and $R^6$ are taken together with the nitrogen atom to which they are attached to form an optionally substituted 3- to 6-membered heterocycloalkyl;

$R^7$ is selected from the group consisting of:
1) Hydrogen;

2) 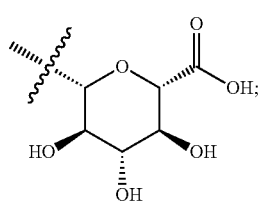

3) Optionally substituted —$C_1$-$C_8$ alkyl;
4) Optionally substituted —$C_2$-$C_8$ alkenyl;
5) Optionally substituted —$C_2$-$C_8$ alkynyl; and
6) Optionally substituted —$C_3$-$C_8$ cycloalkyl;

$R^8$ is selected from the group consisting of:
1) Optionally substituted —$C_1$-$C_8$ alkyl;
2) Optionally substituted —$C_2$-$C_8$ alkenyl;
3) Optionally substituted —$C_2$-$C_8$ alkynyl;
4) Optionally substituted —$C_3$-$C_8$ cycloalkyl;
5) Optionally substituted —$C_3$-$C_8$ cycloalkenyl;
6) Optionally substituted 3- to 8-membered heterocycloalkyl;
7) Optionally substituted 3- to 8-membered heterocycloalkenyl;
8) Optionally substituted aryl;
9) Optionally substituted aryl —$C_1$-$C_8$-alkyl;
10) Optionally substituted heteroaryl;
11) Optionally substituted heteroaryl —$C_1$-$C_8$-alkyl; and
12) $NR^5R^6$;

alternatively, the moiety represented by —$N(R^3)$—Y is an optionally substituted 3- to 8-membered heterocycloalkyl which is fused to (A).

2. The compound of claim 1, wherein $R^1$ is optionally substituted isopropyl, cyclopropyl, or tert-butyl.

3. The compound of claim 1, wherein $R^1$ is optionally substituted phenyl or optionally substituted heteroaryl.

4. The compound of claim 1, wherein $R^1$ is selected from the groups set forth below:

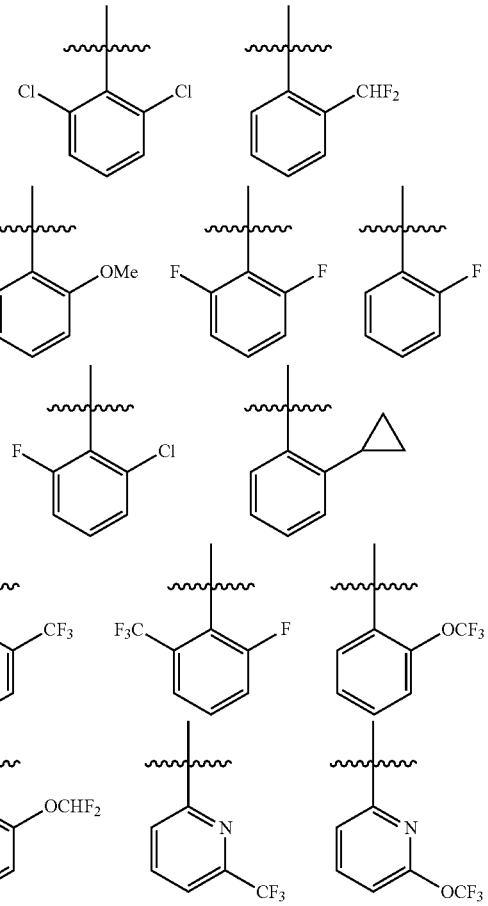

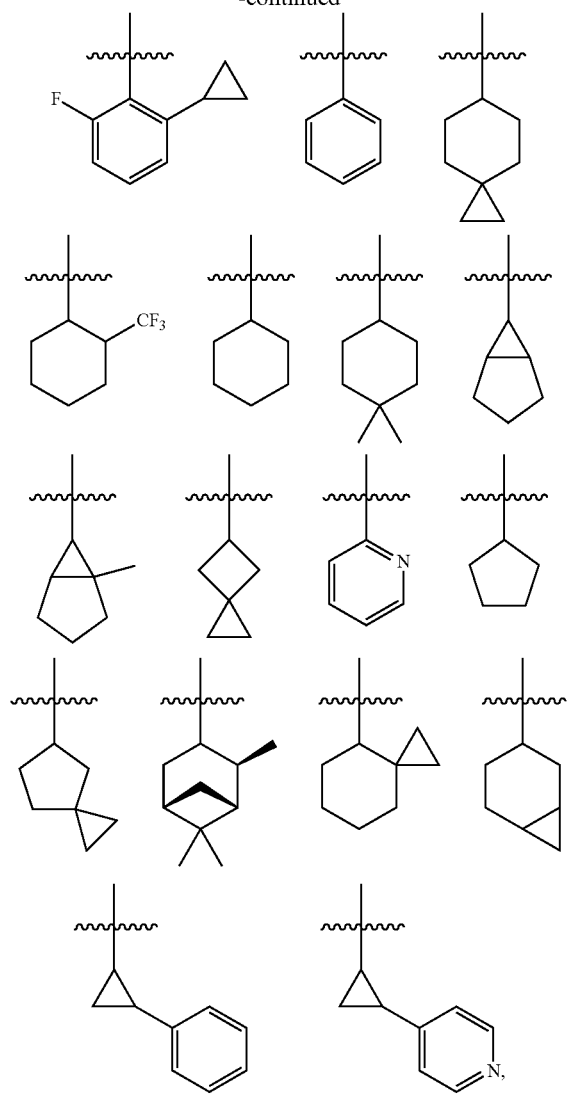

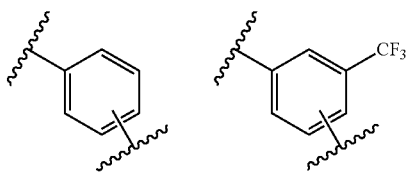
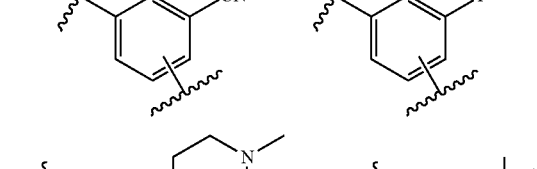
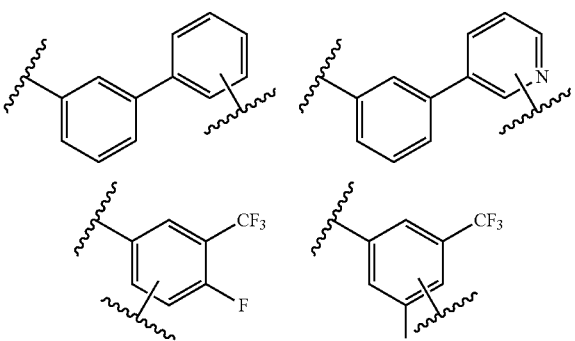
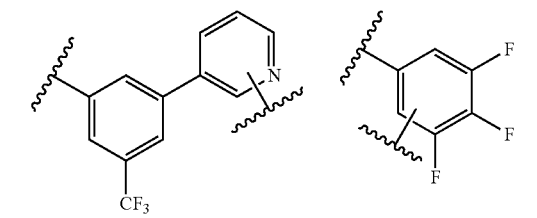

wherein each of said groups is optionally further substituted.

5. The compound of claim 1, wherein  is optionally substituted and selected from phenyl, pyridyl, pyrimidinyl, pyrazolyl, thienyl, thiazolyl, triazolyl, isothiazolyl, pyrrolyl, pyrazolyl, oxazolyl, oxadiazolyl, imidazolyl, furanyl, indolyl, benzothienyl, naphthyl, quinolyl, naphthyridyl, quinoxalyl, pyridopyrazolyl, pyridooxazolyl, pyridothiazolyl, isoquinolyl, pyridofuranyl, indazolyl, benzisoxazolyl, benzofuranyl, benzotriazolyl, and benzothiazolyl.

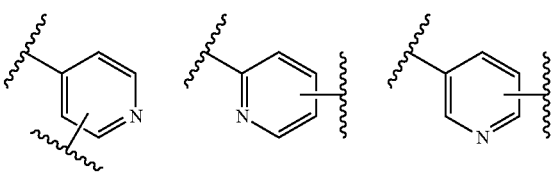
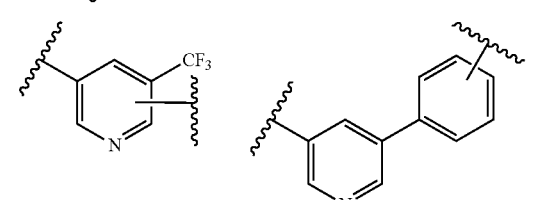

6. The compound of claim 1, wherein  is an optionally substituted biaryl group.

7. The compound of claim 1, wherein  is selected from the groups set forth below:

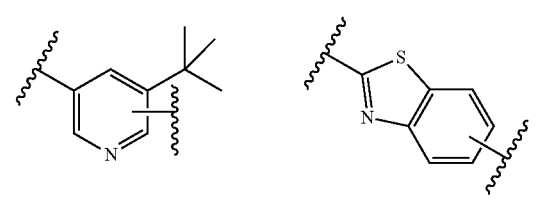

-continued

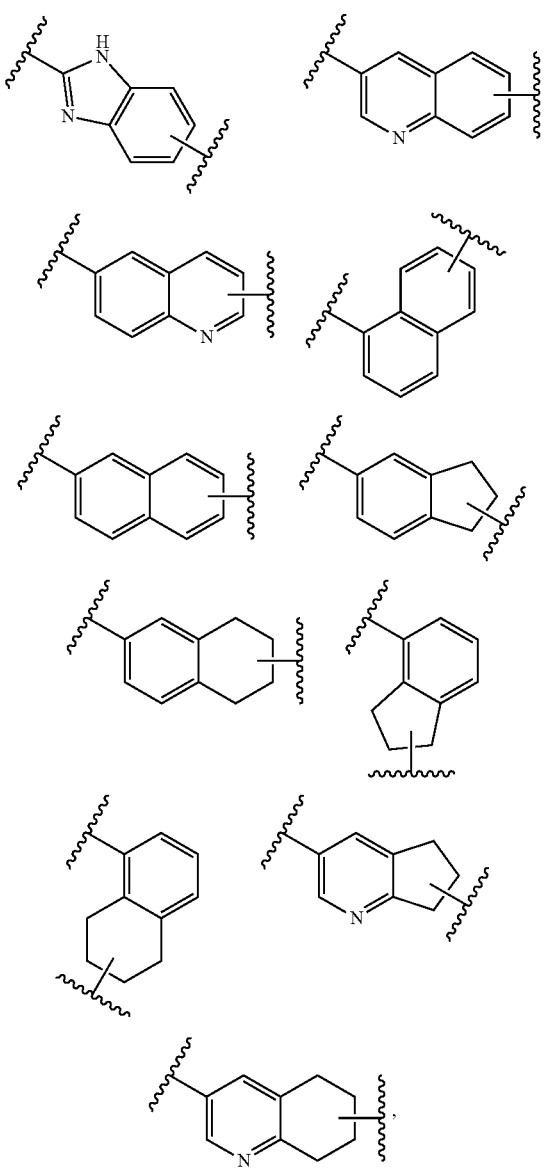

wherein each of said groups is optionally further substituted.

8. The compound of claim 1, represented by Formula (IIa) or (IIb),

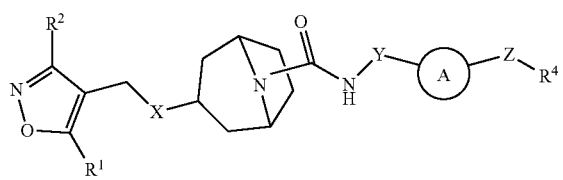
(IIa)

-continued

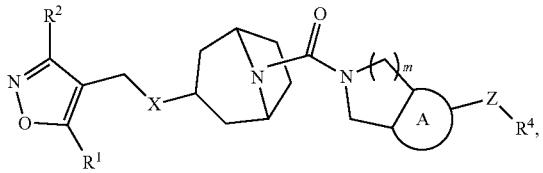
(IIb)

or a pharmaceutically acceptable salt thereof,
wherein m is 0, 1, 2 or 3; and $R^1$, $R^2$, $R^4$, X, Y, Z and (A) are as defined in claim 1.

9. The compound of claim 1, represented by Formula (IIIa) or (IIIb),

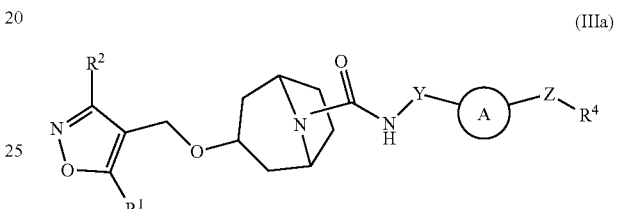
(IIIa)

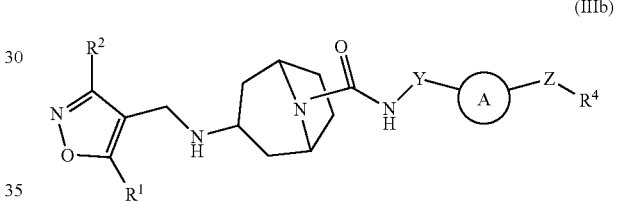
(IIIb)

or a pharmaceutically acceptable salt thereof, wherein $R^1$, $R^2$, $R^4$, Y, Z and (A) are as defined in claim 1.

10. The compound of claim 1, represented by Formula (IVa) or (IVb),

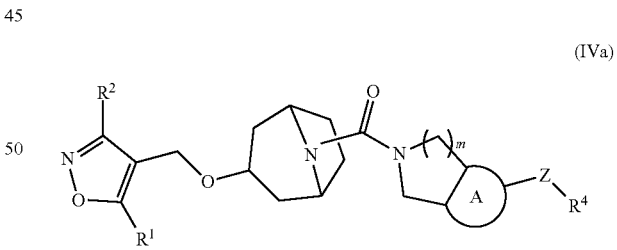
(IVa)

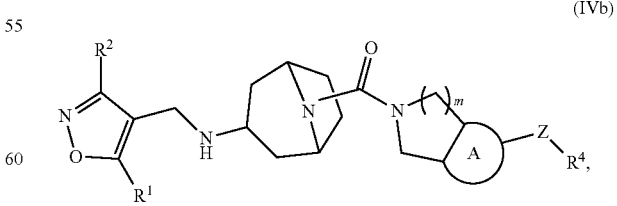
(IVb)

or a pharmaceutically acceptable salt thereof,
wherein m is 0, 1, 2 or 3; and $R^1$, $R^2$, $R^4$, Y, Z and (A) are as defined in claim 1.

11. The compound of claim 1, represented by Formula V,

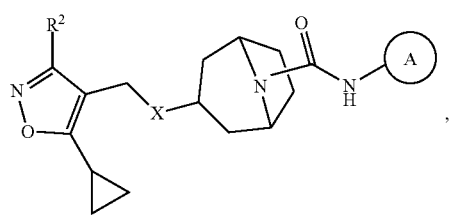

or a pharmaceutically acceptable salt thereof, wherein R², X, and Ⓐ are as defined in claim 1.

12. The compound of claim 11, selected from compounds of Formula (V) wherein R², X, and Ⓐ are delineated for each compound in Table 1, or a pharmaceutically acceptable salt thereof:

TABLE 1

| Compound | R² | X | Ⓐ |
|---|---|---|---|
| 1 | 2,6-diCl-phenyl | O | 3-F-phenyl |
| 2 | 2,6-diCl-phenyl | O | 3-CF₃-phenyl |
| 3 | 2,6-diCl-phenyl | O | 3-CN-phenyl |
| 4 | 2,6-diCl-phenyl | O | 3-tBu-phenyl |
| 5 | 2,6-diCl-phenyl | O | 3-(1-methylpiperidin-4-yl)-phenyl |
| 6 | 2,6-diCl-phenyl | O | 2-CF₃-phenyl |
| 7 | 2,6-diCl-phenyl | O | 2-F-phenyl |
| 8 | 2,6-diCl-phenyl | O | 4-CF₃-phenyl |
| 9 | 2,6-diCl-phenyl | O | 4-CN-phenyl |
| 10 | 2,6-diCl-phenyl | O | 3,4,5-triF-phenyl |
| 11 | 2,6-diCl-phenyl | O | 3-CF₃-5-F-phenyl |
| 12 | 2,6-diCl-phenyl | O | 3-(pyridin-3-yl)-phenyl |
| 13 | 2,6-diCl-phenyl | O | 3-(1-methyl-1H-pyrazol-4-yl)-phenyl |

TABLE 1-continued

| Compound | R² | X | A |
|---|---|---|---|
| 14 | 2,6-dichlorophenyl | O | 3-(pyridin-3-yl)-5-(trifluoromethyl)phenyl |
| 15 | 2,6-dichlorophenyl | O | pyridin-3-yl |
| 16 | 2,6-dichlorophenyl | O | pyridin-2-yl |
| 17 | 2,6-dichlorophenyl | O | pyridin-4-yl |
| 18 | 2,6-dichlorophenyl | O | 5-(trifluoromethyl)pyridin-3-yl |
| 19 | 2,6-dichlorophenyl | O | naphthalen-1-yl |
| 20 | 2,6-dichlorophenyl | O | naphthalen-2-yl |
| 21 | 2,6-dichlorophenyl | O | quinolin-3-yl |
| 22 | 2,6-dichlorophenyl | O | quinolin-6-yl |
| 23 | 2,6-dichlorophenyl | O | benzo[d]thiazol-2-yl |
| 24 | 2,6-dichlorophenyl | O | 3-sulfamoylphenyl |
| 25 | 2,6-dichlorophenyl | O | 3-(N,N-dimethylsulfamoyl)phenyl |
| 26 | 2,6-dichlorophenyl | O | 3-(cyclopropylsulfonyl)phenyl |
| 27 | 2,6-dichlorophenyl | O | 3-(difluoro(pyridin-3-yl)methyl)phenyl |
| 28 | 2,6-dichlorophenyl | O | 5,6,7,8-tetrahydronaphthalen-2-yl |
| 29 | 2,6-dichlorophenyl | O | 5,6,7,8-tetrahydroquinolin-3-yl |

TABLE 1-continued

| Compound | R² | X | A |
|---|---|---|---|
| 30 | 2,6-dichlorophenyl | O | cyclohexyl |
| 31 | 2-(F₃CO)phenyl | O | 3-(CF₃)phenyl |
| 32 | 2-(F₃CO)phenyl | O | 3-fluorophenyl |
| 33 | 2-(F₃CO)phenyl | O | 3-cyanophenyl |
| 34 | 2-(F₃CO)phenyl | O | 3-tert-butylphenyl |
| 35 | 2-(F₃CO)phenyl | O | 3-(1-methylpiperidin-4-yl)phenyl |
| 36 | 2-(F₃CO)phenyl | O | 2-(CF₃)phenyl |
| 37 | 2-(F₃CO)phenyl | O | 2-fluorophenyl |
| 38 | 2-(F₃CO)phenyl | O | 4-(CF₃)phenyl |
| 39 | 2-(F₃CO)phenyl | O | 4-cyanophenyl |
| 40 | 2-(F₃CO)phenyl | O | 3,4,5-trifluorophenyl |
| 41 | 2-(F₃CO)phenyl | O | 3-(CF₃)-5-fluorophenyl |
| 42 | 2-(F₃CO)phenyl | O | 3-(pyridin-3-yl)phenyl |
| 43 | 2-(F₃CO)phenyl | O | 3-(1-methyl-1H-pyrazol-4-yl)phenyl |
| 44 | 2-(F₃CO)phenyl | O | 3-(CF₃)-5-(pyridin-3-yl)phenyl |
| 45 | 2-(F₃CO)phenyl | O | pyridin-3-yl |
| 46 | 2-(F₃CO)phenyl | O | pyridin-2-yl |

TABLE 1-continued

| Compound | R² | X | A |
|---|---|---|---|
| 47 | F₃CO-phenyl | O | pyridin-4-yl |
| 48 | F₃CO-phenyl | O | 5-(trifluoromethyl)pyridin-3-yl |
| 49 | F₃CO-phenyl | O | naphthalen-1-yl |
| 50 | F₃CO-phenyl | O | naphthalen-2-yl |
| 51 | F₃CO-phenyl | O | quinolin-3-yl |
| 52 | F₃CO-phenyl | O | quinolin-6-yl |
| 53 | F₃CO-phenyl | O | benzothiazol-2-yl |
| 54 | F₃CO-phenyl | O | 3-sulfamoylphenyl |
| 55 | F₃CO-phenyl | O | 3-(N,N-dimethylsulfamoyl)phenyl |
| 56 | F₃CO-phenyl | O | 3-(cyclopropylsulfonyl)phenyl |
| 57 | F₃CO-phenyl | O | 3-(difluoro(pyridin-3-yl)methyl)phenyl |
| 58 | F₃CO-phenyl | O | 5,6,7,8-tetrahydronaphthalen-2-yl |
| 59 | F₃CO-phenyl | O | 5,6,7,8-tetrahydroquinolin-3-yl |
| 60 | F₃CO-phenyl | O | cyclohexyl |
| 61 | spiro[2.5]oct-6-yl | O | 3-(trifluoromethyl)phenyl |
| 62 | spiro[2.5]oct-6-yl | O | 3-fluorophenyl |
| 63 | spiro[2.5]oct-6-yl | O | 3-cyanophenyl |
| 64 | spiro[2.5]oct-6-yl | O | 3-tert-butylphenyl |

TABLE 1-continued

| Compound | R² | X | A |
|---|---|---|---|
| 65 | spiro[2.5]octyl | O | 4-(1-methylpiperidin-4-yl)phenyl |
| 66 | spiro[2.5]octyl | O | 2-(trifluoromethyl)phenyl |
| 67 | spiro[2.5]octyl | O | 2-fluorophenyl |
| 68 | spiro[2.5]octyl | O | 4-(trifluoromethyl)phenyl |
| 69 | spiro[2.5]octyl | O | 4-cyanophenyl |
| 70 | spiro[2.5]octyl | O | 3,4,5-trifluorophenyl |
| 71 | spiro[2.5]octyl | O | 3-fluoro-5-(trifluoromethyl)phenyl |
| 72 | spiro[2.5]octyl | O | 3-(pyridin-3-yl)phenyl |
| 73 | spiro[2.5]octyl | O | 3-(1-methyl-1H-pyrazol-4-yl)phenyl |
| 74 | spiro[2.5]octyl | O | 3-(pyridin-3-yl)-5-(trifluoromethyl)phenyl |
| 75 | spiro[2.5]octyl | O | pyridin-3-yl |
| 76 | spiro[2.5]octyl | O | pyridin-2-yl |
| 77 | spiro[2.5]octyl | O | pyridin-4-yl |
| 78 | spiro[2.5]octyl | O | 5-(trifluoromethyl)pyridin-3-yl |
| 79 | spiro[2.5]octyl | O | naphthalen-1-yl |
| 80 | spiro[2.5]octyl | O | naphthalen-2-yl |
| 81 | spiro[2.5]octyl | O | quinolin-3-yl |
| 82 | spiro[2.5]octyl | O | quinolin-6-yl |
| 83 | spiro[2.5]octyl | O | benzo[d]thiazol-2-yl |

TABLE 1-continued

| Compound | R² | X | A |
|---|---|---|---|
| 84 | spiro[2.5]octyl | O | 3-(sulfamoyl)phenyl |
| 85 | spiro[2.5]octyl | O | 3-(N,N-dimethylsulfamoyl)phenyl |
| 86 | spiro[2.5]octyl | O | 3-(cyclopropylsulfonyl)phenyl |
| 87 | spiro[2.5]octyl | O | 3-[difluoro(pyridin-3-yl)methyl]phenyl |
| 88 | spiro[2.5]octyl | O | 5,6,7,8-tetrahydronaphthalen-2-yl |
| 89 | spiro[2.5]octyl | O | 5,6,7,8-tetrahydroquinolin-3-yl |
| 90 | spiro[2.5]octyl | O | cyclohexyl |
| 91 | 2,6-dichlorophenyl | NH | 3-fluorophenyl |
| 92 | 2,6-dichlorophenyl | NH | 3-(trifluoromethyl)phenyl |
| 93 | 2,6-dichlorophenyl | NH | 3-cyanophenyl |
| 94 | 2,6-dichlorophenyl | NH | 3-tert-butylphenyl |
| 95 | 2,6-dichlorophenyl | NH | 3-(1-methylpiperidin-4-yl)phenyl |
| 96 | 2,6-dichlorophenyl | NH | 2-(trifluoromethyl)phenyl |
| 97 | 2,6-dichlorophenyl | NH | 2-fluorophenyl |
| 98 | 2,6-dichlorophenyl | NH | 4-(trifluoromethyl)phenyl |
| 99 | 2,6-dichlorophenyl | NH | 4-cyanophenyl |
| 100 | 2,6-dichlorophenyl | NH | 3,4,5-trifluorophenyl |

TABLE 1-continued

| Compound | R² | X | A |
|---|---|---|---|
| 101 | 2,6-dichlorophenyl | NH | 3-trifluoromethyl-5-fluorophenyl |
| 102 | 2,6-dichlorophenyl | NH | 3-(pyridin-3-yl)phenyl |
| 103 | 2,6-dichlorophenyl | NH | 3-(1-methyl-1H-pyrazol-4-yl)phenyl |
| 104 | 2,6-dichlorophenyl | NH | 3-trifluoromethyl-5-(pyridin-3-yl)phenyl |
| 105 | 2,6-dichlorophenyl | NH | pyridin-3-yl |
| 106 | 2,6-dichlorophenyl | NH | pyridin-2-yl |
| 107 | 2,6-dichlorophenyl | NH | pyridin-4-yl |
| 108 | 2,6-dichlorophenyl | NH | 5-trifluoromethylpyridin-3-yl |
| 109 | 2,6-dichlorophenyl | NH | naphthalen-1-yl |
| 110 | 2,6-dichlorophenyl | NH | naphthalen-2-yl |
| 111 | 2,6-dichlorophenyl | NH | quinolin-3-yl |
| 112 | 2,6-dichlorophenyl | NH | quinolin-6-yl |
| 113 | 2,6-dichlorophenyl | NH | benzothiazol-2-yl |
| 114 | 2,6-dichlorophenyl | NH | 3-sulfamoylphenyl |
| 115 | 2,6-dichlorophenyl | NH | 3-(N,N-dimethylsulfamoyl)phenyl |
| 116 | 2,6-dichlorophenyl | NH | 3-(cyclopropylsulfonyl)phenyl |

TABLE 1-continued

| Compound | R² | X | A |
|---|---|---|---|
| 117 | 2,6-diCl-phenyl | NH | 3-(difluoro(pyridin-3-yl)methyl)phenyl |
| 118 | 2,6-diCl-phenyl | NH | 5,6,7,8-tetrahydronaphthalen-2-yl |
| 119 | 2,6-diCl-phenyl | NH | 5,6,7,8-tetrahydroquinolin-3-yl |
| 120 | 2,6-diCl-phenyl | NH | cyclohexyl |
| 121 | 2-F₃CO-phenyl | NH | 3-CF₃-phenyl |
| 122 | 2-F₃CO-phenyl | NH | 3-F-phenyl |
| 123 | 2-F₃CO-phenyl | NH | 3-CN-phenyl |
| 124 | 2-F₃CO-phenyl | NH | 3-tert-butyl-phenyl |
| 125 | 2-F₃CO-phenyl | NH | 3-(1-methylpiperidin-4-yl)phenyl |
| 126 | 2-F₃CO-phenyl | NH | 2-CF₃-phenyl |
| 127 | 2-F₃CO-phenyl | NH | 2-F-phenyl |
| 128 | 2-F₃CO-phenyl | NH | 4-CF₃-phenyl |
| 129 | 2-F₃CO-phenyl | NH | 4-CN-phenyl |
| 130 | 2-F₃CO-phenyl | NH | 3,4,5-triF-phenyl |
| 131 | 2-F₃CO-phenyl | NH | 3-F-5-CF₃-phenyl |
| 132 | 2-F₃CO-phenyl | NH | 3-(pyridin-3-yl)phenyl |

TABLE 1-continued

| Compound | R² | X | A |
|---|---|---|---|
| 133 | F₃CO-phenyl | NH | phenyl-(1-methyl-pyrazol-4-yl) |
| 134 | F₃CO-phenyl | NH | 3-(CF₃)-5-(pyridin-3-yl)phenyl |
| 135 | F₃CO-phenyl | NH | pyridin-3-yl |
| 136 | F₃CO-phenyl | NH | pyridin-2-yl |
| 137 | F₃CO-phenyl | NH | pyridin-4-yl |
| 138 | F₃CO-phenyl | NH | 5-(CF₃)-pyridin-3-yl |
| 139 | F₃CO-phenyl | NH | naphthalen-1-yl |
| 140 | F₃CO-phenyl | NH | naphthalen-2-yl |
| 141 | F₃CO-phenyl | NH | quinolin-3-yl |
| 142 | F₃CO-phenyl | NH | quinolin-6-yl |
| 143 | F₃CO-phenyl | NH | benzothiazol-2-yl |
| 144 | F₃CO-phenyl | NH | 3-(SO₂NH₂)phenyl |
| 145 | F₃CO-phenyl | NH | 3-(SO₂NMe₂)phenyl |
| 146 | F₃CO-phenyl | NH | 3-(SO₂-cyclopropyl)phenyl |
| 147 | F₃CO-phenyl | NH | 3-(CF₂-pyridin-3-yl)phenyl |
| 148 | F₃CO-phenyl | NH | 5,6,7,8-tetrahydronaphthalen-2-yl |
| 149 | F₃CO-phenyl | NH | 5,6,7,8-tetrahydroquinolin-3-yl |
| 150 | F₃CO-phenyl | NH | cyclohexyl |

TABLE 1-continued

| Compound | R² | X | A |
|---|---|---|---|
| 151 | spiro[2.5]octyl | NH | 3-CF₃-phenyl |
| 152 | spiro[2.5]octyl | NH | 3-F-phenyl |
| 153 | spiro[2.5]octyl | NH | 3-CN-phenyl |
| 154 | spiro[2.5]octyl | NH | 3-tert-butyl-phenyl |
| 155 | spiro[2.5]octyl | NH | 3-(1-methylpiperidin-4-yl)phenyl |
| 156 | spiro[2.5]octyl | NH | 2-CF₃-phenyl |
| 157 | spiro[2.5]octyl | NH | 2-F-phenyl |
| 158 | spiro[2.5]octyl | NH | 4-CF₃-phenyl |
| 159 | spiro[2.5]octyl | NH | 4-CN-phenyl |
| 160 | spiro[2.5]octyl | NH | 3,4,5-trifluorophenyl |
| 161 | spiro[2.5]octyl | NH | 3-CF₃-5-F-phenyl |
| 162 | spiro[2.5]octyl | NH | 3-(pyridin-3-yl)phenyl |
| 163 | spiro[2.5]octyl | NH | 3-(1-methyl-1H-pyrazol-4-yl)phenyl |
| 164 | spiro[2.5]octyl | NH | 3-CF₃-5-(pyridin-3-yl)phenyl |
| 165 | spiro[2.5]octyl | NH | pyridin-3-yl |
| 166 | spiro[2.5]octyl | NH | pyridin-2-yl |
| 167 | spiro[2.5]octyl | NH | pyridin-4-yl |
| 168 | spiro[2.5]octyl | NH | 5-CF₃-pyridin-3-yl |
| 169 | spiro[2.5]octyl | NH | naphthalen-1-yl |

TABLE 1-continued

| Compound | R² | X | A |
|---|---|---|---|
| 170 | spiro[2.5]octyl | NH | naphthalen-2-yl |
| 171 | spiro[2.5]octyl | NH | quinolin-3-yl |
| 172 | spiro[2.5]octyl | NH | quinolin-6-yl |
| 173 | spiro[2.5]octyl | NH | benzothiazol-2-yl |
| 174 | spiro[2.5]octyl | NH | 3-(sulfamoyl)phenyl |
| 175 | spiro[2.5]octyl | NH | 3-(N,N-dimethylsulfamoyl)phenyl |
| 176 | spiro[2.5]octyl | NH | 3-(cyclopropylsulfonyl)phenyl |
| 177 | spiro[2.5]octyl | NH | 3-(difluoro(pyridin-3-yl)methyl)phenyl |
| 178 | spiro[2.5]octyl | NH | 5,6,7,8-tetrahydronaphthalen-2-yl |
| 179 | spiro[2.5]octyl | NH | 5,6,7,8-tetrahydroquinolin-3-yl |
| 180 | spiro[2.5]octyl | NH | cyclohexyl |

13. The compound of claim 1, represented by Formula VI,

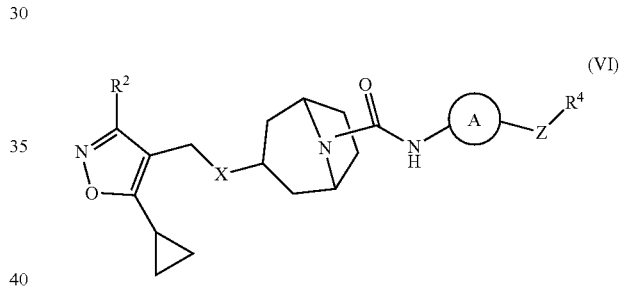

or a pharmaceutically acceptable salt thereof, wherein $R^2$, $R^4$, X, Z and (A) are as defined in claim 1.

14. The compound of claim 13, selected from compounds according to Formula (VI), wherein $R^2$, X, and (A)-Z-$R^4$ are delineated for each compound in Table 2, or a pharmaceutically acceptable salt thereof:

TABLE 2

| Example | R² | X | (A)-Z-R⁴ |
|---|---|---|---|
| 181 | 2,6-dichlorophenyl | O | 3-(CO₂Et)phenyl |

TABLE 2-continued
| Example | R² | X | ⟨A⟩–Z–R⁴ |
|---|---|---|---|
| 182 |  | O | 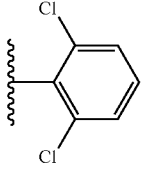 [SMILES: *c1c(Cl)cccc1Cl] |
| 183 | 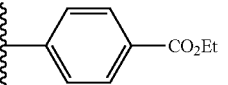 | O | 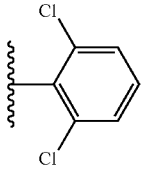 |
| 184 | 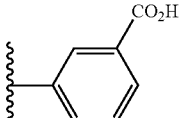 | O | 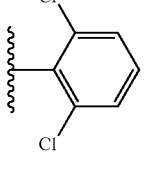 |
| 185 | 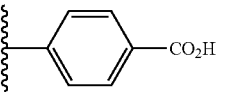 | O | 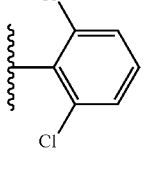 |
| 186 | 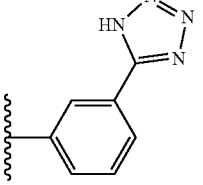 | O | 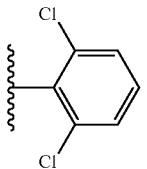 [SMILES: *c1c(Cl)cccc1Cl] |
| 187 | 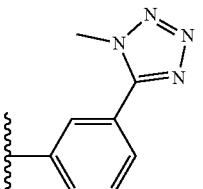 | O | 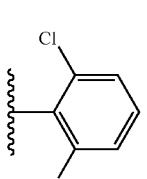 |
| 188 | 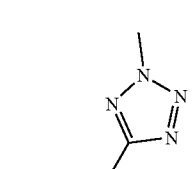 | O | 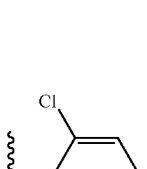 |

TABLE 2-continued

| Example | R² | X | A-Z-R⁴ |
|---|---|---|---|
| 189 | 2,6-diCl-phenyl | O | 4-CF₂H-phenyl |
| 190 | 2,6-diCl-phenyl | O | 3-MeO-4-CO₂Me-phenyl |
| 191 | 2,6-diCl-phenyl | O | 3-F-4-CO₂Me-phenyl |
| 192 | 2,6-diCl-phenyl | O | 3-MeO-4-CO₂H-phenyl |
| 193 | 2,6-diCl-phenyl | O | 3-F-4-CO₂H-phenyl |
| 194 | 2,6-diCl-phenyl | O | 2-CF₃-4-CO₂Me-phenyl (with CO₂Me para) |
| 195 | 2,6-diCl-phenyl | O | 2-CF₃-4-CO₂H-phenyl |
| 196 | 2,6-diCl-phenyl | O | 2-F-4-CO₂Me-phenyl |

TABLE 2-continued
| Example | R² | X | A-Z-R⁴ |
|---|---|---|---|
| 197 |  2,6-dichlorophenyl | O | 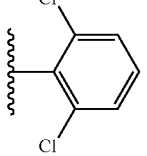 2-F, 4-CO₂H phenyl |
| 198 | 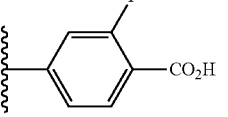 2,6-dichlorophenyl | O | 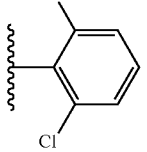 2,6-diF, 4-CO₂Me phenyl |
| 199 | 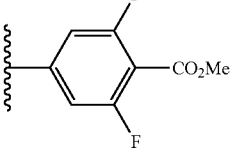 2,6-dichlorophenyl | O | 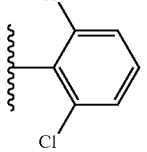 2,6-diF, 4-CO₂H phenyl |
| 200 | 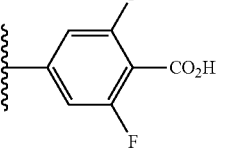 2,6-dichlorophenyl | O | 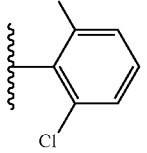 2-phenyl, 4-CO₂Me phenyl |
| 201 | 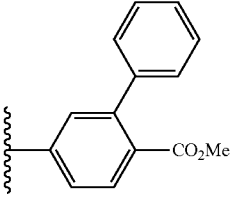 [SMILES: *c1ccc(C(=O)OC)c(-c2ccccc2)c1] 2,6-dichlorophenyl | O | 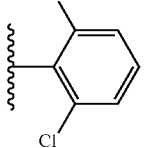 2-phenyl, 4-CO₂H phenyl |
| 202 | 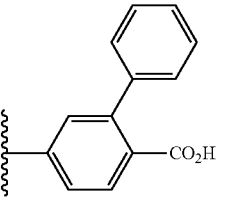 [SMILES: *c1ccc(C(=O)O)c(-c2ccccc2)c1] 2,6-dichlorophenyl | O | 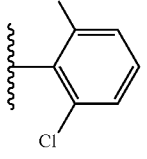 2-(3-pyridyl), 4-CO₂Me phenyl |
| 203 | 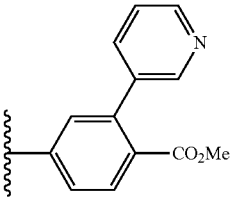 [SMILES: *c1ccc(C(=O)OC)c(-c2cccnc2)c1] 2,6-dichlorophenyl | O | 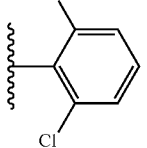 2-(3-pyridyl), 4-CO₂H phenyl |

TABLE 2-continued

| Example | R² | X | A-Z-R⁴ |
|---|---|---|---|
| 204 | 2,6-diCl-phenyl | O | 5-(pyridin-3-yl)-4-methoxy-2-(CO₂Me)-phenyl |
| 205 | 2,6-diCl-phenyl | O | 5-(pyridin-3-yl)-4-methoxy-2-(CO₂H)-phenyl |
| 206 | 2,6-diCl-phenyl | O | 2-(pyridin-3-yl)-3-(CO₂Me)-4-(CF₃)-phenyl |
| 207 | 2,6-diCl-phenyl | O | 2-(pyridin-3-yl)-3-(CO₂H)-4-(CF₃)-phenyl |
| 208 | 2,6-diCl-phenyl | O | 6-(CO₂Me)-naphth-2-yl |
| 209 | 2,6-diCl-phenyl | O | 6-(CO₂H)-naphth-2-yl |
| 210 | 2,6-diCl-phenyl | O | 3-(CO₂Me)-quinolin-6-yl |

TABLE 2-continued

| Example | R² | X | A-Z-R⁴ |
|---|---|---|---|
| 211 | 2,6-dichlorophenyl | O | quinolin-6-yl-3-CO₂H |
| 212 | 2,6-dichlorophenyl | O | 5-(6-CO₂Me)pyridin-3-yl |
| 213 | 2,6-dichlorophenyl | O | 5-(6-CO₂H)pyridin-3-yl |
| 214 | 2,6-dichlorophenyl | O | 3-(morpholine-4-carbonyl)phenyl |
| 215 | 2,6-dichlorophenyl | O | 3-(N,N-dimethylcarbamoyl)phenyl |
| 216 | 2,6-dichlorophenyl | O | 3-(methylsulfonylcarbamoyl)phenyl |
| 217 | 2,6-dichlorophenyl | O | 3-((4-methylphenylsulfonyl)carbamoyl)phenyl |

TABLE 2-continued

| Example | R² | X | (A)–Z–R⁴ |
|---|---|---|---|
| 218 | 2,6-diCl-phenyl | O | 3-(N-cyclopropylsulfonylcarbamoyl)phenyl 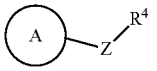 |
| 219 | 2,6-diCl-phenyl | O | 3-(N-(N,N-dimethylsulfamoyl)carbamoyl)phenyl 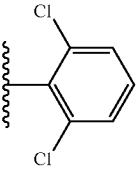 [SMILES: *c1c(Cl)cccc1Cl] |
| 220 | 2,6-diCl-phenyl | O | trans-4-carboxycyclohexyl 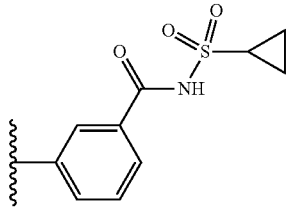 [SMILES: *c1cccc(C(=O)NS(=O)(=O)C2CC2)c1] |
| 221 | 2,6-diCl-phenyl | O | 4-(carboxymethylcarbamoyl)phenyl 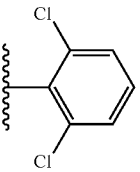 |
| 222 | 2,6-diCl-phenyl | O | 4-(2-sulfoethylcarbamoyl)phenyl 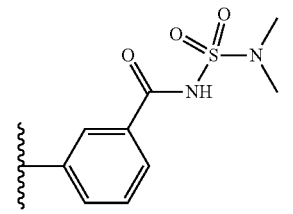 [SMILES: *c1cccc(C(=O)NS(=O)(=O)N(C)C)c1] |
| 223 | 2,6-diCl-phenyl | O | 3-(N-cyclopropylsulfonylureido)phenyl 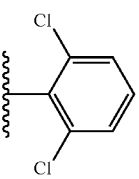 |
| 224 | 2,6-diCl-phenyl | O | 3-(N-(N,N-dimethylsulfamoyl)ureido)phenyl 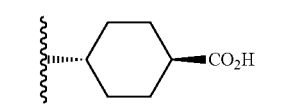 [SMILES: *[C@H]1CC[C@H](C(=O)O)CC1] |

TABLE 2-continued
| Example | R² | X | A—Z—R⁴ |
|---|---|---|---|
| 225 | 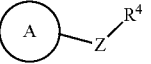 | O | 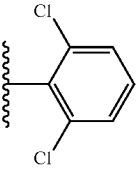 |
| 226 | 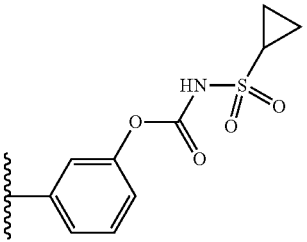 [SMILES: *c1cccc(OC(=O)NS(=O)(=O)C2CC2)c1] | O | 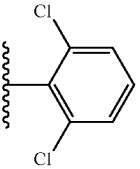 [SMILES: *c1c(Cl)cccc1Cl] |
| 227 | 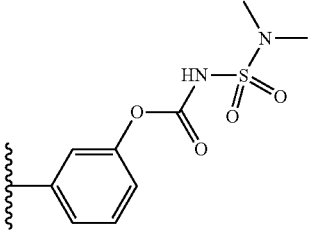 [SMILES: *c1cccc(OC(=O)NS(=O)(=O)N(C)C)c1] | O | 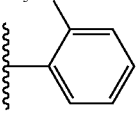 |
| 228 | 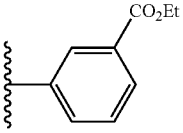 [SMILES: *c1cccc(C(=O)OCC)c1] | O | 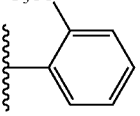 |
| 229 | 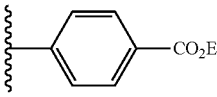 | O | 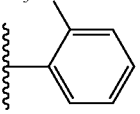 |
| 230 | 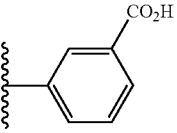 | O | 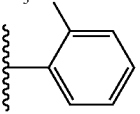 |
| 231 | 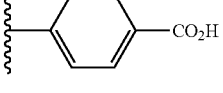 | O | 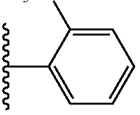 |
| 232 | 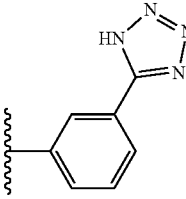 | O | 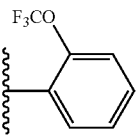 |

TABLE 2-continued
| Example | R² | X | A-Z-R⁴ |
|---|---|---|---|
| 233 | F₃CO- (phenyl) | O | 2-methyl-tetrazol-5-yl-phenyl 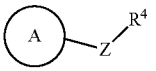 |
| 234 | F₃CO- (phenyl) | O | 1H-tetrazol-1-yl-phenyl 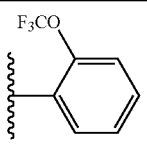 |
| 235 | F₃CO- (phenyl) | O | 4-CF₂H-phenyl 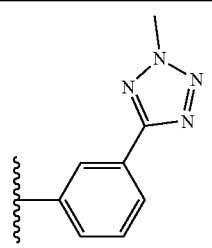 |
| 236 | F₃CO- (phenyl) | O | 3-MeO-4-CO₂Me-phenyl 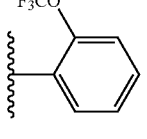 |
| 237 | F₃CO- (phenyl) | O | 3-F-4-CO₂Me-phenyl 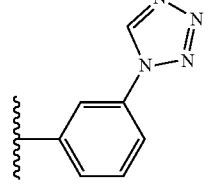 |
| 238 | F₃CO- (phenyl) | O | 3-MeO-4-CO₂H-phenyl 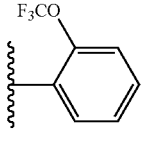 |
| 239 | F₃CO- (phenyl) | O | 3-F-4-CO₂H-phenyl 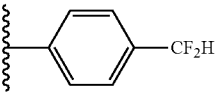 |
| 240 | F₃CO- (phenyl) | O | 2-CF₃-4-CO₂Me-phenyl 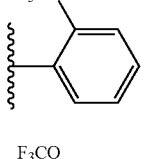 |
| 241 | F₃CO- (phenyl) | O | 2-CF₃-4-CO₂H-phenyl 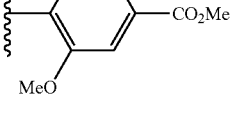 |

TABLE 2-continued

| Example | R² | X | ![A-Z-R⁴] |
|---|---|---|---|
| 242 | F₃CO-(phenyl) | O | (phenyl with F, CO₂Me) |
| 243 | F₃CO-(phenyl) | O | (phenyl with F, CO₂H) |
| 244 | F₃CO-(phenyl) | O | (phenyl with 2F, CO₂Me) |
| 245 | F₃CO-(phenyl) | O | (phenyl with 2F, CO₂H) |
| 246 | F₃CO-(phenyl) | O | (biphenyl, CO₂Me) |
| 247 | F₃CO-(phenyl) | O | (biphenyl, CO₂H) |
| 248 | F₃CO-(phenyl) | O | (pyridinyl-phenyl, CO₂Me) |
| 249 | F₃CO-(phenyl) | O | (pyridinyl-phenyl, CO₂H) |

TABLE 2-continued
| Example | R² | X | (A)–Z–R⁴ |
|---|---|---|---|
| 250 | 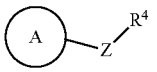 F₃CO- | O | 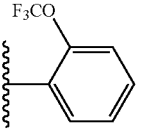 |
| 251 | 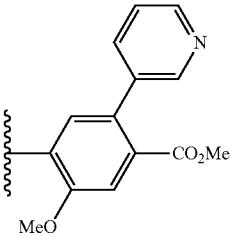 [SMILES: *c1cc(-c2cccnc2)c(C(=O)OC)cc1OC] F₃CO- | O | 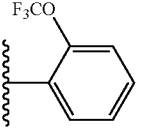 |
| 252 |  F₃CO- | O | 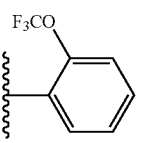 |
| 253 | 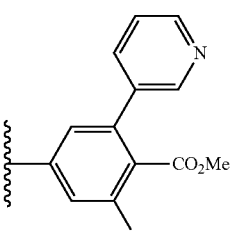 F₃CO- | O | 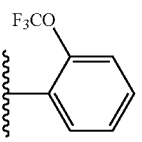 |
| 254 | 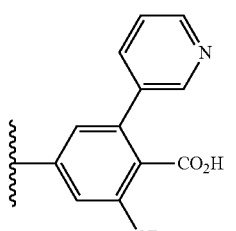 F₃CO- | O | 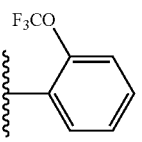 |
| 255 | 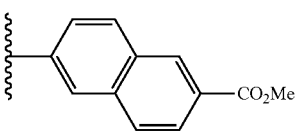 [SMILES: *c1ccc2cc(C(=O)OC)ccc2c1] F₃CO- | O | 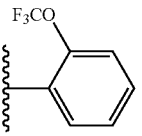 |
| 256 | 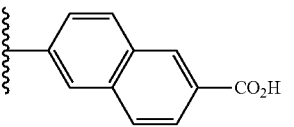 F₃CO- | O | 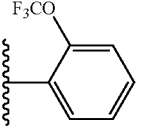 |

TABLE 2-continued

| Example | R² | X | (A)-Z-R⁴ |
|---|---|---|---|
| 257 | F₃CO- (phenyl) | O | quinoline with CO₂H |
| 258 | F₃CO- (phenyl) | O | pyridine with CO₂Me |
| 259 | F₃CO- (phenyl) | O | pyridine with CO₂H |
| 260 | F₃CO- (phenyl) | O | phenyl-C(O)-morpholine |
| 261 | F₃CO- (phenyl) | O | phenyl-C(O)-N(Me)₂ |
| 262 | F₃CO- (phenyl) | O | phenyl-C(O)NH-S(O)₂Me |
| 263 | F₃CO- (phenyl) | O | phenyl-C(O)NH-S(O)₂-(4-tolyl) |
| 264 | F₃CO- (phenyl) | O | phenyl-C(O)NH-S(O)₂-cyclopropyl |

TABLE 2-continued

| Example | R² | X | (A)-Z-R⁴ |
|---|---|---|---|
| 265 | F₃CO-(2-phenyl) | O | 3-phenyl-C(O)NH-S(O)₂-N(CH₃)₂ |
| 266 | F₃CO-(2-phenyl) | O | trans-cyclohexyl-CO₂H |
| 267 | F₃CO-(2-phenyl) | O | 4-phenyl-C(O)NH-CH₂-CO₂H |
| 268 | F₃CO-(2-phenyl) | O | 4-phenyl-C(O)NH-CH₂CH₂-SO₃H |
| 269 | F₃CO-(2-phenyl) | O | 3-phenyl-NH-C(O)-NH-S(O)₂-cyclopropyl |
| 270 | F₃CO-(2-phenyl) | O | 3-phenyl-NH-C(O)-NH-S(O)₂-N(CH₃)₂ |
| 271 | F₃CO-(2-phenyl) | O | 3-phenyl-O-C(O)-NH-S(O)₂-cyclopropyl |

TABLE 2-continued
| Example | R² | X | A-Z-R⁴ |
|---|---|---|---|
| 272 | 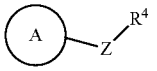 | O | 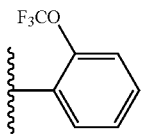 [SMILES: *c1ccccc1OC(F)(F)F] |
| 273 | 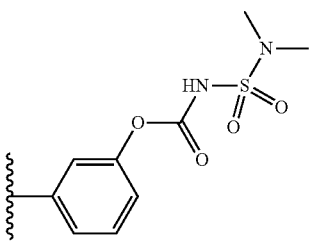 [SMILES: *c1cccc(OC(=O)NS(=O)(=O)N(C)C)c1] | O | 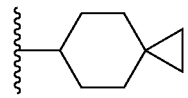 |
| 274 | 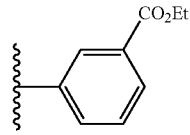 [SMILES: *c1cccc(C(=O)OCC)c1] | O | 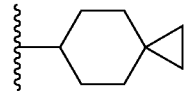 |
| 275 | 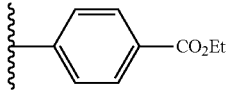 | O | 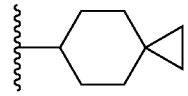 |
| 276 | 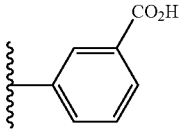 [SMILES: *c1cccc(C(=O)O)c1] | O | 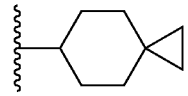 |
| 277 | 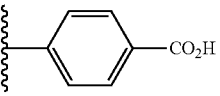 | O | 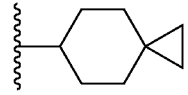 [SMILES: *C1CCC2(CC1)CC2] |
| 278 | 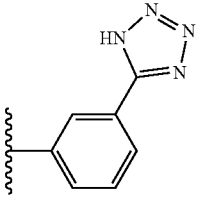 [SMILES: *c1cccc(-c2nnn[nH]2)c1] | O | 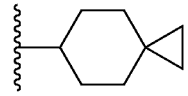 [SMILES: *C1CCC2(CC1)CC2] |
| 279 | 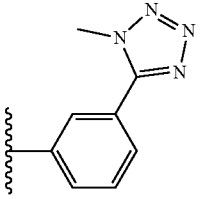 [SMILES: *c1cccc(-c2nnnn2C)c1] | O | 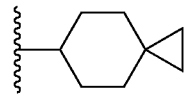 |

TABLE 2-continued

|  | | | A—Z—R⁴ | |
| --- | --- | --- | --- | --- |
| Example | R² | X | | |
| 280 | spiro[2.5]cyclohexyl | O | 3-(1H-tetrazol-1-yl)phenyl | |
| 281 | spiro[2.5]cyclohexyl | O | 4-(CF₂H)phenyl | |
| 282 | spiro[2.5]cyclohexyl | O | 4-CO₂Me-3-MeO-phenyl | |
| 283 | spiro[2.5]cyclohexyl | O | 4-CO₂Me-3-F-phenyl | |
| 284 | spiro[2.5]cyclohexyl | O | 4-CO₂H-3-MeO-phenyl | |
| 285 | spiro[2.5]cyclohexyl | O | 4-CO₂H-3-F-phenyl | |
| 286 | spiro[2.5]cyclohexyl | O | 4-CO₂Me-3-CF₃-phenyl | |
| 287 | spiro[2.5]cyclohexyl | O | 4-CO₂H-3-CF₃-phenyl | |
| 288 | spiro[2.5]cyclohexyl | O | 4-CO₂Me-2-F-phenyl | |
| 289 | spiro[2.5]cyclohexyl | O | 4-CO₂H-2-F-phenyl | |

TABLE 2-continued
| Example | R² | X | (A)—Z—R⁴ |
|---|---|---|---|
| 290 | 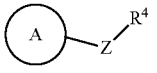 | O |  |
| 291 | 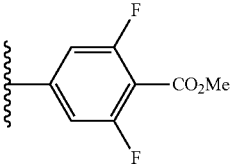 [SMILES: *c1cc(F)c(C(=O)OC)c(F)c1] | O | 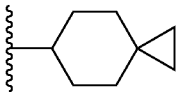 |
| 292 | 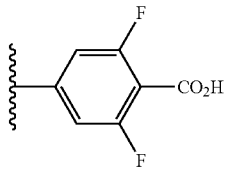 [SMILES: *c1cc(F)c(C(=O)O)c(F)c1] | O | 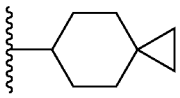 |
| 293 | 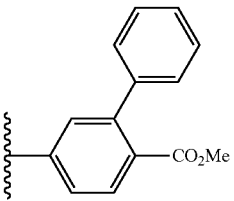 | O | 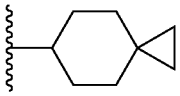 |
| 294 | 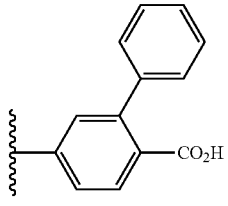 [SMILES: *c1ccc(C(=O)O)c(-c2ccccc2)c1] | O | 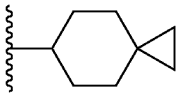 [SMILES: *C1CCC2(CC1)CC2] |
| 295 | 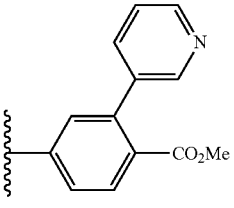 [SMILES: *c1ccc(C(=O)OC)c(-c2cccnc2)c1] | O | 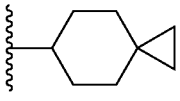 |
| 296 | 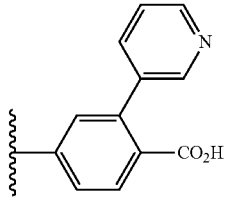 [SMILES: *c1ccc(C(=O)O)c(-c2cccnc2)c1] | O | 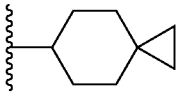 |

TABLE 2-continued
| Example | R² | X | 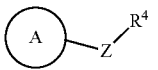 |
|---|---|---|---|
| 297 | 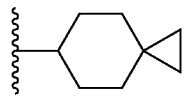 | O | 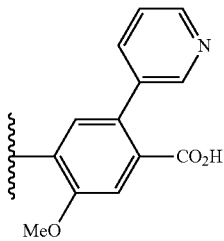 [SMILES: *c1cc(-c2cccnc2)c(C(=O)O)cc1OC] |
| 298 | 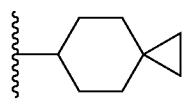 | O | 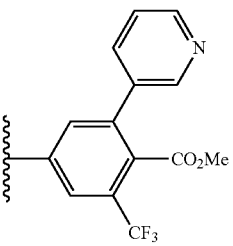 [SMILES: *c1cc(-c2cccnc2)c(C(=O)OC)c(C(F)(F)F)c1] |
| 299 | 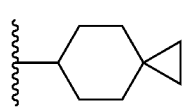 | O | 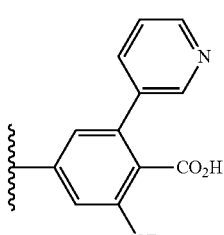 |
| 300 | 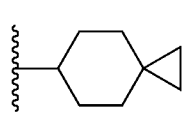 [SMILES: *C1CCC2(CC1)CC2] | O | 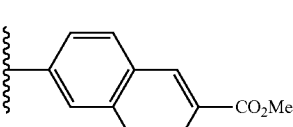 |
| 301 | 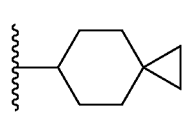 [SMILES: *C1CCC2(CC1)CC2] | O | 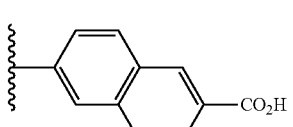 |
| 302 | 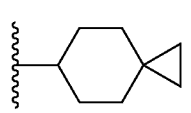 | O | 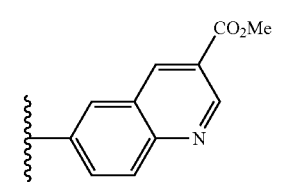 [SMILES: *c1ccc2ncc(C(=O)OC)cc2c1] |
| 303 | 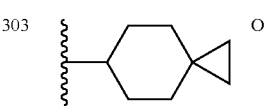 | O | 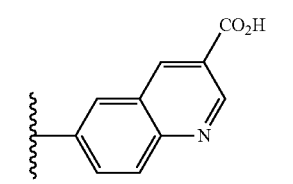 [SMILES: *c1ccc2ncc(C(=O)O)cc2c1] |
| 304 | 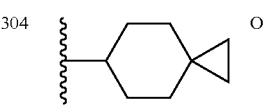 | O | 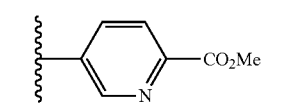 |

TABLE 2-continued
| Example | R² | X | 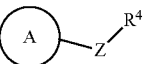 |
|---|---|---|---|
| 305 | 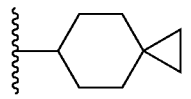 | O | 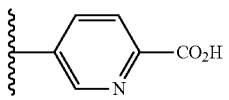 |
| 306 | 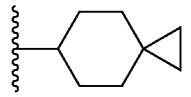 | O | 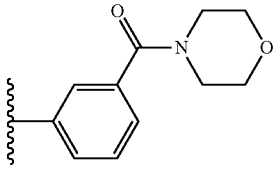 [SMILES: *c1cccc(C(=O)N2CCOCC2)c1] |
| 307 | 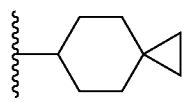 | O | 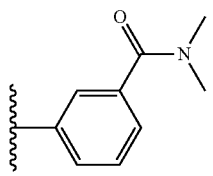 [SMILES: *c1cccc(C(=O)N(C)C)c1] |
| 308 | 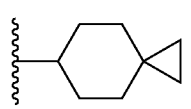 | O | 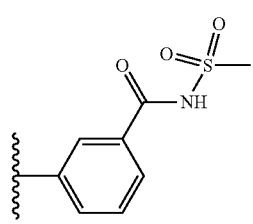 [SMILES: *c1cccc(C(=O)NS(C)(=O)=O)c1] |
| 309 | 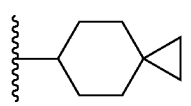 | O | 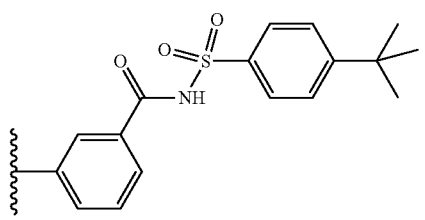 [SMILES: *c1cccc(C(=O)NS(=O)(=O)c2ccc(C(C)(C)C)cc2)c1] |
| 310 | 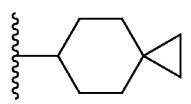 | O | 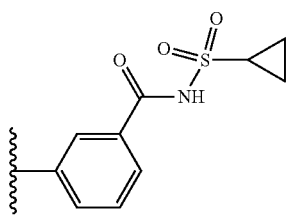 [SMILES: *c1cccc(C(=O)NS(=O)(=O)C2CC2)c1] |
| 311 | 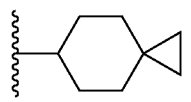 [SMILES: *C1CCC2(CC1)CC2] | O | 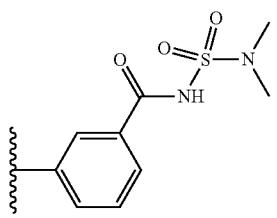 [SMILES: *c1cccc(C(=O)NS(=O)(=O)N(C)C)c1] |
| 312 | 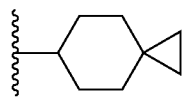 | O | 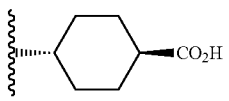 |

TABLE 2-continued
| Example | R² | X | (A)-Z-R⁴ |
|---------|-----|---|----------|
| 313 | 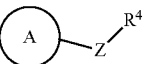 | O | 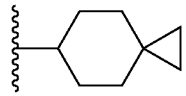 [SMILES: *C1CCC2(CC1)CC2] |
| 314 | 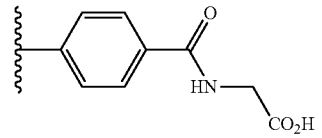 | O | 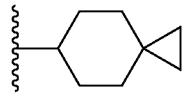 [SMILES: *C1CCC2(CC1)CC2] |
| 315 | 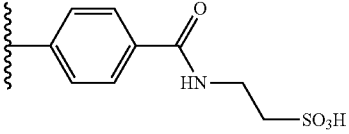 | O | 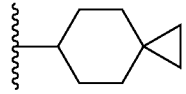 |
| 316 | 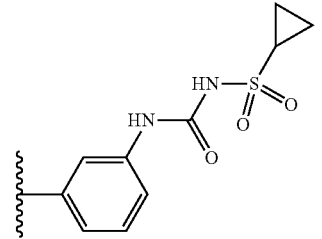 [SMILES: *c1cccc(NC(=O)NS(=O)(=O)C2CC2)c1] | O | 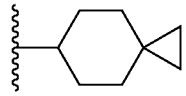 |
| 317 | 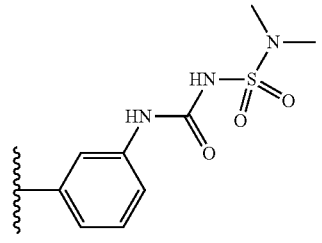 [SMILES: *c1cccc(NC(=O)NS(=O)(=O)N(C)C)c1] | O | 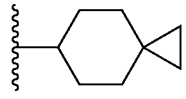 |
| 318 | 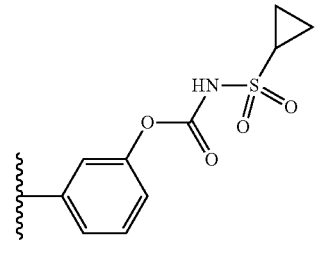 [SMILES: *c1cccc(OC(=O)NS(=O)(=O)C2CC2)c1] | O | 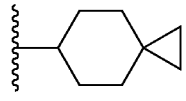 |
| 319 | 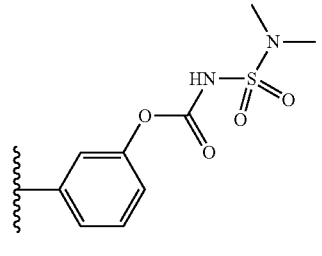 | NH | 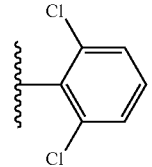 [SMILES: *c1c(Cl)cccc1Cl] |

TABLE 2-continued
| Example | R² | X | ![A-Z-R⁴] |
|---|---|---|---|
| 320 | 2,6-diCl-phenyl  | NH | 4-CO₂Et-phenyl 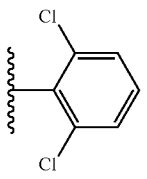 [SMILES: *c1c(Cl)cccc1Cl] |
| 321 | 2,6-diCl-phenyl 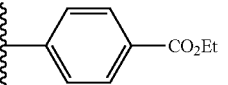 | NH | 3-CO₂H-phenyl 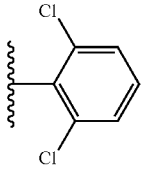 [SMILES: *c1c(Cl)cccc1Cl] |
| 322 | 2,6-diCl-phenyl 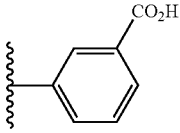 [SMILES: *c1cccc(C(=O)O)c1] | NH | 4-CO₂H-phenyl 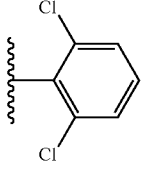 [SMILES: *c1c(Cl)cccc1Cl] |
| 323 | 2,6-diCl-phenyl 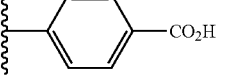 | NH | 3-(1H-tetrazol-5-yl)phenyl 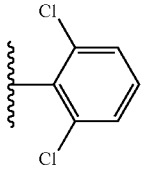 |
| 324 | 2,6-diCl-phenyl 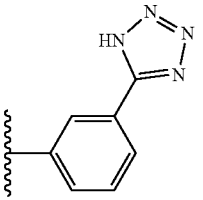 [SMILES: *c1cccc(-c2nnn[nH]2)c1] | NH | 3-(1-methyl-tetrazol-5-yl)phenyl 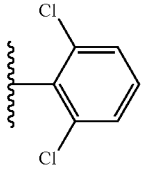 |
| 325 | 2,6-diCl-phenyl 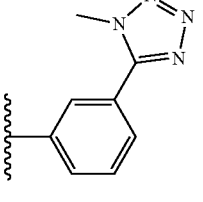 | NH | 3-(2-methyl-tetrazol-5-yl)phenyl 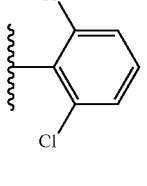 |
| 326 | 2,6-diCl-phenyl 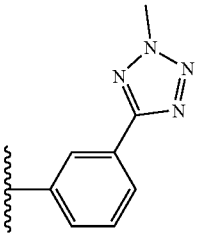 [SMILES: *c1cccc(-c2nnn(C)n2)c1] | NH | 3-(tetrazol-1-yl)phenyl 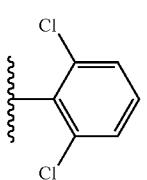 [SMILES: *c1c(Cl)cccc1Cl] |

TABLE 2-continued

| Example | R² | X | A–Z–R⁴ |
|---|---|---|---|
| 327 | 2,6-diCl-phenyl | NH | 4-CF₂H-phenyl |
| 328 | 2,6-diCl-phenyl | NH | 3-MeO-4-CO₂Me-phenyl |
| 329 | 2,6-diCl-phenyl | NH | 3-F-4-CO₂Me-phenyl |
| 330 | 2,6-diCl-phenyl | NH | 3-MeO-4-CO₂H-phenyl |
| 331 | 2,6-diCl-phenyl | NH | 3-F-4-CO₂H-phenyl |
| 332 | 2,6-diCl-phenyl | NH | 2-CF₃-4-CO₂Me-phenyl |
| 333 | 2,6-diCl-phenyl | NH | 2-CF₃-4-CO₂H-phenyl |
| 334 | 2,6-diCl-phenyl | NH | 2-F-4-CO₂Me-phenyl |

TABLE 2-continued

| Example | R² | X | (A)–Z–R⁴ |
|---|---|---|---|
| 335 | 2,6-diCl-phenyl | NH | 3-F, 4-CO₂H-phenyl |
| 336 | 2,6-diCl-phenyl | NH | 3,5-diF, 4-CO₂Me-phenyl |
| 337 | 2,6-diCl-phenyl | NH | 3,5-diF, 4-CO₂H-phenyl |
| 338 | 2,6-diCl-phenyl | NH | 3-phenyl, 4-CO₂Me-phenyl |
| 339 | 2,6-diCl-phenyl | NH | 3-phenyl, 4-CO₂H-phenyl |
| 340 | 2,6-diCl-phenyl | NH | 3-(pyridin-3-yl), 4-CO₂Me-phenyl |
| 341 | 2,6-diCl-phenyl | NH | 3-(pyridin-3-yl), 4-CO₂H-phenyl |

TABLE 2-continued
| Example | R² | X | 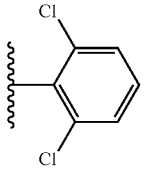 [SMILES: *c1c(Cl)cccc1Cl] |
|---|---|---|---|
| 342 | 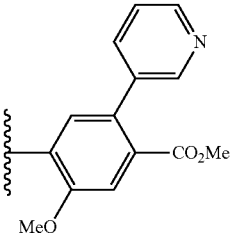 [SMILES: *c1cc(-c2cccnc2)c(C(=O)OC)cc1OC] | NH | 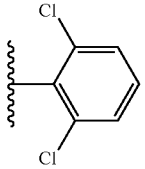 |
| 343 | 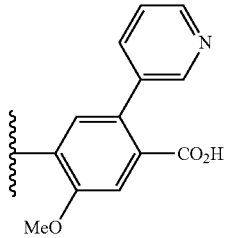 [SMILES: *c1cc(-c2cccnc2)c(C(=O)O)cc1OC] | NH | 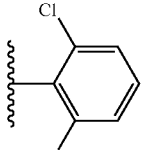 |
| 344 | 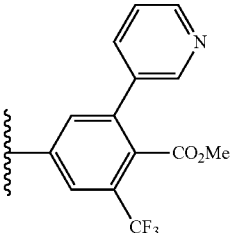 | NH | 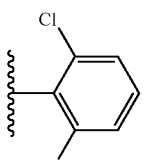 |
| 345 | 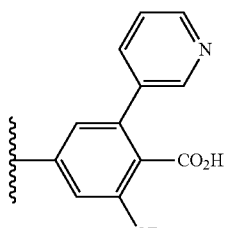 | NH | 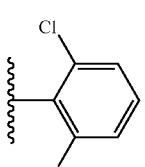 |
| 346 | 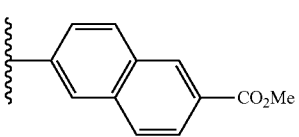 [SMILES: *c1ccc2cc(C(=O)OC)ccc2c1] | NH | 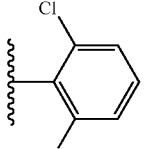 |
| 347 | 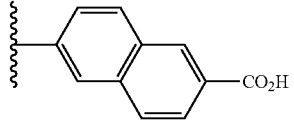 | NH | 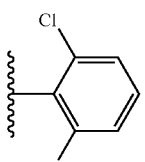 |
| 348 | 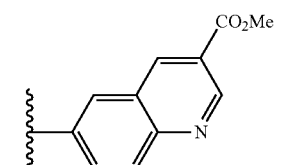 | NH |  |

TABLE 2-continued

| Example | R² | X | A–Z–R⁴ |
|---|---|---|---|
| 349 | 2,6-diCl-phenyl | NH | quinoline-3-CO₂H (6-yl) |
| 350 | 2,6-diCl-phenyl | NH | 5-(pyridin-2-yl)-CO₂Me |
| 351 | 2,6-diCl-phenyl | NH | 5-(pyridin-2-yl)-CO₂H |
| 352 | 2,6-diCl-phenyl | NH | 3-(morpholin-4-ylcarbonyl)phenyl |
| 353 | 2,6-diCl-phenyl | NH | 3-(N,N-dimethylcarbamoyl)phenyl |
| 354 | 2,6-diCl-phenyl | NH | 3-(methylsulfonylaminocarbonyl)phenyl |
| 355 | 2,6-diCl-phenyl | NH | 3-(4-methylphenylsulfonylaminocarbonyl)phenyl |

TABLE 2-continued

| Example | R² | X | (A)–Z–R⁴ |
|---|---|---|---|
| 356 | 2,6-diCl-phenyl | NH | 3-(cyclopropylsulfonylaminocarbonyl)phenyl |
| 357 | 2,6-diCl-phenyl | NH | 3-(N,N-dimethylsulfamoylaminocarbonyl)phenyl |
| 358 | 2,6-diCl-phenyl | NH | trans-4-carboxycyclohexyl |
| 359 | 2,6-diCl-phenyl | NH | 4-(carboxymethylaminocarbonyl)phenyl |
| 360 | 2,6-diCl-phenyl | NH | 4-(2-sulfoethylaminocarbonyl)phenyl |
| 361 | 2,6-diCl-phenyl | NH | 3-(cyclopropylsulfonylaminocarbonylamino)phenyl |
| 362 | 2,6-diCl-phenyl | NH | 3-(N,N-dimethylsulfamoylaminocarbonylamino)phenyl |

TABLE 2-continued

| Example | R² | X | A-Z-R⁴ |
|---|---|---|---|
| 363 | 2,6-dichlorophenyl | NH | 3-(cyclopropylsulfonylaminocarbonyloxy)phenyl 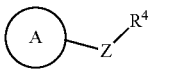 |
| 364 | 2,6-dichlorophenyl | NH | 3-(dimethylaminosulfonylaminocarbonyloxy)phenyl 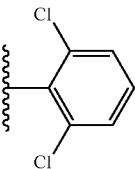 [SMILES: *c1c(Cl)cccc1Cl] |
| 365 | 2-(trifluoromethoxy)phenyl | NH | 3-(CO₂Et)phenyl 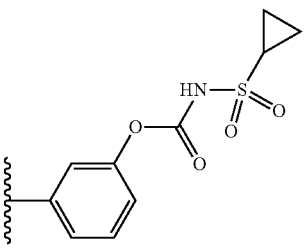 |
| 366 | 2-(trifluoromethoxy)phenyl | NH | 4-(CO₂Et)phenyl 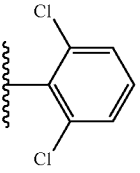 [SMILES: *c1c(Cl)cccc1Cl] |
| 367 | 2-(trifluoromethoxy)phenyl | NH | 3-(CO₂H)phenyl 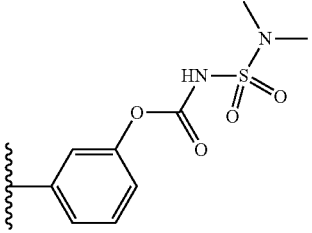 [SMILES: *c1cccc(OC(=O)NS(=O)(=O)N(C)C)c1] |
| 368 | 2-(trifluoromethoxy)phenyl | NH | 4-(CO₂H)phenyl 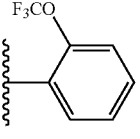 |
| 369 | 2-(trifluoromethoxy)phenyl | NH | 3-(1H-tetrazol-5-yl)phenyl 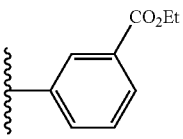 [SMILES: *c1cccc(C(=O)OCC)c1] |
| 370 | 2-(trifluoromethoxy)phenyl | NH | 3-(1-methyl-1H-tetrazol-5-yl)phenyl 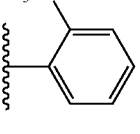 |

TABLE 2-continued
| Example | R² | X | A–Z–R⁴ |
|---|---|---|---|
| 371 | F₃CO– 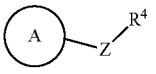 | NH |  |
| 372 | F₃CO– 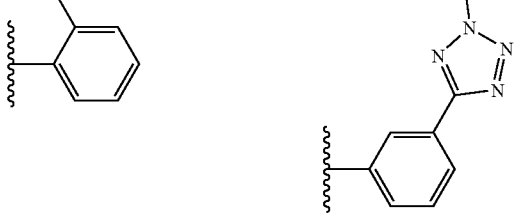 | NH |  |
| 373 | F₃CO– 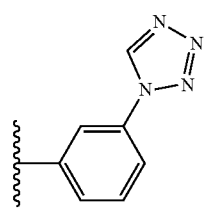 [SMILES: *c1cccc(-n2cnnn2)c1] | NH |  —CF₂H |
| 374 | F₃CO– 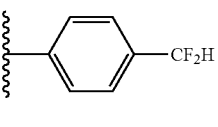 | NH |  —CO₂H, F |
| 375 | F₃CO– 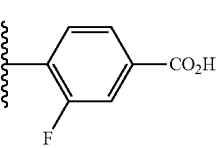 [SMILES: *c1ccc(C(=O)O)cc1F] | NH |  —CO₂Me, F |
| 376 | F₃CO– 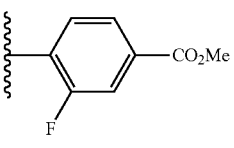 | NH |  —CO₂H, MeO |
| 377 | F₃CO– 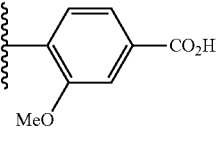 [SMILES: *c1ccc(C(=O)O)cc1OC] | NH |  —CO₂H, F |
| 378 | F₃CO– 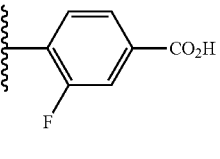 [SMILES: *c1ccc(C(=O)O)cc1F] | NH |  CF₃, —CO₂Me |
| 379 | F₃CO– 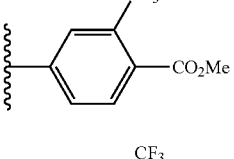 | NH |  CF₃, —CO₂H |

TABLE 2-continued

| Example | R² | X | A–Z–R⁴ |
|---|---|---|---|
| 380 | F₃CO-phenyl | NH | 2-fluoro-4-(CO₂Me)-phenyl |
| 381 | F₃CO-phenyl | NH | 2-fluoro-4-(CO₂H)-phenyl |
| 382 | F₃CO-phenyl | NH | 2,6-difluoro-4-(CO₂Me)-phenyl |
| 383 | F₃CO-phenyl | NH | 2,6-difluoro-4-(CO₂H)-phenyl |
| 384 | F₃CO-phenyl | NH | 2-phenyl-4-(CO₂Me)-phenyl |
| 385 | F₃CO-phenyl | NH | 2-phenyl-4-(CO₂H)-phenyl |
| 386 | F₃CO-phenyl | NH | 2-(pyridin-3-yl)-4-(CO₂Me)-phenyl |
| 387 | F₃CO-phenyl | NH | 2-(pyridin-3-yl)-4-(CO₂H)-phenyl |

TABLE 2-continued
| Example | R² | X | A-Z-R⁴ |
|---|---|---|---|
| 388 | 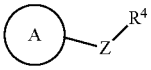 | NH | 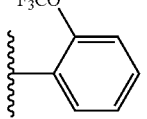 |
| 389 | 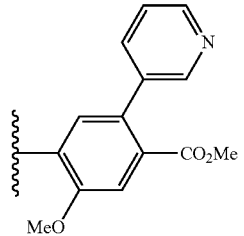 [SMILES: *c1cc(-c2cccnc2)c(C(=O)OC)cc1OC] | NH | 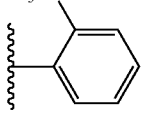 |
| 390 | 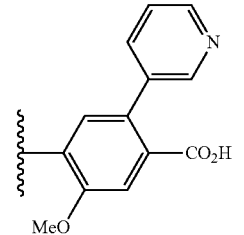 [SMILES: *c1cc(-c2cccnc2)c(C(=O)O)cc1OC] | NH | 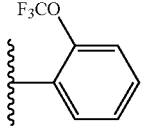 |
| 391 | 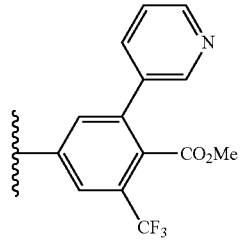 | NH | 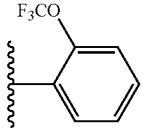 |
| 392 | 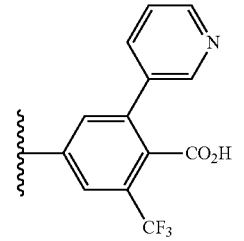 [SMILES: *c1cc(-c2cccnc2)c(C(=O)O)c(C(F)(F)F)c1] | NH | 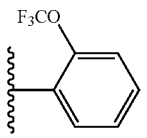 |
| 393 | 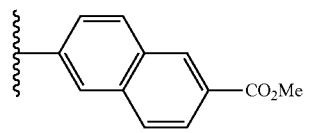 [SMILES: *c1ccc2cc(C(=O)OC)ccc2c1] | NH | 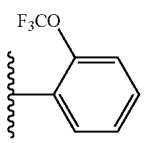 |
| 394 | 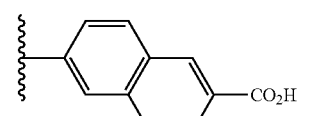 | NH | 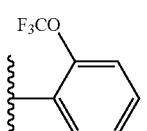 |

TABLE 2-continued

| Example | R² | X | A—Z—R⁴ |
|---|---|---|---|
| 395 | F₃CO-phenyl | NH | quinoline-CO₂H |
| 396 | F₃CO-phenyl | NH | pyridine-CO₂Me |
| 397 | F₃CO-phenyl | NH | pyridine-CO₂H |
| 398 | F₃CO-phenyl | NH | phenyl-C(O)-morpholine |
| 399 | F₃CO-phenyl | NH | F₃CO-phenyl |
| 400 | F₃CO-phenyl | NH | phenyl-C(O)NH-SO₂-Me |
| 401 | F₃CO-phenyl | NH | phenyl-C(O)NH-SO₂-(4-methylphenyl) |
| 402 | F₃CO-phenyl | NH | phenyl-C(O)NH-SO₂-cyclopropyl |

TABLE 2-continued
| Example | R² | X |  |
|---|---|---|---|
| 403 | F₃CO 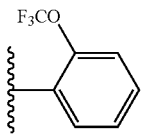 | NH | 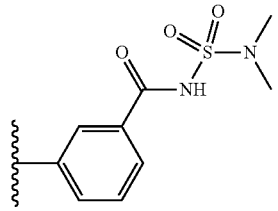 |
| 404 | F₃CO 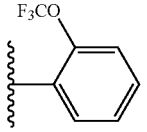 | NH | 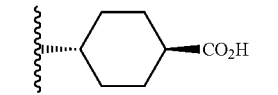 |
| 405 | F₃CO 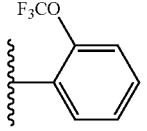 | NH | 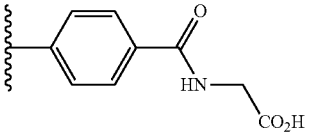 |
| 406 | F₃CO 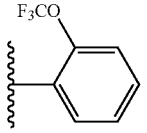 | NH | 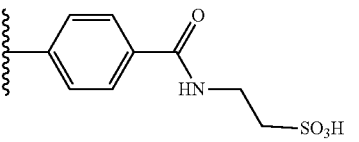 |
| 407 | F₃CO 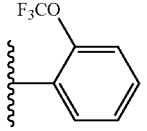 | NH | 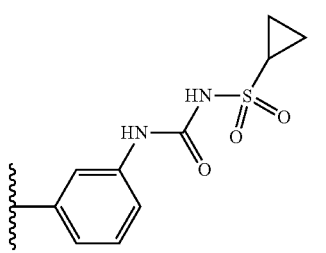 |
| 408 | F₃CO 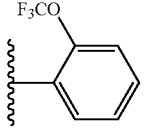 | NH | 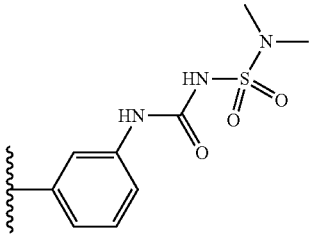 [SMILES: *c1cccc(NC(=O)NS(=O)(=O)N(C)C)c1] |
| 409 | F₃CO 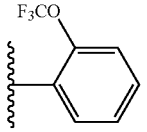 | NH | 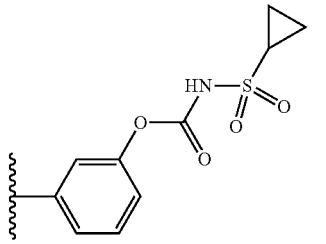 [SMILES: *c1cccc(OC(=O)NS(=O)(=O)C2CC2)c1] |

TABLE 2-continued

| Example | R² | X | (structure) |
|---|---|---|---|
| 410 | F₃CO-phenyl | NH | 3-(N,N-dimethylsulfamoylcarbamoyloxy)phenyl |
| 411 | spiro[2.5]octyl | NH | 3-CO₂Et-phenyl |
| 412 | spiro[2.5]octyl | NH | 4-CO₂Et-phenyl |
| 413 | spiro[2.5]octyl | NH | 3-CO₂H-phenyl |
| 414 | spiro[2.5]octyl | NH | 4-CO₂H-phenyl |
| 415 | spiro[2.5]octyl | NH | 3-(1H-tetrazol-5-yl)phenyl |
| 416 | spiro[2.5]octyl | NH | 3-(1-methyl-1H-tetrazol-5-yl)phenyl |
| 417 | spiro[2.5]octyl | NH | 3-(2-methyl-2H-tetrazol-5-yl)phenyl |

TABLE 2-continued
| Example | R² | X | (A)–Z–R⁴ |
|---|---|---|---|
| 418 | 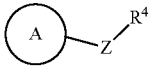 | NH | 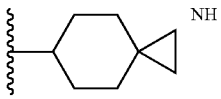 |
| 419 | 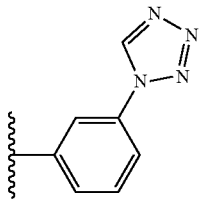 [SMILES: *c1cccc(-n2cnnn2)c1] | NH | 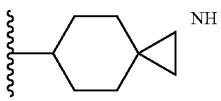 -CF₂H |
| 420 | 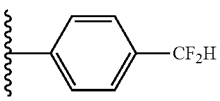 | NH | 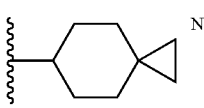 -CO₂Me, MeO |
| 421 | 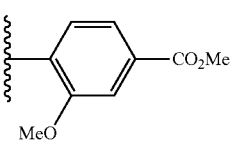 [SMILES: *c1ccc(C(=O)OC)cc1OC] | NH | 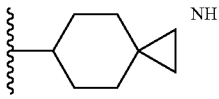 -CO₂Me, F |
| 422 | 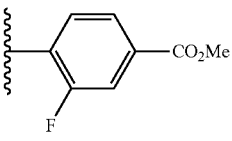 [SMILES: *c1ccc(C(=O)OC)cc1F] | NH | 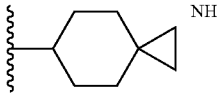 -CO₂H, MeO |
| 423 | 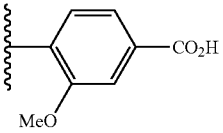 [SMILES: *c1ccc(C(=O)O)cc1OC] | NH | 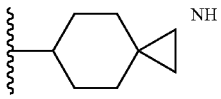 -CO₂H, F |
| 424 | 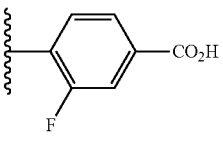 [SMILES: *c1ccc(C(=O)O)cc1F] | NH | 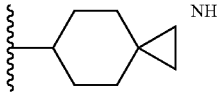 CF₃, -CO₂Me |
| 425 | 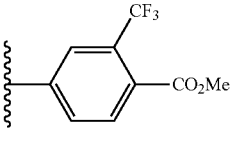 | NH | 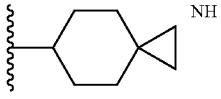 CF₃, -CO₂H |
| 426 | 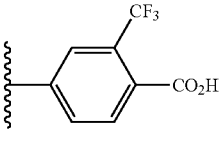 | NH | 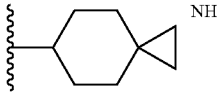 F, -CO₂Me |
| 427 | 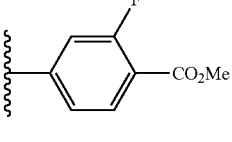 | NH | 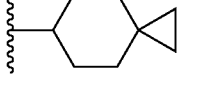 F, -CO₂H |

TABLE 2-continued
| Example | R² | X | (A)-Z-R⁴ |
|---|---|---|---|
| 428 |  | NH | 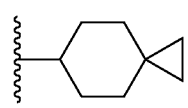 [SMILES: *C1CCC2(CC1)CC2] |
| 429 | 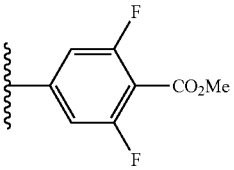 [SMILES: *c1cc(F)c(C(=O)OC)c(F)c1] | NH | 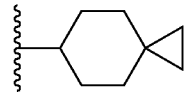 |
| 430 | 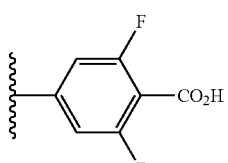 | NH | 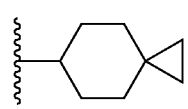 |
| 431 | 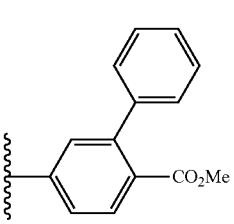 [SMILES: *c1ccc(C(=O)OC)c(-c2ccccc2)c1] | NH | 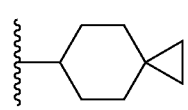 |
| 432 | 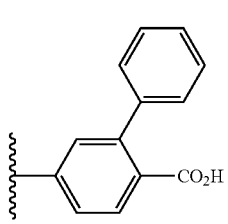 | NH | 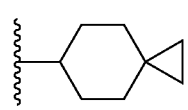 |
| 433 | 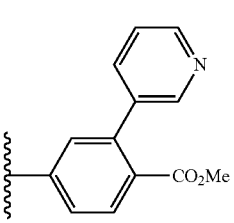 [SMILES: *c1ccc(C(=O)OC)c(-c2cccnc2)c1] | NH | 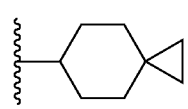 |
| 434 | 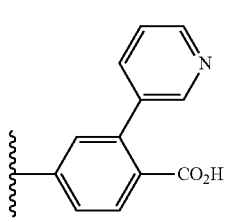 [SMILES: *c1ccc(C(=O)O)c(-c2cccnc2)c1] | NH | 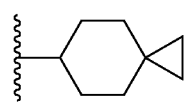 |

TABLE 2-continued
| Example | R² | X | (A)-Z-R⁴ |
|---|---|---|---|
| 435 | 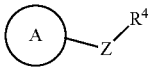 | NH | 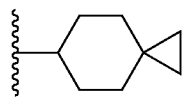 |
| 436 |  | NH | 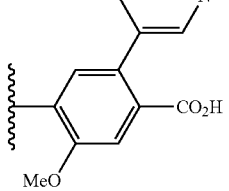 |
| 437 | 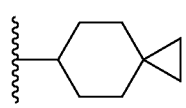 | NH |  |
| 438 | 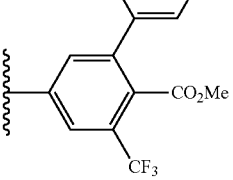 | NH | 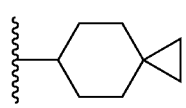 |
| 439 |  | NH | 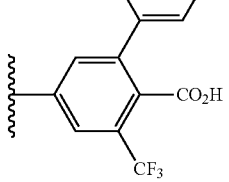 |
| 440 | 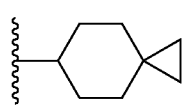 | NH |  |
| 441 | 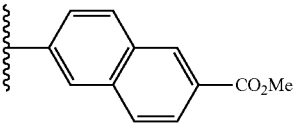 | NH | 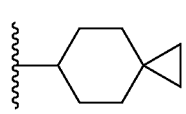 [SMILES: *C1CCC2(CC1)CC2] |
| 442 |  | NH | 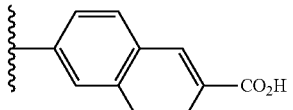 |

TABLE 2-continued
| Example | R² | X | (A)-Z-R⁴ |
|---|---|---|---|
| 443 | 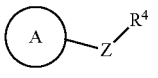 | NH | 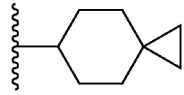 |
| 444 | 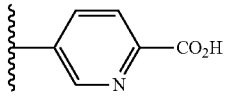 | NH | 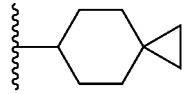 |
| 445 | 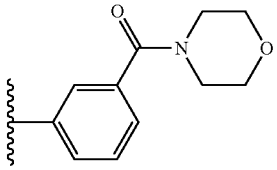 [SMILES: *c1cccc(C(=O)N2CCOCC2)c1] | NH | 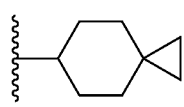 [SMILES: *C1CCC2(CC1)CC2] |
| 446 | 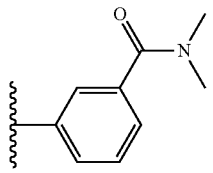 [SMILES: *c1cccc(C(=O)N(C)C)c1] | NH | 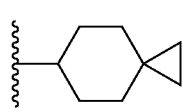 |
| 447 | 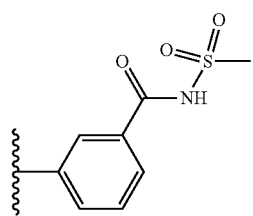 [SMILES: *c1cccc(C(=O)NS(C)(=O)=O)c1] | NH | 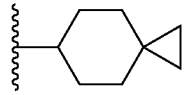 |
| 448 | 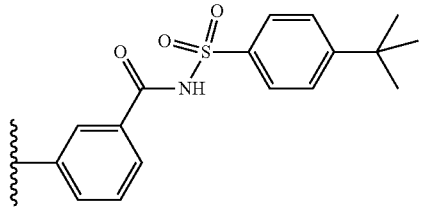 [SMILES: *c1cccc(C(=O)NS(=O)(=O)c2ccc(C(C)(C)C)cc2)c1] | NH | 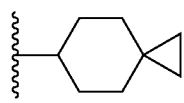 |
| 449 | 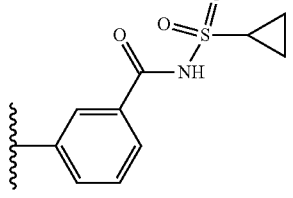 | NH | 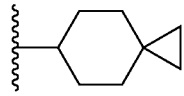 |
| 450 | 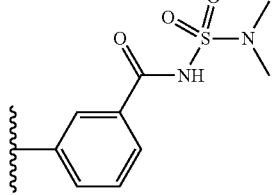 | NH | 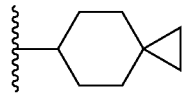 |

TABLE 2-continued
| Example | R² | X | (A)-Z-R⁴ |
|---|---|---|---|
| 451 | 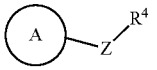 | NH | 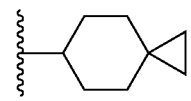 |
| 452 | 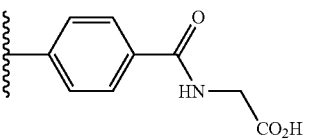 | NH | 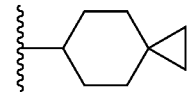 |
| 453 | 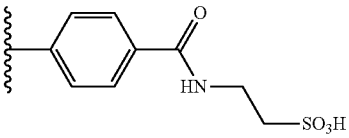 [SMILES: *c1ccc(C(=O)NCCS(=O)(=O)O)cc1] | NH | 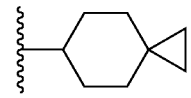 |
| 454 | 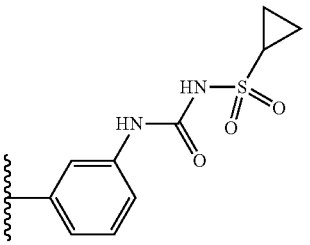 | NH | 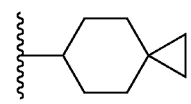 [SMILES: *C1CCC2(CC1)CC2] |
| 455 | 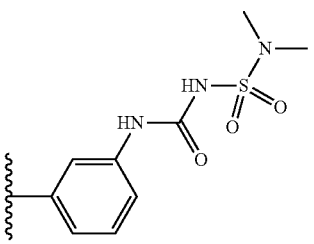 | NH | 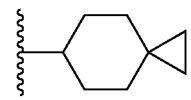 |
| 456 | 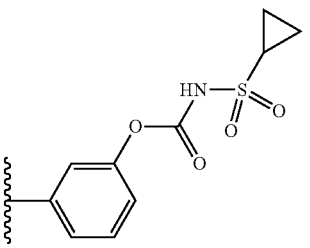 [SMILES: *c1cccc(OC(=O)NS(=O)(=O)C2CC2)c1] | NH | 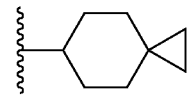 |

15. The compound of claim 1, represented by Formula VII,

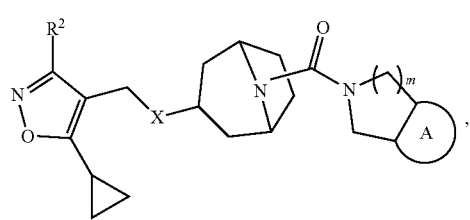

or a pharmaceutically acceptable salt thereof, wherein m is 0, 1, 2 or 3; and $R^2$, X, and 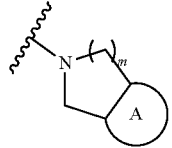 are as defined in claim 1.

16. The compound of claim 15, selected from compounds according to Formula (VII), wherein $R^2$, X, and

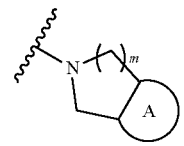

are delineated for each compound in Table 3, or a pharmaceutically acceptable salt thereof:

TABLE 3

| Example | $R^2$ | X |  |
|---|---|---|---|
| 457 | 2,6-dichlorophenyl | O | isoindoline |
| 458 | 2,6-dichlorophenyl | O | 5-CF₃-isoindoline |
| 459 | 2,6-dichlorophenyl | O | 4-CF₃-isoindoline |
| 460 | 2,6-dichlorophenyl | O | 5-(pyridin-3-yl)-isoindoline |
| 461 | 2,6-dichlorophenyl | O | 4-(pyridin-3-yl)-isoindoline |

TABLE 3-continued

| Example | R² | X | |
|---|---|---|---|
| 462 | 2,6-diCl-phenyl | O | 5-CF₃, 6-F isoindoline |
| 463 | 2,6-diCl-phenyl | O | 4-F, 5-CF₃ isoindoline |
| 464 | 2,6-diCl-phenyl | O | 5-tBu isoindoline |
| 465 | 2,6-diCl-phenyl | O | 4-tBu isoindoline |
| 466 | 2,6-diCl-phenyl | O | pyrrolo-pyridine |
| 467 | 2,6-diCl-phenyl | O | CF₃-pyrrolo-pyridine |
| 468 | 2,6-diCl-phenyl | O | CF₃-pyrrolo-pyridine |

TABLE 3-continued

| Example | R² | X | (structure) |
|---|---|---|---|
| 469 | 2,6-dichlorophenyl | O | 1,2,3,4-tetrahydroisoquinolin-2-yl |
| 470 | 2,6-dichlorophenyl | O | 1,2,3,4-tetrahydroquinolin-1-yl |
| 471 | 2,6-dichlorophenyl | O | 5,6,7,8-tetrahydro-2,7-naphthyridin-7-yl |
| 472 | 2,6-dichlorophenyl | O | 1,2,3,4-tetrahydro-1,8-naphthyridin-1-yl |
| 473 | 2-(trifluoromethoxy)phenyl | O | isoindolin-2-yl |
| 474 | 2-(trifluoromethoxy)phenyl | O | 5-(trifluoromethyl)isoindolin-2-yl |
| 475 | 2-(trifluoromethoxy)phenyl | O | 4-(trifluoromethyl)isoindolin-2-yl |
| 476 | 2-(trifluoromethoxy)phenyl | O | 5-(pyridin-3-yl)isoindolin-2-yl |

TABLE 3-continued

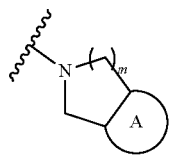

| Example | R² | X | |
|---|---|---|---|
| 477 | F₃CO- (ortho phenyl) | O | isoindoline with 4-(pyridin-3-yl) |
| 478 | F₃CO- (ortho phenyl) | O | isoindoline with CF₃ and F |
| 479 | F₃CO- (ortho phenyl) | O | isoindoline with F and CF₃ |
| 480 | F₃CO- (ortho phenyl) | O | isoindoline with t-Bu |
| 481 | F₃CO- (ortho phenyl) | O | isoindoline with t-Bu |
| 482 | F₃CO- (ortho phenyl) | O | isoindoline |
| 483 | F₃CO- (ortho phenyl) | O | pyrido-isoindoline with CF₃ |
| 484 | F₃CO- (ortho phenyl) | O | pyrido-isoindoline with CF₃ |

TABLE 3-continued
| Example | R² | X | |
|---|---|---|---|
| 485 | F₃CO- 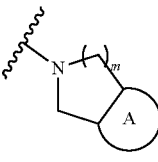 | O | 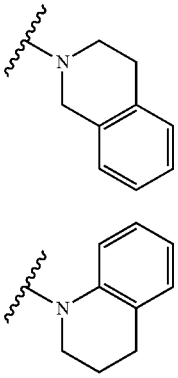 |
| 486 | F₃CO- 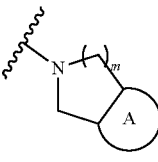 | O | 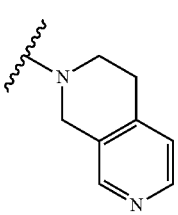 [SMILES: *N1CCc2ccncc2C1] |
| 487 | F₃CO- 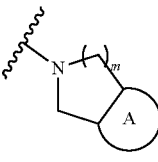 | O | 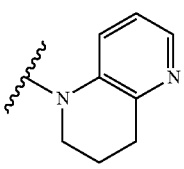 [SMILES: *N1CCCc2ncccc21] |
| 488 | F₃CO- 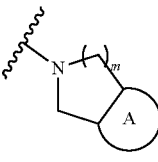 | O | 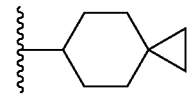 |
| 489 | 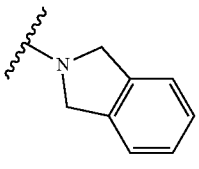 [SMILES: *N1Cc2ccccc2C1] | O | 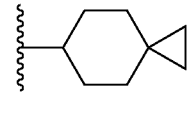 [SMILES: *C1CCC2(CC1)CC2] |
| 490 | 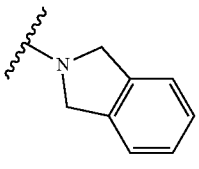 [SMILES: *N1Cc2ccccc2C1] | O | 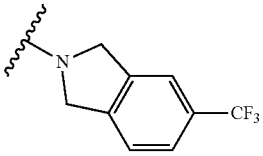 [SMILES: *N1Cc2ccc(C(F)(F)F)cc2C1] |
| 491 | 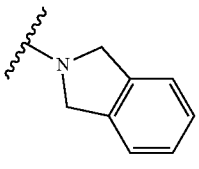 [SMILES: *N1Cc2ccccc2C1] | O | 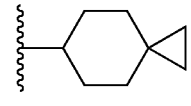 |
| 492 | 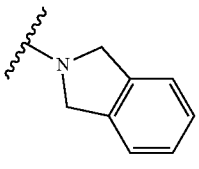 [SMILES: *N1Cc2ccccc2C1] | O | 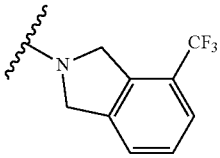 [SMILES: *N1Cc2cccc(C(F)(F)F)c2C1] |

TABLE 3-continued

| Example | R² | X | (structure) |
|---|---|---|---|
| 493 | spiro[5.2]cyclohexane-cyclopropane | O | isoindoline with 3-pyridyl substituent |
| 494 | spiro[5.2]cyclohexane-cyclopropane | O | isoindoline with CF₃ and F substituents |
| 495 | spiro[5.2]cyclohexane-cyclopropane | O | isoindoline with F and CF₃ substituents |
| 496 | spiro[5.2]cyclohexane-cyclopropane | O | isoindoline with t-Bu substituent |
| 497 | spiro[5.2]cyclohexane-cyclopropane | O | isoindoline with t-Bu substituent |
| 498 | spiro[5.2]cyclohexane-cyclopropane | O | pyrrolo-pyridine |
| 499 | spiro[5.2]cyclohexane-cyclopropane | O | pyrrolo-pyridine with CF₃ |
| 500 | spiro[5.2]cyclohexane-cyclopropane | O | pyrrolo-pyridine with CF₃ |

TABLE 3-continued

| Example | R² | X | (structure) |
|---|---|---|---|
| 501 | spiro[2.5]oct-6-yl | O | 1,2,3,4-tetrahydroisoquinolin-2-yl |
| 502 | spiro[2.5]oct-6-yl | O | 1,2,3,4-tetrahydroquinolin-1-yl |
| 503 | spiro[2.5]oct-6-yl | O | 5,6,7,8-tetrahydro-2,7-naphthyridin-7-yl |
| 504 | spiro[2.5]oct-6-yl | O | 1,2,3,4-tetrahydro-1,8-naphthyridin-1-yl |
| 505 | 2,6-dichlorophenyl | NH | isoindolin-2-yl |
| 506 | 2,6-dichlorophenyl | NH | 5-(trifluoromethyl)isoindolin-2-yl |
| 507 | 2,6-dichlorophenyl | NH | 4-(trifluoromethyl)isoindolin-2-yl |
| 508 | 2,6-dichlorophenyl | NH | 5-(pyridin-3-yl)isoindolin-2-yl |

TABLE 3-continued
| Example | R² | X | |
|---|---|---|---|
| 509 | 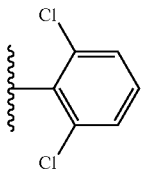 [SMILES: *c1c(Cl)cccc1Cl] | NH | 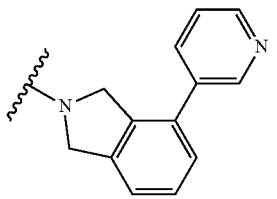 [SMILES: *N1Cc2cccc(-c3cccnc3)c2C1] |
| 510 | 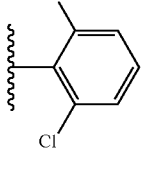 | NH | 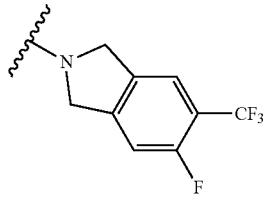 [SMILES: *N1Cc2cc(F)c(C(F)(F)F)cc2C1] |
| 511 | 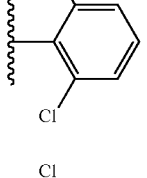 | NH | 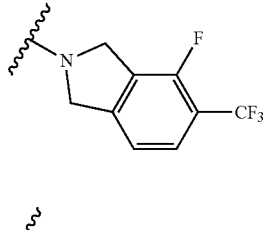 |
| 512 | 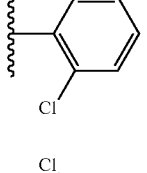 | NH | 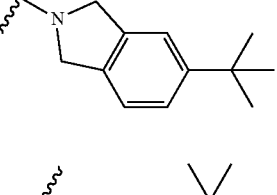 |
| 513 | 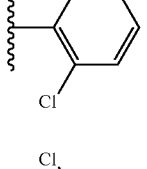 | NH | 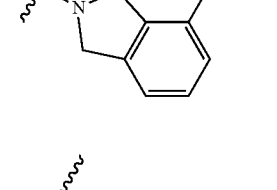 |
| 514 | 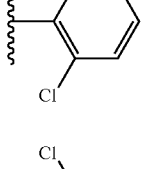 | NH | 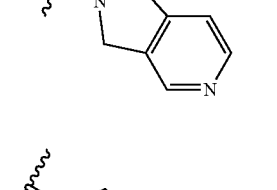 |
| 515 | 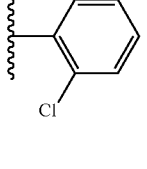 | NH | 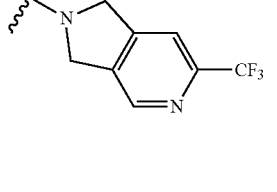 |

TABLE 3-continued

| Example | R² | X |
|---|---|---|
| 516 | 2,6-diCl-phenyl | NH |
| 517 | 2,6-diCl-phenyl | NH |
| 518 | 2,6-diCl-phenyl | NH |
| 519 | 2,6-diCl-phenyl | NH |
| 520 | 2,6-diCl-phenyl | NH |
| 521 | 2-F₃CO-phenyl | NH |
| 522 | 2-F₃CO-phenyl | NH |
| 523 | 2-F₃CO-phenyl | NH |

TABLE 3-continued

| Example | R² | X | (structure) |
|---|---|---|---|
| 524 | F₃CO-phenyl | NH | isoindoline-pyridin-3-yl |
| 525 | F₃CO-phenyl | NH | isoindoline-pyridin-3-yl |
| 526 | F₃CO-phenyl | NH | isoindoline-CF₃,F |
| 527 | F₃CO-phenyl | NH | isoindoline-F,CF₃ |
| 528 | F₃CO-phenyl | NH | isoindoline-tBu |
| 529 | F₃CO-phenyl | NH | isoindoline-tBu |
| 530 | F₃CO-phenyl | NH | pyrrolo-pyridine |
| 531 | F₃CO-phenyl | NH | pyrrolo-pyridine-CF₃ |

TABLE 3-continued

| Example | R² | X | [A ring structure] |
|---|---|---|---|
| 532 | F₃CO-phenyl | NH | pyrrolo-pyridine with CF₃ |
| 533 | F₃CO-phenyl | NH | tetrahydroisoquinoline |
| 534 | F₃CO-phenyl | NH | tetrahydroquinoline |
| 535 | F₃CO-phenyl | NH | tetrahydro-2,7-naphthyridine |
| 536 | F₃CO-phenyl | NH | tetrahydro-1,8-naphthyridine |
| 537 | spiro[2.5]octyl | NH | isoindoline |
| 538 | spiro[2.5]octyl | NH | isoindoline-CF₃ |
| 539 | spiro[2.5]octyl | NH | isoindoline-CF₃ |

TABLE 3-continued

| Example | R² | X | (structure) |
|---|---|---|---|
| 540 | spiro[2.5]octyl | NH | 5-(pyridin-3-yl)isoindoline |
| 541 | spiro[2.5]octyl | NH | 4-(pyridin-3-yl)isoindoline |
| 542 | spiro[2.5]octyl | NH | 5-CF₃, 6-F isoindoline |
| 543 | spiro[2.5]octyl | NH | 4-F, 5-CF₃ isoindoline |
| 544 | spiro[2.5]octyl | NH | 5-tert-butyl isoindoline |
| 545 | spiro[2.5]octyl | NH | 4-tert-butyl isoindoline |
| 546 | spiro[2.5]octyl | NH | 1,2,3,4-tetrahydroisoquinoline |
| 547 | spiro[2.5]octyl | NH | 6-CF₃-pyrrolo-pyridine |

TABLE 3-continued

| Example | R² | X | (structure) |
|---------|----|----|-------------|
| 548 | (cyclohexane-spiro-cyclopropane) | NH | (pyrrolo-pyridine with CF₃) |
| 549 | (cyclohexane-spiro-cyclopropane) | NH | (tetrahydroisoquinoline) |
| 550 | (cyclohexane-spiro-cyclopropane) | NH | (tetrahydroquinoline) |
| 551 | (cyclohexane-spiro-cyclopropane) | NH | (tetrahydro-naphthyridine) |
| 552 | (cyclohexane-spiro-cyclopropane) | NH | (tetrahydro-1,8-naphthyridine) |

17. The compound of claim 1, represented by Formula VIII,

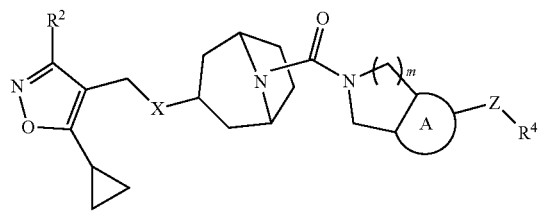

(VIII)

or a pharmaceutically acceptable salt thereof, wherein m is 0, 1, 2 or 3; and R², R⁴, X, Z, and

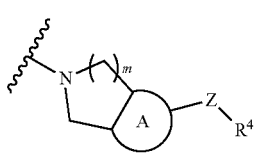

are as defined in claim 1.

18. The compound of claim 17, selected from compounds according to Formula (VIII), wherein R², X, and are delineated for each compound in Table 4, or a pharmaceutically acceptable salt thereof:

TABLE 4
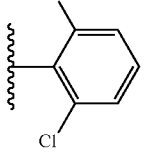
| Example | R² | X | |
|---|---|---|---|
| 553 | 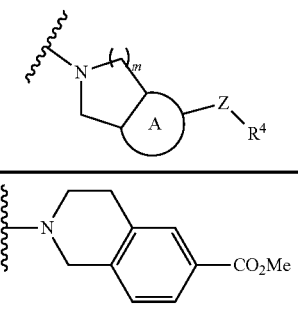 | O | 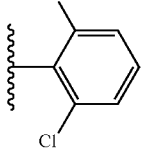 |
| 554 | 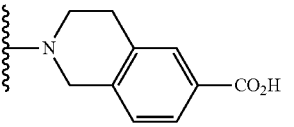 [SMILES: *N1CCc2cc(C(=O)O)ccc2C1] | O | 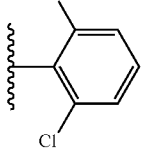 |
| 555 | 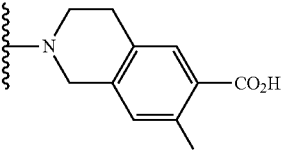 | O | 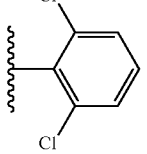 |
| 556 | 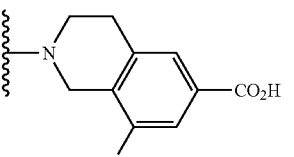 | O | 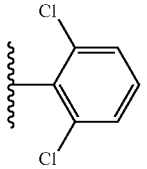 [SMILES: *c1c(Cl)cccc1Cl] |
| 557 | 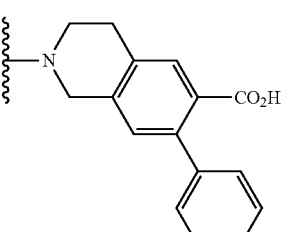 | O | 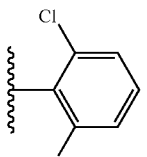 |
| 558 | 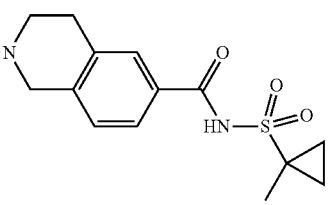 | O | 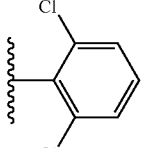 |
| 559 | 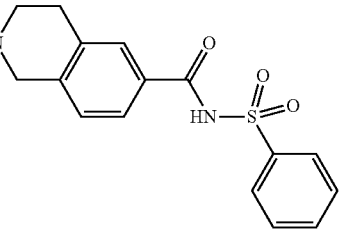 | O | 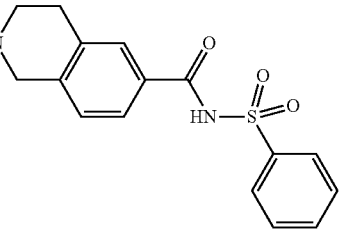 |

TABLE 4-continued

| Example | R² | X | (structure) |
|---|---|---|---|
| 560 | 2,6-diCl-phenyl | O | tetrahydroisoquinoline-6-C(O)NH-S(O)₂-N(CH₃)₂ |
| 561 | 2,6-diCl-phenyl | O | tetrahydroisoquinolin-6-yl-NH-C(O)-NH-S(O)₂-(1-methylcyclopropyl) |
| 562 | 2,6-diCl-phenyl | O | tetrahydroisoquinolin-6-yl-O-C(O)-NH-S(O)₂-(1-methylcyclopropyl) |
| 563 | 2,6-diCl-phenyl | O | tetrahydroisoquinoline-6-(1H-tetrazol-5-yl) |
| 564 | 2,6-diCl-phenyl | O | tetrahydroisoquinoline-6-C(O)NH-CH₂-CO₂H |
| 565 | 2,6-diCl-phenyl | O | tetrahydroisoquinoline-6-C(O)NH-CH₂-SO₃H |
| 566 | 2,6-diCl-phenyl | O | 6-(MeO₂C)-indoline |

TABLE 4-continued
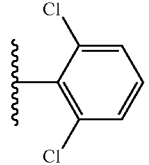 [SMILES: *c1c(Cl)cccc1Cl]
| Example | R² | X | |
|---|---|---|---|
| 567 | 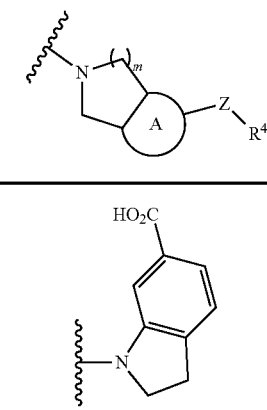 | O | 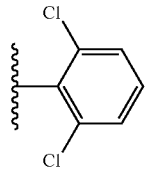 |
| 568 | 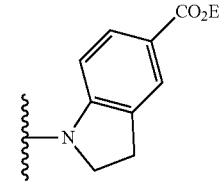 | O | 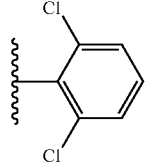 [SMILES: *c1c(Cl)cccc1Cl] |
| 569 | 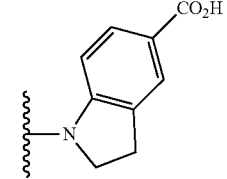 [SMILES: *N1CCc2cc(C(=O)O)ccc21] | O | 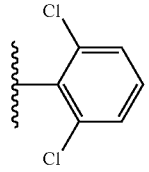 [SMILES: *c1c(Cl)cccc1Cl] |
| 570 | 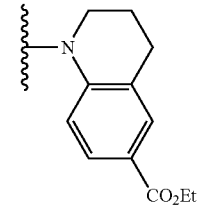 [SMILES: *N1CCCc2cc(C(=O)OCC)ccc21] | O | 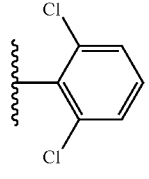 |
| 571 | 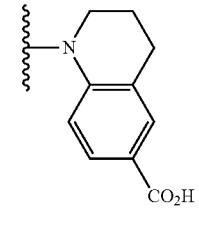 [SMILES: *N1CCCc2cc(C(=O)O)ccc21] | O | 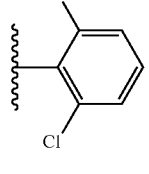 |
| 572 | 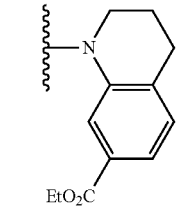 | O |  |

TABLE 4-continued

| Example | R² | X | |
|---|---|---|---|
| 573 | 2,6-dichlorophenyl | O | 1,2,3,4-tetrahydroquinoline-7-carboxylic acid (N-linked) |
| 574 | 2,6-dichlorophenyl | O | isoindoline-5-carboxylic acid methyl ester (N-linked) |
| 575 | 2,6-dichlorophenyl | O | isoindoline-5-carboxylic acid (N-linked) |
| 576 | 2-(trifluoromethoxy)phenyl | O | 1,2,3,4-tetrahydroisoquinoline-6-carboxylic acid methyl ester (N-linked) |
| 577 | 2-(trifluoromethoxy)phenyl | O | 1,2,3,4-tetrahydroisoquinoline-6-carboxylic acid (N-linked) |
| 578 | 2-(trifluoromethoxy)phenyl | O | 7-(trifluoromethyl)-1,2,3,4-tetrahydroisoquinoline-6-carboxylic acid (N-linked) |
| 579 | 2-(trifluoromethoxy)phenyl | O | 8-(trifluoromethyl)-1,2,3,4-tetrahydroisoquinoline-6-carboxylic acid (N-linked) |

TABLE 4-continued

| Example | R² | X | |
|---|---|---|---|
| 580 | F₃CO-phenyl | O | tetrahydroisoquinoline-CO₂H with pyridin-3-yl |
| 581 | F₃CO-phenyl | O | tetrahydroisoquinoline-C(O)NH-S(O)₂-(1-methylcyclopropyl) |
| 582 | F₃CO-phenyl | O | tetrahydroisoquinoline-C(O)NH-S(O)₂-phenyl |
| 583 | F₃CO-phenyl | O | tetrahydroisoquinoline-C(O)NH-S(O)₂-N(CH₃)₂ |
| 584 | F₃CO-phenyl | O | tetrahydroisoquinoline-NH-C(O)NH-S(O)₂-(1-methylcyclopropyl) |
| 585 | F₃CO-phenyl | O | tetrahydroisoquinoline-O-C(O)NH-S(O)₂-(1-methylcyclopropyl) |

TABLE 4-continued

| Example | R² | X | |
|---|---|---|---|
| 586 | F₃CO-(2-phenyl) | O | tetrahydroisoquinoline-6-yl-tetrazole |
| 587 | F₃CO-(2-phenyl) | O | tetrahydroisoquinoline-6-carboxamide-N-CH₂CO₂H |
| 588 | F₃CO-(2-phenyl) | O | tetrahydroisoquinoline-6-carboxamide-N-CH₂CH₂SO₃H |
| 589 | F₃CO-(2-phenyl) | O | indoline-N-yl, 6-CO₂Me |
| 590 | F₃CO-(2-phenyl) | O | indoline-N-yl, 6-CO₂H |
| 591 | F₃CO-(2-phenyl) | O | indoline-N-yl, 5-CO₂Et |
| 592 | F₃CO-(2-phenyl) | O | indoline-N-yl, 5-CO₂H |

TABLE 4-continued
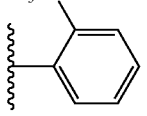
| Example | R² | X | |
|---|---|---|---|
| 593 | F₃CO- 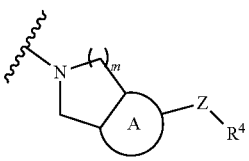 | O | 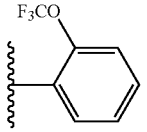 (N-tetrahydroquinoline-6-CO₂Et) |
| 594 | F₃CO- 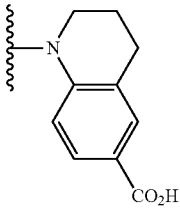 | O | 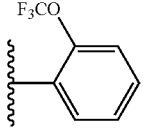 (N-tetrahydroquinoline-6-CO₂H) |
| 595 | F₃CO- 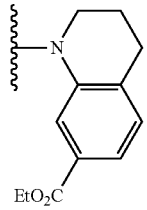 | O | 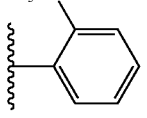 (N-tetrahydroquinoline-7-CO₂Et) |
| 596 | F₃CO- 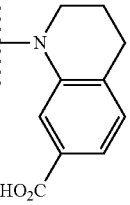 | O | 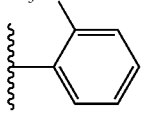 (N-tetrahydroquinoline-7-CO₂H) |
| 597 | F₃CO- 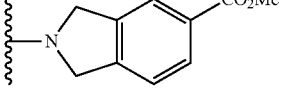 | O | 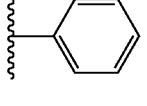 (isoindoline-CO₂Me) |
| 598 | F₃CO- 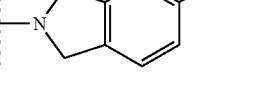 | O | 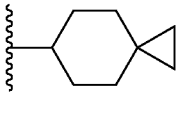 (isoindoline-CO₂H) |
| 599 | 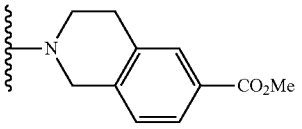 (spiro[2.5]octyl) | O | 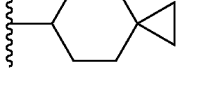 (tetrahydroisoquinoline-CO₂Me) |
| 600 | 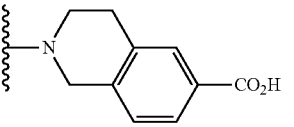 [SMILES: *N1CCc2cc(C(=O)O)ccc2C1] (spiro[2.5]octyl) | O | (tetrahydroisoquinoline-CO₂H) |

TABLE 4-continued
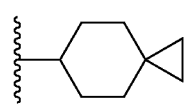
| Example | R² | X | |
|---|---|---|---|
| 601 | 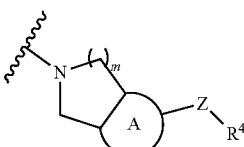 | O | 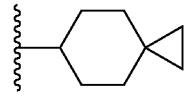 |
| 602 | 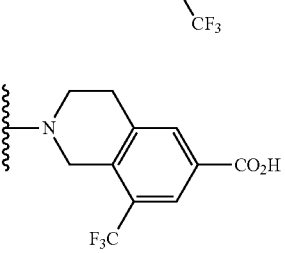 | O | 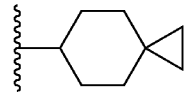 |
| 603 | 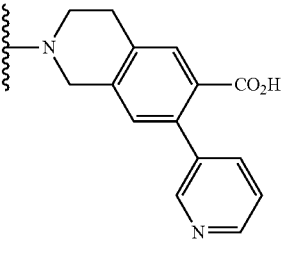 [SMILES: *N1CCc2cc(C(=O)O)c(-c3cccnc3)cc2C1] | O | 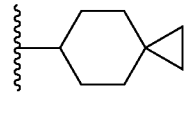 |
| 604 | 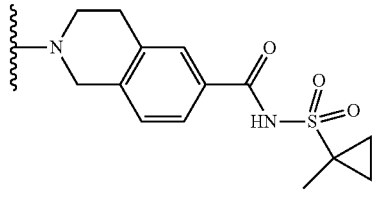 [SMILES: *N1CCc2cc(C(=O)NS(=O)(=O)C3(C)CC3)ccc2C1] | O | 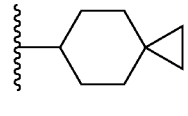 |
| 605 | 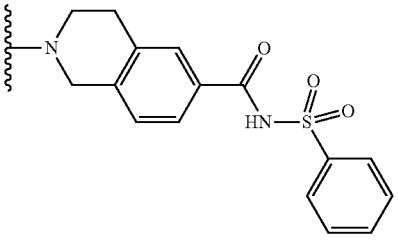 [SMILES: *N1CCc2cc(C(=O)NS(=O)(=O)c3ccccc3)ccc2C1] | O | 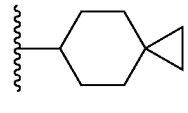 |
| 606 | 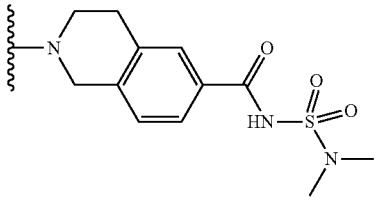 [SMILES: *N1CCc2cc(C(=O)NS(=O)(=O)N(C)C)ccc2C1] | O |  |

TABLE 4-continued

| Example | R² | X | (structure with A, Z, R⁴) |
|---|---|---|---|
| 607 | spiro[2.5]octyl | O | tetrahydroisoquinoline-6-NH-C(O)-NH-S(O)₂-(1-methylcyclopropyl) |
| 608 | spiro[2.5]octyl | O | tetrahydroisoquinoline-6-O-C(O)-NH-S(O)₂-(1-methylcyclopropyl) |
| 609 | spiro[2.5]octyl | O | tetrahydroisoquinoline-6-(1H-tetrazol-5-yl) |
| 610 | spiro[2.5]octyl | O | tetrahydroisoquinoline-6-C(O)-NH-CH₂-CO₂H |
| 611 | spiro[2.5]octyl | O | tetrahydroisoquinoline-6-C(O)-NH-CH₂CH₂-SO₃H |
| 612 | spiro[2.5]octyl | O | indoline-1-yl, 6-CO₂Me |
| 613 | spiro[2.5]octyl | O | indoline-1-yl, 6-CO₂H |

TABLE 4-continued

| Example | R² | X | (structure shown in header: N-pyrrolidine fused to ring A with Z-R⁴) |
|---|---|---|---|
| 614 | spiro[2.5]octyl | O | 5-(ethoxycarbonyl)indolin-1-yl |
| 615 | spiro[2.5]octyl | O | 5-carboxyindolin-1-yl |
| 616 | spiro[2.5]octyl | O | 6-(ethoxycarbonyl)-1,2,3,4-tetrahydroquinolin-1-yl |
| 617 | spiro[2.5]octyl | O | 6-carboxy-1,2,3,4-tetrahydroquinolin-1-yl |
| 618 | spiro[2.5]octyl | O | 7-(ethoxycarbonyl)-1,2,3,4-tetrahydroquinolin-1-yl |
| 619 | spiro[2.5]octyl | O | 7-carboxy-1,2,3,4-tetrahydroquinolin-1-yl |
| 620 | spiro[2.5]octyl | O | 5-(methoxycarbonyl)isoindolin-2-yl |

TABLE 4-continued

| Example | R² | X | (structure with A ring) |
|---|---|---|---|
| 621 | cyclohexane-spiro-cyclopropane | O | isoindoline-5-CO₂H |
| 622 | 2,6-dichlorophenyl | NH | tetrahydroisoquinoline-6-CO₂Me |
| 623 | 2,6-dichlorophenyl | NH | tetrahydroisoquinoline-6-CO₂H |
| 624 | 2,6-dichlorophenyl | NH | tetrahydroisoquinoline-6-CO₂H, 7-CF₃ |
| 625 | 2,6-dichlorophenyl | NH | tetrahydroisoquinoline-6-CO₂H, 8-CF₃ |
| 626 | 2,6-dichlorophenyl | NH | tetrahydroisoquinoline-6-CO₂H, 7-(pyridin-3-yl) |
| 627 | 2,6-dichlorophenyl | NH | tetrahydroisoquinoline-6-C(O)NHS(O)₂-(1-methylcyclopropyl) |

TABLE 4-continued

| Example | R² | X | |
|---|---|---|---|
| 628 | 2,6-diCl-phenyl | NH | tetrahydroisoquinoline-6-C(O)NH-SO₂-phenyl |
| 629 | 2,6-diCl-phenyl | NH | tetrahydroisoquinoline-6-C(O)NH-SO₂-N(CH₃)₂ |
| 630 | 2,6-diCl-phenyl | NH | tetrahydroisoquinoline-6-NH-C(O)-NH-SO₂-(1-methylcyclopropyl) |
| 631 | 2,6-diCl-phenyl | NH | tetrahydroisoquinoline-6-O-C(O)-NH-SO₂-(1-methylcyclopropyl) |
| 632 | 2,6-diCl-phenyl | NH | tetrahydroisoquinoline-6-tetrazole |
| 633 | 2,6-diCl-phenyl | NH | tetrahydroisoquinoline-6-C(O)NH-CH₂-CO₂H |
| 634 | 2,6-diCl-phenyl | NH | tetrahydroisoquinoline-6-C(O)NH-CH₂-SO₃H |

TABLE 4-continued
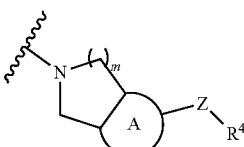
| Example | R² | X | |
|---|---|---|---|
| 635 | 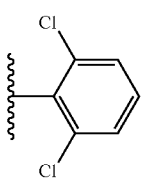 [SMILES: *c1c(Cl)cccc1Cl] | NH | 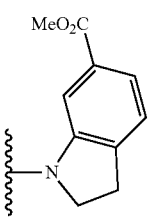 [SMILES: *N1CCc2ccc(C(=O)OC)cc21] |
| 636 | 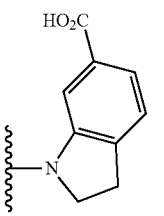 [SMILES: *N1CCc2ccc(C(=O)O)cc21] | NH | 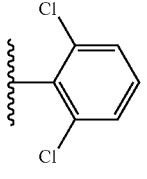 |
| 637 | 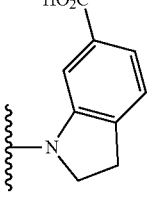 | NH | 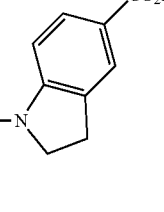 |
| 638 | 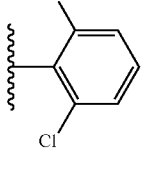 | NH | 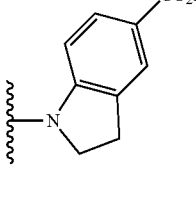 |
| 639 | 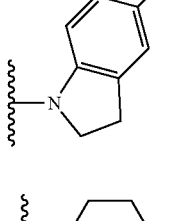 | NH | 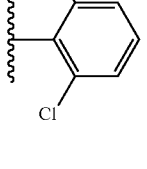 |
| 640 | 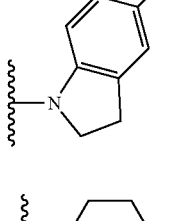 | NH | 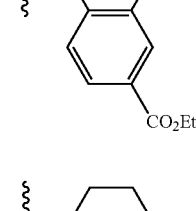 |

TABLE 4-continued

| Example | R² | X | |
|---|---|---|---|
| 641 | 2,6-diCl-phenyl | NH | 1,2,3,4-tetrahydroquinoline-7-CO₂Et (N-linked) |
| 642 | 2,6-diCl-phenyl | NH | 1,2,3,4-tetrahydroquinoline-7-CO₂H (N-linked) |
| 643 | 2,6-diCl-phenyl | NH | isoindoline-5-CO₂Me (N-linked) |
| 644 | 2,6-diCl-phenyl | NH | isoindoline-5-CO₂H (N-linked) |
| 645 | 2-OCF₃-phenyl | NH | 1,2,3,4-tetrahydroisoquinoline-6-CO₂Me (N-linked) |
| 646 | 2-OCF₃-phenyl | NH | 1,2,3,4-tetrahydroisoquinoline-6-CO₂H (N-linked) |
| 647 | 2-OCF₃-phenyl | NH | 7-CF₃-1,2,3,4-tetrahydroisoquinoline-6-CO₂H (N-linked) |
| 648 | 2-OCF₃-phenyl | NH | 8-CF₃-1,2,3,4-tetrahydroisoquinoline-6-CO₂H (N-linked) |

TABLE 4-continued

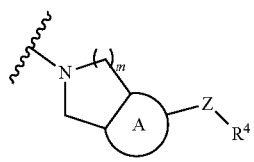

| Example | R² | X | |
|---|---|---|---|
| 649 | F₃CO-phenyl | NH | tetrahydroisoquinoline-6-(pyridin-3-yl)-7-CO₂H |
| 650 | F₃CO-phenyl | NH | tetrahydroisoquinoline-6-C(O)NH-S(O)₂-(1-methylcyclopropyl) |
| 651 | F₃CO-phenyl | NH | tetrahydroisoquinoline-6-C(O)NH-S(O)₂-phenyl |
| 652 | F₃CO-phenyl | NH | tetrahydroisoquinoline-6-C(O)NH-S(O)₂-N(CH₃)₂ |
| 653 | F₃CO-phenyl | NH | tetrahydroisoquinoline-6-NH-C(O)NH-S(O)₂-(1-methylcyclopropyl) |
| 654 | F₃CO-phenyl | NH | tetrahydroisoquinoline-6-O-C(O)NH-S(O)₂-(1-methylcyclopropyl) |

TABLE 4-continued

| Example | R² | X | [A-Z-R⁴ group] |
|---|---|---|---|
| 655 | F₃CO-phenyl | NH | tetrahydroisoquinoline-tetrazole |
| 656 | F₃CO-phenyl | NH | tetrahydroisoquinoline-C(O)NH-CH₂-CO₂H |
| 657 | F₃CO-phenyl | NH | tetrahydroisoquinoline-C(O)NH-CH₂CH₂-SO₃H |
| 658 | F₃CO-phenyl | NH | indoline-6-CO₂Me |
| 659 | F₃CO-phenyl | NH | indoline-6-CO₂H |
| 660 | F₃CO-phenyl | NH | indoline-5-CO₂Et |
| 661 | F₃CO-phenyl | NH | indoline-5-CO₂H |

TABLE 4-continued

| Example | R² | X | [structure] |
|---|---|---|---|
| 662 | F₃CO-phenyl | NH | 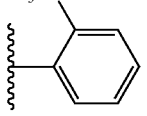 tetrahydroquinoline-6-CO₂Et |
| 663 | F₃CO-phenyl | NH | 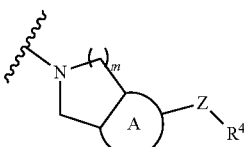 tetrahydroquinoline-6-CO₂H |
| 664 | F₃CO-phenyl | NH | 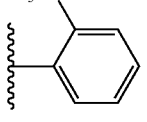 tetrahydroquinoline-7-CO₂Et |
| 665 | F₃CO-phenyl | NH | 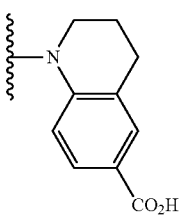 [SMILES: *N1CCCc2cc(C(=O)O)ccc21] tetrahydroquinoline-7-CO₂Et |
| 666 | F₃CO-phenyl | NH | 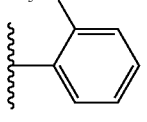 isoindoline-5-CO₂Me |
| 667 | F₃CO-phenyl | NH | 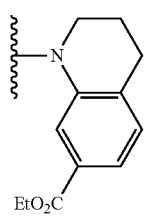 isoindoline-5-CO₂H |
| 668 | spiro[2.5]octyl | NH | 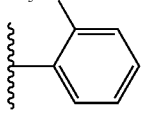 tetrahydroisoquinoline-6-CO₂Me |
| 669 | spiro[2.5]octyl | NH | 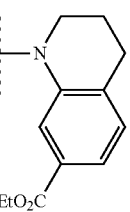 tetrahydroisoquinoline-6-CO₂H |

TABLE 4-continued

| Example | R² | X | (structure) |
|---|---|---|---|
| 670 | spiro[2.5]octyl | NH | 1,2,3,4-tetrahydroisoquinolin-2-yl, 6-CO₂H, 7-CF₃ |
| 671 | spiro[2.5]octyl | NH | 1,2,3,4-tetrahydroisoquinolin-2-yl, 6-CO₂H, 8-CF₃ |
| 672 | spiro[2.5]octyl | NH | 1,2,3,4-tetrahydroisoquinolin-2-yl, 6-CO₂H, 7-(pyridin-3-yl) |
| 673 | spiro[2.5]octyl | NH | 1,2,3,4-tetrahydroisoquinolin-2-yl, 6-C(O)NHS(O)₂-(1-methylcyclopropyl) |
| 674 | spiro[2.5]octyl | NH | 1,2,3,4-tetrahydroisoquinolin-2-yl, 6-C(O)NHS(O)₂-phenyl |
| 675 | spiro[2.5]octyl | NH | 1,2,3,4-tetrahydroisoquinolin-2-yl, 6-C(O)NHS(O)₂-N(CH₃)₂ |

TABLE 4-continued

| Example | R² | X | (structure) |
|---|---|---|---|
| 676 | spiro[2.5]octyl | NH | tetrahydroisoquinoline-6-yl-NH-C(O)-NH-S(O)₂-(1-methylcyclopropyl) |
| 677 | spiro[2.5]octyl | NH | tetrahydroisoquinoline-6-yl-O-C(O)-NH-S(O)₂-(1-methylcyclopropyl) |
| 678 | spiro[2.5]octyl | NH | tetrahydroisoquinoline-6-yl-(1H-tetrazol-5-yl) |
| 679 | spiro[2.5]octyl | NH | tetrahydroisoquinoline-6-yl-C(O)-NH-CH₂-CO₂H |
| 680 | spiro[2.5]octyl | NH | tetrahydroisoquinoline-6-yl-C(O)-NH-CH₂CH₂-SO₃H |
| 681 | spiro[2.5]octyl | NH | 6-(MeO₂C)-indolin-1-yl |
| 682 | spiro[2.5]octyl | NH | 6-(HO₂C)-indolin-1-yl |

TABLE 4-continued

| Example | R² | X | (structure with A, Z, R⁴) |
|---|---|---|---|
| 683 | spiro[2.5]octyl | NH | 1-indolinyl-5-CO₂Et |
| 684 | spiro[2.5]octyl | NH | 1-indolinyl-5-CO₂H |
| 685 | spiro[2.5]octyl | NH | 1,2,3,4-tetrahydroquinolin-1-yl-6-CO₂Et |
| 686 | spiro[2.5]octyl | NH | 1,2,3,4-tetrahydroquinolin-1-yl-6-CO₂H |
| 687 | spiro[2.5]octyl | NH | 1,2,3,4-tetrahydroquinolin-1-yl-7-CO₂Et |
| 688 | spiro[2.5]octyl | NH | 1,2,3,4-tetrahydroquinolin-1-yl-7-CO₂H |
| 689 | spiro[2.5]octyl | NH | 2-isoindolinyl-5-CO₂Me |

TABLE 4-continued

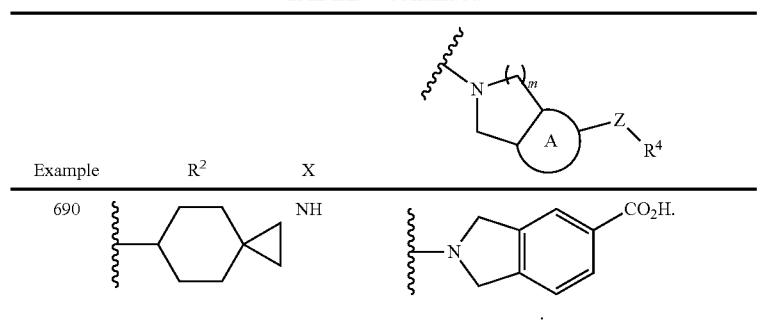

| Example | R² | X | |
|---|---|---|---|
| 690 | (cyclohexane-spirocyclopropane) | NH | (isoindoline-CO₂H) |

19. The compound of claim 1, selected from the compounds set forth below or a pharmaceutically acceptable salt thereof:

| Compound | Structure |
|---|---|
| 1 | (structure with 5-cyclopropyl-3-(2,6-dichlorophenyl)isoxazole linked via CH₂O to bicyclic amine bearing urea with 3-fluorophenyl) |
| 2 | (structure with 5-cyclopropyl-3-(2,6-dichlorophenyl)isoxazole linked via CH₂O to bicyclic amine bearing urea with 3-trifluoromethylphenyl) |
| 3 | (structure with 5-cyclopropyl-3-(2,6-dichlorophenyl)isoxazole linked via CH₂O to bicyclic amine bearing urea with 3-cyanophenyl) |

-continued
| Compound | Structure |
|---|---|
| 4 | 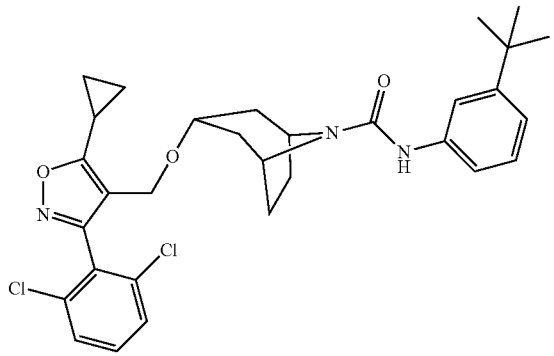 [SMILES: CC(C)(C)c1cccc(NC(=O)N2C3CCC2CC(OCc2c(-c4c(Cl)cccc4Cl)noc2C2CC2)C3)c1] |
| 5 | 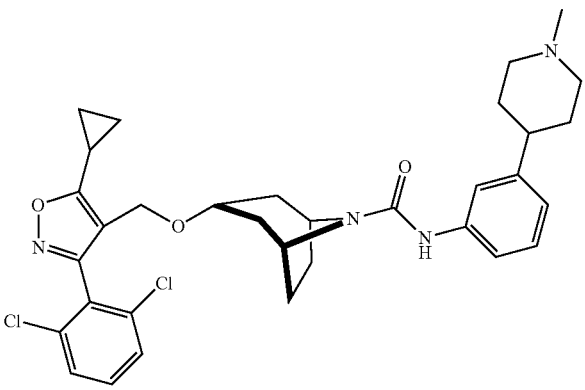 |
| 6 | 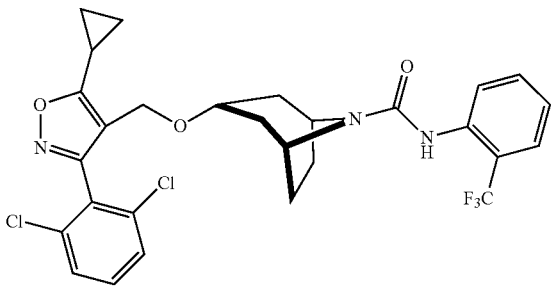 |
| 7 | 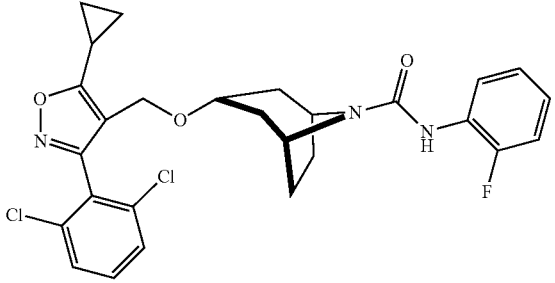 |

-continued
| Compound | Structure |
|---|---|
| 8 | 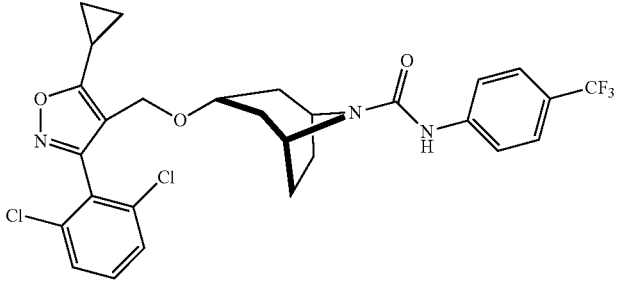 |
| 9 | 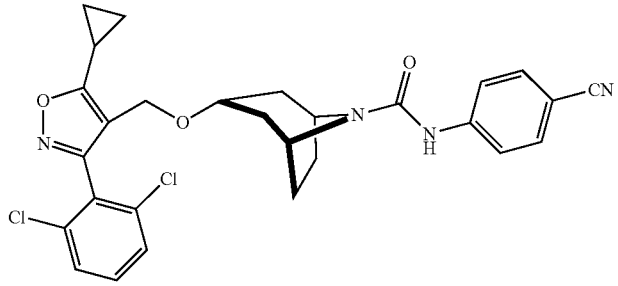 |
| 10 | 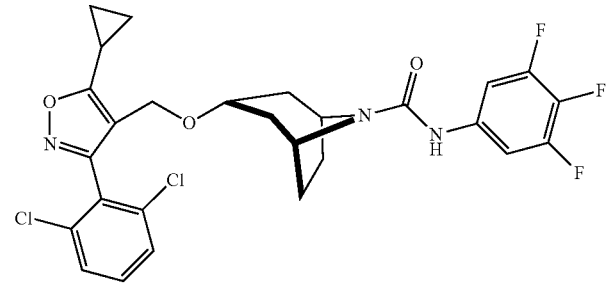 |
| 11 | 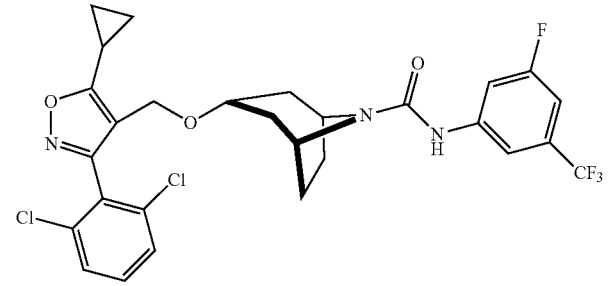 |
| 12 | 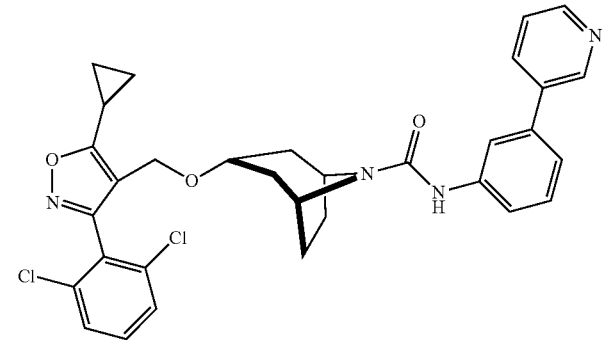 |

| Compound | Structure |
|---|---|
| 13 | 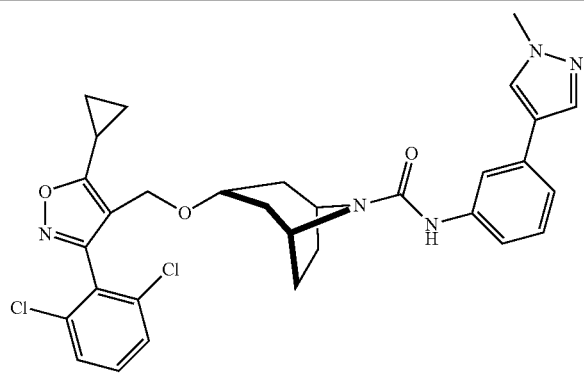 |
| 14 | 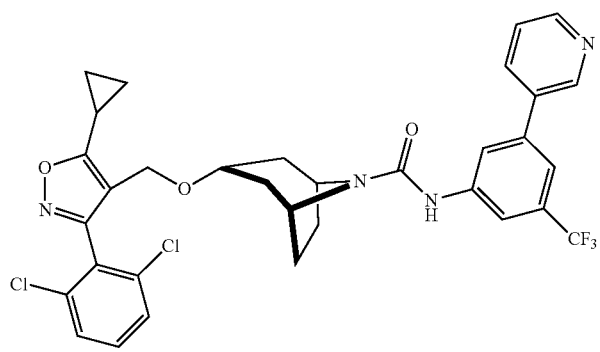 |
| 15 | 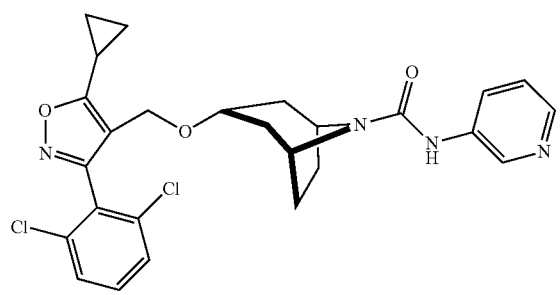 |
| 16 | 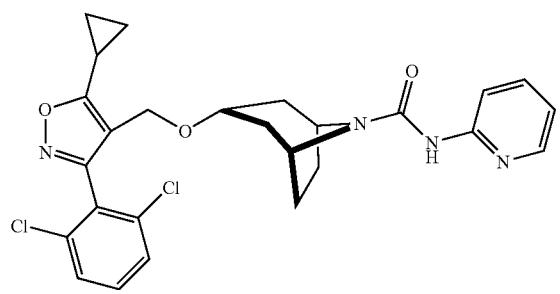 |
| 17 | 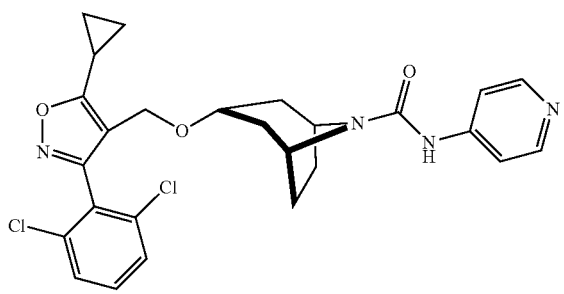 |

| Compound | Structure |
|---|---|
| 18 | 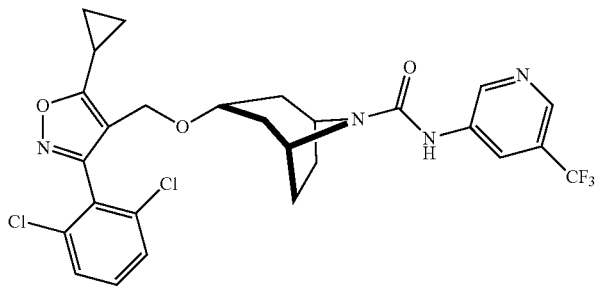 |
| 19 | 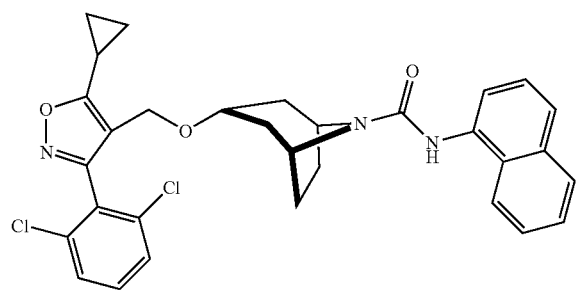 |
| 20 | 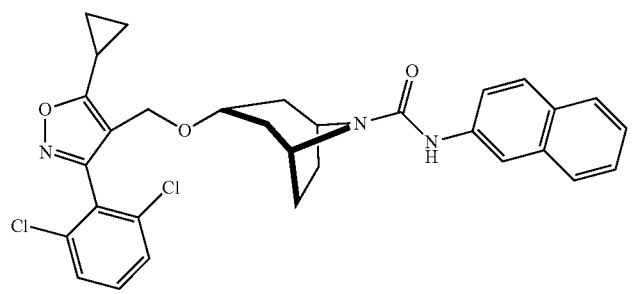 |
| 21 | 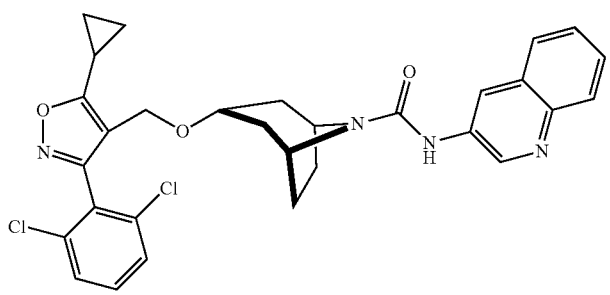 |
| 22 | 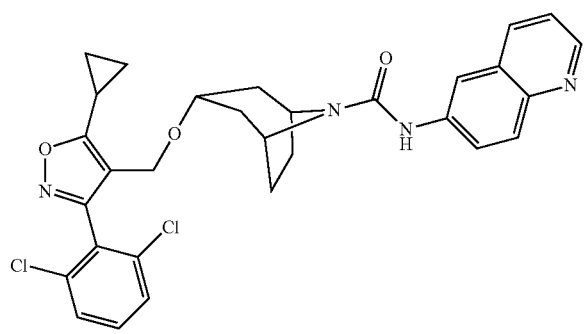 [SMILES: O=C(Nc1ccc2ncccc2c1)N1C2CCC1CC(OCc1c(-c3c(Cl)cccc3Cl)noc1C1CC1)C2] |

-continued
| Compound | Structure |
|---|---|
| 23 | 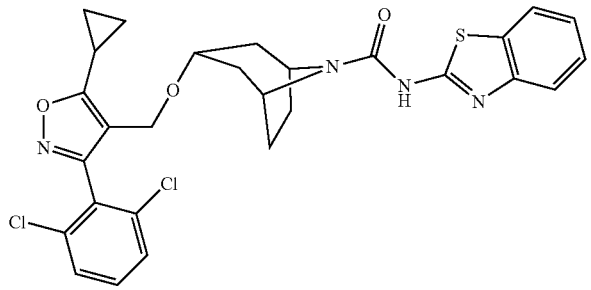 [SMILES: O=C(Nc1nc2ccccc2s1)N1C2CCC1CC(OCc1c(-c3c(Cl)cccc3Cl)noc1C1CC1)C2] |
| 24 | 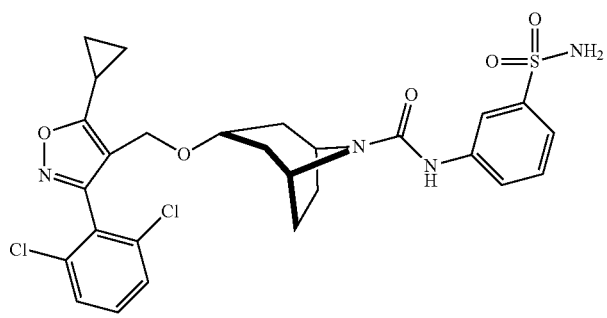 |
| 25 | 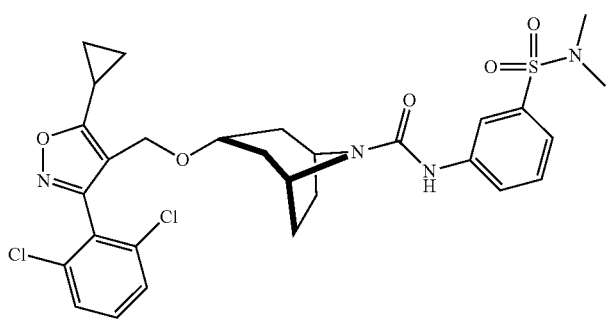 |
| 30 | 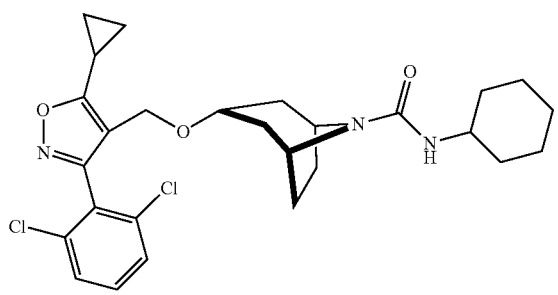 |
| 93 | 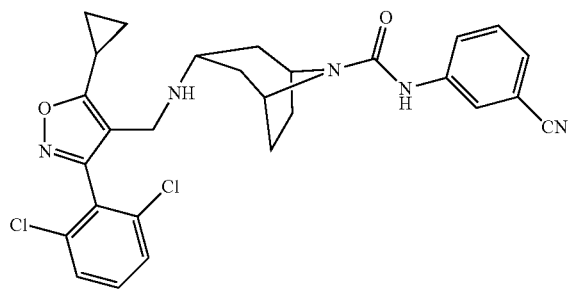 [SMILES: N#Cc1cccc(NC(=O)N2C3CCC2CC(NCc2c(-c4c(Cl)cccc4Cl)noc2C2CC2)C3)c1] |

| Compound | Structure |
|---|---|
| 121 | 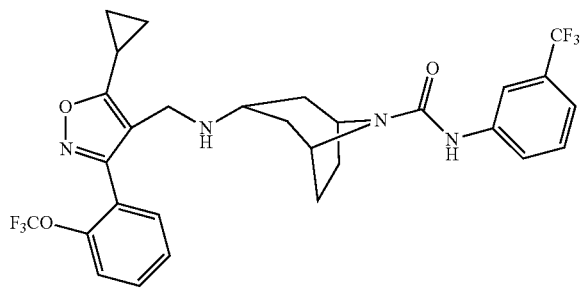 [SMILES: O=C(Nc1cccc(C(F)(F)F)c1)N1C2CCC1CC(NCc1c(-c3ccccc3OC(F)(F)F)noc1C1CC1)C2] |
| 181 | 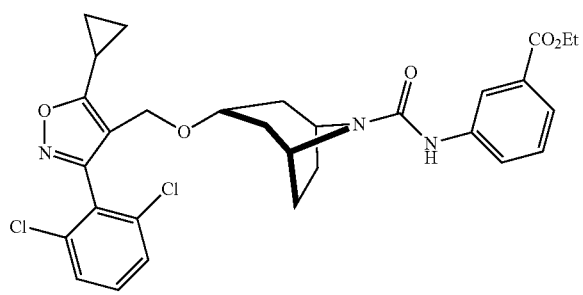 |
| 182 | 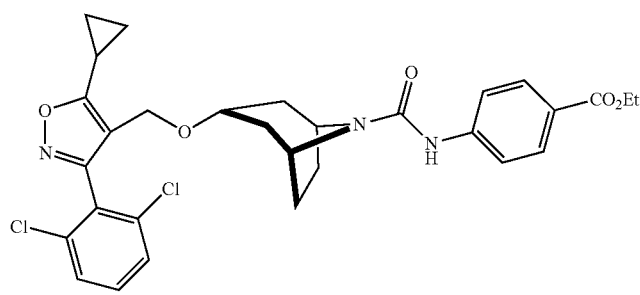 |
| 183 | 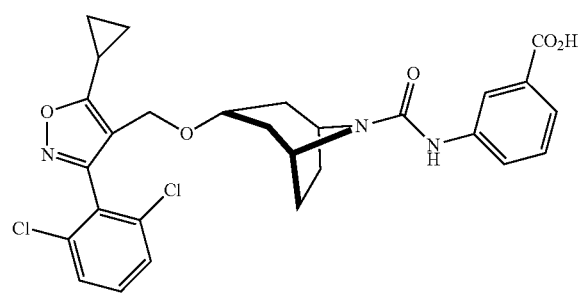 |
| 184 | 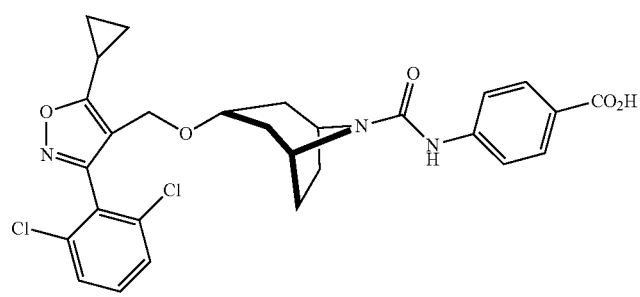 |

| Compound | Structure |
|---|---|
| 185 | 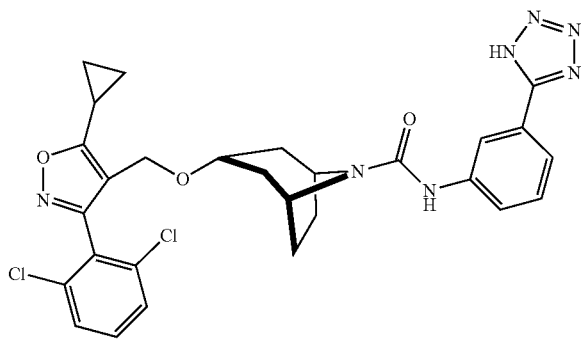 |
| 186 | 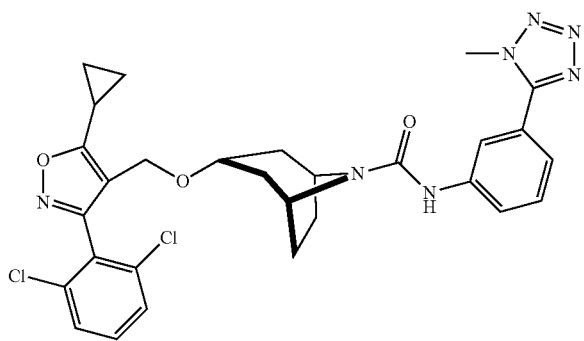 |
| 187 | 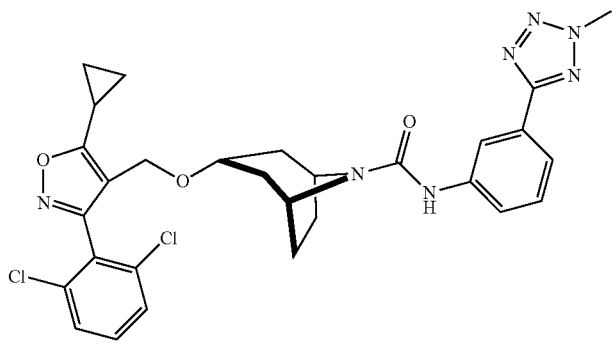 |
| 189 | 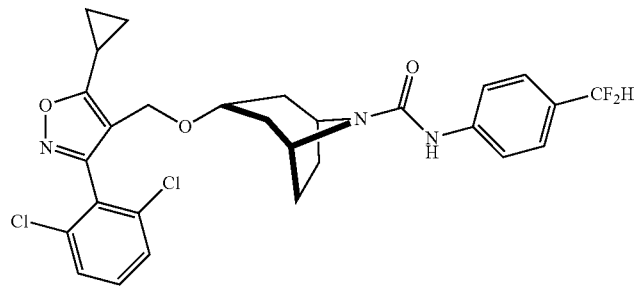 |

-continued
| Compound | Structure |
|---|---|
| 190 | 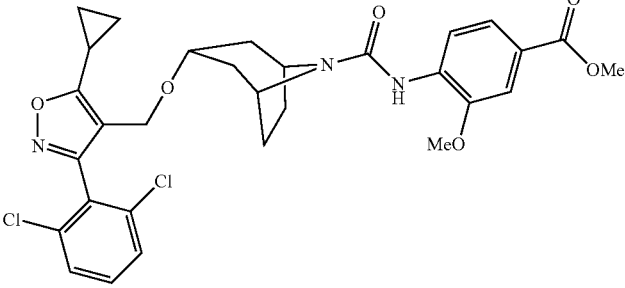 |
| 192 | 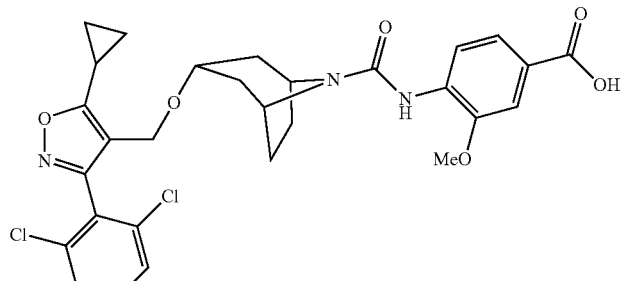 |
| 194 | 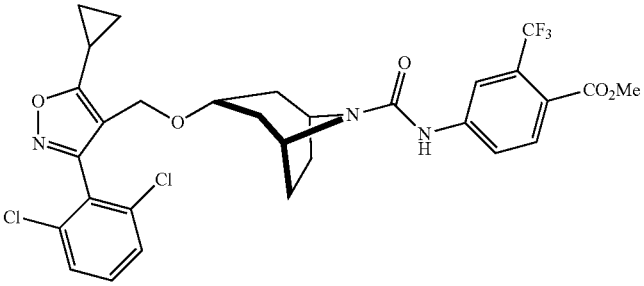 |
| 195 | 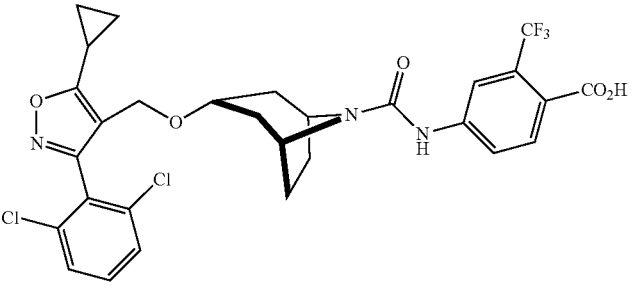 |
| 196 | 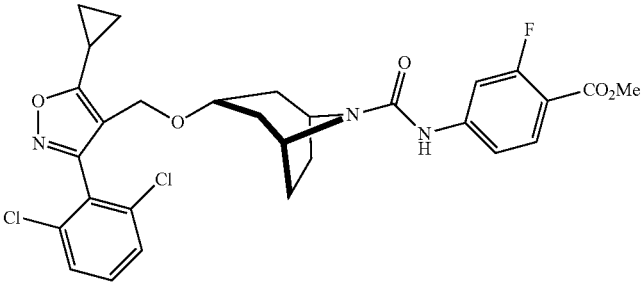 |

-continued
| Compound | Structure |
|---|---|
| 197 | 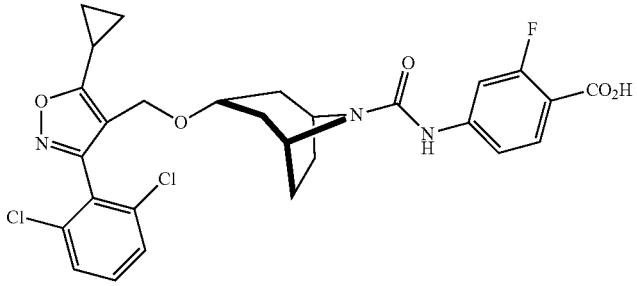 |
| 198 | 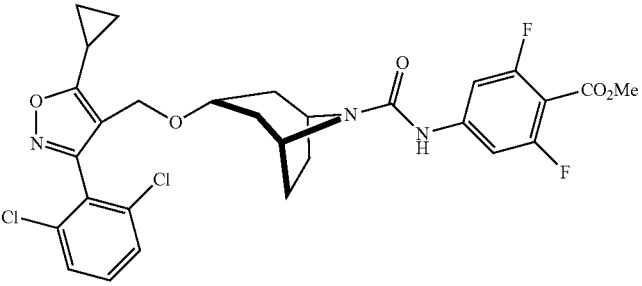 |
| 199 | 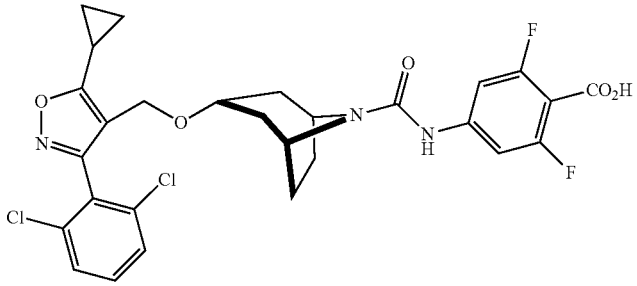 |
| 200 | 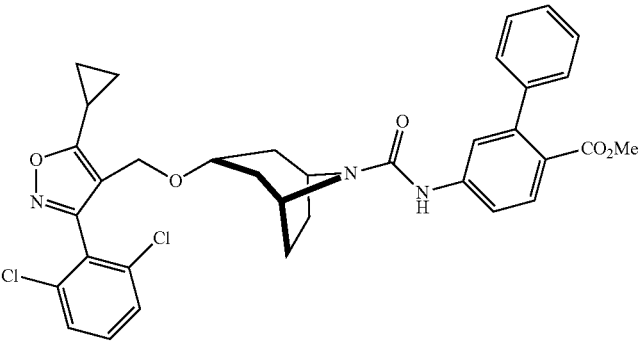 |
| 201 | 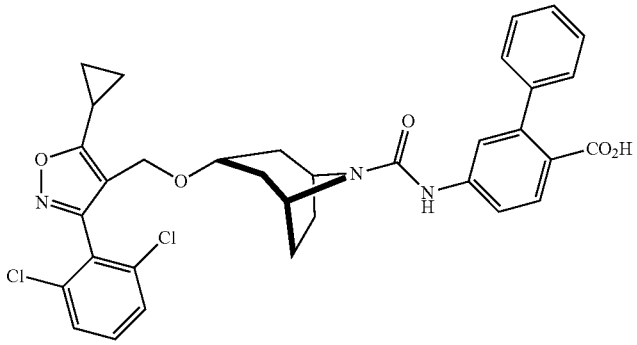 |

| Compound | Structure |
|---|---|
| 211 | 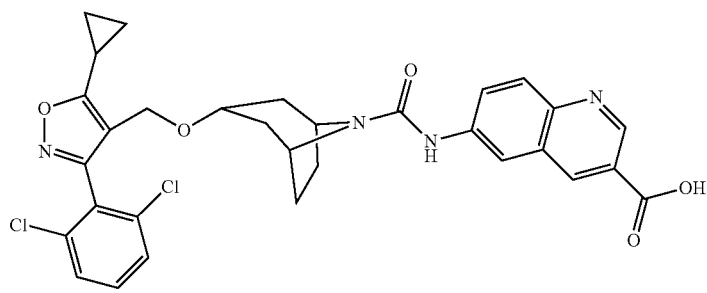 [SMILES: O=C(O)c1cnc2ccc(NC(=O)N3C4CCC3CC(OCc3c(-c5c(Cl)cccc5Cl)noc3C3CC3)C4)cc2c1] |
| 212 | 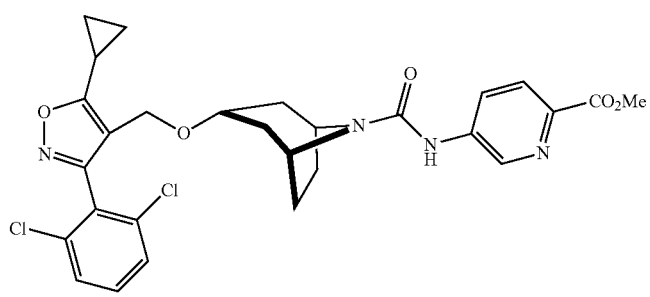 |
| 213 | 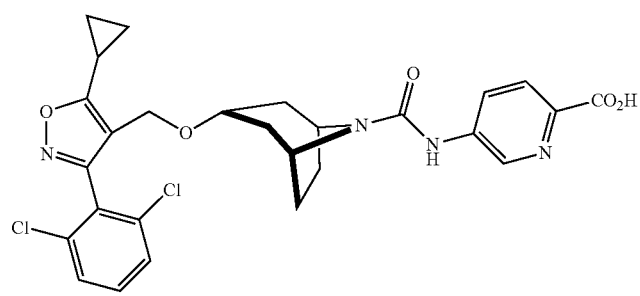 |
| 214 | 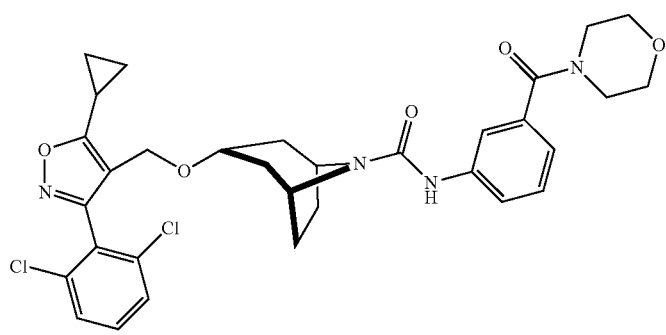 |
| 215 | 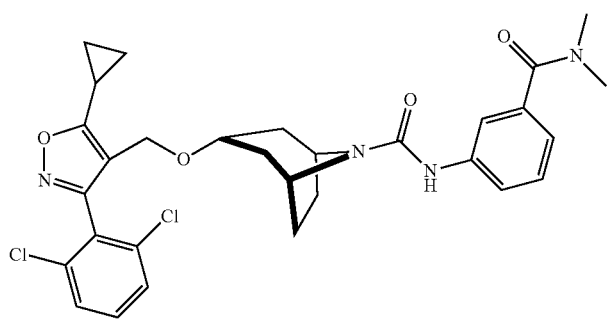 |

| Compound | Structure |
|---|---|
| 216 | 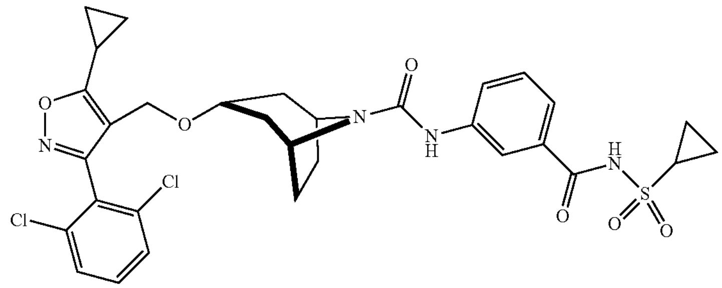 |
| 217 | 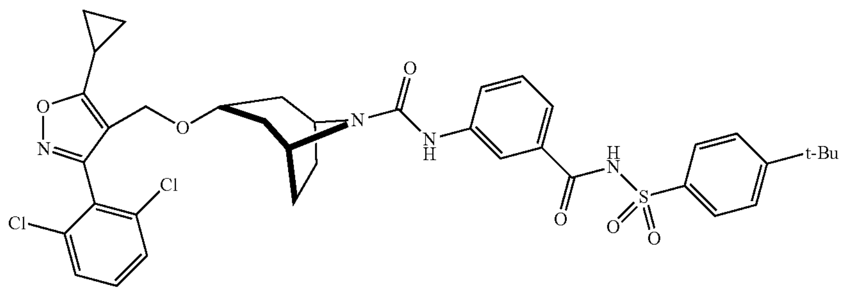 |
| 219 | 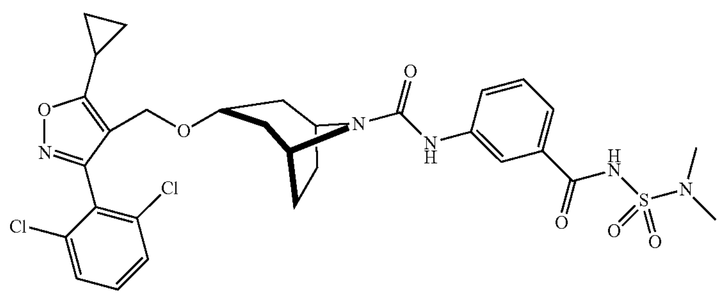 |
| 227 | 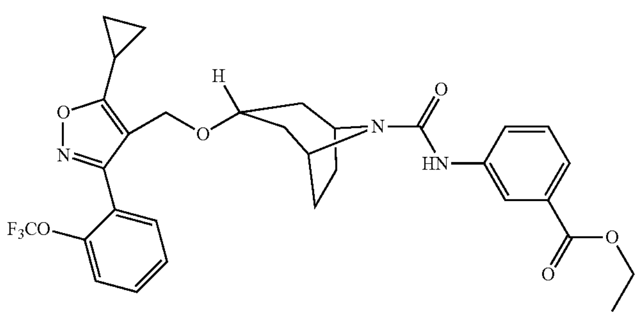 [SMILES: CCOC(=O)c1cccc(NC(=O)N2C3CCC2CC(OCc2c(-c4ccccc4OC(F)(F)F)noc2C2CC2)C3)c1] |
| 228 | 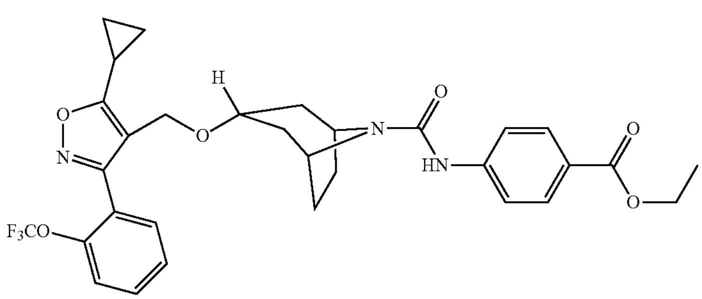 [SMILES: CCOC(=O)c1ccc(NC(=O)N2C3CCC2CC(OCc2c(-c4ccccc4OC(F)(F)F)noc2C2CC2)C3)cc1] |

| Compound | Structure |
|---|---|
| 229 | 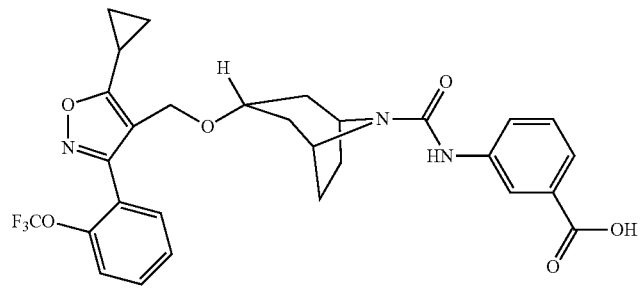 [SMILES: O=C(O)c1cccc(NC(=O)N2C3CCC2CC(OCc2c(-c4ccccc4OC(F)(F)F)noc2C2CC2)C3)c1] |
| 230 | 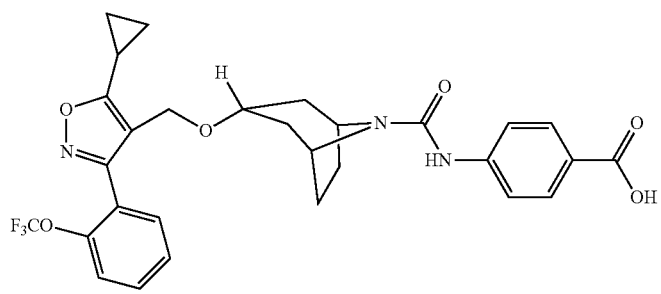 [SMILES: O=C(O)c1ccc(NC(=O)N2C3CCC2CC(OCc2c(-c4ccccc4OC(F)(F)F)noc2C2CC2)C3)cc1] |
| 236 | 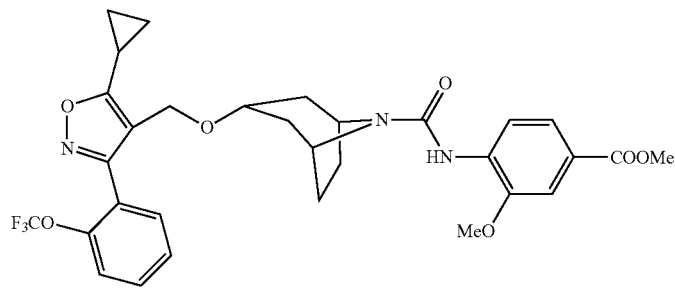 [SMILES: COC(=O)c1ccc(NC(=O)N2C3CCC2CC(OCc2c(-c4ccccc4OC(F)(F)F)noc2C2CC2)C3)c(OC)c1] |
| 237 | 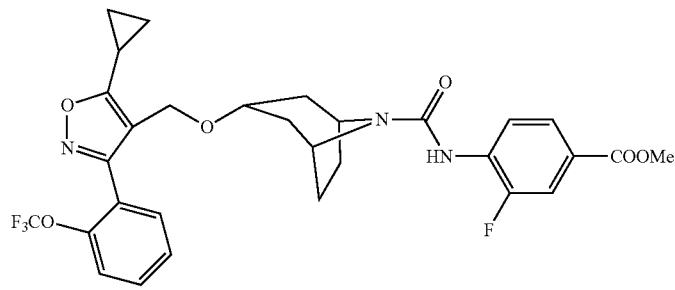 [SMILES: COC(=O)c1ccc(NC(=O)N2C3CCC2CC(OCc2c(-c4ccccc4OC(F)(F)F)noc2C2CC2)C3)c(F)c1] |
| 238 | 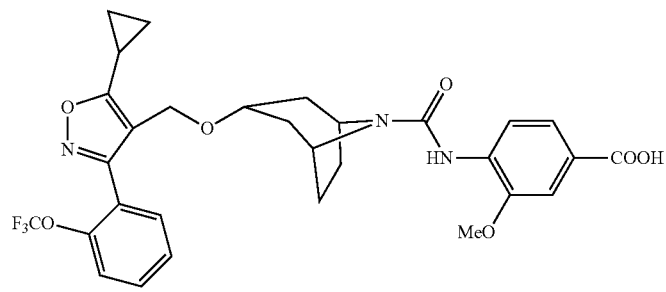 [SMILES: COc1cc(C(=O)O)ccc1NC(=O)N1C2CCC1CC(OCc1c(-c3ccccc3OC(F)(F)F)noc1C1CC1)C2] |

| Compound | Structure |
|---|---|
| 239 | 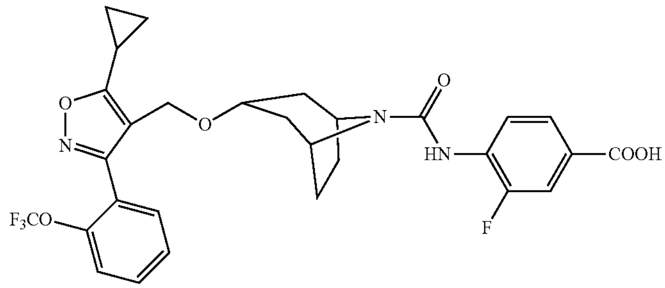 |
| 247 | 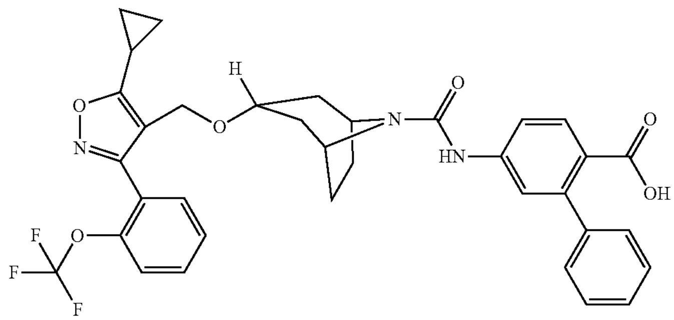 [SMILES: O=C(O)c1ccc(NC(=O)N2C3CCC2CC(OCc2c(-c4ccccc4OC(F)(F)F)noc2C2CC2)C3)cc1-c1ccccc1] |
| 262 | 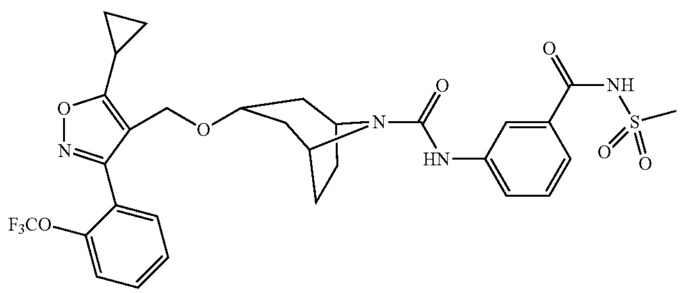 [SMILES: CS(=O)(=O)NC(=O)c1cccc(NC(=O)N2C3CCC2CC(OCc2c(-c4ccccc4OC(F)(F)F)noc2C2CC2)C3)c1] |
| 263 | 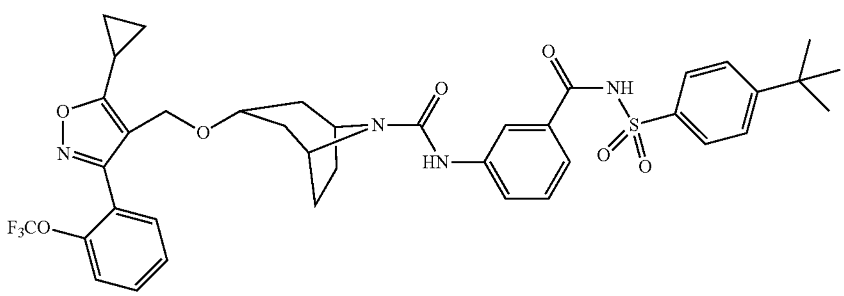 [SMILES: CC(C)(C)c1ccc(S(=O)(=O)NC(=O)c2cccc(NC(=O)N3C4CCC3CC(OCc3c(-c5ccccc5OC(F)(F)F)noc3C3CC3)C4)c2)cc1] |
| 264 | 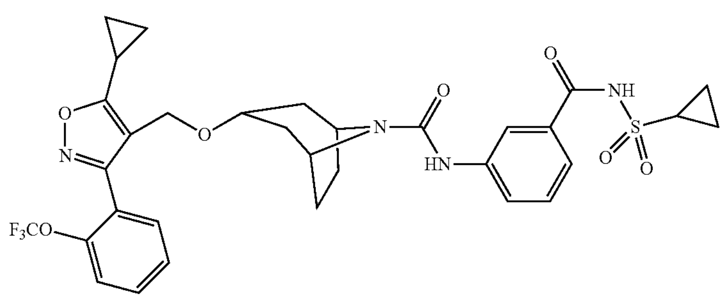 [SMILES: O=C(NS(=O)(=O)C1CC1)c1cccc(NC(=O)N2C3CCC2CC(OCc2c(-c4ccccc4OC(F)(F)F)noc2C2CC2)C3)c1] |

| Compound | Structure |
|---|---|
| 265 | 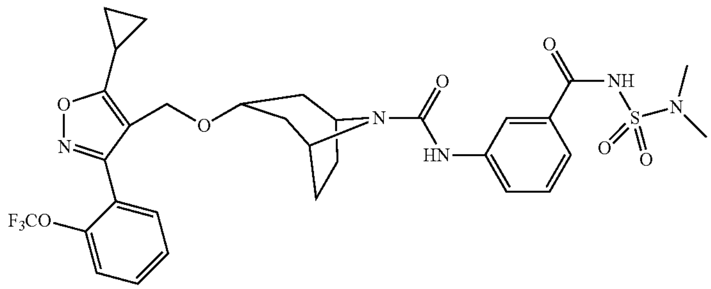 [SMILES: CN(C)S(=O)(=O)NC(=O)c1cccc(NC(=O)N2C3CCC2CC(OCc2c(-c4ccccc4OC(F)(F)F)noc2C2CC2)C3)c1] |
| 266 | 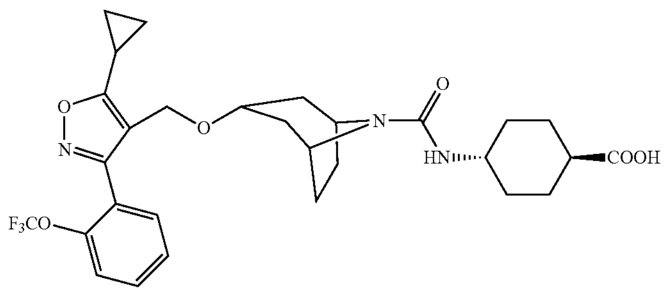 [SMILES: O=C(N[C@H]1CC[C@H](C(=O)O)CC1)N1C2CCC1CC(OCc1c(-c3ccccc3OC(F)(F)F)noc1C1CC1)C2] |
| 285 | 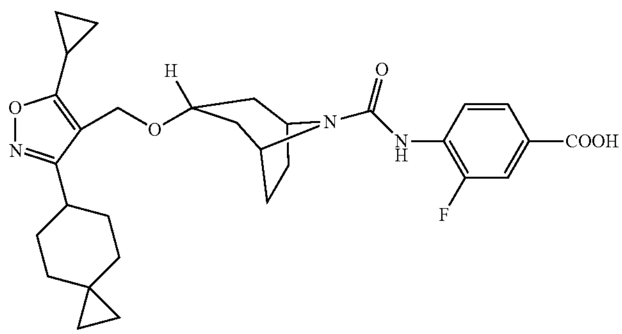 [SMILES: O=C(O)c1ccc(NC(=O)N2C3CCC2CC(OCc2c(C4CCC5(CC4)CC5)noc2C2CC2)C3)c(F)c1] |
| 293 | 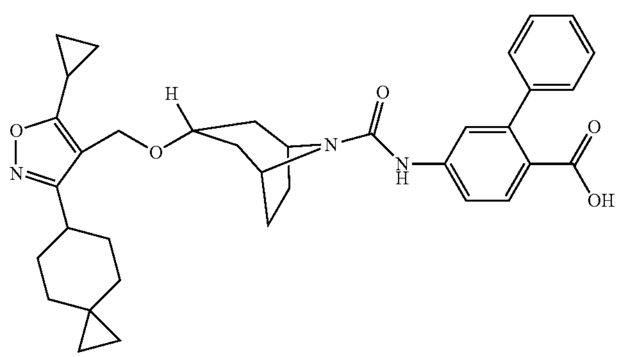 [SMILES: O=C(O)c1ccc(NC(=O)N2C3CCC2CC(OCc2c(C4CCC5(CC4)CC5)noc2C2CC2)C3)cc1-c1ccccc1] |
| 589 | 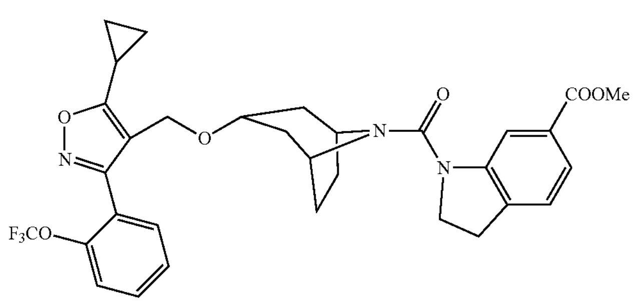 [SMILES: COC(=O)c1ccc2c(c1)N(C(=O)N1C3CCC1CC(OCc1c(-c4ccccc4OC(F)(F)F)noc1C1CC1)C3)CC2] |

| Compound | Structure |
|---|---|
| 590 | 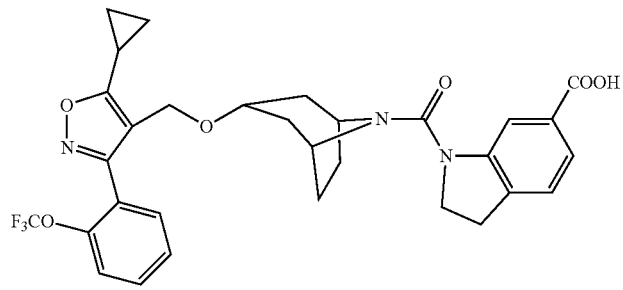 [SMILES: O=C(O)c1ccc2c(c1)N(C(=O)N1C3CCC1CC(OCc1c(-c4ccccc4OC(F)(F)F)noc1C1CC1)C3)CC2] |
| 591 | 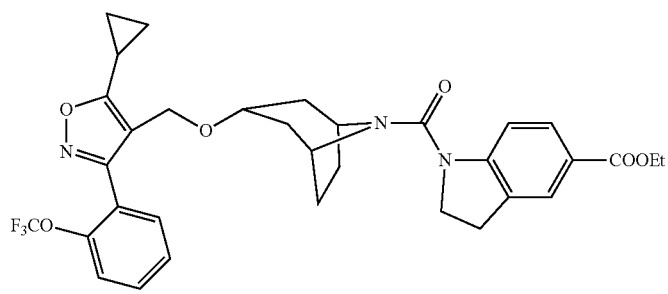 [SMILES: CCOC(=O)c1ccc2c(c1)CCN2C(=O)N1C2CCC1CC(OCc1c(-c3ccccc3OC(F)(F)F)noc1C1CC1)C2] |
| 592 | 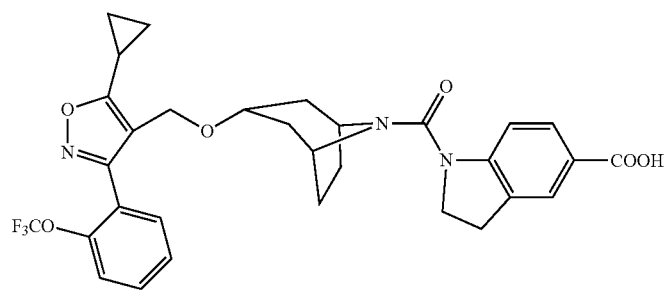 [SMILES: O=C(O)c1ccc2c(c1)CCN2C(=O)N1C2CCC1CC(OCc1c(-c3ccccc3OC(F)(F)F)noc1C1CC1)C2] |
| 593 | 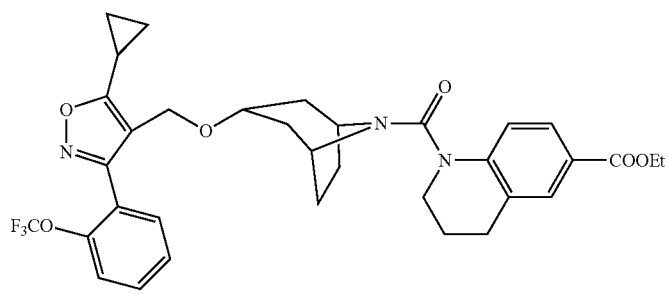 [SMILES: CCOC(=O)c1ccc2c(c1)CCCN2C(=O)N1C2CCC1CC(OCc1c(-c3ccccc3OC(F)(F)F)noc1C1CC1)C2] |
| 594 | 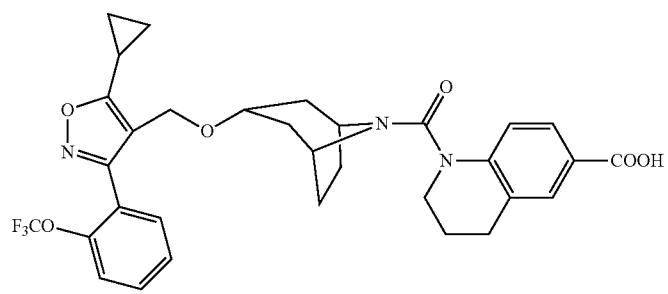 |

| Compound | Structure |
|---|---|
| 595 | 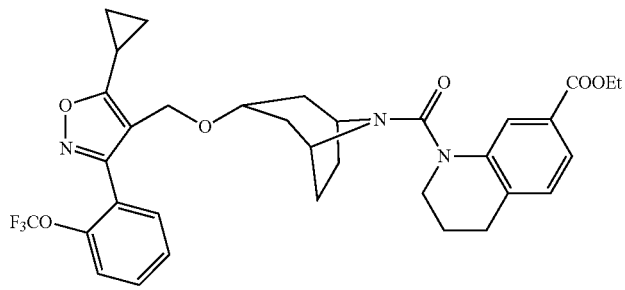 [SMILES: CCOC(=O)c1ccc2c(c1)N(C(=O)N1C3CCC1CC(OCc1c(-c4ccccc4OC(F)(F)F)noc1C1CC1)C3)CCC2] |
| 596 | 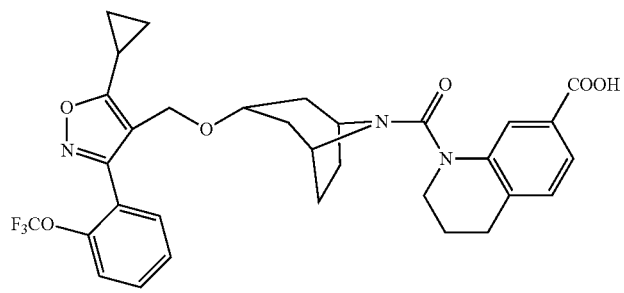 [SMILES: O=C(O)c1ccc2c(c1)N(C(=O)N1C3CCC1CC(OCc1c(-c4ccccc4OC(F)(F)F)noc1C1CC1)C3)CCC2] |
| 597 | 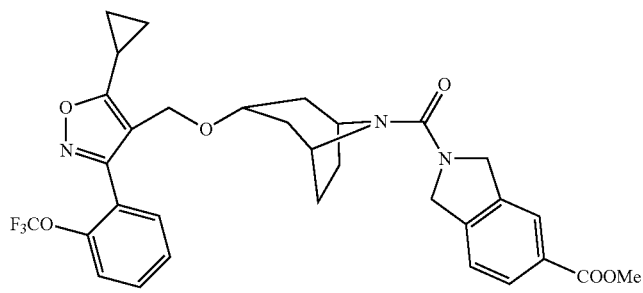 [SMILES: COC(=O)c1ccc2c(c1)CN(C(=O)N1C3CCC1CC(OCc1c(-c4ccccc4OC(F)(F)F)noc1C1CC1)C3)C2] |
| 598 | 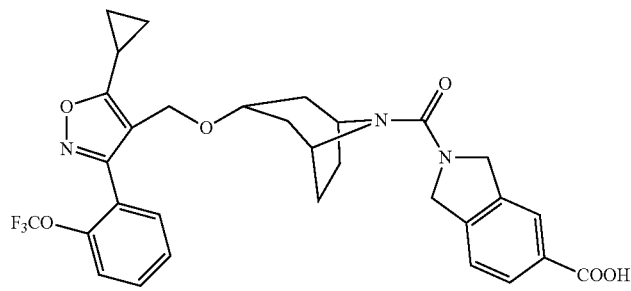 [SMILES: O=C(O)c1ccc2c(c1)CN(C(=O)N1C3CCC1CC(OCc1c(-c4ccccc4OC(F)(F)F)noc1C1CC1)C3)C2] |
| 691 | 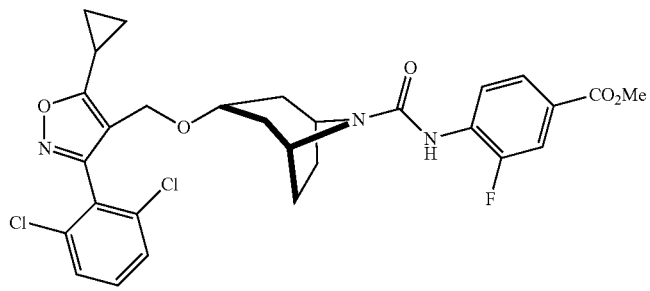 |

| Compound | Structure |
|---|---|
| 692 | 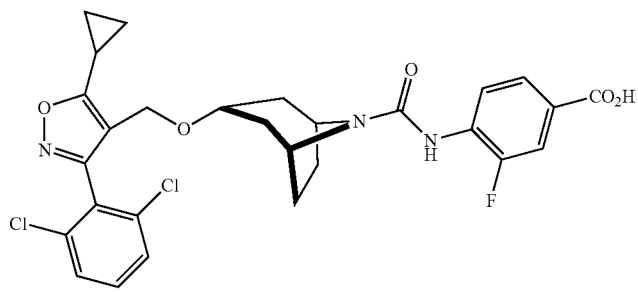 |
| 693 | 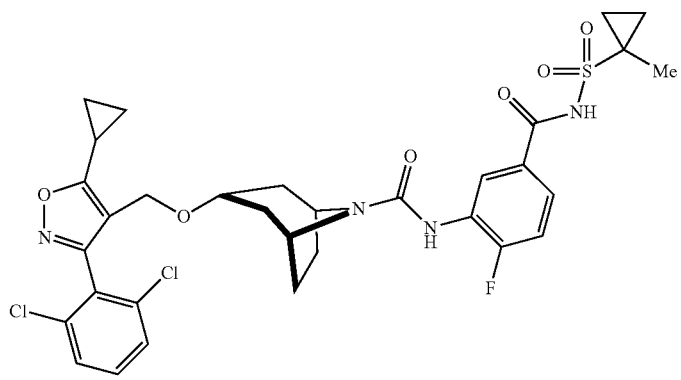 |
| 694 | 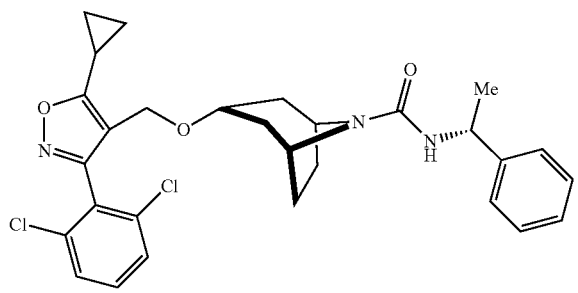 |
| 695 | 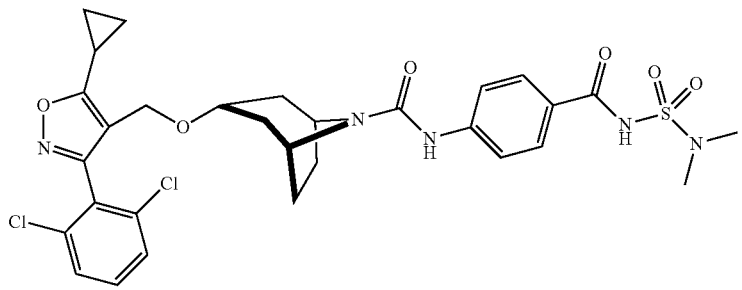 |
| 696 | 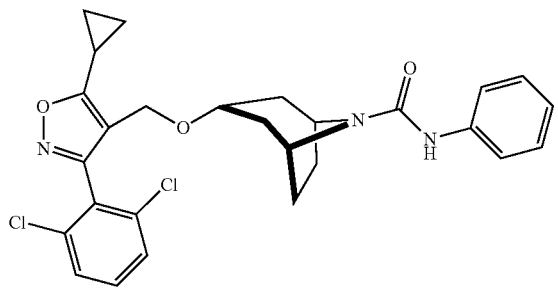 |

| Compound | Structure |
|---|---|
| 697 | 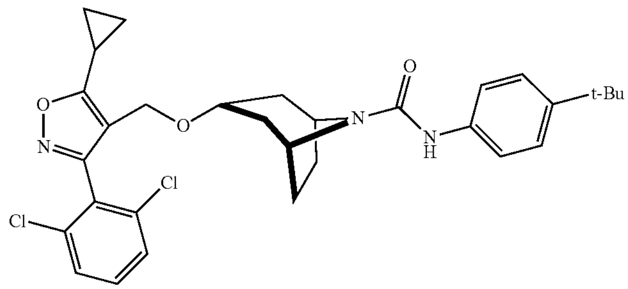 |
| 698 | 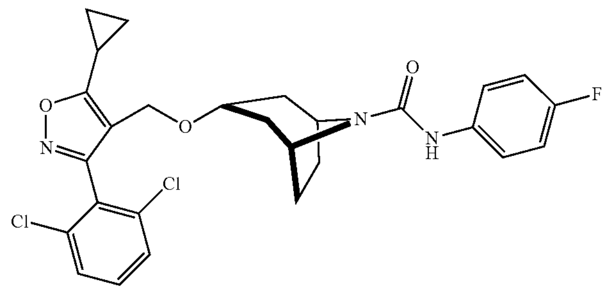 |
| 699 | 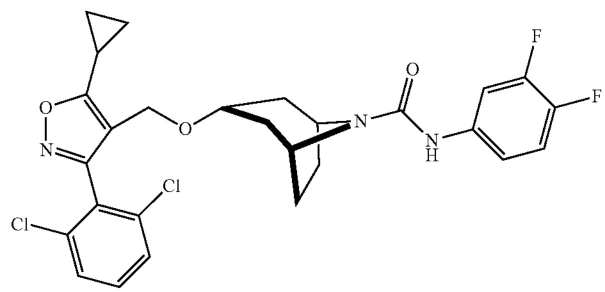 |
| 700 | 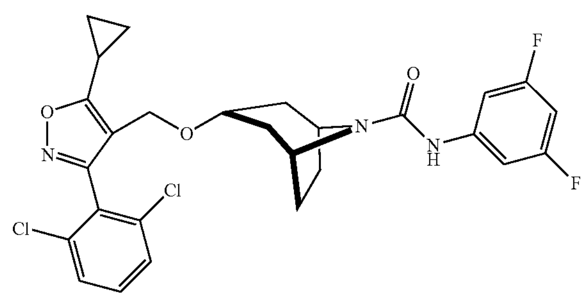 |
| 701 | 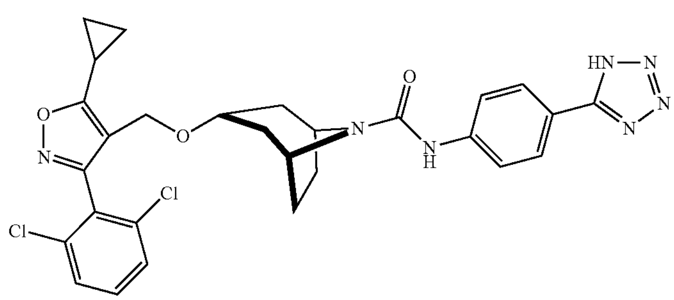 |

-continued
| Compound | Structure |
|---|---|
| 702 | 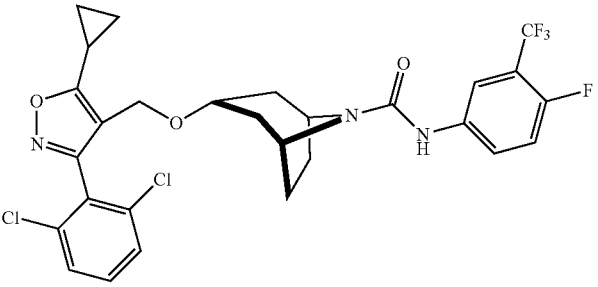 |
| 703 | 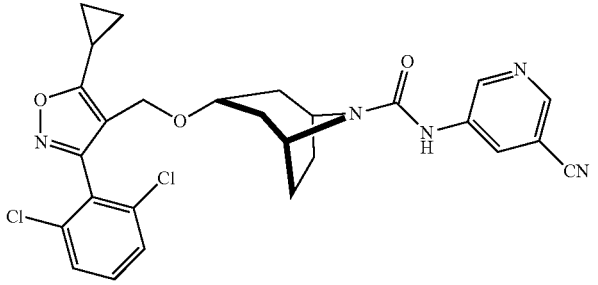 |
| 704 | 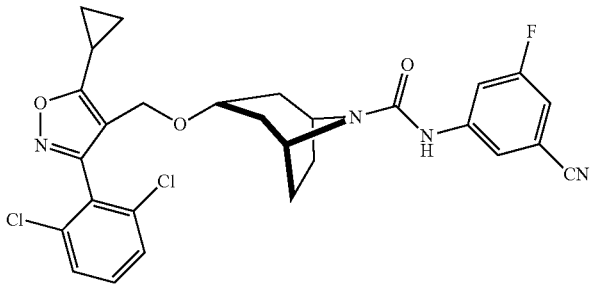 |
| 705 | 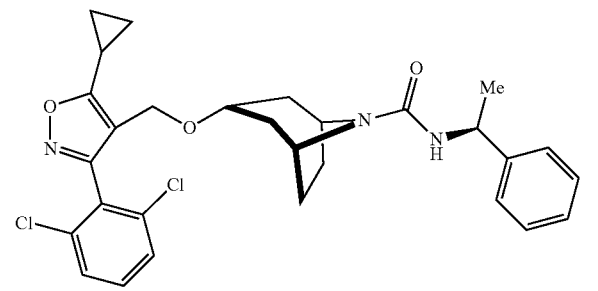 |
| 706 | 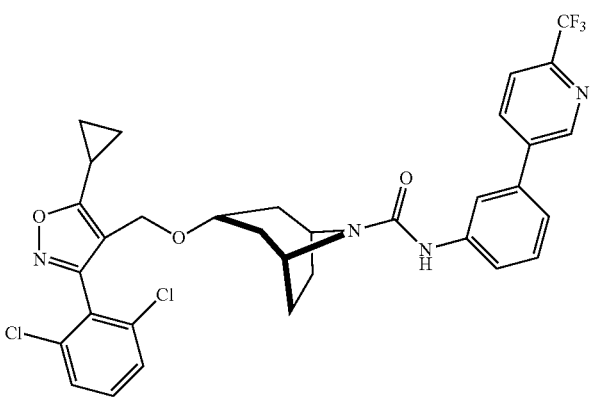 |

-continued

| Compound | Structure |
|---|---|
| 707 | 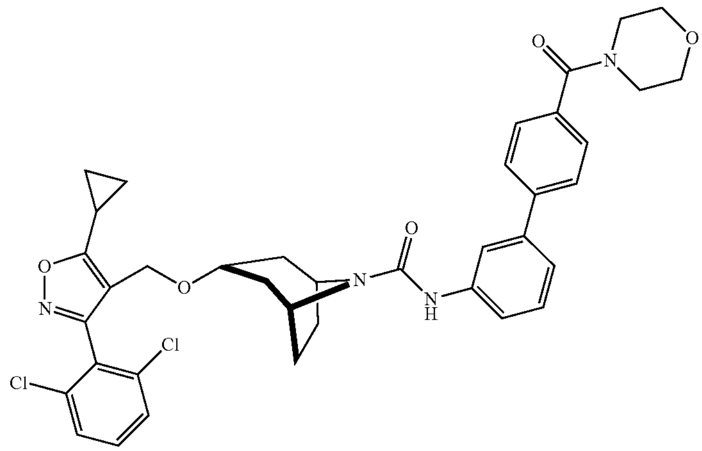 |
| 708 | 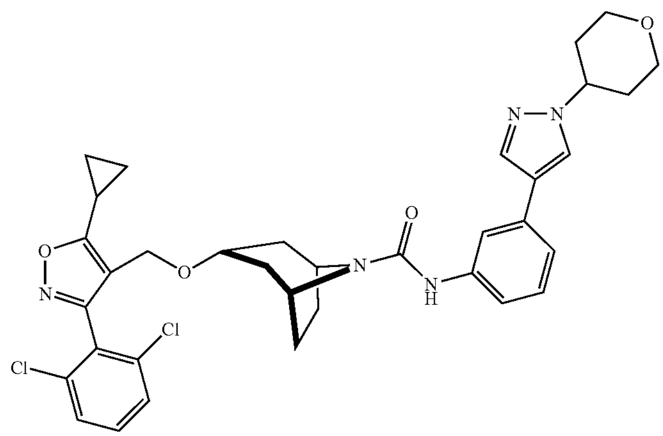 |
| 709 | 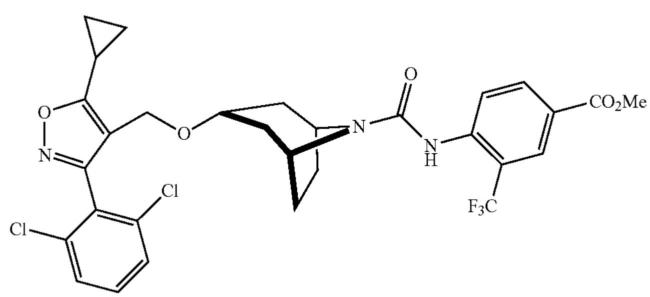 |
| 710 | 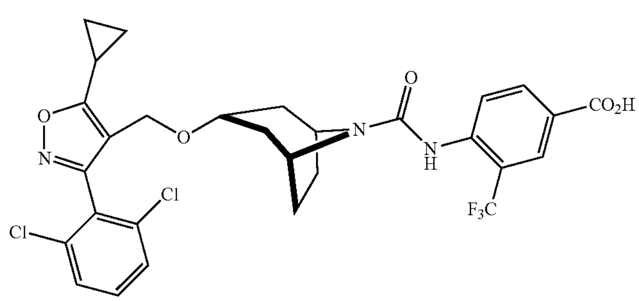 |

| Compound | Structure |
|---|---|
| 711 | 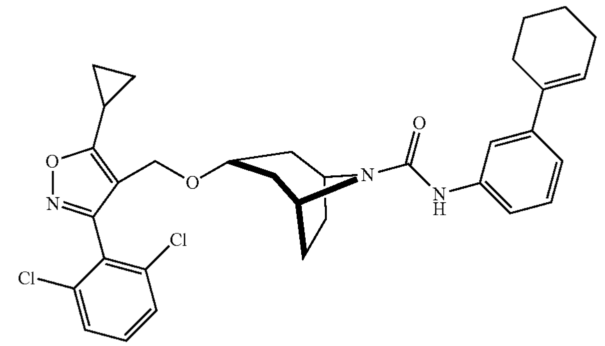 |
| 712 | 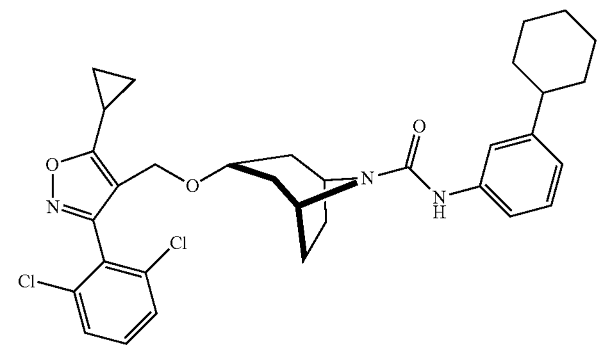 |
| 713 | 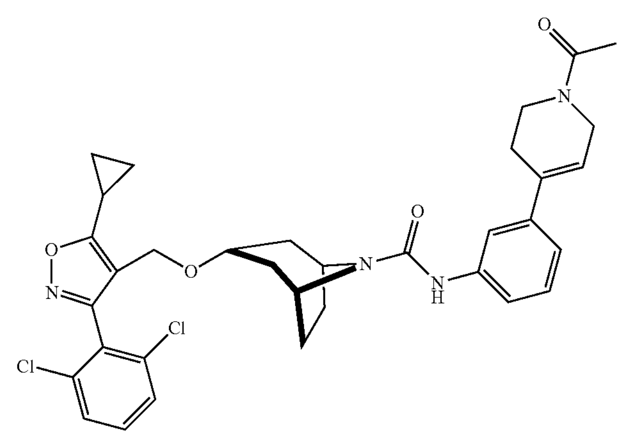 |
| 714 | 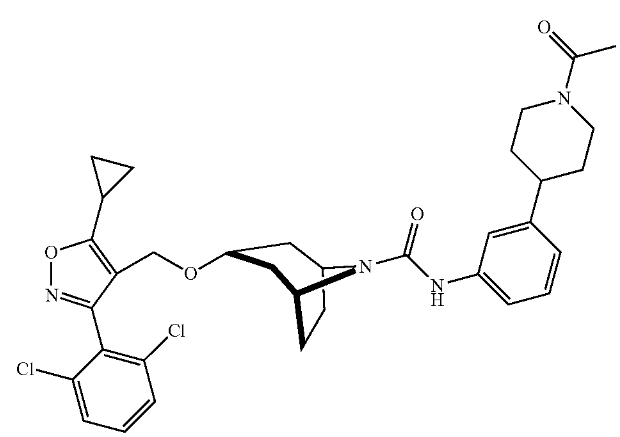 |

| Compound | Structure |
|---|---|
| 715 | 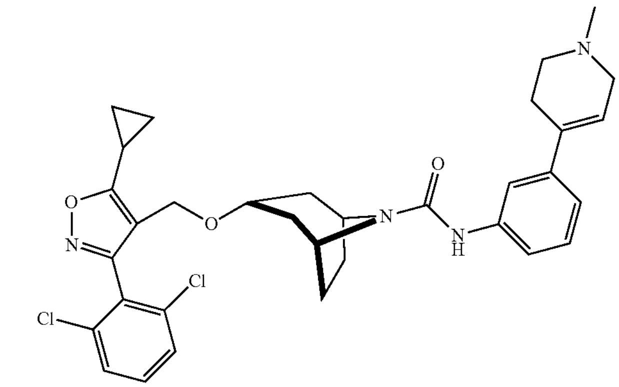 |
| 716 | 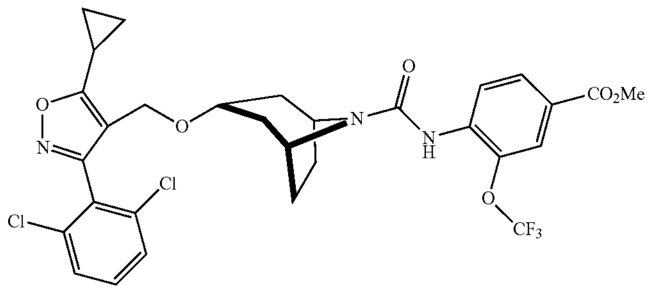 |
| 717 | 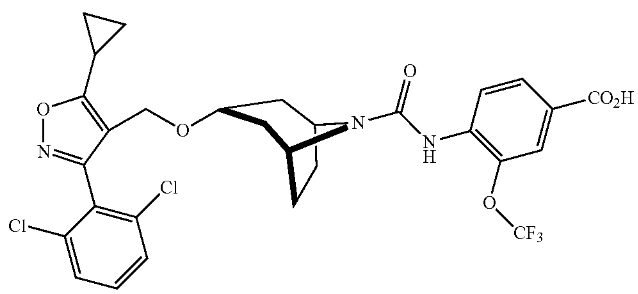 |
| 718 | 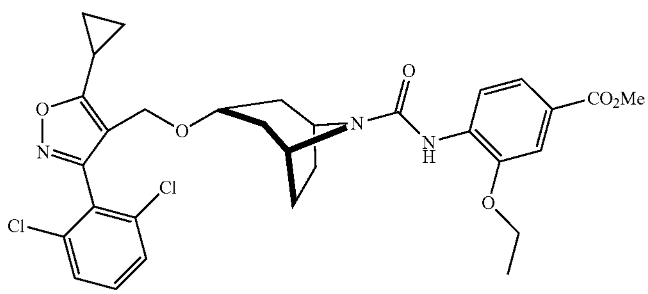 |
| 719 | 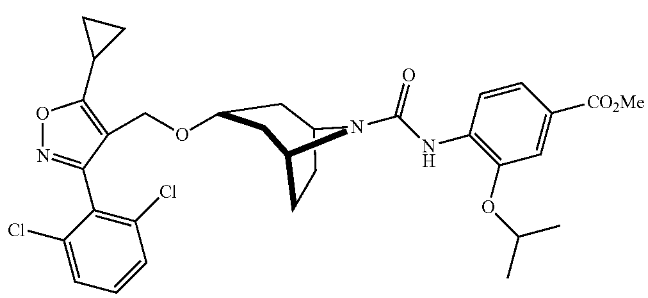 |

-continued

| Compound | Structure |
|---|---|
| 720 | 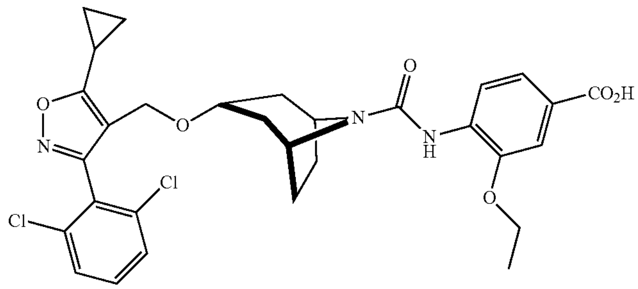 |
| 721 | 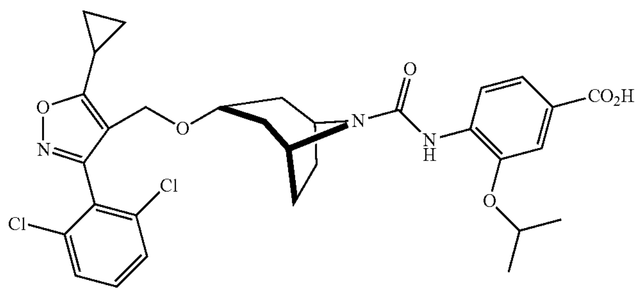 |
| 722 | 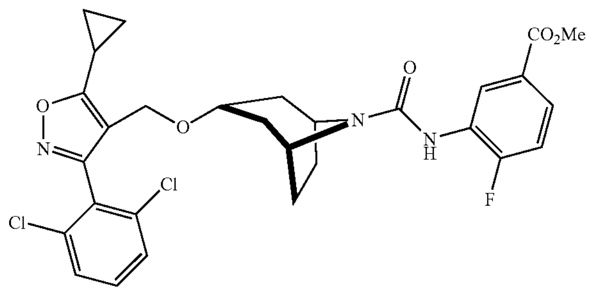 |
| 723 | 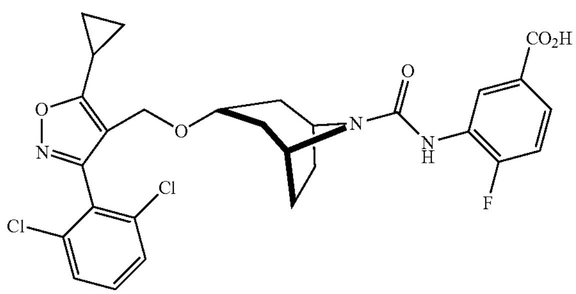 |
| 724 | 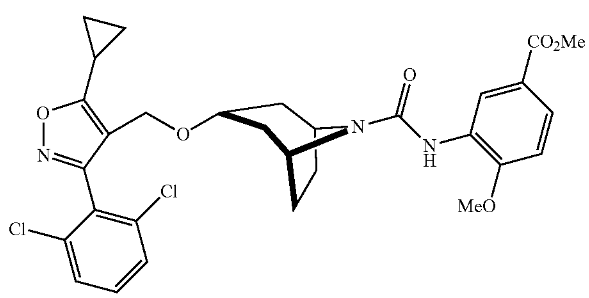 |

| Compound | Structure |
|---|---|
| 725 | 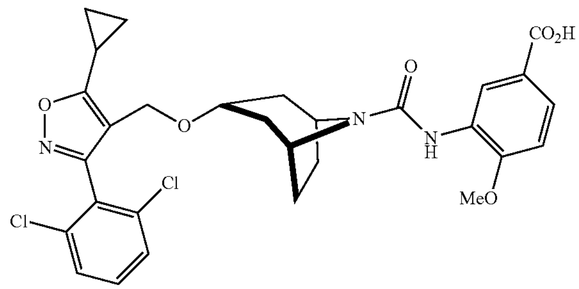 |
| 726 | 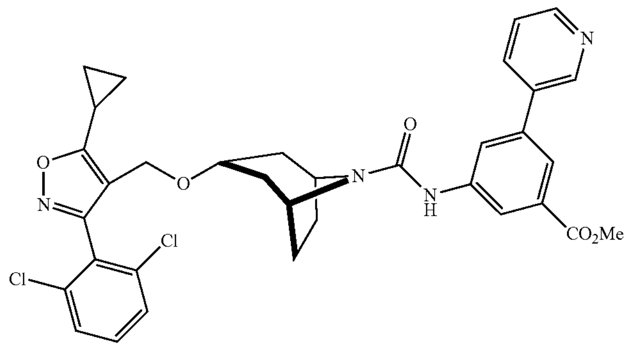 |
| 727 | 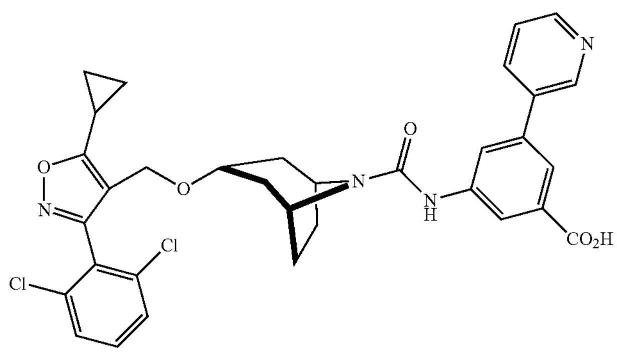 |
| 728 | 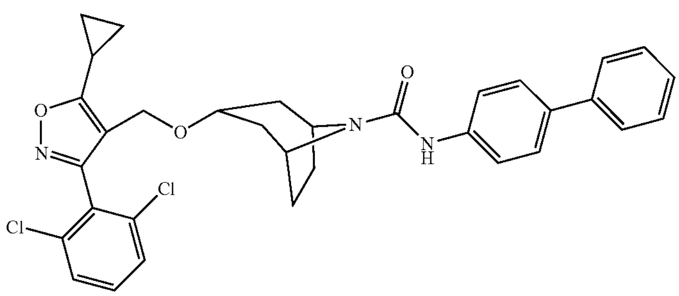 [SMILES: O=C(Nc1ccc(-c2ccccc2)cc1)N1C2CCC1CC(OCc1c(-c3c(Cl)cccc3Cl)noc1C1CC1)C2] |
| 729 | 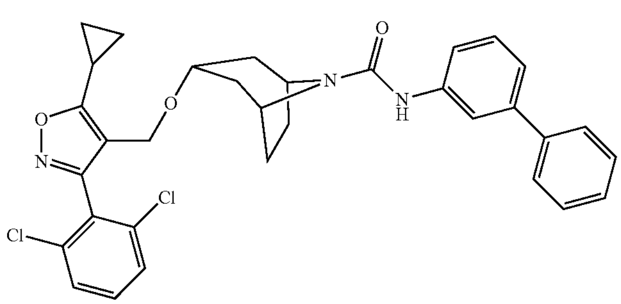 [SMILES: O=C(Nc1cccc(-c2ccccc2)c1)N1C2CCC1CC(OCc1c(-c3c(Cl)cccc3Cl)noc1C1CC1)C2] |

| Compound | Structure |
|---|---|
| 730 | 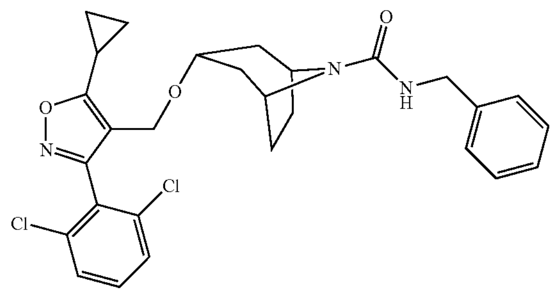 [SMILES: O=C(NCc1ccccc1)N1C2CCC1CC(OCc1c(-c3c(Cl)cccc3Cl)noc1C1CC1)C2] |
| 731 | 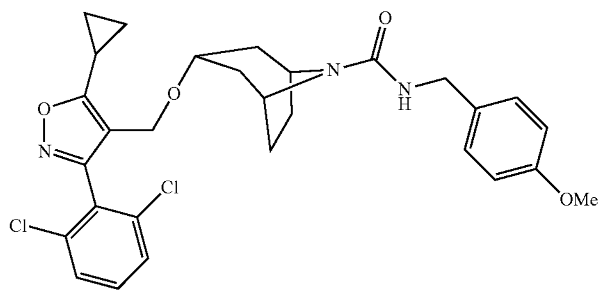 [SMILES: COc1ccc(CNC(=O)N2C3CCC2CC(OCc2c(-c4c(Cl)cccc4Cl)noc2C2CC2)C3)cc1] |
| 732 | 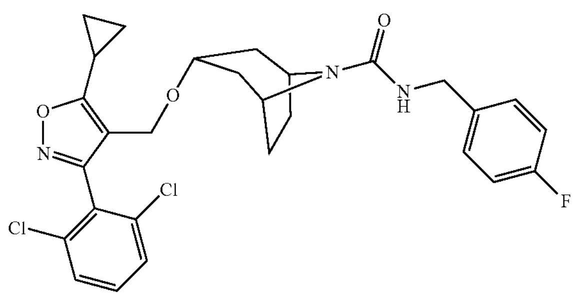 [SMILES: O=C(NCc1ccc(F)cc1)N1C2CCC1CC(OCc1c(-c3c(Cl)cccc3Cl)noc1C1CC1)C2] |
| 733 | 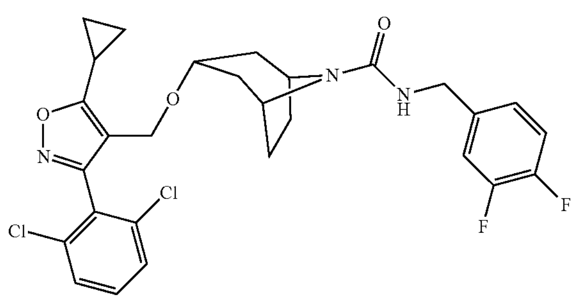 [SMILES: O=C(NCc1ccc(F)c(F)c1)N1C2CCC1CC(OCc1c(-c3c(Cl)cccc3Cl)noc1C1CC1)C2] |
| 734 | 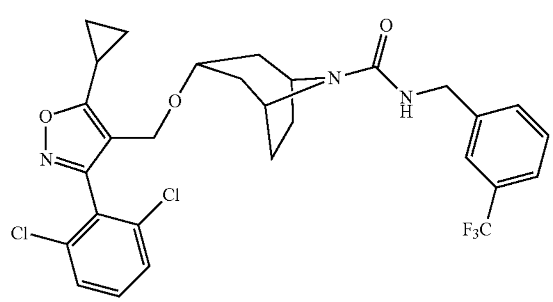 [SMILES: O=C(NCc1cccc(C(F)(F)F)c1)N1C2CCC1CC(OCc1c(-c3c(Cl)cccc3Cl)noc1C1CC1)C2] |

-continued

| Compound | Structure |
|---|---|
| 735 | 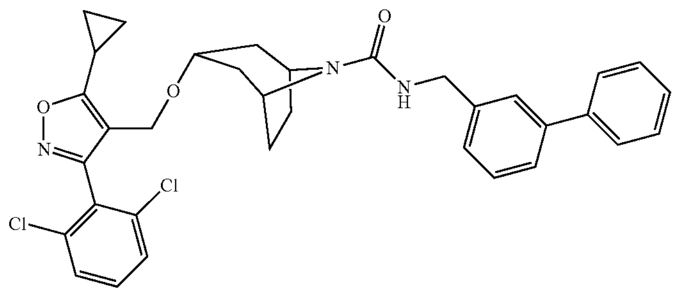 [SMILES: O=C(NCc1cccc(-c2ccccc2)c1)N1C2CCC1CC(OCc1c(-c3c(Cl)cccc3Cl)noc1C1CC1)C2] |
| 736 | 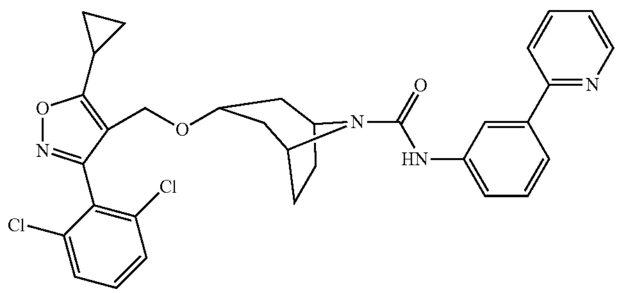 [SMILES: O=C(Nc1cccc(-c2ccccn2)c1)N1C2CCC1CC(OCc1c(-c3c(Cl)cccc3Cl)noc1C1CC1)C2] |
| 737 | 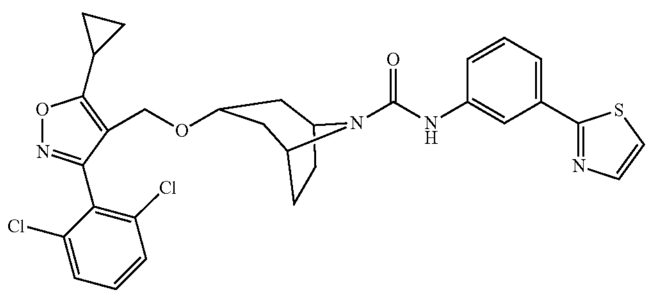 [SMILES: O=C(Nc1cccc(-c2nccs2)c1)N1C2CCC1CC(OCc1c(-c3c(Cl)cccc3Cl)noc1C1CC1)C2] |
| 738 | 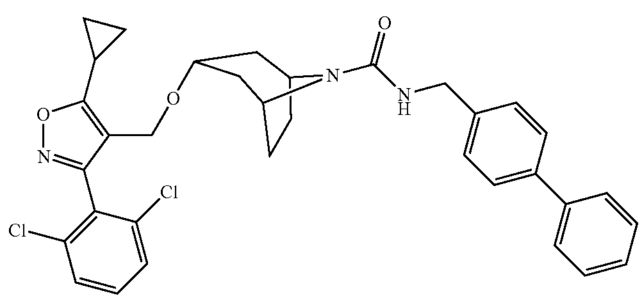 [SMILES: O=C(NCc1ccc(-c2ccccc2)cc1)N1C2CCC1CC(OCc1c(-c3c(Cl)cccc3Cl)noc1C1CC1)C2] |
| 739 | 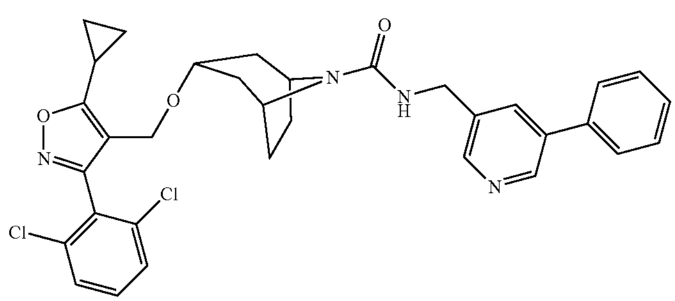 |

| Compound | Structure |
|---|---|
| 740 | 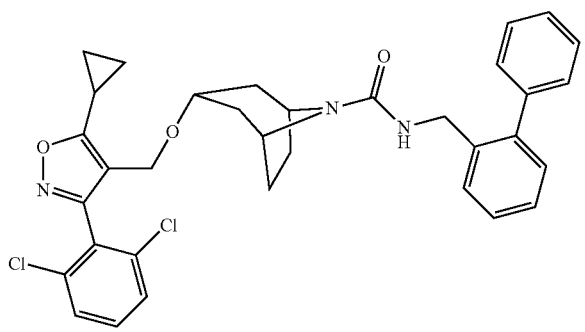 [SMILES: O=C(NCc1ccccc1-c1ccccc1)N1C2CCC1CC(OCc1c(-c3c(Cl)cccc3Cl)noc1C1CC1)C2] |
| 741 | 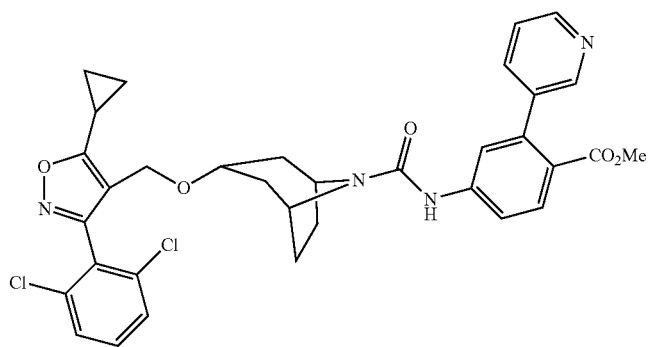 [SMILES: COC(=O)c1ccc(NC(=O)N2C3CCC2CC(OCc2c(-c4c(Cl)cccc4Cl)noc2C2CC2)C3)cc1-c1cccnc1] |
| 742 | 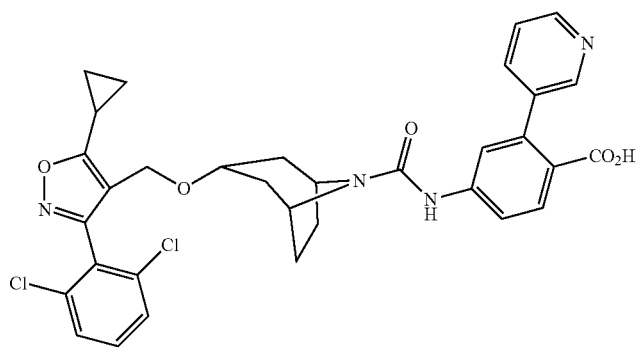 [SMILES: O=C(O)c1ccc(NC(=O)N2C3CCC2CC(OCc2c(-c4c(Cl)cccc4Cl)noc2C2CC2)C3)cc1-c1cccnc1] |
| 743 | 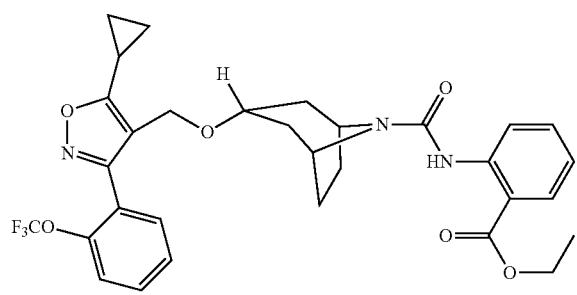 [SMILES: CCOC(=O)c1ccccc1NC(=O)N1C2CCC1CC(OCc1c(-c3ccccc3OC(F)(F)F)noc1C1CC1)C2] |

| Compound | Structure |
|---|---|
| 744 | 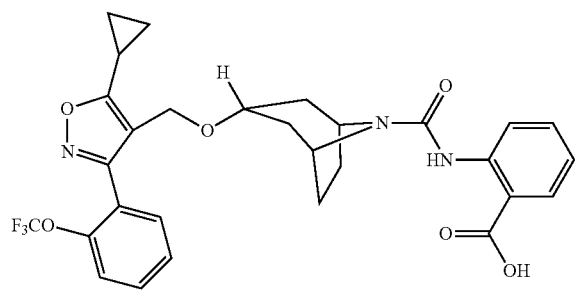 [SMILES: O=C(O)c1ccccc1NC(=O)N1C2CCC1CC(OCc1c(-c3ccccc3OC(F)(F)F)noc1C1CC1)C2] |
| 745 | 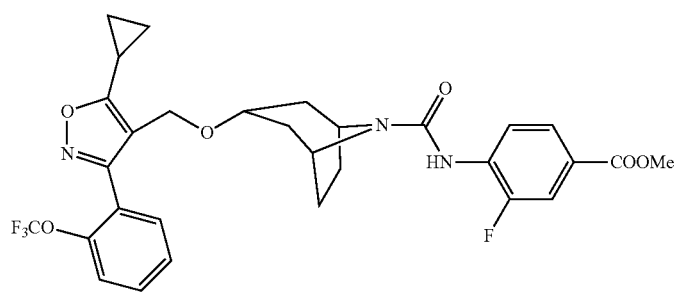 [SMILES: COC(=O)c1ccc(NC(=O)N2C3CCC2CC(OCc2c(-c4ccccc4OC(F)(F)F)noc2C2CC2)C3)c(F)c1] |
| 746 | 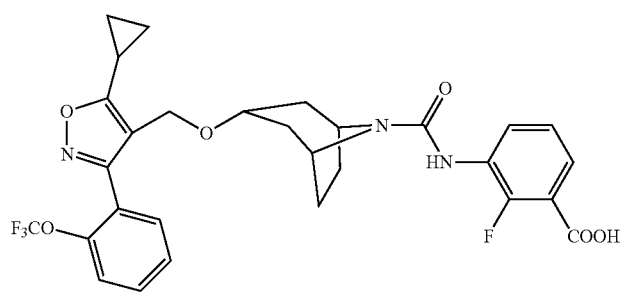 [SMILES: O=C(O)c1cccc(NC(=O)N2C3CCC2CC(OCc2c(-c4ccccc4OC(F)(F)F)noc2C2CC2)C3)c1F] |
| 747 | 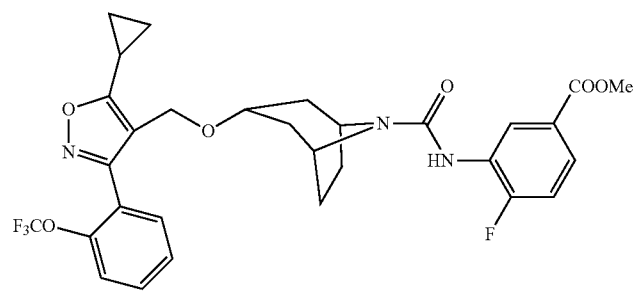 [SMILES: COC(=O)c1ccc(F)c(NC(=O)N2C3CCC2CC(OCc2c(-c4ccccc4OC(F)(F)F)noc2C2CC2)C3)c1] |
| 748 | 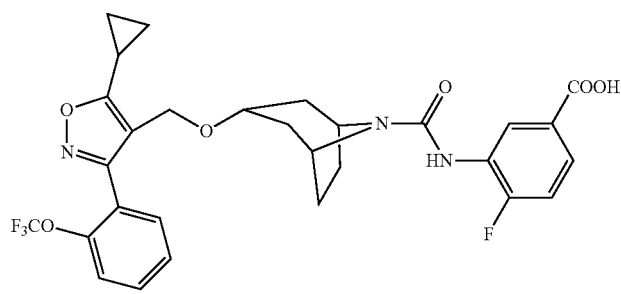 [SMILES: O=C(O)c1ccc(F)c(NC(=O)N2C3CCC2CC(OCc2c(-c4ccccc4OC(F)(F)F)noc2C2CC2)C3)c1] |

| Compound | Structure |
|---|---|
| 749 | 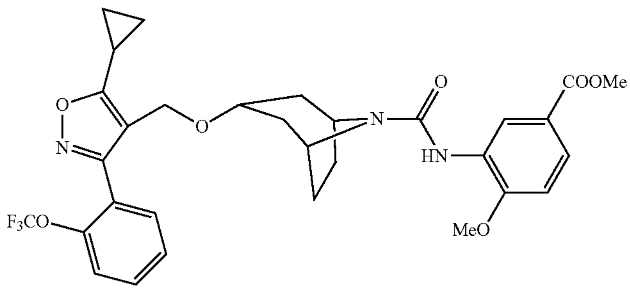 [SMILES: COC(=O)c1ccc(OC)c(NC(=O)N2C3CCC2CC(OCc2c(-c4ccccc4OC(F)(F)F)noc2C2CC2)C3)c1] |
| 750 | 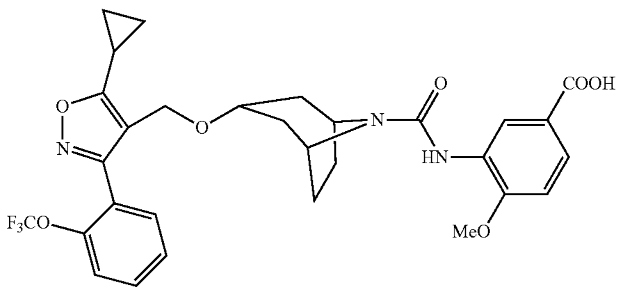 [SMILES: COc1ccc(C(=O)O)cc1NC(=O)N1C2CCC1CC(OCc1c(-c3ccccc3OC(F)(F)F)noc1C1CC1)C2] |
| 751 | 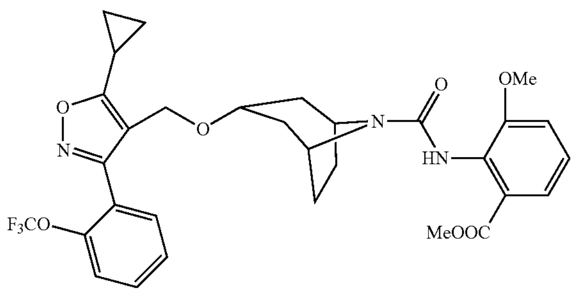 [SMILES: COC(=O)c1cccc(OC)c1NC(=O)N1C2CCC1CC(OCc1c(-c3ccccc3OC(F)(F)F)noc1C1CC1)C2] |
| 752 | 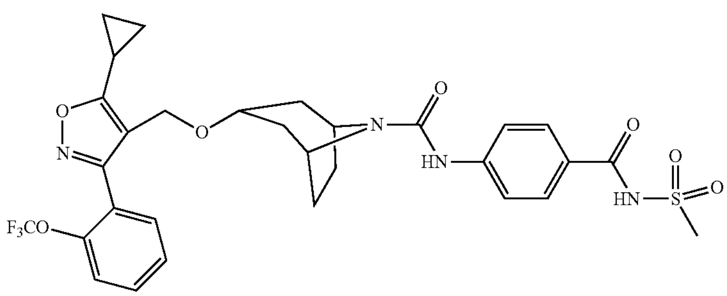 [SMILES: CS(=O)(=O)NC(=O)c1ccc(NC(=O)N2C3CCC2CC(OCc2c(-c4ccccc4OC(F)(F)F)noc2C2CC2)C3)cc1] |
| 753 | 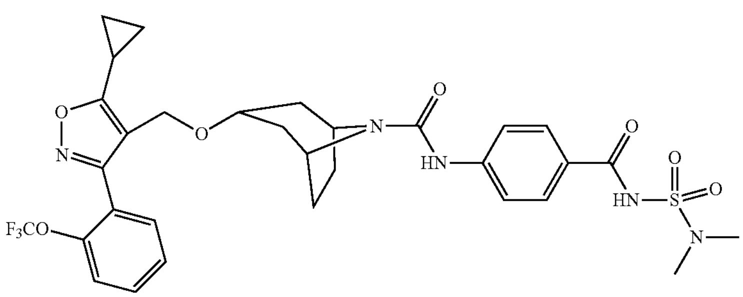 [SMILES: CN(C)S(=O)(=O)NC(=O)c1ccc(NC(=O)N2C3CCC2CC(OCc2c(-c4ccccc4OC(F)(F)F)noc2C2CC2)C3)cc1] |

| Compound | Structure |
|---|---|
| 754 | 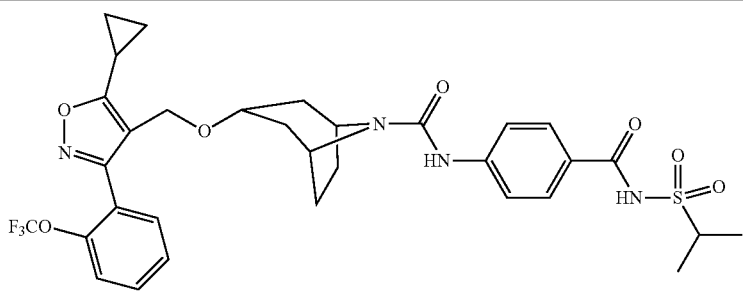 |
| 755 | 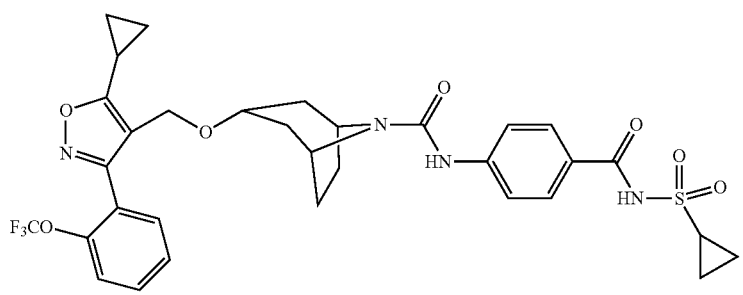 [SMILES: O=C(NS(=O)(=O)C1CC1)c1ccc(NC(=O)N2C3CCC2CC(OCc2c(-c4ccccc4OC(F)(F)F)noc2C2CC2)C3)cc1] |
| 756 | 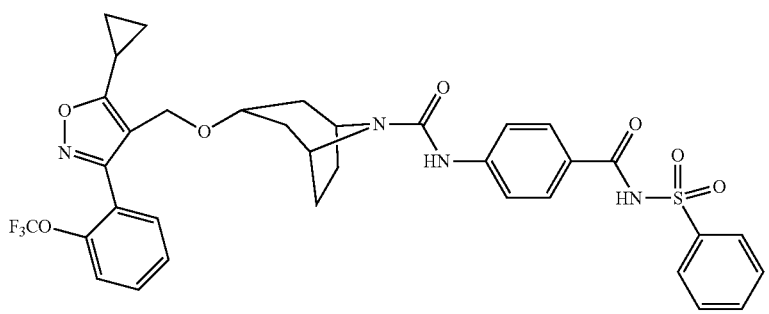 [SMILES: O=C(NS(=O)(=O)c1ccccc1)c1ccc(NC(=O)N2C3CCC2CC(OCc2c(-c4ccccc4OC(F)(F)F)noc2C2CC2)C3)cc1] |
| 757 | 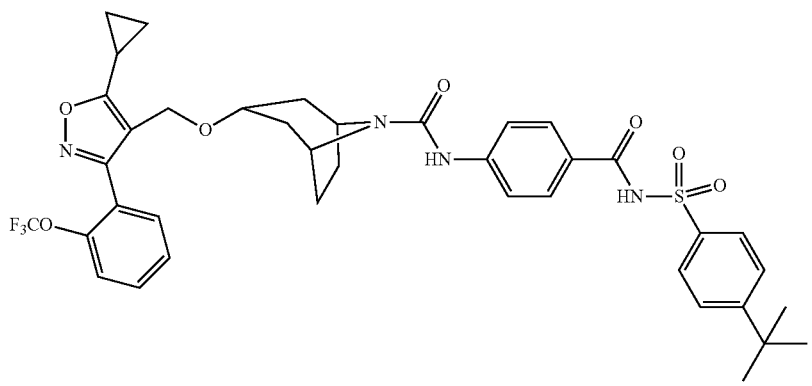 [SMILES: CC(C)(C)c1ccc(S(=O)(=O)NC(=O)c2ccc(NC(=O)N3C4CCC3CC(OCc3c(-c5ccccc5OC(F)(F)F)noc3C3CC3)C4)cc2)cc1] |
| 758 | 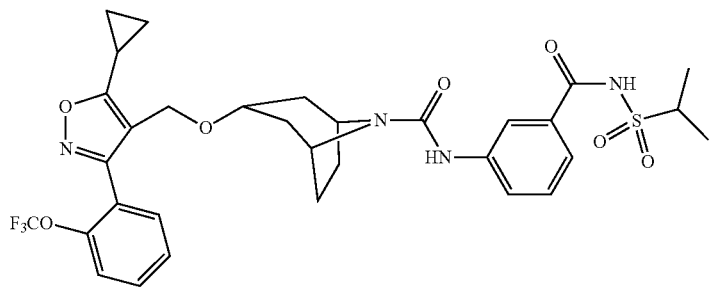 [SMILES: CC(C)S(=O)(=O)NC(=O)c1cccc(NC(=O)N2C3CCC2CC(OCc2c(-c4ccccc4OC(F)(F)F)noc2C2CC2)C3)c1] |

-continued

| Compound | Structure |
|---|---|
| 759 | 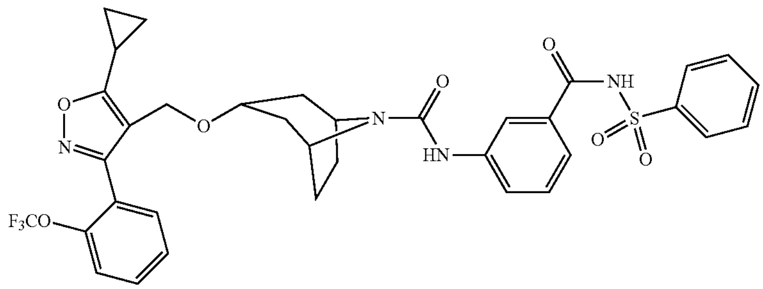 [SMILES: O=C(NS(=O)(=O)c1ccccc1)c1cccc(NC(=O)N2C3CCC2CC(OCc2c(-c4ccccc4OC(F)(F)F)noc2C2CC2)C3)c1] |
| 760 | 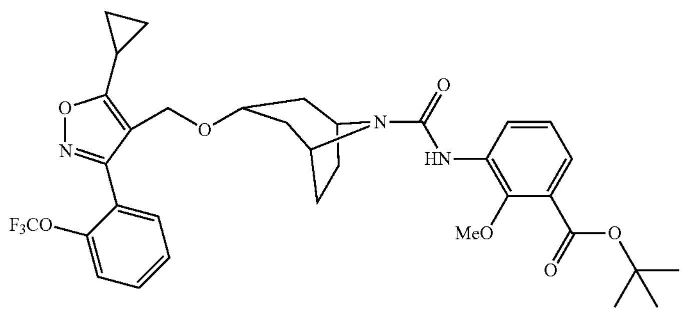 [SMILES: COc1c(NC(=O)N2C3CCC2CC(OCc2c(-c4ccccc4OC(F)(F)F)noc2C2CC2)C3)cccc1C(=O)OC(C)(C)C] |
| 761 | 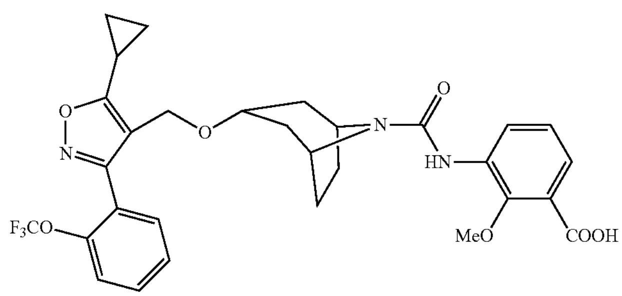 [SMILES: COc1c(NC(=O)N2C3CCC2CC(OCc2c(-c4ccccc4OC(F)(F)F)noc2C2CC2)C3)cccc1C(=O)O] |
| 762 | 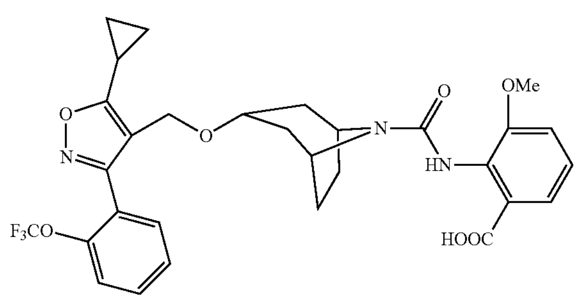 [SMILES: COc1cccc(C(=O)O)c1NC(=O)N1C2CCC1CC(OCc1c(-c3ccccc3OC(F)(F)F)noc1C1CC1)C2] |
| 763 | 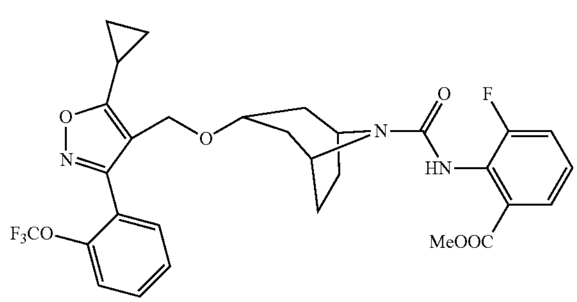 [SMILES: COC(=O)c1cccc(F)c1NC(=O)N1C2CCC1CC(OCc1c(-c3ccccc3OC(F)(F)F)noc1C1CC1)C2] |

| Compound | Structure |
|---|---|
| 764 | 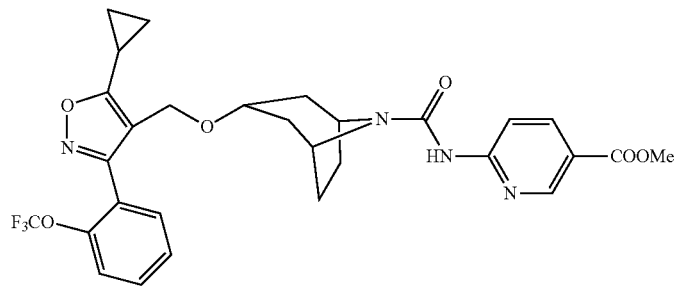 [SMILES: COC(=O)c1ccc(NC(=O)N2C3CCC2CC(OCc2c(-c4ccccc4OC(F)(F)F)noc2C2CC2)C3)nc1] |
| 765 | 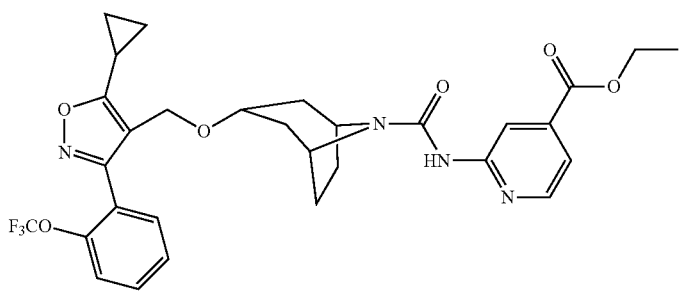 [SMILES: CCOC(=O)c1ccnc(NC(=O)N2C3CCC2CC(OCc2c(-c4ccccc4OC(F)(F)F)noc2C2CC2)C3)c1] |
| 766 | 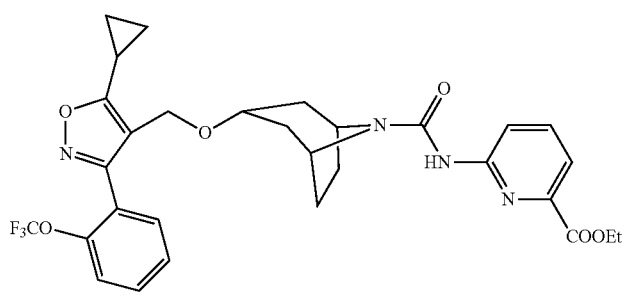 [SMILES: CCOC(=O)c1cccc(NC(=O)N2C3CCC2CC(OCc2c(-c4ccccc4OC(F)(F)F)noc2C2CC2)C3)n1] |
| 767 | 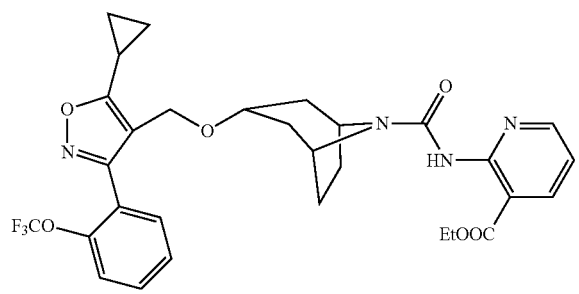 |
| 768 | 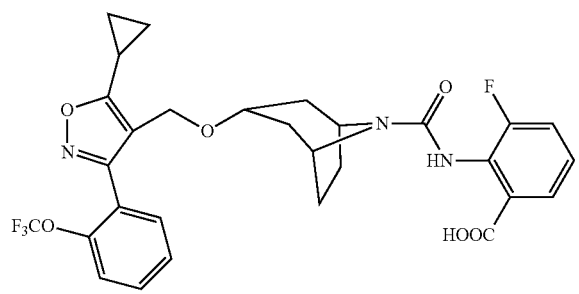 [SMILES: O=C(O)c1cccc(F)c1NC(=O)N1C2CCC1CC(OCc1c(-c3ccccc3OC(F)(F)F)noc1C1CC1)C2] |

-continued

| Compound | Structure |
|---|---|
| 769 | 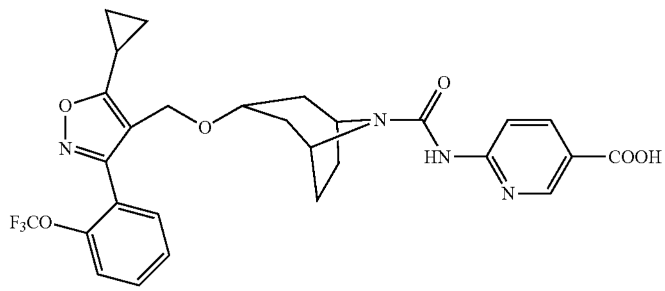 [SMILES: O=C(O)c1ccc(NC(=O)N2C3CCC2CC(OCc2c(-c4ccccc4OC(F)(F)F)noc2C2CC2)C3)nc1] |
| 770 | 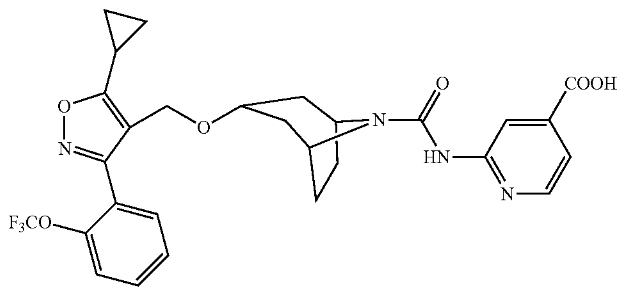 [SMILES: O=C(O)c1ccnc(NC(=O)N2C3CCC2CC(OCc2c(-c4ccccc4OC(F)(F)F)noc2C2CC2)C3)c1] |
| 771 | 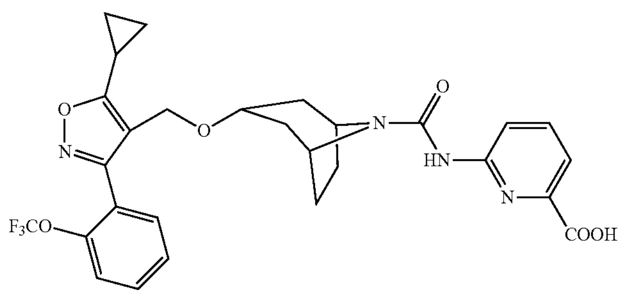 [SMILES: O=C(O)c1cccc(NC(=O)N2C3CCC2CC(OCc2c(-c4ccccc4OC(F)(F)F)noc2C2CC2)C3)n1] |
| 772 | 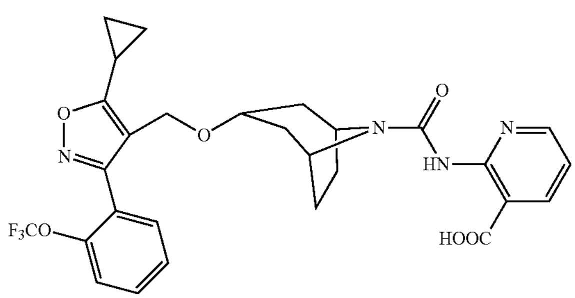 [SMILES: O=C(O)c1cccnc1NC(=O)N1C2CCC1CC(OCc1c(-c3ccccc3OC(F)(F)F)noc1C1CC1)C2] |
| 773 | 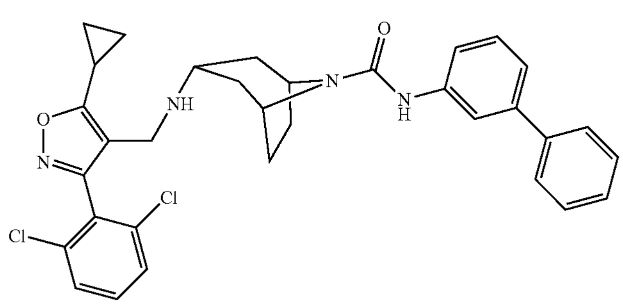 [SMILES: O=C(Nc1cccc(-c2ccccc2)c1)N1C2CCC1CC(NCc1c(-c3c(Cl)cccc3Cl)noc1C1CC1)C2] |

| Compound | Structure |
|---|---|
| 774 | 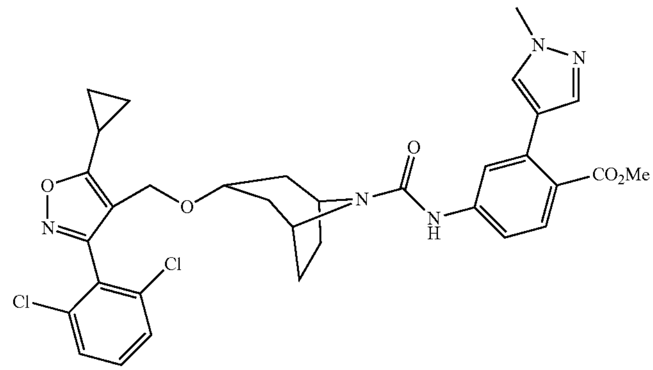 [SMILES: COC(=O)c1ccc(NC(=O)N2C3CCC2CC(OCc2c(-c4c(Cl)cccc4Cl)noc2C2CC2)C3)cc1-c1cnn(C)c1] |
| 775 | 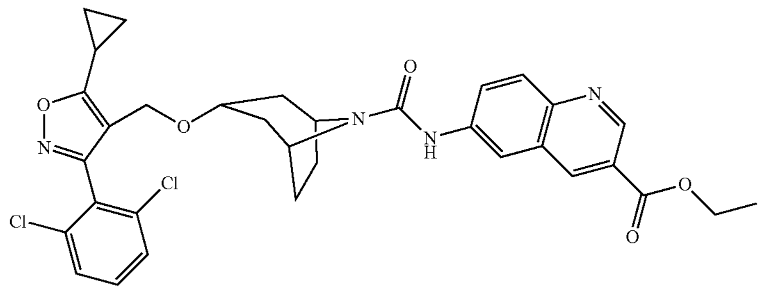 [SMILES: CCOC(=O)c1cnc2ccc(NC(=O)N3C4CCC3CC(OCc3c(-c5c(Cl)cccc5Cl)noc3C3CC3)C4)cc2c1] |
| 776 | 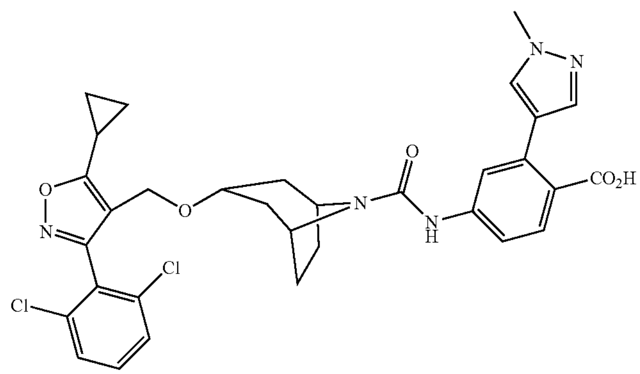 [SMILES: Cn1cc(-c2cc(NC(=O)N3C4CCC3CC(OCc3c(-c5c(Cl)cccc5Cl)noc3C3CC3)C4)ccc2C(=O)O)cn1] |
| 777 | 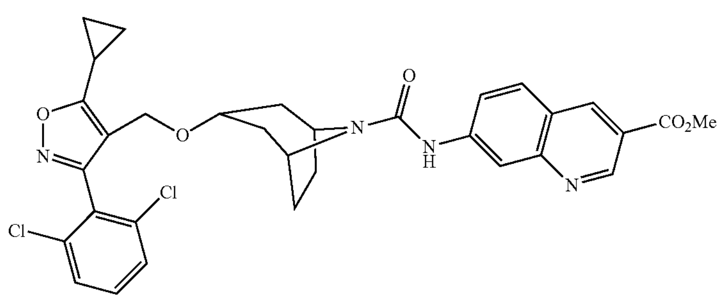 [SMILES: COC(=O)c1cnc2cc(NC(=O)N3C4CCC3CC(OCc3c(-c5c(Cl)cccc5Cl)noc3C3CC3)C4)ccc2c1] |

| Compound | Structure |
|---|---|
| 778 | 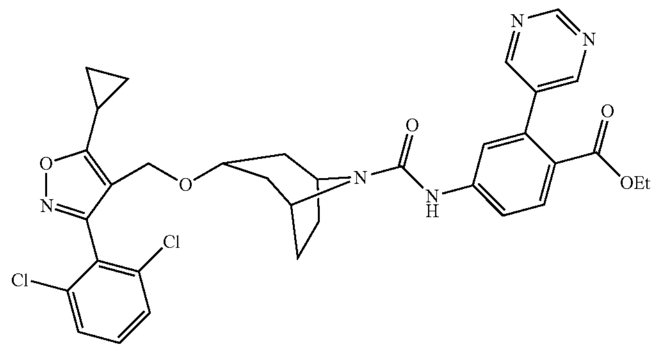 [SMILES: CCOC(=O)c1ccc(NC(=O)N2C3CCC2CC(OCc2c(-c4c(Cl)cccc4Cl)noc2C2CC2)C3)cc1-c1cncnc1] |
| 779 | 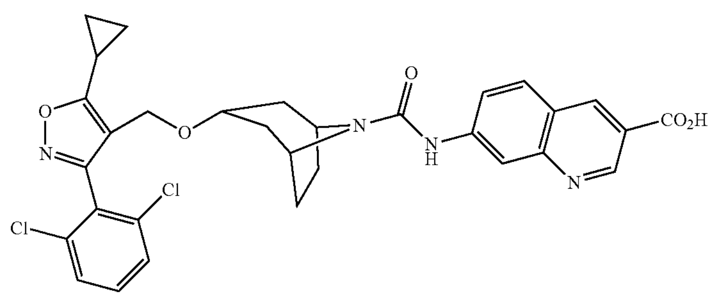 [SMILES: O=C(O)c1cnc2cc(NC(=O)N3C4CCC3CC(OCc3c(-c5c(Cl)cccc5Cl)noc3C3CC3)C4)ccc2c1] |
| 780 | 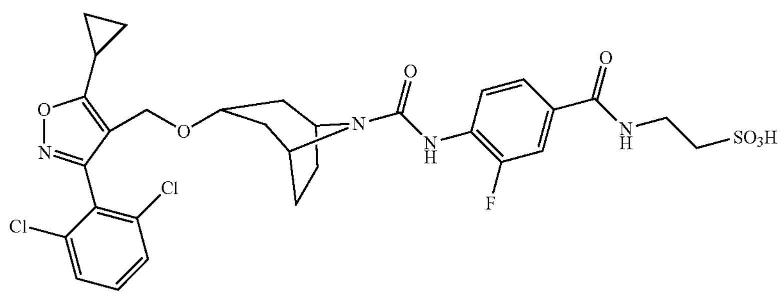 [SMILES: O=C(NCCS(=O)(=O)O)c1ccc(NC(=O)N2C3CCC2CC(OCc2c(-c4c(Cl)cccc4Cl)noc2C2CC2)C3)c(F)c1] |
| 781 | 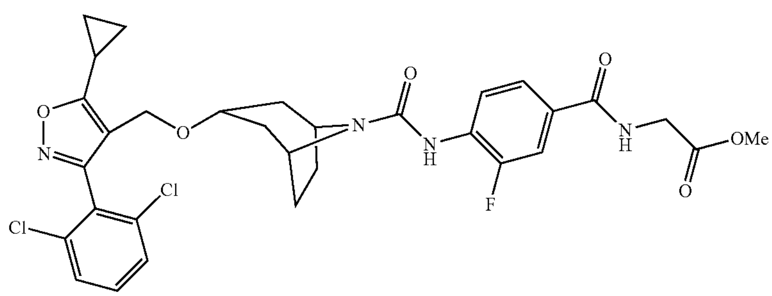 [SMILES: COC(=O)CNC(=O)c1ccc(NC(=O)N2C3CCC2CC(OCc2c(-c4c(Cl)cccc4Cl)noc2C2CC2)C3)c(F)c1] |
| 782 | 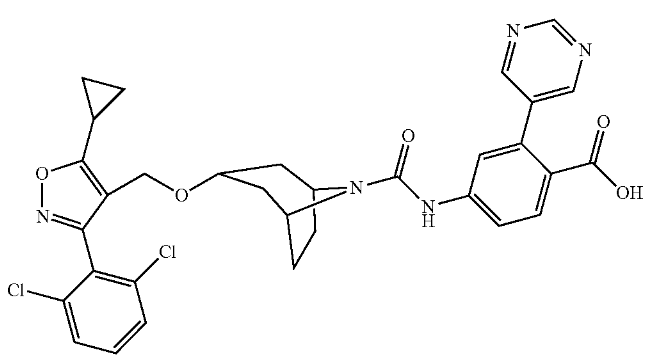 [SMILES: O=C(O)c1ccc(NC(=O)N2C3CCC2CC(OCc2c(-c4c(Cl)cccc4Cl)noc2C2CC2)C3)cc1-c1cncnc1] |

| Compound | Structure |
|---|---|
| 783 | 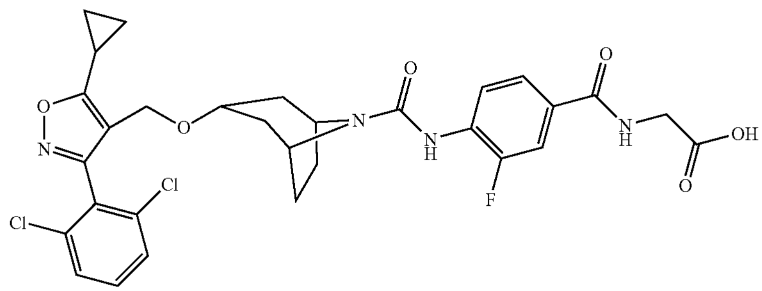 [SMILES: O=C(O)CNC(=O)c1ccc(NC(=O)N2C3CCC2CC(OCc2c(-c4c(Cl)cccc4Cl)noc2C2CC2)C3)c(F)c1] |
| 784 | 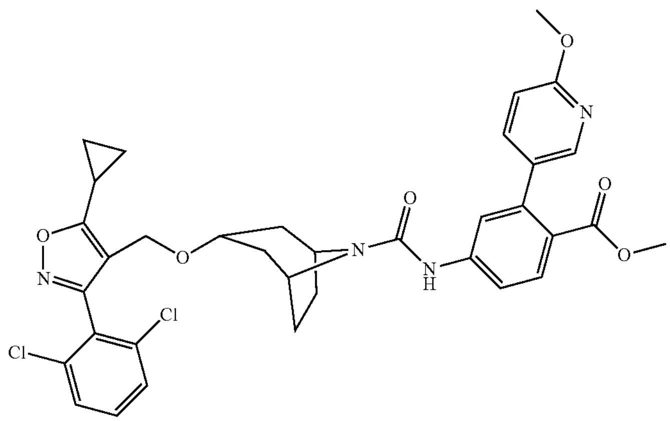 [SMILES: COC(=O)c1ccc(NC(=O)N2C3CCC2CC(OCc2c(-c4c(Cl)cccc4Cl)noc2C2CC2)C3)cc1-c1ccc(OC)nc1] |
| 785 | 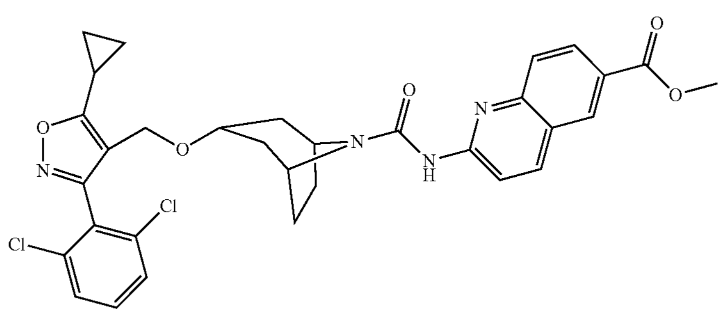 [SMILES: COC(=O)c1ccc2nc(NC(=O)N3C4CCC3CC(OCc3c(-c5c(Cl)cccc5Cl)noc3C3CC3)C4)ccc2c1] |
| 786 | 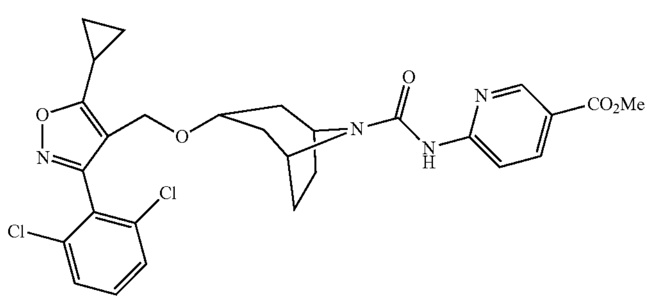 [SMILES: COC(=O)c1ccc(NC(=O)N2C3CCC2CC(OCc2c(-c4c(Cl)cccc4Cl)noc2C2CC2)C3)nc1] |

| Compound | Structure |
|---|---|
| 787 | 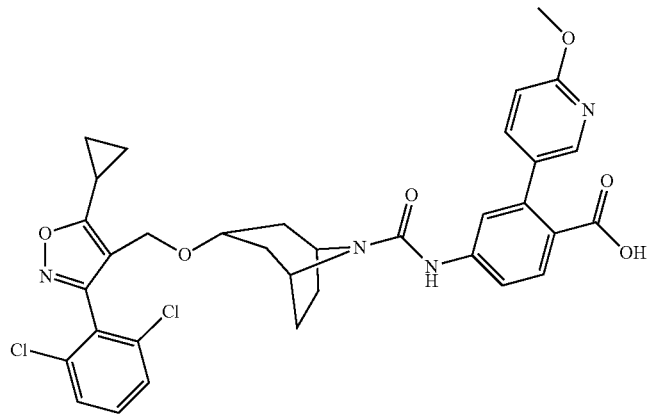 [SMILES: COc1ccc(-c2cc(NC(=O)N3C4CCC3CC(OCc3c(-c5c(Cl)cccc5Cl)noc3C3CC3)C4)ccc2C(=O)O)cn1] |
| 788 | 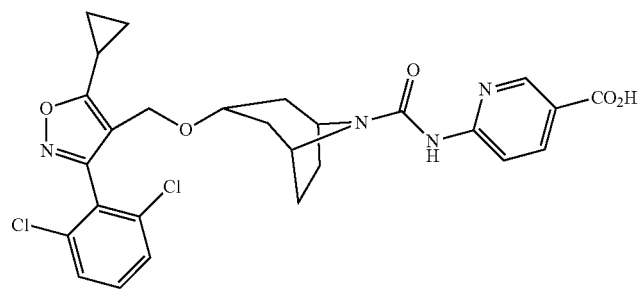 [SMILES: O=C(O)c1ccc(NC(=O)N2C3CCC2CC(OCc2c(-c4c(Cl)cccc4Cl)noc2C2CC2)C3)nc1] |
| 789 | 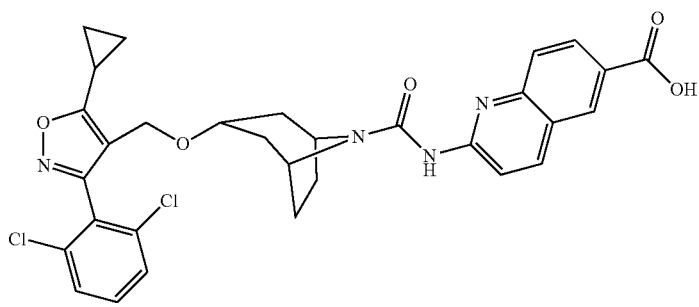 [SMILES: O=C(O)c1ccc2nc(NC(=O)N3C4CCC3CC(OCc3c(-c5c(Cl)cccc5Cl)noc3C3CC3)C4)ccc2c1] |
| 790 | 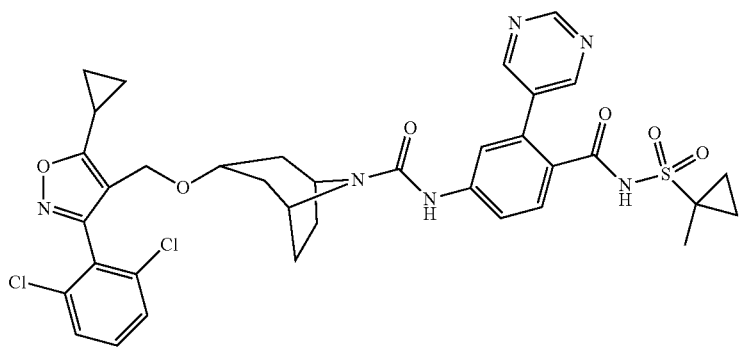 [SMILES: CC1(S(=O)(=O)NC(=O)c2ccc(NC(=O)N3C4CCC3CC(OCc3c(-c5c(Cl)cccc5Cl)noc3C3CC3)C4)cc2-c2cncnc2)CC1] |

| Compound | Structure |
|---|---|
| 791 | 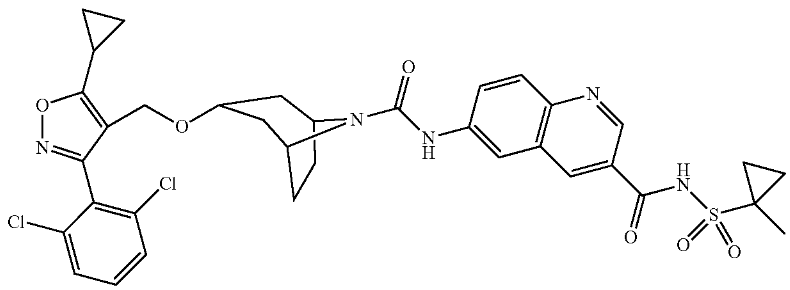 [SMILES: CC1(S(=O)(=O)NC(=O)c2cnc3ccc(NC(=O)N4C5CCC4CC(OCc4c(-c6c(Cl)cccc6Cl)noc4C4CC4)C5)cc3c2)CC1] |
| 792 | 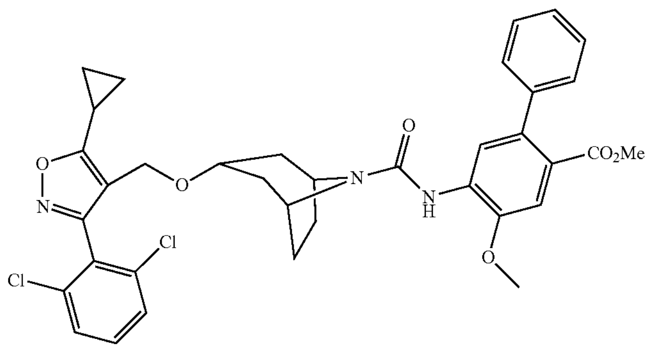 [SMILES: COC(=O)c1cc(OC)c(NC(=O)N2C3CCC2CC(OCc2c(-c4c(Cl)cccc4Cl)noc2C2CC2)C3)cc1-c1ccccc1] |
| 793 | 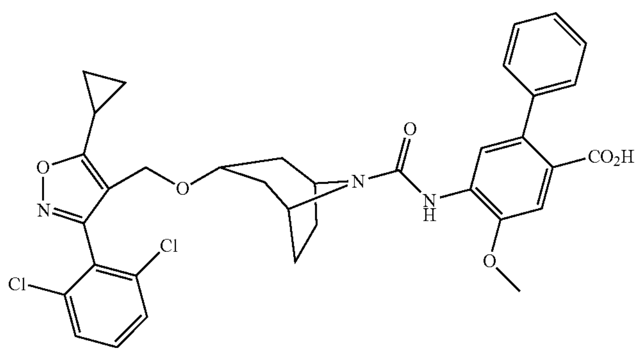 [SMILES: COc1cc(C(=O)O)c(-c2ccccc2)cc1NC(=O)N1C2CCC1CC(OCc1c(-c3c(Cl)cccc3Cl)noc1C1CC1)C2] |
| 794 | 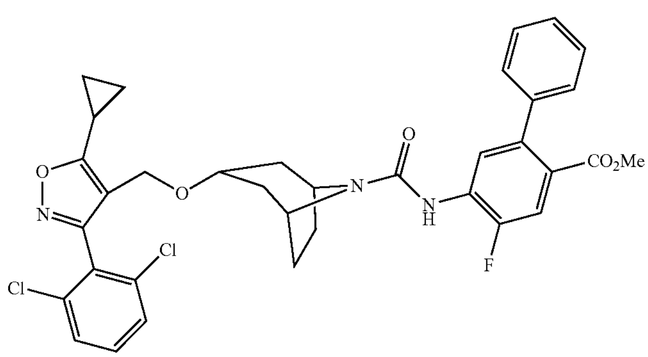 [SMILES: COC(=O)c1cc(F)c(NC(=O)N2C3CCC2CC(OCc2c(-c4c(Cl)cccc4Cl)noc2C2CC2)C3)cc1-c1ccccc1] |

| Compound | Structure |
|---|---|
| 795 | 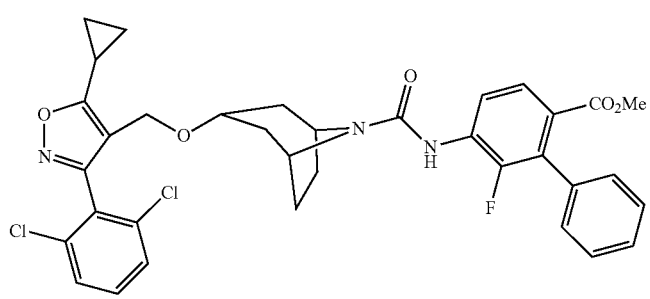 [SMILES: COC(=O)c1ccc(NC(=O)N2C3CCC2CC(OCc2c(-c4c(Cl)cccc4Cl)noc2C2CC2)C3)c(F)c1-c1ccccc1] |
| 796 | 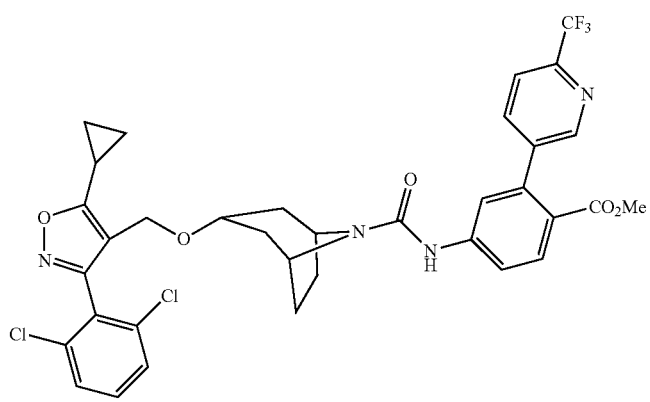 [SMILES: COC(=O)c1ccc(NC(=O)N2C3CCC2CC(OCc2c(-c4c(Cl)cccc4Cl)noc2C2CC2)C3)cc1-c1ccc(C(F)(F)F)nc1] |
| 797 | 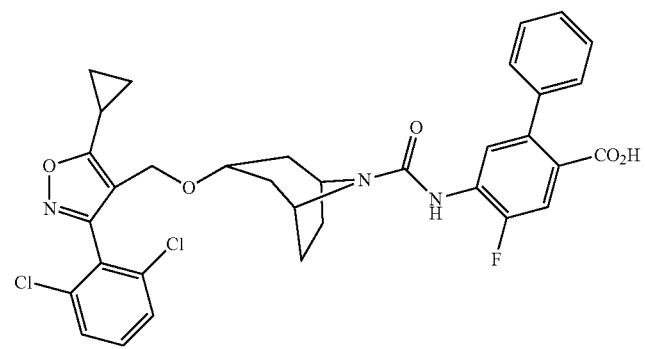 [SMILES: O=C(O)c1cc(F)c(NC(=O)N2C3CCC2CC(OCc2c(-c4c(Cl)cccc4Cl)noc2C2CC2)C3)cc1-c1ccccc1] |
| 798 | 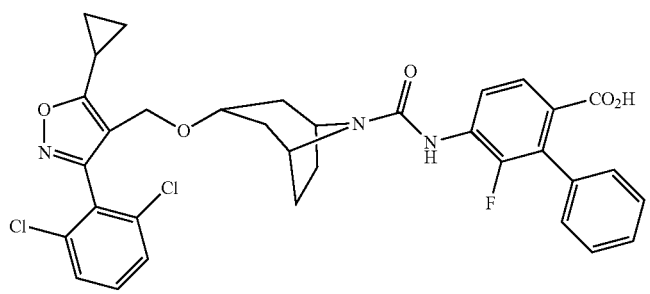 [SMILES: O=C(O)c1ccc(NC(=O)N2C3CCC2CC(OCc2c(-c4c(Cl)cccc4Cl)noc2C2CC2)C3)c(F)c1-c1ccccc1] |

| Compound | Structure |
|---|---|
| 799 | 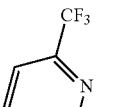 |
| 800 | 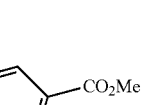 |
| 801 | 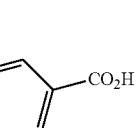 |
| 802 | 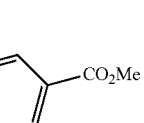 |
| 803 | 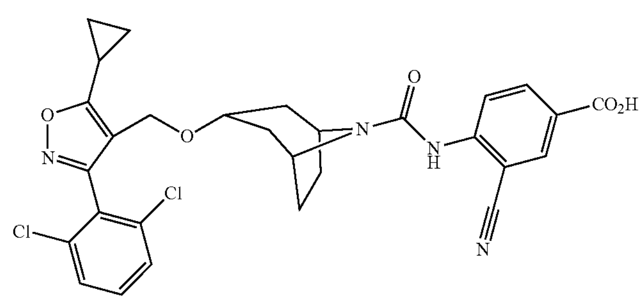 [SMILES: N#Cc1cc(C(=O)O)ccc1NC(=O)N1C2CCC1CC(OCc1c(-c3c(Cl)cccc3Cl)noc1C1CC1)C2] |

-continued
| Compound | Structure |
|---|---|
| 804 | 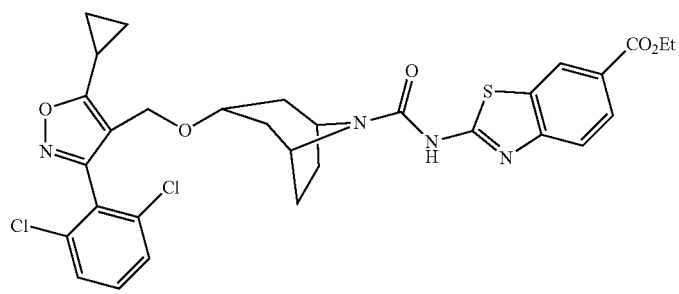 [SMILES: CCOC(=O)c1ccc2nc(NC(=O)N3C4CCC3CC(OCc3c(-c5c(Cl)cccc5Cl)noc3C3CC3)C4)sc2c1] |
| 805 | 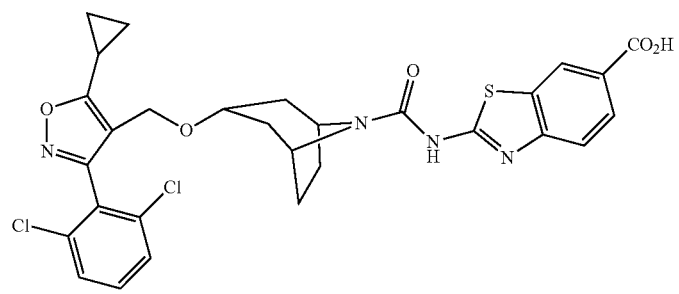 [SMILES: O=C(O)c1ccc2nc(NC(=O)N3C4CCC3CC(OCc3c(-c5c(Cl)cccc5Cl)noc3C3CC3)C4)sc2c1] |
| 806 | 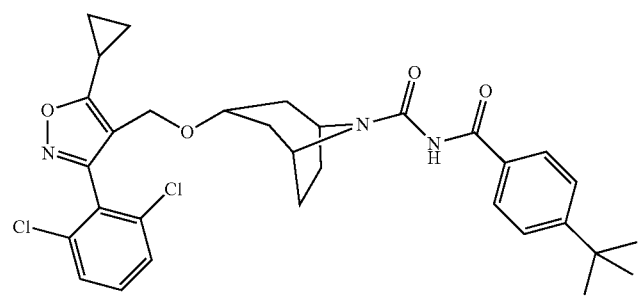 [SMILES: CC(C)(C)c1ccc(C(=O)NC(=O)N2C3CCC2CC(OCc2c(-c4c(Cl)cccc4Cl)noc2C2CC2)C3)cc1] |
| 807 | 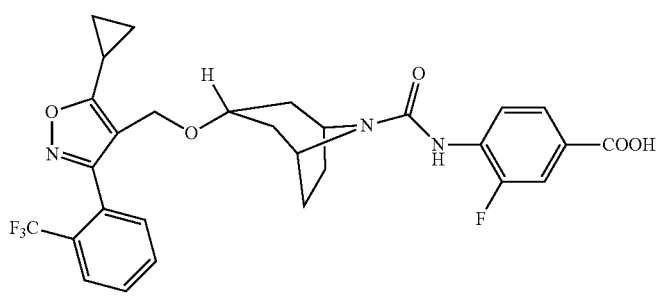 [SMILES: O=C(O)c1ccc(NC(=O)N2C3CCC2CC(OCc2c(-c4ccccc4C(F)(F)F)noc2C2CC2)C3)c(F)c1] |
| 808 | 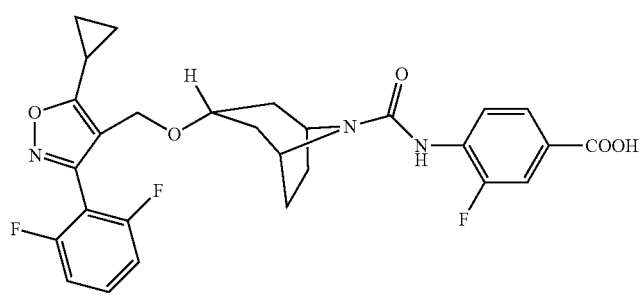 [SMILES: O=C(O)c1ccc(NC(=O)N2C3CCC2CC(OCc2c(-c4c(F)cccc4F)noc2C2CC2)C3)c(F)c1] |

| Compound | Structure |
|---|---|
| 809 | 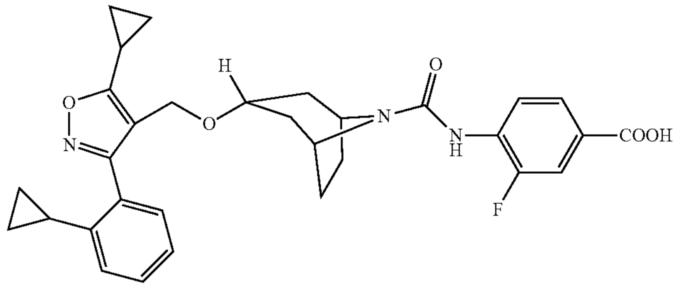 [SMILES: O=C(O)c1ccc(NC(=O)N2C3CCC2CC(OCc2c(-c4ccccc4C4CC4)noc2C2CC2)C3)c(F)c1] |
| 810 | 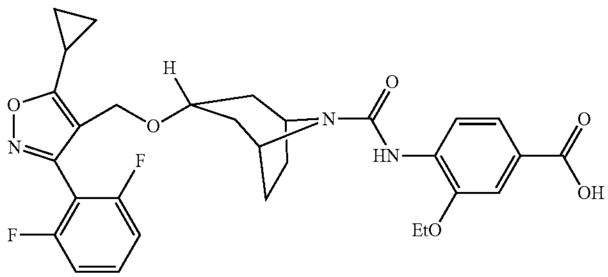 [SMILES: CCOc1cc(C(=O)O)ccc1NC(=O)N1C2CCC1CC(OCc1c(-c3c(F)cccc3F)noc1C1CC1)C2] |
| 811 | 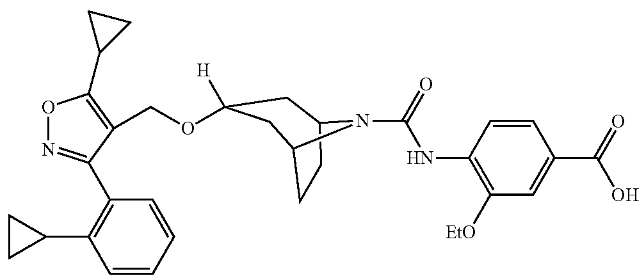 [SMILES: CCOc1cc(C(=O)O)ccc1NC(=O)N1C2CCC1CC(OCc1c(-c3ccccc3C3CC3)noc1C1CC1)C2] |
| 812 | 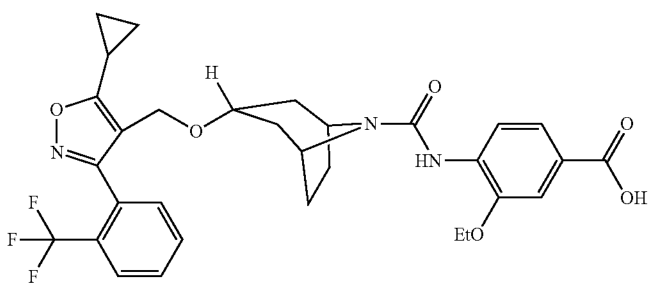 [SMILES: CCOc1cc(C(=O)O)ccc1NC(=O)N1C2CCC1CC(OCc1c(-c3ccccc3C(F)(F)F)noc1C1CC1)C2] |
| 813 | 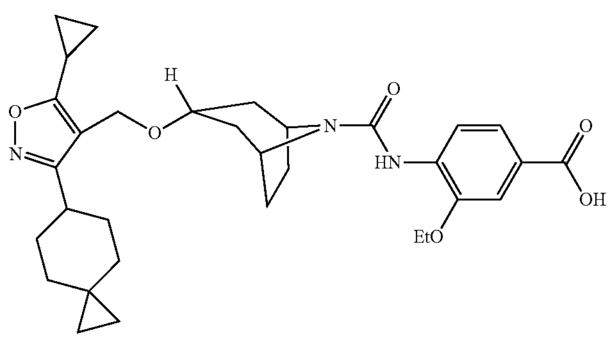 [SMILES: CCOc1cc(C(=O)O)ccc1NC(=O)N1C2CCC1CC(OCc1c(C3CCC4(CC3)CC4)noc1C1CC1)C2] |

-continued
| Compound | Structure |
|---|---|
| 814 | 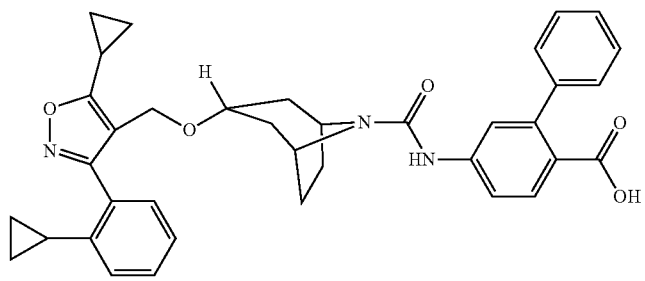 [SMILES: O=C(O)c1ccc(NC(=O)N2C3CCC2CC(OCc2c(-c4ccccc4C4CC4)noc2C2CC2)C3)cc1-c1ccccc1] |
| 815 | 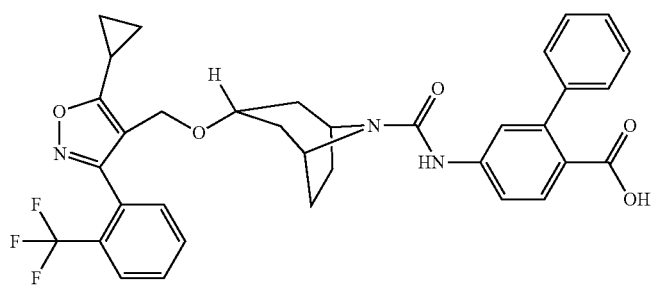 [SMILES: O=C(O)c1ccc(NC(=O)N2C3CCC2CC(OCc2c(-c4ccccc4C(F)(F)F)noc2C2CC2)C3)cc1-c1ccccc1] |
| 816 | 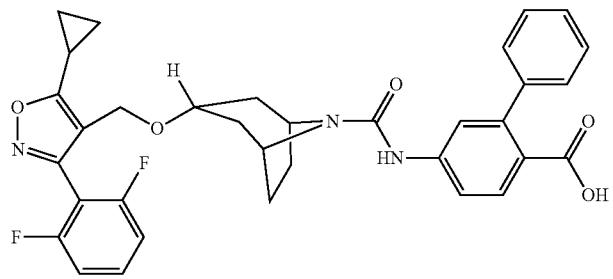 [SMILES: O=C(O)c1ccc(NC(=O)N2C3CCC2CC(OCc2c(-c4c(F)cccc4F)noc2C2CC2)C3)cc1-c1ccccc1] |
| 817 | 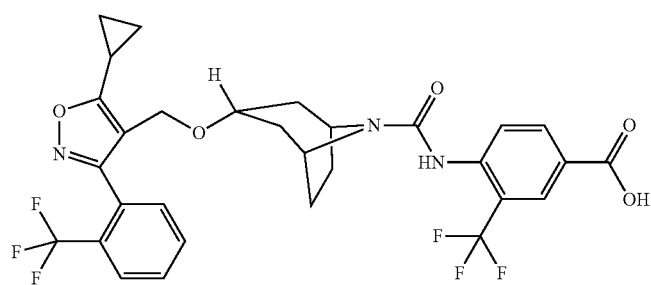 [SMILES: O=C(O)c1ccc(NC(=O)N2C3CCC2CC(OCc2c(-c4ccccc4C(F)(F)F)noc2C2CC2)C3)c(C(F)(F)F)c1] |
| 818 | 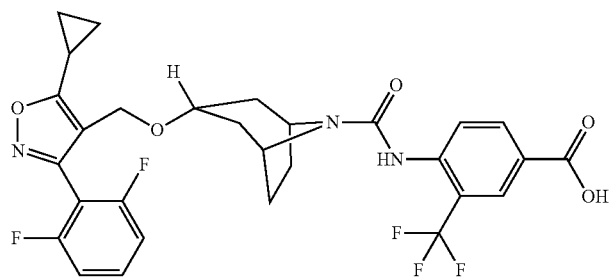 [SMILES: O=C(O)c1ccc(NC(=O)N2C3CCC2CC(OCc2c(-c4c(F)cccc4F)noc2C2CC2)C3)c(C(F)(F)F)c1] |

| Compound | Structure |
|---|---|
| 819 | 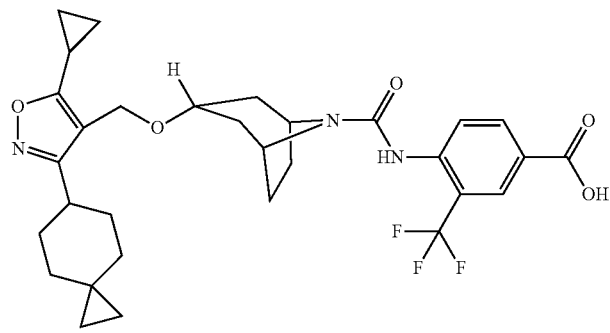 [SMILES: O=C(O)c1ccc(NC(=O)N2C3CCC2CC(OCc2c(C4CCC5(CC4)CC5)noc2C2CC2)C3)c(C(F)(F)F)c1] |
| 820 | 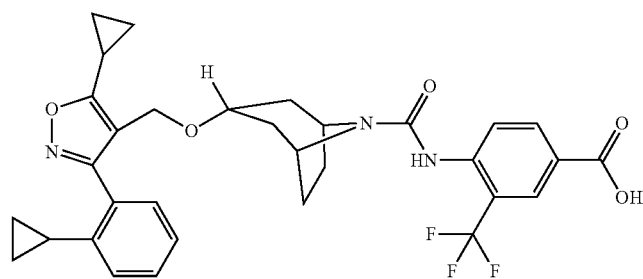 [SMILES: O=C(O)c1ccc(NC(=O)N2C3CCC2CC(OCc2c(-c4ccccc4C4CC4)noc2C2CC2)C3)c(C(F)(F)F)c1] |
| 821 | 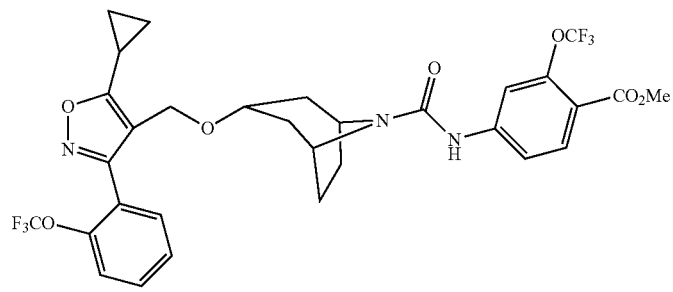 [SMILES: COC(=O)c1ccc(NC(=O)N2C3CCC2CC(OCc2c(-c4ccccc4OC(F)(F)F)noc2C2CC2)C3)cc1OC(F)(F)F] |
| 822 | 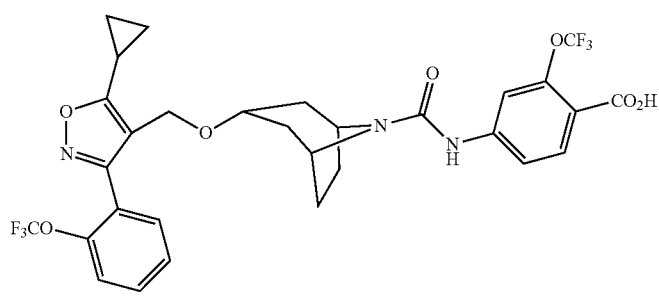 [SMILES: O=C(O)c1ccc(NC(=O)N2C3CCC2CC(OCc2c(-c4ccccc4OC(F)(F)F)noc2C2CC2)C3)cc1OC(F)(F)F] |
| 823 | 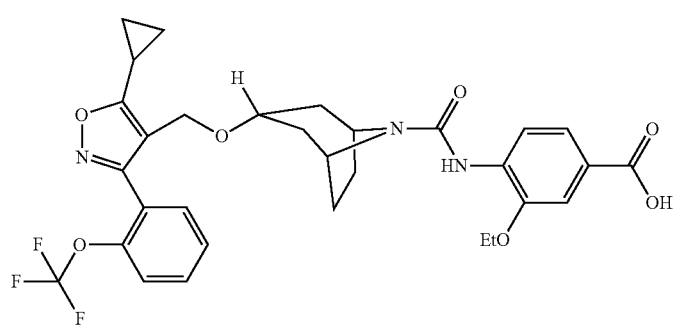 [SMILES: CCOc1cc(C(=O)O)ccc1NC(=O)N1C2CCC1CC(OCc1c(-c3ccccc3OC(F)(F)F)noc1C1CC1)C2] |

| Compound | Structure |
|---|---|
| 824 | 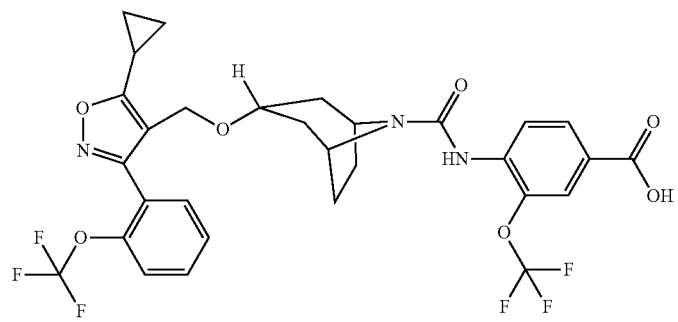 [SMILES: O=C(O)c1ccc(NC(=O)N2C3CCC2CC(OCc2c(-c4ccccc4OC(F)(F)F)noc2C2CC2)C3)c(OC(F)(F)F)c1] |
| 825 | 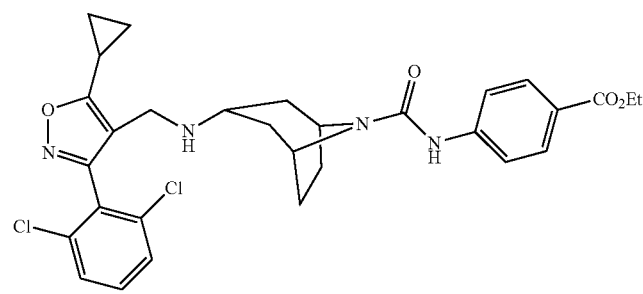 [SMILES: CCOC(=O)c1ccc(NC(=O)N2C3CCC2CC(NCc2c(-c4c(Cl)cccc4Cl)noc2C2CC2)C3)cc1] |
| 826 | 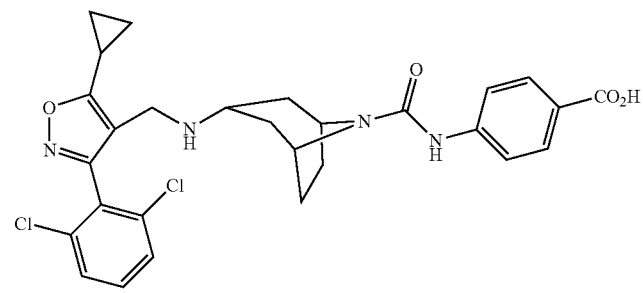 [SMILES: O=C(O)c1ccc(NC(=O)N2C3CCC2CC(NCc2c(-c4c(Cl)cccc4Cl)noc2C2CC2)C3)cc1] |
| 827 | 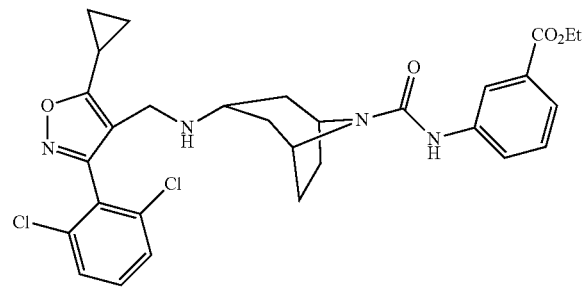 [SMILES: CCOC(=O)c1cccc(NC(=O)N2C3CCC2CC(NCc2c(-c4c(Cl)cccc4Cl)noc2C2CC2)C3)c1] |
| 828 | 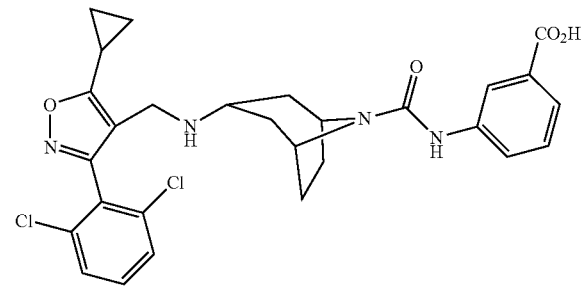 [SMILES: O=C(O)c1cccc(NC(=O)N2C3CCC2CC(NCc2c(-c4c(Cl)cccc4Cl)noc2C2CC2)C3)c1] |

| Compound | Structure |
|---|---|
| 829 | 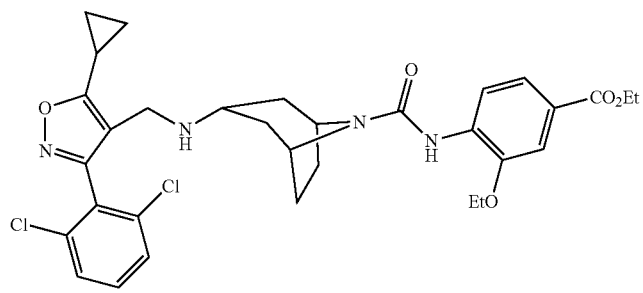 [SMILES: CCOC(=O)c1ccc(NC(=O)N2C3CCC2CC(NCc2c(-c4c(Cl)cccc4Cl)noc2C2CC2)C3)c(OCC)c1] |
| 830 | 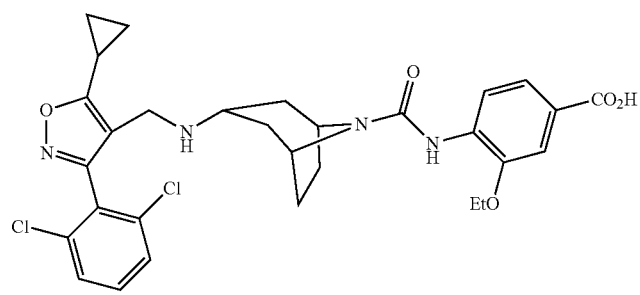 [SMILES: CCOc1cc(C(=O)O)ccc1NC(=O)N1C2CCC1CC(NCc1c(-c3c(Cl)cccc3Cl)noc1C1CC1)C2] |
| 831 | 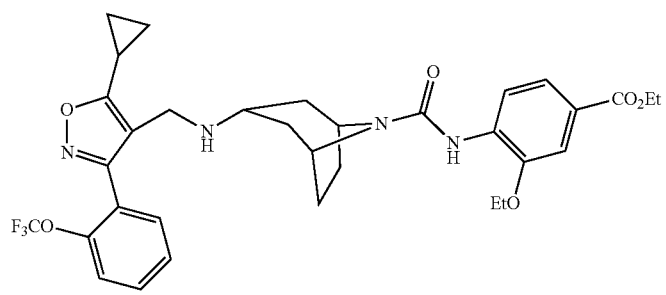 [SMILES: CCOC(=O)c1ccc(NC(=O)N2C3CCC2CC(NCc2c(-c4ccccc4OC(F)(F)F)noc2C2CC2)C3)c(OCC)c1] |
| 832 | 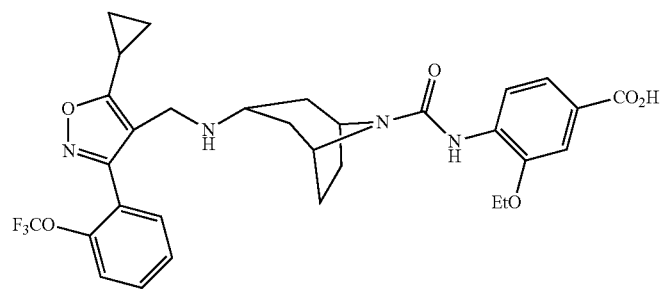 [SMILES: CCOc1cc(C(=O)O)ccc1NC(=O)N1C2CCC1CC(NCc1c(-c3ccccc3OC(F)(F)F)noc1C1CC1)C2] |
| 833 | 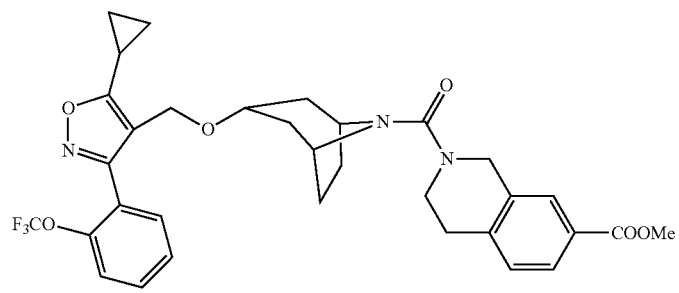 [SMILES: COC(=O)c1ccc2c(c1)CN(C(=O)N1C3CCC1CC(OCc1c(-c4ccccc4OC(F)(F)F)noc1C1CC1)C3)CC2] |

| Compound | Structure |
|---|---|
| 834 | (structure with cyclopropyl-isoxazole, F₃CO-phenyl, bicyclic amine linked to tetrahydroisoquinoline-COOH via urea) |
| 835 | (structure with cyclopropyl-isoxazole, 2,6-dichlorophenyl, bicyclic amine linked via urea to 5-phenylpyridin-3-yl amine) |
| 836 | (structure with cyclopropyl-isoxazole, 2,6-dichlorophenyl, bicyclic amine linked via urea to 3-(pyridin-4-yl)phenyl amine) |

20. A method for treating a disease or condition selected from the group consisting of primary biliary cirrhosis, cerebrotendinous xanthomatosis, primary sclerosing cholangitis, alcoholic liver disease, nonalcoholic fatty liver disease, nonalcoholic steatohepatitis, dyslipidemia, atherosclerosis, hypercholesterolemia, hypertriglyceridemia, and Type II diabetes in a subject in need thereof, comprising administering to the subject a therapeutically effective amount of a compound according to claim 1.

21. The method according to claim 20, wherein the disease or condition is selected from primary biliary cirrhosis, primary sclerosing cholangitis, and cerebrotendinous xanthomatosis.

22. A pharmaceutical composition comprising a compound of claim 1 and a pharmaceutically acceptable carrier.

23. A method for treating nonalcoholic steatohepatitis in a subject in need thereof, comprising administering to the subject a therapeutically effective amount of a compound according to claim 1.

24. A method for treating primary biliary cirrhosis in a subject in need thereof, comprising administering to the subject a therapeutically effective amount of a compound according to claim 1.

25. A method for treating nonalcoholic fatty liver disease in a subject in need thereof, comprising administering to the subject a therapeutically effective amount of a compound according to claim 1.

* * * * *

UNITED STATES PATENT AND TRADEMARK OFFICE
CERTIFICATE OF CORRECTION

PATENT NO. : 10,597,391 B2
APPLICATION NO. : 15/793554
DATED : March 24, 2020
INVENTOR(S) : Jing He et al.

It is certified that error appears in the above-identified patent and that said Letters Patent is hereby corrected as shown below:

In the Claims

At Column 278
In Claim 3, Line 27, after wherein delete "$R^1$" and insert -- $R^2$ --; and
In Claim 4, Line 29, after wherein delete "$R^1$" and insert -- $R^2$ --.

At Column 356
In Claim 14, at Example 374 2nd formula delete " 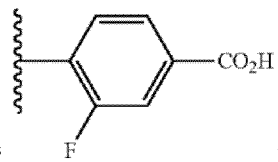 " and insert 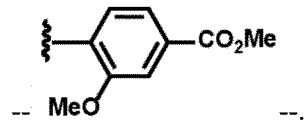 --.

At Column 362
In Claim 14, at Example 399 2nd formula delete " 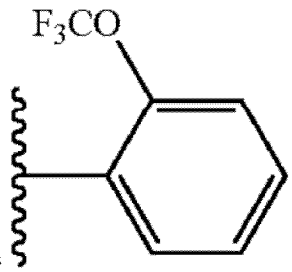 " and insert Signed and Sealed this
Twenty-seventh Day of October, 2020

Andrei Iancu
*Director of the United States Patent and Trademark Office*